(12) United States Patent
Meyers et al.

(10) Patent No.: US 12,268,847 B1
(45) Date of Patent: Apr. 8, 2025

(54) DEVICES AND METHODS FOR DELIVERY OF SUBSTANCES WITHIN A MEDICAMENT CONTAINER

(71) Applicant: kaleo, Inc., Richmond, VA (US)

(72) Inventors: Paul F. Meyers, Fishers, IN (US); Michael J. Roe, Powhatan, VA (US)

(73) Assignee: kaleo, Inc., Richmond, VA (US)

( * ) Notice: Subject to any disclaimer, the term of this patent is extended or adjusted under 35 U.S.C. 154(b) by 293 days.

(21) Appl. No.: 17/668,228

(22) Filed: Feb. 9, 2022

Related U.S. Application Data

(60) Provisional application No. 63/147,785, filed on Feb. 10, 2021.

(51) Int. Cl.
*A61M 5/20* (2006.01)
*A61M 5/315* (2006.01)
*A61M 5/32* (2006.01)

(52) U.S. Cl.
CPC ...... *A61M 5/2046* (2013.01); *A61M 5/31548* (2013.01); *A61M 5/3158* (2013.01);
(Continued)

(58) Field of Classification Search
CPC .............. A61M 5/2053; A61M 5/2046; A61M 5/3158; A61M 5/322
See application file for complete search history.

(56) References Cited

U.S. PATENT DOCUMENTS

| | | |
|---|---|---|
| 2,409,656 A | 10/1946 | Austin |
| 2,960,087 A | 11/1960 | Uytenbogaart |

(Continued)

FOREIGN PATENT DOCUMENTS

| | | |
|---|---|---|
| DE | 2019296 | 11/1971 |
| EP | 1287840 A1 | 3/2003 |

(Continued)

OTHER PUBLICATIONS

"Anaphylaxis Canada Product Catalogue," Anaphylaxis Canada > Living with Anaphylaxis > Tools and Resources [online] [retrieved on Jan. 24, 2007] Retrieved from the Internet <URL: http://anaphylaxis.org/content/livingwith/product catalogue.asp >, 9 pages.
(Continued)

*Primary Examiner* — Nathan R Price
*Assistant Examiner* — Tania Isma
(74) *Attorney, Agent, or Firm* — Mills IP Law, PLLC

(57) ABSTRACT

An apparatus includes a housing, an energy storage member, a carrier, a medicament container, and a delivery control mechanism. The housing defines a gas chamber configured to receive pressurized gas from the energy storage member to pressurize the gas chamber. The carrier has a proximal surface that defines a portion of the gas chamber. The medicament container is coupled to the carrier and has a distal end portion coupled to a delivery member. The medicament container contains at least 5 mL of medicament and includes an elastomeric member that seals the medicament within the medicament container. The delivery control mechanism is coupled to a proximal end portion of the medicament container and includes a flow restriction member for regulating a pressure supplied by the gas chamber and entering into the medicament container that acts on the elastomeric member.

25 Claims, 60 Drawing Sheets

(52) U.S. Cl.
CPC ........... *A61M 5/322* (2013.01); *A61M 5/2053* (2013.01); *A61M 2005/2093* (2013.01)

(56) References Cited

U.S. PATENT DOCUMENTS

| | | | |
|---|---|---|---|
| 3,055,362 A | 9/1962 | Uytenbogaart |
| 3,115,133 A | 12/1963 | Morando |
| 3,426,448 A | 2/1969 | Sarnoff |
| 3,563,373 A | 2/1971 | Paulson |
| 3,565,070 A | 2/1971 | Hanson et al. |
| 3,688,765 A | 9/1972 | Gasaway |
| 3,768,472 A | 10/1973 | Hodosh et al. |
| 3,795,061 A | 3/1974 | Sarnoff et al. |
| 3,797,489 A | 3/1974 | Sarnoff |
| 3,941,130 A | 3/1976 | Tibbs |
| 3,945,379 A | 3/1976 | Pritz et al. |
| 4,031,889 A | 6/1977 | Pike |
| 4,108,177 A | 8/1978 | Pistor |
| 4,124,024 A | 11/1978 | Schwebel et al. |
| 4,226,235 A | 10/1980 | Sarnoff et al. |
| 4,227,528 A | 10/1980 | Wardlaw |
| 4,258,713 A | 3/1981 | Wardlaw |
| 4,360,019 A | 11/1982 | Portner et al. |
| 4,378,015 A | 3/1983 | Wardlaw |
| 4,394,863 A | 7/1983 | Bartner |
| 4,424,057 A | 1/1984 | House |
| 4,441,629 A | 4/1984 | Mackal |
| 4,484,910 A | 11/1984 | Sarnoff |
| 4,573,976 A | 3/1986 | Sampson et al. |
| 4,596,556 A | 6/1986 | Morrow et al. |
| 4,610,666 A | 9/1986 | Pizzino |
| 4,617,557 A | 10/1986 | Gordon |
| 4,624,660 A | 11/1986 | Mijers et al. |
| 4,640,686 A | 2/1987 | Dalling et al. |
| 4,643,721 A | 2/1987 | Brunet |
| 4,664,653 A | 5/1987 | Sagstetter et al. |
| 4,666,430 A | 5/1987 | Brown et al. |
| 4,673,657 A | 6/1987 | Christian |
| 4,689,042 A | 8/1987 | Sarnoff et al. |
| 4,693,708 A | 9/1987 | Wanderer et al. |
| 4,755,169 A | 7/1988 | Sarnoff et al. |
| 4,781,697 A | 11/1988 | Slaughter |
| 4,782,841 A | 11/1988 | Lopez |
| 4,784,652 A | 11/1988 | Wikström |
| 4,790,824 A | 12/1988 | Morrow et al. |
| 4,795,433 A | 1/1989 | Sarnoff |
| 4,820,286 A | 4/1989 | van der Wal |
| 4,822,340 A | 4/1989 | Kamstra |
| 4,826,489 A | 5/1989 | Haber |
| 4,853,521 A | 8/1989 | Claeys et al. |
| 4,874,381 A | 10/1989 | Vetter |
| 4,874,382 A | 10/1989 | Lindemann et al. |
| 4,894,054 A | 1/1990 | Miskinyar |
| 4,906,235 A | 3/1990 | Roberts |
| 4,915,695 A | 4/1990 | Koobs |
| 4,941,880 A | 7/1990 | Burns |
| 4,959,056 A | 9/1990 | Dombrowski et al. |
| 4,968,302 A | 11/1990 | Schluter et al. |
| 4,983,164 A | 1/1991 | Hook et al. |
| 5,000,736 A | 3/1991 | Kaufhold, Jr. et al. |
| 5,024,656 A | 6/1991 | Gasaway et al. |
| 5,037,306 A | 8/1991 | van Schoonhoven |
| 5,038,023 A | 8/1991 | Saliga |
| 5,041,088 A | 8/1991 | Ritson et al. |
| 5,042,977 A | 8/1991 | Bechtold et al. |
| 5,062,603 A | 11/1991 | Smith et al. |
| 5,064,413 A | 11/1991 | McKinnon et al. |
| 5,071,353 A | 12/1991 | van der Wal |
| 5,080,649 A | 1/1992 | Vetter |
| 5,085,642 A | 2/1992 | Sarnoff et al. |
| 5,092,842 A | 3/1992 | Bechtold et al. |
| 5,092,843 A | 3/1992 | Monroe et al. |
| 5,104,380 A | 4/1992 | Holman et al. |
| 5,125,898 A | 6/1992 | Kaufhold, Jr. et al. |
| 5,139,490 A | 8/1992 | Vetter et al. |
| 5,147,311 A | 9/1992 | Pickhard |
| 5,167,641 A | 12/1992 | Schmitz |
| 5,199,949 A | 4/1993 | Haber et al. |
| 5,224,936 A | 7/1993 | Gallagher |
| 5,240,146 A | 8/1993 | Smedley et al. |
| 5,244,465 A | 9/1993 | Michel |
| 5,271,527 A | 12/1993 | Haber et al. |
| 5,281,198 A | 1/1994 | Haber et al. |
| 5,286,258 A | 2/1994 | Haber et al. |
| 5,295,965 A | 3/1994 | Wilmot |
| 5,298,023 A | 3/1994 | Haber et al. |
| 5,298,024 A | 3/1994 | Richmond |
| 5,312,326 A | 5/1994 | Myers et al. |
| 5,314,412 A | 5/1994 | Rex |
| 5,318,544 A | 6/1994 | Drypen et al. |
| 5,336,180 A | 8/1994 | Kriesel et al. |
| 5,343,519 A | 8/1994 | Feldman |
| 5,344,407 A | 9/1994 | Ryan |
| 5,354,284 A | 10/1994 | Haber et al. |
| 5,356,376 A | 10/1994 | Milijasevic et al. |
| 5,358,489 A | 10/1994 | Wyrick |
| 5,363,842 A | 11/1994 | Mishelevich et al. |
| 5,380,281 A | 1/1995 | Tomellini et al. |
| 5,383,851 A | 1/1995 | McKinnon, Jr. et al. |
| 5,383,864 A | 1/1995 | van den Heuvel |
| 5,394,866 A | 3/1995 | Ritson et al. |
| 5,395,345 A | 3/1995 | Gross |
| 5,399,163 A | 3/1995 | Peterson et al. |
| 5,405,362 A | 4/1995 | Kramer et al. |
| 5,417,660 A | 5/1995 | Martin |
| 5,451,210 A | 9/1995 | Kramer et al. |
| 5,466,217 A | 11/1995 | Myers et al. |
| 5,478,316 A | 12/1995 | Bitdinger et al. |
| 5,514,097 A | 5/1996 | Knauer |
| 5,514,135 A | 5/1996 | Earle |
| 5,527,287 A | 6/1996 | Miskinyar |
| 5,540,664 A | 7/1996 | Wyrick |
| 5,558,679 A | 9/1996 | Tuttle |
| 5,567,160 A | 10/1996 | Massino |
| 5,568,555 A | 10/1996 | Shamir |
| 5,569,192 A | 10/1996 | van der Wal |
| 5,584,815 A | 12/1996 | Pawelka et al. |
| 5,615,771 A | 4/1997 | Hollister |
| 5,616,132 A | 4/1997 | Newman |
| 5,645,534 A | 7/1997 | Chanoch |
| 5,658,259 A | 8/1997 | Pearson et al. |
| 5,681,291 A | 10/1997 | Galli |
| 5,681,292 A | 10/1997 | Tober et al. |
| 5,692,492 A | 12/1997 | Bruna et al. |
| 5,695,476 A | 12/1997 | Harris |
| 5,697,916 A | 12/1997 | Schraga |
| 5,716,338 A | 2/1998 | Hjertman et al. |
| 5,728,074 A | 3/1998 | Castellano et al. |
| 5,772,635 A | 6/1998 | Dastur et al. |
| 5,779,677 A | 7/1998 | Frezza |
| 5,792,190 A | 8/1998 | Olson et al. |
| 5,800,397 A | 9/1998 | Wilson et al. |
| 5,805,423 A | 9/1998 | Wever et al. |
| 5,809,997 A | 9/1998 | Wolf |
| 5,814,020 A | 9/1998 | Gross |
| 5,823,346 A | 10/1998 | Weiner |
| 5,832,488 A | 11/1998 | Eberhardt |
| 5,837,546 A | 11/1998 | Allen et al. |
| RE35,986 E | 12/1998 | Ritson et al. |
| 5,846,089 A | 12/1998 | Weiss et al. |
| 5,848,990 A | 12/1998 | Cirelli et al. |
| 5,852,590 A | 12/1998 | de la Huerga |
| 5,853,292 A | 12/1998 | Eggert et al. |
| 5,858,001 A | 1/1999 | Tsals et al. |
| 5,865,795 A | 2/1999 | Schiff et al. |
| 5,868,711 A | 2/1999 | Kramer et al. |
| 5,868,713 A | 2/1999 | Klippenstein |
| 5,868,721 A | 2/1999 | Marinacci |
| D407,487 S | 3/1999 | Greubel et al. |
| 5,876,380 A | 3/1999 | Manganini et al. |
| 5,925,021 A | 7/1999 | Castellano et al. |
| 5,928,195 A | 7/1999 | Malamud |
| 5,941,857 A | 8/1999 | Nguyen et al. |
| 5,964,739 A | 10/1999 | Champ |

(56) References Cited

U.S. PATENT DOCUMENTS

| | | | |
|---|---|---|---|
| 5,970,457 A | 10/1999 | Brant et al. |
| 5,971,953 A | 10/1999 | Bachynsky |
| 6,015,438 A | 1/2000 | Shaw |
| 6,030,363 A | 2/2000 | Kriesel |
| 6,039,713 A | 3/2000 | Botich et al. |
| 6,045,534 A | 4/2000 | Jacobsen et al. |
| 6,050,977 A | 4/2000 | Adams |
| 6,056,728 A | 5/2000 | von Schuckmann |
| 6,062,901 A | 5/2000 | Liu et al. |
| 6,063,053 A | 5/2000 | Castellano et al. |
| 6,074,213 A | 6/2000 | Hon |
| 6,077,106 A | 6/2000 | Mish |
| 6,080,130 A | 6/2000 | Castellano |
| 6,083,199 A | 7/2000 | Thorley et al. |
| 6,084,526 A | 7/2000 | Blotky et al. |
| 6,086,562 A | 7/2000 | Jacobsen et al. |
| 6,096,002 A | 8/2000 | Landau |
| 6,099,504 A | 8/2000 | Gross et al. |
| 6,102,896 A | 8/2000 | Roser |
| 6,119,684 A | 9/2000 | Nöhl et al. |
| 6,120,786 A | 9/2000 | Cheikh |
| 6,123,685 A | 9/2000 | Reynolds |
| 6,149,626 A | 11/2000 | Rachynsky et al. |
| 6,158,613 A | 12/2000 | Novosel et al. |
| 6,161,281 A | 12/2000 | Dando et al. |
| 6,165,155 A | 12/2000 | Jacobsen et al. |
| 6,179,812 B1 | 1/2001 | Botich et al. |
| 6,192,891 B1 | 2/2001 | Gravel et al. |
| 6,193,695 B1 | 2/2001 | Rippstein, Jr. |
| 6,202,642 B1 | 3/2001 | McKinnon et al. |
| 6,210,359 B1 | 4/2001 | Patel et al. |
| 6,210,369 B1 | 4/2001 | Wilmot et al. |
| 6,219,587 B1 | 4/2001 | Ahlin et al. |
| 6,221,045 B1 | 4/2001 | Duchon et al. |
| 6,221,055 B1 | 4/2001 | Shaw et al. |
| 6,223,936 B1 | 5/2001 | Jeanbourquin |
| 6,245,046 B1 | 6/2001 | Sibbitt |
| 6,258,063 B1 | 7/2001 | Haar et al. |
| 6,258,068 B1 | 7/2001 | Kirchhofer et al. |
| 6,259,654 B1 | 7/2001 | de la Huerga |
| 6,264,629 B1 | 7/2001 | Landau |
| 6,270,479 B1 | 8/2001 | Bergens et al. |
| 6,280,421 B1 | 8/2001 | Kirchhofer et al. |
| 6,312,412 B1 | 11/2001 | Saied et al. |
| 6,317,630 B1 | 11/2001 | Gross et al. |
| 6,334,070 B1 | 12/2001 | Nova et al. |
| 6,364,866 B1 | 4/2002 | Furr et al. |
| 6,371,939 B2 | 4/2002 | Bergens et al. |
| 6,383,168 B1 | 5/2002 | Landau et al. |
| 6,387,078 B1 | 5/2002 | Gillespie, III |
| 6,405,912 B2 | 6/2002 | Giannou |
| 6,406,455 B1 | 6/2002 | Willis et al. |
| 6,411,567 B1 | 6/2002 | Niemiec et al. |
| 6,413,236 B1 | 7/2002 | Van Dyke |
| 6,419,656 B1 | 7/2002 | Vetter et al. |
| 6,425,897 B2 | 7/2002 | Overes et al. |
| 6,427,684 B2 | 8/2002 | Ritsche et al. |
| 6,428,517 B1 | 8/2002 | Hochman et al. |
| 6,428,528 B2 | 8/2002 | Sadowski |
| 6,454,746 B1 | 9/2002 | Bydlon et al. |
| 6,475,181 B1 | 11/2002 | Potter et al. |
| 6,478,771 B1 | 11/2002 | Lavi et al. |
| 6,482,186 B1 | 11/2002 | Douglas et al. |
| 6,494,863 B1 | 12/2002 | Shaw et al. |
| 6,500,150 B1 | 12/2002 | Gross et al. |
| 6,514,230 B1 | 2/2003 | Munk et al. |
| 6,529,446 B1 | 3/2003 | de la Huerga |
| 6,530,900 B1 | 3/2003 | Daily et al. |
| 6,530,904 B1 | 3/2003 | Edwards et al. |
| 6,535,714 B2 | 3/2003 | Melker et al. |
| 6,540,672 B1 | 4/2003 | Simonsen et al. |
| 6,540,675 B2 | 4/2003 | Aceti et al. |
| 6,544,234 B1 | 4/2003 | Gabriel |
| 6,551,276 B1 | 4/2003 | Mann et al. |
| 6,551,298 B1 | 4/2003 | Zhang |
| 6,554,798 B1 | 4/2003 | Mann et al. |
| 6,558,320 B1 | 5/2003 | Causey et al. |
| 6,565,533 B1 | 5/2003 | Smith et al. |
| 6,569,123 B2 | 5/2003 | Alchas |
| 6,572,584 B1 | 6/2003 | Shaw et al. |
| 6,574,166 B2 | 6/2003 | Niemiec |
| 6,575,939 B1 | 6/2003 | Brunel |
| RE38,189 E | 7/2003 | Walker et al. |
| 6,585,685 B2 | 7/2003 | Staylor et al. |
| 6,585,698 B1 | 7/2003 | Packman et al. |
| 6,589,158 B2 | 7/2003 | Winkler |
| 6,595,956 B1 | 7/2003 | Gross et al. |
| 6,599,272 B1 | 7/2003 | Hjertman et al. |
| 6,613,010 B2 | 9/2003 | Castellano |
| 6,613,011 B2 | 9/2003 | Castellano |
| 6,616,627 B2 | 9/2003 | Willis et al. |
| 6,633,796 B1 | 10/2003 | Pool et al. |
| 6,641,566 B2 | 11/2003 | Douglas et al. |
| 6,645,171 B1 | 11/2003 | Robinson et al. |
| 6,645,181 B1 | 11/2003 | Lavi et al. |
| 6,648,850 B2 | 11/2003 | Landau |
| 6,656,150 B2 | 12/2003 | Hill et al. |
| 6,656,163 B1 | 12/2003 | Marshall et al. |
| 6,659,980 B2 | 12/2003 | Moberg et al. |
| 6,673,035 B1 | 1/2004 | Rice et al. |
| 6,676,630 B2 | 1/2004 | Landau et al. |
| 6,679,862 B2 | 1/2004 | Diaz et al. |
| 6,689,093 B2 | 2/2004 | Landau |
| 6,692,469 B1 | 2/2004 | Weekes et al. |
| 6,699,218 B2 | 3/2004 | Flaherty et al. |
| 6,702,778 B2 | 3/2004 | Hill et al. |
| 6,706,019 B1 | 3/2004 | Parker et al. |
| 6,707,763 B2 | 3/2004 | Osberg et al. |
| 6,708,050 B2 | 3/2004 | Carim |
| 6,722,916 B2 | 4/2004 | Buccinna et al. |
| 6,723,077 B2 | 4/2004 | Pickup et al. |
| 6,726,657 B1 | 4/2004 | Dedig et al. |
| 6,726,661 B2 | 4/2004 | Munk et al. |
| 6,736,796 B2 | 5/2004 | Shekalim |
| 6,743,203 B1 | 6/2004 | Pickhard |
| 6,743,635 B2 | 6/2004 | Neel et al. |
| 6,749,437 B2 | 6/2004 | Chan |
| 6,752,781 B2 | 6/2004 | Landau et al. |
| 6,764,469 B2 | 7/2004 | Broselow |
| 6,767,336 B1 | 7/2004 | Kaplan |
| 6,770,052 B2 | 8/2004 | Hill et al. |
| 6,770,056 B2 | 8/2004 | Price et al. |
| 6,783,509 B1 | 8/2004 | Landau et al. |
| 6,786,875 B2 | 9/2004 | Barker et al. |
| 6,786,885 B2 | 9/2004 | Hochman et al. |
| 6,793,646 B1 | 9/2004 | Giambattista et al. |
| 6,803,856 B1 | 10/2004 | Murphy et al. |
| 6,805,686 B1 | 10/2004 | Fathallah et al. |
| 6,808,514 B2 | 10/2004 | Schneider et al. |
| 6,809,653 B1 | 10/2004 | Mann et al. |
| 6,817,986 B2 | 11/2004 | Slate et al. |
| 6,830,560 B1 | 12/2004 | Gross et al. |
| 6,839,304 B2 | 1/2005 | Niemiec et al. |
| 6,872,200 B2 | 3/2005 | Mann et al. |
| 6,875,195 B2 | 4/2005 | Choi |
| 6,883,222 B2 | 4/2005 | Landau |
| 6,923,764 B2 | 8/2005 | Aceti et al. |
| 6,936,029 B2 | 8/2005 | Mann et al. |
| 6,936,032 B1 | 8/2005 | Bush, Jr. et al. |
| 6,937,150 B2 | 8/2005 | Medema et al. |
| 6,942,646 B2 | 9/2005 | Langley et al. |
| 6,946,299 B2 | 9/2005 | Neel et al. |
| 6,949,082 B2 | 9/2005 | Langley et al. |
| 6,952,604 B2 | 10/2005 | DeNuzzio et al. |
| 6,953,445 B2 | 10/2005 | Wilmot et al. |
| 6,953,693 B2 | 10/2005 | Neel et al. |
| 6,958,691 B1 | 10/2005 | Anderson et al. |
| 6,959,247 B2 | 10/2005 | Neel et al. |
| 6,960,192 B1 | 11/2005 | Flaherty et al. |
| 6,961,285 B2 | 11/2005 | Niemiec et al. |
| 6,964,650 B2 | 11/2005 | Alexandre et al. |
| 6,969,259 B2 | 11/2005 | Pastrick et al. |
| 6,979,316 B1 | 12/2005 | Rubin et al. |
| 6,979,326 B2 | 12/2005 | Mann et al. |

(56) References Cited

U.S. PATENT DOCUMENTS

| | | |
|---|---|---|
| 6,985,870 B2 | 1/2006 | Martucci et al. |
| 6,997,911 B2 | 2/2006 | Klitmose |
| 7,014,470 B2 | 3/2006 | Vann |
| 7,029,455 B2 | 4/2006 | Flaherty et al. |
| 7,074,211 B1 | 7/2006 | Heiniger et al. |
| 7,104,972 B2 | 9/2006 | Moller et al. |
| 7,113,101 B2 | 9/2006 | Peterson et al. |
| 7,116,233 B2 | 10/2006 | Zhurin |
| 7,118,553 B2 | 10/2006 | Scherer |
| 7,126,879 B2 | 10/2006 | Snyder |
| 7,158,011 B2 | 1/2007 | Brue |
| 7,299,981 B2 | 11/2007 | Hickle et al. |
| 7,329,241 B2 | 2/2008 | Horvath et al. |
| 7,357,790 B2 | 4/2008 | Hommann et al. |
| 7,416,540 B2 | 8/2008 | Edwards et al. |
| 7,465,294 B1 | 12/2008 | Vladimirsky |
| 7,500,963 B2 | 3/2009 | Westbye et al. |
| 7,500,967 B2 | 3/2009 | Thorley et al. |
| 7,503,907 B1 | 3/2009 | Lesch, Jr. |
| 7,544,188 B2 | 6/2009 | Edwards et al. |
| 7,611,491 B2 | 11/2009 | Pickhard |
| 7,611,495 B1 | 11/2009 | Gianturco |
| 7,637,891 B2 | 12/2009 | Wall |
| 7,648,482 B2 | 1/2010 | Edwards et al. |
| 7,648,483 B2 | 1/2010 | Edwards et al. |
| 7,654,983 B2 | 2/2010 | De La Sema et al. |
| 7,674,246 B2 | 3/2010 | Gillespie et al. |
| 7,678,073 B2 | 3/2010 | Griffiths et al. |
| 7,686,788 B2 | 3/2010 | Freyman et al. |
| 7,708,719 B2 | 5/2010 | Wilmot et al. |
| 7,731,686 B2 | 6/2010 | Edwards et al. |
| 7,731,690 B2 | 6/2010 | Edwards et al. |
| 7,749,194 B2 | 7/2010 | Edwards et al. |
| 7,758,550 B2 | 7/2010 | Bollenbach et al. |
| 7,771,397 B1 | 8/2010 | Olson |
| 7,806,866 B2 | 10/2010 | Hommann et al. |
| 7,850,662 B2 | 12/2010 | Veasey et al. |
| 7,871,393 B2 | 1/2011 | Monroe |
| 7,901,377 B1 | 3/2011 | Harrison et al. |
| 7,901,384 B2 | 3/2011 | Kleyman et al. |
| 7,918,823 B2 | 4/2011 | Edwards et al. |
| 7,918,832 B2 | 4/2011 | Veasey et al. |
| 7,931,614 B2 | 4/2011 | Gonnelli et al. |
| 7,938,802 B2 | 5/2011 | Bicknell et al. |
| 7,938,808 B2 | 5/2011 | Pessin |
| 7,947,017 B2 | 5/2011 | Edwards et al. |
| 8,016,788 B2 | 9/2011 | Edwards et al. |
| 8,021,335 B2 | 9/2011 | Lesch, Jr. |
| 8,105,281 B2 | 1/2012 | Edwards et al. |
| 8,105,293 B2 | 1/2012 | Pickhard |
| 8,123,719 B2 | 2/2012 | Edwards et al. |
| 8,162,886 B2 | 4/2012 | Sadowski et al. |
| 8,172,082 B2 | 5/2012 | Edwards et al. |
| 8,172,790 B2 | 5/2012 | Hunter et al. |
| 8,177,749 B2 | 5/2012 | Slate et al. |
| 8,206,360 B2 | 6/2012 | Edwards et al. |
| 8,221,347 B2 | 7/2012 | Toles et al. |
| 8,231,573 B2 | 7/2012 | Edwards et al. |
| 8,251,947 B2 | 8/2012 | Kramer et al. |
| 8,276,583 B2 | 10/2012 | Farieta et al. |
| 8,313,466 B2 | 11/2012 | Edwards et al. |
| 8,317,756 B2 | 11/2012 | Krumme et al. |
| 8,361,029 B2 | 1/2013 | Edwards et al. |
| 8,409,141 B2 | 4/2013 | Johansen et al. |
| 8,425,462 B2 | 4/2013 | Edwards et al. |
| 8,574,214 B2 | 11/2013 | Kühn et al. |
| 8,608,698 B2 | 12/2013 | Edwards et al. |
| 8,613,720 B2 | 12/2013 | Bendek et al. |
| 8,632,504 B2 | 1/2014 | Young |
| 8,647,306 B2 | 2/2014 | Schwirtz et al. |
| 8,662,349 B2 | 3/2014 | Genosar et al. |
| 8,663,188 B2 | 3/2014 | Genosar et al. |
| 8,684,968 B2 | 4/2014 | Genosar |
| 8,690,827 B2 | 4/2014 | Edwards et al. |
| 8,728,042 B2 | 5/2014 | Pickhard |
| 8,734,394 B2 | 5/2014 | Adams et al. |
| 8,747,357 B2 | 6/2014 | Stamp et al. |
| 8,900,197 B2 | 12/2014 | Crow |
| 8,920,377 B2 | 12/2014 | Edwards et al. |
| 8,945,048 B2 | 2/2015 | Thorley et al. |
| 8,961,455 B2 | 2/2015 | Holmqvist et al. |
| 8,986,242 B2 | 3/2015 | Auld et al. |
| 8,992,477 B2 | 3/2015 | Raday et al. |
| 9,022,980 B2 | 5/2015 | Edwards et al. |
| 9,044,549 B2 | 6/2015 | Niklasson |
| 9,056,170 B2 | 6/2015 | Edwards et al. |
| 9,084,849 B2 | 7/2015 | Edwards et al. |
| 9,149,579 B2 | 10/2015 | Edwards et al. |
| 9,173,999 B2 | 11/2015 | Edwards et al. |
| 9,289,563 B2 | 3/2016 | Pickhard et al. |
| 9,345,831 B2 | 5/2016 | Raday et al. |
| 9,352,099 B2 | 5/2016 | Roberts et al. |
| 9,517,307 B2 * | 12/2016 | Blondino ............ A61M 5/2053 |
| 9,586,010 B2 | 3/2017 | Mesa et al. |
| 9,586,011 B2 | 3/2017 | Roberts et al. |
| 9,820,913 B2 | 11/2017 | Genosar |
| 9,821,113 B2 | 11/2017 | Cole et al. |
| 9,925,333 B2 | 3/2018 | Hooven et al. |
| 10,028,886 B2 | 7/2018 | Genosar |
| 10,071,203 B2 | 9/2018 | Edwards et al. |
| 10,105,499 B2 | 10/2018 | Schwirtz et al. |
| 10,251,999 B2 | 4/2019 | Cole et al. |
| 10,363,374 B2 | 7/2019 | Nazzaro et al. |
| 10,507,285 B2 | 12/2019 | Dunki-Jacobs et al. |
| 10,695,485 B2 | 6/2020 | Nazzaro |
| 10,716,901 B2 | 7/2020 | Genosar |
| 10,729,842 B2 | 8/2020 | Hooven et al. |
| 10,864,139 B2 | 12/2020 | Genosar |
| 10,960,134 B2 | 3/2021 | Salter et al. |
| 10,981,713 B2 | 4/2021 | Genosar |
| 11,001,435 B2 | 5/2021 | Genosar |
| 11,167,087 B2 | 11/2021 | Meyers et al. |
| 11,185,634 B2 | 11/2021 | Genosar |
| 11,638,794 B2 | 5/2023 | Genosar |
| 11,648,180 B2 | 5/2023 | Genosar |
| 2001/0005781 A1 | 6/2001 | Bergens et al. |
| 2001/0037087 A1 | 11/2001 | Knauer |
| 2002/0016567 A1 | 2/2002 | Hochman et al. |
| 2002/0042596 A1 | 4/2002 | Hartlaub et al. |
| 2002/0055711 A1 | 5/2002 | Lavi et al. |
| 2002/0076679 A1 | 6/2002 | Aman |
| 2002/0079326 A1 | 6/2002 | Fuchs |
| 2002/0095120 A1 | 7/2002 | Larsen et al. |
| 2002/0096543 A1 | 7/2002 | Juselius |
| 2003/0028145 A1 | 2/2003 | Duchon et al. |
| 2003/0040717 A1 | 2/2003 | Saulenas et al. |
| 2003/0105430 A1 | 6/2003 | Lavi et al. |
| 2003/0106824 A1 | 6/2003 | Wilmot et al. |
| 2003/0120222 A1 | 6/2003 | Vaillancourt |
| 2003/0132128 A1 | 7/2003 | Mazur |
| 2003/0233070 A1 | 12/2003 | De La Serna et al. |
| 2004/0015125 A1 | 1/2004 | Alexandre et al. |
| 2004/0019326 A1 | 1/2004 | Gilbert et al. |
| 2004/0024361 A1 | 2/2004 | Fago et al. |
| 2004/0024367 A1 | 2/2004 | Gilbert |
| 2004/0039336 A1 | 2/2004 | Amark et al. |
| 2004/0039337 A1 | 2/2004 | Letzing |
| 2004/0039368 A1 | 2/2004 | Reilly et al. |
| 2004/0054327 A1 | 3/2004 | Gillespie, III |
| 2004/0073169 A1 | 4/2004 | Amisar et al. |
| 2004/0092874 A1 | 5/2004 | Mazidji et al. |
| 2004/0094146 A1 | 5/2004 | Schiewe et al. |
| 2004/0116854 A1 | 6/2004 | Abulhaj et al. |
| 2004/0138611 A1 | 7/2004 | Griffiths et al. |
| 2004/0143298 A1 | 7/2004 | Nova et al. |
| 2004/0159364 A1 | 8/2004 | Landau et al. |
| 2004/0210199 A1 | 10/2004 | Atterbury et al. |
| 2004/0220524 A1 | 11/2004 | Sadowski et al. |
| 2004/0249358 A1 | 12/2004 | McWethy et al. |
| 2004/0267204 A1 | 12/2004 | Brustowicz |
| 2005/0027255 A1 | 2/2005 | Lavi et al. |
| 2005/0033234 A1 | 2/2005 | Sadowski et al. |
| 2005/0033386 A1 | 2/2005 | Osborn et al. |
| 2005/0049561 A1 | 3/2005 | Hommann et al. |

(56) References Cited

U.S. PATENT DOCUMENTS

| | | |
|---|---|---|
| 2005/0062603 A1 | 3/2005 | Fuerst et al. |
| 2005/0070848 A1 | 3/2005 | Kim et al. |
| 2005/0089517 A1 | 4/2005 | Shames |
| 2005/0090781 A1 | 4/2005 | Baba et al. |
| 2005/0090782 A1 | 4/2005 | Marshall et al. |
| 2005/0101912 A1 | 5/2005 | Faust et al. |
| 2005/0134433 A1 | 6/2005 | Sweeney, II |
| 2005/0148931 A1 | 7/2005 | Juhasz |
| 2005/0148945 A1 | 7/2005 | Chen |
| 2005/0159705 A1 | 7/2005 | Crawford et al. |
| 2005/0165360 A1 | 7/2005 | Stamp |
| 2005/0168337 A1 | 8/2005 | Mahoney |
| 2005/0171477 A1 | 8/2005 | Rubin et al. |
| 2005/0182358 A1 | 8/2005 | Veit et al. |
| 2005/0183982 A1 | 8/2005 | Giewercer |
| 2005/0192530 A1 | 9/2005 | Castellano |
| 2005/0192534 A1 | 9/2005 | Wolbring et al. |
| 2005/0197654 A1 | 9/2005 | Edman et al. |
| 2005/0203466 A1 | 9/2005 | Hommann et al. |
| 2005/0222539 A1 | 10/2005 | Gonzales et al. |
| 2005/0261742 A1 | 11/2005 | Nova et al. |
| 2005/0267403 A1 | 12/2005 | Landau et al. |
| 2005/0273059 A1 | 12/2005 | Mernoe et al. |
| 2005/0277891 A1 | 12/2005 | Sibbitt |
| 2006/0030819 A1 | 2/2006 | Young et al. |
| 2006/0053036 A1 | 3/2006 | Coffman et al. |
| 2006/0058848 A1 | 3/2006 | Piraino et al. |
| 2006/0111666 A1 | 5/2006 | Hommann et al. |
| 2006/0111671 A1 | 5/2006 | Klippenstein |
| 2006/0116639 A1 | 6/2006 | Russell |
| 2006/0129089 A1 | 6/2006 | Stamp |
| 2006/0129090 A1 | 6/2006 | Moberg et al. |
| 2006/0173408 A1 | 8/2006 | Wyrick |
| 2006/0184133 A1 | 8/2006 | Pessin |
| 2006/0189938 A1 | 8/2006 | Hommann et al. |
| 2006/0200077 A1 | 9/2006 | Righi et al. |
| 2006/0223027 A1 | 10/2006 | Smith et al. |
| 2006/0235354 A1 | 10/2006 | Kaal et al. |
| 2006/0247578 A1 | 11/2006 | Arguedas et al. |
| 2006/0247579 A1 | 11/2006 | Friedman |
| 2006/0265186 A1 | 11/2006 | Holland et al. |
| 2007/0008113 A1 | 1/2007 | Spoonhower et al. |
| 2007/0021720 A1 | 1/2007 | Guillermo |
| 2007/0074722 A1 | 4/2007 | Giroux et al. |
| 2007/0079777 A1 | 4/2007 | Hurlstone et al. |
| 2007/0088268 A1 | 4/2007 | Edwards |
| 2007/0100288 A1 | 5/2007 | Bozeman et al. |
| 2007/0129686 A1 | 6/2007 | Daily et al. |
| 2007/0135767 A1 | 6/2007 | Gillespie, III et al. |
| 2007/0173772 A1 | 7/2007 | Liversidge |
| 2007/0184847 A1 | 8/2007 | Hansen et al. |
| 2007/0210147 A1 | 9/2007 | Morrone et al. |
| 2007/0213598 A1 | 9/2007 | Howard et al. |
| 2007/0233001 A1 | 10/2007 | Burroughs et al. |
| 2007/0265568 A1 | 11/2007 | Tsals et al. |
| 2007/0276320 A1 | 11/2007 | Wall et al. |
| 2007/0293826 A1 | 12/2007 | Wall et al. |
| 2008/0111685 A1 | 5/2008 | Olson et al. |
| 2008/0147006 A1 | 6/2008 | Brunnberg et al. |
| 2008/0154200 A1 | 6/2008 | Lesch |
| 2008/0171995 A1 | 7/2008 | Vitullo et al. |
| 2008/0188798 A1 | 8/2008 | Weber |
| 2008/0208114 A1 | 8/2008 | Landau et al. |
| 2008/0228143 A1 | 9/2008 | Stamp |
| 2008/0255513 A1 | 10/2008 | Kaal et al. |
| 2008/0262443 A1 | 10/2008 | Hommann |
| 2009/0093759 A1 | 4/2009 | Judd et al. |
| 2009/0192486 A1 | 7/2009 | Wilmot et al. |
| 2009/0209939 A1 | 8/2009 | Verespej et al. |
| 2009/0221962 A1 | 9/2009 | Kaal et al. |
| 2009/0240200 A1 | 9/2009 | Heneveld et al. |
| 2009/0299279 A1 | 12/2009 | Richter |
| 2009/0318361 A1 | 12/2009 | Noera et al. |
| 2010/0010454 A1 | 1/2010 | Marshall et al. |
| 2010/0049125 A1 | 2/2010 | James et al. |
| 2010/0137808 A1 | 6/2010 | Wilmot et al. |
| 2010/0152659 A1 | 6/2010 | Streit et al. |
| 2010/0160894 A1 | 6/2010 | Julian et al. |
| 2010/0185148 A1 | 7/2010 | Gillespie, III et al. |
| 2010/0185178 A1 | 7/2010 | Sharp et al. |
| 2010/0280460 A1 | 11/2010 | Markussen |
| 2011/0046565 A1 | 2/2011 | Radmer et al. |
| 2011/0060274 A1 | 3/2011 | Kuhn |
| 2011/0092954 A1 | 4/2011 | Jennings |
| 2011/0098655 A1 | 4/2011 | Jennings et al. |
| 2011/0144594 A1 | 6/2011 | Sund et al. |
| 2011/0201999 A1 | 8/2011 | Cronenberg et al. |
| 2011/0202011 A1 | 8/2011 | Wozencroft |
| 2011/0213314 A1 | 9/2011 | Guillermo |
| 2011/0270220 A1 | 11/2011 | Genosar |
| 2011/0319864 A1 | 12/2011 | Beller et al. |
| 2012/0046613 A1 | 2/2012 | Plumptre |
| 2012/0056019 A1 | 3/2012 | Renz et al. |
| 2012/0101446 A1 | 4/2012 | Heald |
| 2012/0101475 A1 | 4/2012 | Wilmot et al. |
| 2012/0103328 A1 | 5/2012 | Smith et al. |
| 2012/0103462 A1 | 5/2012 | Levy |
| 2012/0107783 A1 | 5/2012 | Julian et al. |
| 2012/0116319 A1 | 5/2012 | Grunhut |
| 2012/0125951 A1 | 5/2012 | Leak et al. |
| 2012/0130318 A1 | 5/2012 | Young |
| 2012/0143144 A1 | 6/2012 | Young |
| 2012/0172804 A1 | 7/2012 | Plumptre |
| 2012/0172817 A1 | 7/2012 | Bruggemann et al. |
| 2012/0191049 A1 | 7/2012 | Harms et al. |
| 2012/0209200 A1 | 8/2012 | Jones et al. |
| 2012/0233834 A1 | 9/2012 | Szechinski et al. |
| 2012/0238960 A1 | 9/2012 | Smith et al. |
| 2012/0253288 A1 | 10/2012 | Dasbach et al. |
| 2012/0259285 A1 | 10/2012 | Schabbach et al. |
| 2012/0268741 A1 | 10/2012 | Pommerau et al. |
| 2012/0271243 A1 | 10/2012 | Plumptre et al. |
| 2012/0283648 A1 | 11/2012 | Veasey et al. |
| 2012/0283651 A1 | 11/2012 | Veasey et al. |
| 2012/0283662 A1 | 11/2012 | MacDonald et al. |
| 2012/0289906 A1 | 11/2012 | Jones et al. |
| 2012/0289929 A1 | 11/2012 | Boyd et al. |
| 2012/0310168 A1 | 12/2012 | Plumptre et al. |
| 2012/0310206 A1 | 12/2012 | Kouyoumjian et al. |
| 2012/0323186 A1 | 12/2012 | Karlsen et al. |
| 2012/0325865 A1 | 12/2012 | Forstreuter et al. |
| 2012/0330244 A1 | 12/2012 | Helmer et al. |
| 2013/0060231 A1 | 3/2013 | Adlon et al. |
| 2013/0060232 A1 | 3/2013 | Adlon et al. |
| 2013/0079718 A1 | 3/2013 | Shang et al. |
| 2013/0079725 A1 | 3/2013 | Shang |
| 2013/0096512 A1 | 4/2013 | Ekman et al. |
| 2013/0110050 A1 | 5/2013 | Boyd et al. |
| 2013/0131602 A1 | 5/2013 | Kemp et al. |
| 2013/0138049 A1 | 5/2013 | Kemp et al. |
| 2013/0150800 A1 | 6/2013 | Kemp et al. |
| 2013/0172822 A1 | 7/2013 | Ekman et al. |
| 2013/0204199 A1 | 8/2013 | Hourmand et al. |
| 2013/0218074 A1 | 8/2013 | Holmqvist et al. |
| 2013/0226084 A1 | 8/2013 | Samandi et al. |
| 2013/0236872 A1 | 9/2013 | Laurusonis et al. |
| 2013/0245562 A1 | 9/2013 | Kouyoumjian et al. |
| 2013/0266919 A1 | 10/2013 | Baker et al. |
| 2013/0274662 A1 | 10/2013 | Hourmand et al. |
| 2013/0274707 A1 | 10/2013 | Wilmot et al. |
| 2013/0296796 A1 | 11/2013 | Hourmand et al. |
| 2013/0317427 A1 | 11/2013 | Brereton et al. |
| 2013/0317477 A1 | 11/2013 | Edwards et al. |
| 2013/0317480 A1 | 11/2013 | Reber et al. |
| 2014/0008366 A1 | 1/2014 | Genosar |
| 2014/0025014 A1 | 1/2014 | Radmer et al. |
| 2014/0031760 A1 | 1/2014 | Mercer et al. |
| 2014/0046259 A1 | 2/2014 | Reber et al. |
| 2014/0081234 A1 | 3/2014 | Eggert et al. |
| 2014/0103075 A1 | 4/2014 | Bennison et al. |
| 2014/0114250 A1 | 4/2014 | Desalvo et al. |
| 2014/0128840 A1 | 5/2014 | Rao et al. |
| 2014/0135705 A1 | 5/2014 | Hourmand et al. |
| 2014/0257185 A1 | 9/2014 | Bechmann et al. |

(56) References Cited

U.S. PATENT DOCUMENTS

| | | |
|---|---|---|
| 2014/0257241 A1 | 9/2014 | Sutkin et al. |
| 2015/0051538 A1 | 2/2015 | Hata et al. |
| 2015/0144793 A1 | 5/2015 | Whalley et al. |
| 2015/0165129 A1 | 6/2015 | Row et al. |
| 2015/0174325 A1 | 6/2015 | Young et al. |
| 2015/0238695 A1 | 8/2015 | Edwards et al. |
| 2015/0283323 A1 | 10/2015 | Young et al. |
| 2016/0015907 A1 | 1/2016 | Edwards et al. |
| 2016/0045670 A1 | 2/2016 | Edwards et al. |
| 2016/0074584 A1 | 3/2016 | Carmel et al. |
| 2016/0114110 A1 | 4/2016 | Kerns |
| 2016/0184521 A1 | 6/2016 | Edwards et al. |
| 2016/0193412 A1 | 7/2016 | Cereda et al. |
| 2016/0250414 A1 | 9/2016 | Edwards et al. |
| 2016/0354556 A1 | 12/2016 | Zucker et al. |
| 2016/0361496 A1 | 12/2016 | Guillermo et al. |
| 2017/0246393 A1 | 8/2017 | Genosar |
| 2017/0290982 A1 | 10/2017 | Edwards et al. |
| 2018/0008774 A1 | 1/2018 | Edwards et al. |
| 2018/0104413 A1 | 4/2018 | Mcloughlin et al. |
| 2018/0117251 A1 | 5/2018 | Rioux et al. |
| 2018/0200451 A1 | 7/2018 | Shekalim |
| 2018/0204636 A1 | 7/2018 | Edwards et al. |
| 2018/0207369 A1 | 7/2018 | Converse et al. |
| 2018/0235840 A1 | 8/2018 | Genosar |
| 2018/0289901 A1 | 10/2018 | Bøggild-damkvist et al. |
| 2018/0296760 A1 | 10/2018 | Csenar et al. |
| 2018/0304017 A1 | 10/2018 | Edwards et al. |
| 2018/0304018 A1 | 10/2018 | Blondino et al. |
| 2019/0009025 A1 | 1/2019 | Chakrabarti et al. |
| 2019/0009027 A1 | 1/2019 | Edwards et al. |
| 2019/0151548 A1 | 5/2019 | Edwards et al. |
| 2019/0175837 A1 | 6/2019 | Edwards et al. |
| 2019/0275253 A1 | 9/2019 | Edwards et al. |
| 2019/0282763 A1 | 9/2019 | Edwards et al. |
| 2020/0197612 A1 | 6/2020 | Edwards et al. |
| 2020/0214625 A1 | 7/2020 | Hooven et al. |
| 2020/0316290 A1 | 10/2020 | Bourelle et al. |
| 2020/0345937 A1 | 11/2020 | Genosar |
| 2020/0360231 A1 | 11/2020 | Genosar |
| 2021/0138152 A1 | 5/2021 | Edwards et al. |
| 2021/0154098 A1 | 5/2021 | Genosar |
| 2021/0213201 A1 | 7/2021 | Meyers et al. |
| 2021/0292073 A1 | 9/2021 | Genosar |
| 2021/0402097 A1 | 12/2021 | Genosar et al. |
| 2022/0040413 A1 | 2/2022 | Edwards et al. |
| 2022/0054753 A1 | 2/2022 | Meyers et al. |
| 2022/0071844 A1 | 3/2022 | Genosar |
| 2022/0088310 A1 | 3/2022 | Genosar |
| 2023/0076855 A1 | 3/2023 | Edwards et al. |
| 2023/0099753 A1 | 3/2023 | Genosar |
| 2023/0210526 A1 | 7/2023 | Genosar |

FOREIGN PATENT DOCUMENTS

| | | |
|---|---|---|
| EP | 1462134 A1 | 9/2004 |
| EP | 1518575 A1 | 3/2005 |
| EP | 1712178 A2 | 10/2006 |
| FR | 1514210 | 2/1968 |
| FR | 2506161 | 11/1982 |
| FR | 2509615 | 1/1983 |
| FR | 2700959 | 2/1993 |
| GB | 2490807 | 11/2012 |
| MX | PA04009276 | 1/2005 |
| WO | WO 91/04760 | 4/1991 |
| WO | WO 93/02720 | 2/1993 |
| WO | WO 93/23096 | 11/1993 |
| WO | WO 95/13838 | 5/1995 |
| WO | WO 95/26009 | 9/1995 |
| WO | WO 95/35126 | 12/1995 |
| WO | WO 98/52632 | 11/1998 |
| WO | WO 99/10031 | 3/1999 |
| WO | WO 2001/024690 | 4/2001 |
| WO | WO 2001/026020 | 4/2001 |
| WO | WO 2001/041849 | 6/2001 |
| WO | WO 2001/088828 | 11/2001 |
| WO | WO 2001/093926 | 12/2001 |
| WO | WO 2002/083205 | 10/2002 |
| WO | WO 2002/083212 | 10/2002 |
| WO | WO 2003/011378 | 2/2003 |
| WO | WO 2003/013632 | 2/2003 |
| WO | WO 2003/095001 | 11/2003 |
| WO | WO 2003/097133 | 11/2003 |
| WO | WO 2004/047890 | 6/2004 |
| WO | WO 2004/047891 | 6/2004 |
| WO | WO 2004/047892 | 6/2004 |
| WO | WO 2004/047893 | 6/2004 |
| WO | WO 2004/054644 | 7/2004 |
| WO | WO 2005/050526 | 6/2005 |
| WO | WO 2005/070481 | 8/2005 |
| WO | WO 2005/077441 | 8/2005 |
| WO | WO 2005/039673 | 5/2006 |
| WO | WO 2006/058426 | 6/2006 |
| WO | WO 2006/109778 | 10/2006 |
| WO | WO 2006/125692 | 11/2006 |
| WO | WO 2008/005315 | 1/2008 |
| WO | WO 2008/148864 | 12/2008 |
| WO | WO 2009/095735 | 8/2009 |
| WO | WO 2010/033806 | 3/2010 |
| WO | WO 2011/157930 | 12/2011 |
| WO | WO 2013/044172 | 3/2013 |
| WO | WO2015/055588 | 4/2015 |
| WO | WO 2016/160341 A1 | 10/2016 |
| WO | WO 2017/033193 A2 | 3/2017 |
| WO | WO 2017/034618 A1 | 3/2017 |
| WO | WO 2017/210011 | 12/2017 |
| WO | WO 2018/078121 | 5/2018 |
| WO | WO 2020/140040 | 7/2020 |
| WO | WO 2020/168412 A1 | 8/2020 |
| WO | WO 2021/012035 A1 | 1/2021 |
| WO | WO 2023/009742 | 2/2023 |
| WO | WO 2023/019209 | 2/2023 |
| WO | WO 2023/034826 | 3/2023 |
| WO | WO 2023/070096 | 4/2023 |
| WO | WO 2023/141627 | 7/2023 |

OTHER PUBLICATIONS

"Merck Serono Launches easypod(R), First Electronic Growth Hormone Injection Device," Jan. 30, 2007 [online] [retrieved on Feb. 5, 2007] Retrieved from the Internet <URL: http://www.biz.yahoo.com/prnews/070130/ukm028.html?.v=8>, 3 pages.

Examination Report for British Patent Application No. GB 0708523.6, mailed Dec. 8, 2008.

Office Action for JP2007-543005, mailed Feb. 1, 2010.

Examination Report for British Patent Application No. GB 0822532.8, mailed Jan. 21, 2009.

Examination Report for British Patent Application No. GB 0822532.8, mailed May 21, 2009.

Office Action for U.S. Appl. No. 11/562,061, mailed Feb. 3, 2009.

Office Action for U.S. Appl. No. 11/758,393, mailed May 13, 2009.

Search Report and Written Opinion for International Patent Application No. PCT/US07/84891 mailed Sep. 15, 2008, 7 pages.

Office Action for U.S. Appl. No. 12/138,987, mailed Oct. 5, 2009.

Office Action for U.S. Appl. No. 13/053,451, mailed Nov. 15, 2012.

Office Action for U.S. Appl. No. 13/090,392, mailed Feb. 29, 2012.

International Search Report and Written Opinion for International Patent Application No. PCT/US06/03415, mailed Jul. 13, 2006, 10 pages.

Office Action for U.S. Appl. No. 12/119,016, mailed Nov. 3, 2011.

Examination Report for Australian Patent Application No. 2012211307, mailed Mar. 3, 2014, 3 pages.

Supplementary Search Report for European Patent Application No. 12740010.9, mailed Aug. 5, 2014.

International Search Report and Written Opinion for International Application No. PCT/US2012/022675, mailed May 25, 2012.

Third Party Observations filed in European Patent Application No. 07864490.3, mailed Aug. 22, 2016.

International Search Report and Written Opinion for International Application No. PCT/US2016/40333 mailed Dec. 12, 2016.

(56) References Cited

OTHER PUBLICATIONS

Office Action for Canadian Patent Application No. 2,825,600, mailed Feb. 1, 2018.
Extended European Search Report for European Patent Application No. 16818770.6, mailed Jul. 3, 2019.
Office Action for U.S. Appl. No. 15/738,008, mailed Aug. 22, 2019.
Office Action for CN Application No. 201680038520.9, mailed Mar. 2, 2020.
International Search Report and Written Opinion for PCT/US19/68750, mailed Mar. 20, 2020.
Office Action for JP Application No. 2017-560704, mailed May 13, 2020.
Invitation to Pay Additional Fees for PCT Application No. PCT/US2020/045467, mailed Oct. 14, 2020.
Office Action for AU Application No. 2016287571, mailed Nov. 5, 2020.
International Search Report and Written Opinion for PCT Application No. PCT/US2020/045467, mailed Jan. 4, 2021.
Office Action for U.S. Appl. No. 17/269,510, mailed Apr. 30, 2021.
Office Action for IN Application No. 201718041270, mailed May 24, 2021.

\* cited by examiner

| Test No. | Starting Pressure | Dispensing Time (min:sec) and Pressure (psi) | | | | | | | | |
|---|---|---|---|---|---|---|---|---|---|---|
| | | 20% of 10mL Dispensed | | 40% of 10mL Dispensed | | 60% of 10mL Dispensed | | 80% of 10mL Dispensed | | 100% of 10mL Dispensed | |
| 1 | 100 | 0:18 | 98 | 0:37 | 95 | 0:59 | 92 | 1:25 | 88 | 1:55 | 84 |
| 2 | 100 | 0:17 | 98 | 0:36 | 95 | 0:58 | 92 | 1:23 | 89 | 1:52 | 85 |
| 3 | 99 | 0:17 | 97 | 0:36 | 94 | 0:58 | 91 | 1:24 | 88 | 1:55 | 84 |
| 4 | 98 | 0:18 | 95 | 0:37 | 92 | 0:57 | 90 | 1:25 | 87 | 1:50 | 83 |
| 5 | 100 | 0:18 | 98 | 0:37 | 95 | 0:57 | 92 | 1:21 | 89 | 1:56 | 85 |
| 6 | 100 | 0:18 | 98 | 0:36 | 95 | 0:56 | 92 | 1:22 | 89 | 1:55 | 84 |
| 7 | 101 | 0:17 | 99 | 0:36 | 96 | 0:57 | 93 | 1:22 | 90 | 1:51 | 86 |
| 8 | 99 | 0:17 | 97 | 0:35 | 94 | 0:54 | 92 | 1:17 | 88 | 1:46 | 85 |
| 9 | 98 | 0:17 | 96 | 0:36 | 93 | 0:56 | 90 | 1:20 | 88 | 1:55 | 83 |
| 10 | 102 | 0:16 | 100 | 0:35 | 97 | 0:56 | 94 | 1:20 | 91 | 1:50 | 87 |
| 11 | 100 | 0:17 | 96 | 0:36 | 89 | 0:58 | 82 | 1:29 | 76 | 2:15 | 66 |
| 12 | 98 | 0:17 | 96 | 0:38 | 93 | 1:01 | 90 | 1:28 | 87 | 2:01 | 83 |
| 13 | 99 | 0:18 | 96 | 0:38 | 94 | 1:00 | 90 | 1:25 | 87 | 1:55 | 84 |
| 14 | 100 | 0:17 | 97 | 0:38 | 94 | 1:01 | 91 | 1:28 | 88 | 1:57 | 84 |
| 15 | 100 | 0:17 | 98 | 0:37 | 94 | 0:59 | 91 | 1:22 | 89 | 1:53 | 85 |
| 16 | 100 | 0:17 | 98 | 0:36 | 95 | 0:57 | 92 | 1:20 | 89 | 1:46 | 86 |
| 17 | 100 | 0:17 | 98 | 0:36 | 95 | 0:58 | 92 | 1:31 | 89 | 1:52 | 84 |
| 18 | 99 | 0:18 | 96 | 0:37 | 93 | 0:59 | 90 | 1:25 | 87 | 1:55 | 83 |
| 19 | 98 | 0:18 | 95 | 0:39 | 92 | 1:00 | 89 | 1:25 | 86 | 1:58 | 82 |
| 20 | 101 | 0:16 | 98 | 0:35 | 96 | 0:54 | 93 | 1:17 | 90 | 1:45 | 86 |
| 21 | 99 | 0:18 | 96 | 0:37 | 94 | 0:57 | 90 | 1:20 | 88 | 1:45 | 85 |
| 22 | 100 | 0:18 | 98 | 0:37 | 94 | 0:58 | 91 | 1:23 | 89 | 1:57 | 84 |
| 23 | 100 | 0:18 | 97 | 0:38 | 94 | 0:59 | 91 | 1:24 | 88 | 1:56 | 84 |
| 24 | 97 | 0:18 | 95 | 0:39 | 92 | 1:01 | 89 | 1:28 | 86 | 2:01 | 82 |
| | Average Time | 0:17 | | 0:36 | | 0:57 | | 1:23 | | 1:53 | |
| | Elapsed Time | 0:17 | | 0:19 | | 0:21 | | 0:25 | | 0:31 | |

*FIG. 64*

DEVICES AND METHODS FOR DELIVERY OF SUBSTANCES WITHIN A MEDICAMENT CONTAINER

CROSS-REFERENCE TO RELATED APPLICATIONS

This application claims benefit of priority to U.S. Provisional Application No. 63/147,785, entitled "Devices and Methods for Delivery of Substances within a Prefilled Syringe," filed Feb. 10, 2021, which is incorporated herein by reference in its entirety.

BACKGROUND

The embodiments described herein relate to medicament delivery devices, pharmaceutical compositions, and drug products. More particularly, the embodiments described herein relate to medicament delivery devices for controlled delivery of medicaments from a medicament container (e.g., a prefilled syringe or cartridge).

Known autoinjectors often include a spring-based actuation system that moves a piston rod to insert the needle and inject the medicament. The size (e.g., length) of such known systems, however, can be larger than desired because of the need to incorporate the piston rod. The length of the piston rod is related to the desired dose to be delivered, and thus as the desired dosage to be delivered increases, the injector size can increase significantly. Moreover, known medicaments or therapeutic substances are formulated to include high molecular weight compounds, compounds with complex molecular structures, living cells, and/or biologics. Such medicaments often have a very high viscosity (e.g., greater than about 100 centipoise at room temperature), which must be accommodated by the delivery system. For example, the force and pressure generated by a spring-based actuation system in an autoinjector may be incompatible with the force and pressure required for the proper delivery of medicaments or therapeutic substances including high molecular weight compounds. Accordingly, many known auto-injectors may not be able to provide appropriate force and/or develop the desired flow rate for effective delivery of such higher viscosity substances. Moreover, even if an auto-injector is capable of producing the desired force, such devices may result in undesirable delivery conditions or rates, which can compromise the substance being delivered or cause excessive pain or discomfort during the delivery process. For example, if the rate of delivery is too high, the resulting shear forces may damage the molecules within the substance, thereby reducing efficacy.

Furthermore, known auto-injectors that include automatic needle retraction after delivery of the medicament to prevent accidental needle prick may include one or more guide shafts or linkages to detect the completion of the medicament delivery in order to initiate the retraction process. The guide shafts and linkages introduce additional friction during the medicament delivery process that works against providing desirable delivery rates and conditions. The guide shafts and linkages also require additional internal housing space, thereby increasing the overall size and bulk of the auto-injector.

Additionally, known prefilled syringes are often filled with a predetermined volume of the medicament (e.g., sufficient for a 1 mL delivered dose). Some therapeutic regimens, however, now require higher delivered volumes (e.g., 2 mL or more). Moreover, known devices and methods for parenterally delivering higher volumes (especially of high-viscosity substances) can often result in unmanageable pain, swelling or even leaking of the delivered substance out of the delivery site. Such undesirable results can be exacerbated when the substance is delivered at a high rate (which, as described above, can damage some therapeutic agents) or with an uneven delivery rate. Thus, to accommodate the standard fill volumes available, known methods and devices for delivering higher volumes can include multiple delivery events (e.g., injections) or infusions (either in a clinic or via an on-body pump), which are often undesirable for patients.

Thus, a need exists for improved methods and devices for delivering medicaments contained within a prefilled syringe. A need also exists for improved methods of controlling medicament delivery to maintain a consistent delivery rate during the course of an extended delivery event.

SUMMARY

Medicament delivery devices for administration of medicaments contained within a medicament container are described herein. In some embodiments, an apparatus includes a housing, an energy storage member, a carrier disposed within the housing, a container coupled to the carrier, a control assembly coupled to a proximal end portion of the container, and a valve assembly. The housing defines a gas chamber. A side wall of the housing defines an opening configured to selectively place the gas chamber in fluid communication with an exterior volume. The energy storage member is configured to release a pressurized gas when the energy storage member is actuated. The carrier includes a proximal surface defining a portion of a boundary of the gas chamber, and the gas chamber configured to receive the pressurized gas to pressurize the gas chamber. A distal end portion of the container is configured to be coupled to a needle, the container containing at least 10 mL of a composition with a viscosity of at least 4 centipoise. The container further includes an elastomeric member that seals the composition within the container. The control assembly coupled to a proximal end portion of the container. The control assembly is configured to regulate a flow of the pressurized gas into the container that acts on the elastomeric member. The valve assembly includes a valve member and a release member. The valve member is configured to seal the opening of the housing when the valve member is in a first position and unseal the opening of the housing when the valve member is in a second position to place the gas chamber in fluid communication with the exterior volume. The release member extends beyond a perimeter of the housing, and the release member is configured to be actuated to move the valve member from the first position to the second position.

In some embodiments, an apparatus includes a housing, a base portion, an energy storage member, a carrier, a container, and a delivery control assembly. The housing defines a gas chamber. The base portion is coupled to the housing, and the base portion is configured to contact a target surface of a body during delivery. The energy storage member is configured to release a pressurized gas when the energy storage member is actuated. The carrier is disposed within the housing. A proximal surface of the carrier defines a portion of a boundary of the gas chamber. The gas chamber is configured to receive the pressurized gas to pressurize the gas chamber. The container is coupled to the carrier. A distal end portion of the container is configured to be coupled to a needle, the container containing a delivery volume of a composition with a viscosity of at least 4 centipoise. The container includes an elastomeric member that seals the composition within the container. The delivery control assembly is coupled to a proximal end portion of the container. The delivery control assembly includes a flow restriction member configured to regulate movement of the elastomer member to dispense a first 20% of the delivered volume of the composition over a first time duration, and to dispense a last 20% of the delivered volume of the composition over a second time duration. The second time duration being less than 2 times the first time duration.

In some embodiments, a method of delivering a dose of a composition includes placing a medical injector against a body. The medical injector includes a housing defining an internal volume, a container disposed within the housing, a needle coupled to the container, an elastomeric member disposed within the container, an actuating assembly including an energy storage member; and a control assembly disposed between the internal volume of the housing and the internal volume of the container. The container contains the dose of the composition within an internal volume of the container, and the dose of the composition has a delivered volume of at least 10 mL. The method includes actuating the medical injector such that the energy storage member produces a force within the internal volume of the housing applied on the container and on the control assembly. The control assembly regulates a portion of the force applied on the elastomeric member such that the elastomeric member moves within the container to deliver the dose of the composition from the container, via the needle and into the body, over a duration of time greater than about 15 seconds and less than about 3 minutes.

In some embodiments, a method of delivering a dose of a composition includes placing a medical injector against a body. The medical injector includes a housing defining an internal volume, a container disposed within the housing, a needle coupled to the container, an elastomeric member disposed within the container, an actuating assembly including an energy storage member; and a gas vent assembly including a valve disposed between the internal volume of the housing and an exterior volume surrounding the housing, the valve being configured to selectively seal the vent opening. The container contains the dose of the composition within an internal volume of the container, and the dose of the composition has a delivered volume of at least 10 mL. The method includes actuating the medical injector such that the energy storage member produces a force within the internal volume of the housing applied on the container. The gas vent assembly regulates a portion of the force applied on the elastomeric member to move the elastomeric member within the container to deliver the dose of the composition from the container via the needle into the body over a delivery time greater than about 15 seconds and less than about 3 minutes.

In some embodiments, a method of delivering a dose of a composition includes actuating a medical injector such that an energy storage member produces a force via a compressed gas within an internal volume of a housing of the medical injector on a container containing a dose of the composition. The force causes the container to move within the housing to cause a needle to extend from the housing. The movement of the container compresses a retraction spring of the medical injector. The method also includes regulating, via a control assembly of the medical injector, a portion of the force applied on an elastomeric member of the container to cause a movement of the elastomeric member within the container to deliver an initial portion of the dose. A venting of the internal volume is initiated via a vent opening defined by the container. The vent opening is sized to maintain the force produced by the compressed gas on the container at a magnitude that is greater than a force applied by the retraction spring during a time to deliver a final portion the dose. The force produced by the compressed gas decreases to a magnitude that is less than the force applied by the retraction spring concurrent with the delivery of the final portion of the dose. Additionally, the method includes retracting the needle via a movement of the container within the housing in response to the force applied by the retraction spring.

In some embodiments, an apparatus for delivering a composition includes a housing defining a gas chamber. A side wall of the housing defines an opening configured to selectively place the gas chamber in fluid communication with an exterior volume. The apparatus also includes an energy storage member configured to release a pressurized gas when the energy storage member is actuated. A carrier is disposed within the housing. A proximal surface of the carrier defines a portion of a boundary of the gas chamber. The gas chamber is configured to receive the pressurized gas to pressurize the gas chamber. A container is coupled to the carrier. A distal end portion of the container is configured to be coupled to a needle. The container contains at least 10 mL of a composition with a viscosity of at least 4 centipoise. The container includes an elastomeric member that seals the composition within the container. Additionally, the apparatus includes a control assembly coupled to a proximal end portion of the container. The control assembly is configured to regulate a flow of the pressurized gas into the container that acts on the elastomeric member. Further, the apparatus includes a valve assembly including a valve member and a valve actuator. The valve member is configured to seal the opening of the housing when the valve member is in a first position and unseal the opening of the housing when the valve member is in a second position. Unsealing the opening places the gas chamber in fluid communication with the exterior volume. The valve actuator extends beyond a perimeter of the housing. The release member is configured to be actuated to move the valve member from the first position to the second position.

BRIEF DESCRIPTION OF THE DRAWINGS

FIG. 64 is a chart showing pressures and delivery times of 10 mL of a composition via the medical injector shown in FIG. 60.

DETAILED DESCRIPTION

Figure 1:
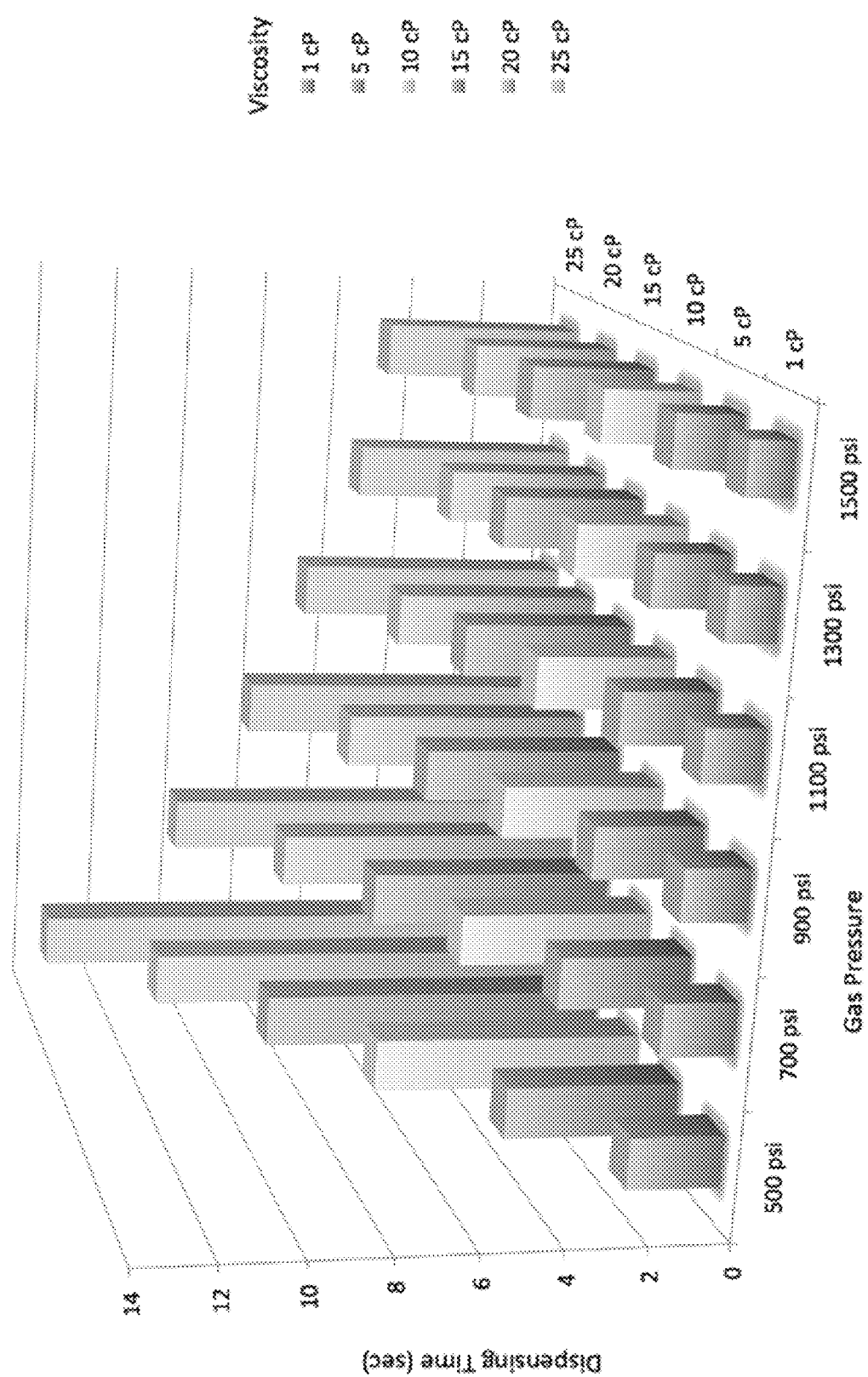
FIG. 1 is a chart showing the time for delivery of 1 mL of a substance via a medicament delivery device according to an embodiment, as a function of the gas pressure and viscosity.

Medicament delivery devices for administration of medicaments are described herein. In some embodiments, an apparatus includes a housing, an energy storage member, a carrier, a medicament container, and a delivery control mechanism. The energy storage member is configured to produce a pressurized gas when the energy storage member is actuated. The housing defines a gas chamber configured to receive pressurized gas from the energy storage member to pressurize the gas chamber. The carrier has a proximal surface that defines a portion of a boundary of the gas chamber. The medicament container is coupled to the carrier and has a distal end portion coupled to a delivery member. The medicament container contains a medicament and includes an elastomeric member that seals the medicament within the medicament container. The delivery control mechanism is coupled to a proximal end portion of the medicament container. The delivery control mechanism includes a flow restriction member that regulates a pressure supplied by the gas chamber that enters into the medicament container. The pressurized gas that builds up within the medicament container acts on the elastomeric member. In some embodiments, the flow restriction member includes at least a single port valve, a multi-port valve, or a porous member.

In some embodiments, it may be desirable to vent the gas chamber to reduce the pressure within the gas chamber. Venting the gas chamber facilitates retraction of the delivery member (e.g., a needle) in response to a retraction force applied by a retraction spring when the retraction force exceeds the force generated by the pressure within the gas chamber. In order to ensure delivery of the full dose of the medicament, the apparatus, in some embodiments, includes a vent opening that is sized to maintain the force produced by the compressed gas at a magnitude that is greater that the retraction force for a time to deliver a final portion of the dose. The force produced by the compressed gas decreases in response to the venting to a magnitude that is less than the force applied by the retraction spring concurrent with the delivery of the final portion of the dose.

In some embodiments, the delivery member is a needle coupled to the distal end portion of the medicament container. The carrier is configured to move from a first carrier position to a second carrier position in response to the pressurized gas being conveyed into the gas chamber. Movement of the carrier from the first carrier position to the second carrier position moves the needle from a first needle position, where the needle is disposed within the housing, to a second needle position, where the needle extends from the housing. The flow restriction member is configured to limit movement of the elastomeric member prior to the carrier being placed in the second carrier position.

In some embodiments, the gas chamber is a first gas chamber and the portion of the boundary of the first gas chamber is a first portion of the boundary. A proximal end portion of the flow restriction member defines a second portion of the boundary of the first gas chamber. A distal end portion of the flow restriction member defines a first portion of the boundary of a second gas chamber. A proximal end portion of the elastomeric member defines a second portion of the boundary of the second gas chamber. After the carrier is placed in the second carrier position, the flow restriction member is configured to permit pressurized gas to pass from the first gas chamber into the second gas chamber via the flow restriction member. In some embodiments, the elastomeric member moves within the medicament container in response to the pressurized gas being conveyed into the second gas chamber. The elastomeric member moves through a stroke distance to convey a dose of medicament from the medicament container via the needle.

In some embodiments, the delivery control mechanism includes a first body portion and a second body portion. The second body portion extends from the first body portion and the first body portion defines a first axis. The second body portion defines a second axis, and the second axis is non-parallel with the first axis. In some embodiments, the medicament container defines a third axis, and the third axis is parallel with the first axis. In some embodiments, the second body portion of the delivery control mechanism includes a flow restriction retainer. The flow restriction member is supported at least partially within the flow restriction retainer.

In some embodiments, the first body portion of the delivery control mechanism includes a proximal end portion and a distal end portion. The distal end portion of the delivery control mechanism is opposite the proximal end portion of the delivery control mechanism. The distal end portion of the delivery mechanism includes a radially extending flange configured to mount on at least the carrier or the proximal end portion of the medicament container. In some embodiments, the distal end portion of the first body portion extends into the proximal end portion of the medicament container.

In some embodiments, the flow restriction member includes a flow restriction retainer and a flow restriction member disposed within the flow restriction retainer. The flow restriction retainer includes a radially extending flange configured to mount on at least the carrier or the proximal end portion of the medicament container. In some embodiments, a distal end portion of the flow restriction retainer extends into the proximal end of the medicament container. The flow restriction retainer defines a first axis, the medicament container defines a second axis, and the second axis is parallel with the first axis.

In some embodiments, the first body portion of the delivery control mechanism includes an annular groove configured to retain a seal member. In some embodiments, the seal member is an O-ring.

In some embodiments, the apparatus further includes a retraction spring coupled to the housing. The retraction spring is configured to bias the carrier towards the first carrier position. The retraction spring is configured to move the carrier towards the first carrier position in response to the pressurized gas being conveyed out of the gas chamber via an opening in the housing.

In some embodiments, the medicament container is a prefilled syringe with a container body. The delivery member includes a needle and the needle is staked to a distal end portion of the container body.

In some embodiments, the medicament within the medicament container includes a drug and/or a biologic product. In some embodiments, the medicament within the medicament container has a viscosity of greater than or equal to 100 centipoise at room temperature. In some embodiments, the medicament within the medicament container includes high molecule weight compounds greater than 5 kDa.

In some embodiments, the carrier is a first carrier, the portion of the boundary of the gas chamber is a first portion of the boundary, the medicament container is a first medicament container, the elastomeric member is a first elastomeric member, the medicament is a first medicament, the delivery control mechanism is a first delivery control mechanism, and the flow restriction member is a first flow restriction member. The apparatus further includes a second carrier disposed within the housing. A second medicament container is coupled to the second carrier. A proximal surface of the second carrier defines a second portion of the boundary of the gas chamber. A distal end portion of the second medicament container is configured to couple to a second delivery member. The second medicament container contains a second medicament and includes a second elastomeric member that seals the second medicament within the second medicament container. A second delivery control mechanism is coupled to a proximal end portion of the second medicament container. The second delivery control mechanism includes a second flow restriction member configured to regulate flow of the pressurized gas into the second medicament container. The pressurized gas that builds up within the second medicament container acts on the second elastomeric member.

In some embodiments, the first delivery member is a first needle coupled to the distal end of the first medicament container. The second delivery member is a second needle coupled to the distal end of the second medicament container. In some embodiments, the first medicament container is non-coaxial with the second medicament container. In some embodiments, the first medicament container and the second medicament container are configured to move within the housing simultaneously in response to the pressurized gas being conveyed into the gas chamber of the housing.

In some embodiments, an apparatus includes a housing, an energy storage member, a carrier, a medicament container, a delivery control mechanism, and a valve member. The housing defines a gas chamber and includes a side wall. The side wall of the housing defines an opening configured to selectively place the gas chamber in fluid communication with an exterior volume. The energy storage member is configured to produce a pressurized gas when the energy storage member is actuated. The carrier is disposed within the housing. A proximal surface of the carrier defines a portion of a boundary of the gas chamber. The gas chamber is configured to receive the pressurized gas from the energy storage member to pressurize the gas chamber. The medicament container is coupled to the carrier. A distal end portion of the medicament container is configured to be coupled to a delivery member. The medicament container contains a medicament and includes an elastomeric member that seals the medicament within the medicament container. The delivery control mechanism is coupled to a proximal end portion of the medicament container. The medicament container includes a flow restriction member that is configured to regulate a flow of the pressurized gas into the medicament container. The pressurized gas in the medicament container acts on the elastomeric member. The valve member is configured to seal the opening of the housing when the valve member is in a first position. The valve member is configured to unseal the opening of the housing when the valve member is in a second position. When the valve member is in the second position, the unsealed opening places the gas chamber in fluid communication with the exterior volume.

In some embodiments, the apparatus further includes an expandable assembly. The expandable assembly includes a first member, a second member, and a third member. The first member is coupled to the elastomeric member. The second member is coupled between the first member and the third member. A portion of the second member is movably disposed within the delivery control mechanism. The third member is coupled to the valve member. The expandable assembly is configured to transition from a first configuration to a second configuration when the elastomeric member moves within the medicament container. The valve member moves from the first position to the second position when the expandable assembly transitions from the first configuration to the second configuration to release pressurized gas from the gas chamber to the exterior volume.

In some embodiments, the delivery control mechanism defines a bore within which the portion of the second member of the expandable assembly is movably disposed. An outer surface of the second member and an inner surface of the bore define an annulus in fluid communication with the flow restriction member. In some embodiments, the annulus is configured to convey pressurized gas received from the flow restriction member to the medicament container.

In some embodiments, the elastomeric member moves within the medicament container through a stroke distance to convey a dose of the medicament from the medicament container in response to the pressurized gas being conveyed into the medicament container. In some embodiments, the delivery control mechanism includes a seal member configured to limit pressurized gas received from passing between the second member of the expandable assembly and the bore of the delivery control mechanism.

In some embodiments, the second member of the expandable assembly includes a flange portion configured to contact a distal end portion of the delivery control member in at least the first configuration of the expandable assembly. In some embodiments, the second member and the delivery control mechanism are configured to move together from a first position to a second position in response to pressurized gas being conveyed into the gas chamber. In some embodiments, the first member is a flexible member configured to transition when the elastomeric member moves within the medicament container. The flexible member transitions from having a first length when the flexible member is in a collapsed state to a second length when the flexible member is in an expanded state. The flexible member is configured to exert a release force on the second member to move the second member axially relative to the delivery control mechanism when the flexible member transitions from the collapsed state to the expanded state. In some embodiments, axial movement of the second member transfers the release force to the third member to move the valve member relative to the opening.

In some embodiments, the second member defines an inner bore. The third member includes a shaft with a proximal end portion and a distal end portion. The proximal end portion of the third member is coupled to the valve member. The distal end portion of the third member includes an end stop member. The inner bore of the second member is configured to ride along the shaft of the third member. The second member rides along the shaft between the valve member and the end stop of the third member in response to pressurized gas being conveyed into the gas chamber.

In some embodiments, the valve member includes a valve portion that defines a gas release path. The valve portion is disposed within the opening of the housing such that the gas release path is fluidically isolated from the gas chamber via a seal member when the expandable assembly is in the first configuration. In some embodiments, the expandable assembly has a first size when in the first configuration and a second size when in the second configuration. The second size is such that the valve member actuates and places the gas chamber in fluid communication with the exterior volume after a medicament is conveyed from the medicament container.

In some embodiments, the first configuration is a collapsed configuration and the second configuration is an expanded configuration. The first member is a flexible member configured to transition when the elastomeric member moves within the medicament container having a first length when the expandable member is in a collapsed state to having a second length when the expandable member is in an expanded state. The flexible member is configured to exert a release force on the valve member to move valve member relative to the opening when the expandable assembly transitions from the collapsed configuration to the expanded configuration. When the valve member is moved relative to the opening, the gas chamber is placed in fluid communication with the exterior volume. In some embodiments, the flexible member is at least a filament and/or a band.

In some embodiments, the valve member moves in a distal direction when the flexible member transitions from the collapsed configuration to the expanded configuration and as the elastomeric member continues to move in the distal direction. In some embodiments, the first member of the expandable assembly is coupled to the elastomeric member via a coupling member. The coupling member includes a retention structure. The third member of the expandable assembly includes a locking protrusion configured to engage the retention structure of the first member when the flexible member is in the collapsed configuration. The locking protrusion is configured to release from the retention structure when a gas pressure within the medicament container exceeds a threshold pressure value.

In some embodiments, the apparatus includes a housing, a medicament container, an electronic circuit system, a sensing unit, a delivery module, and an output module. The medicament container is disposed within the housing. A distal end portion of the medicament container is configured to be coupled to a delivery member. The medicament container contains a medicament and includes an elastomeric member that seals the medicament within the medicament container. The electronic circuit system is coupled to the housing. The electronic circuit system includes a sensing unit, a delivery module, and an output module. The sensing unit is configured to detect a position of the elastomeric member relative to the medicament container and to produce an electronic signal associated with at least one of a position, a velocity, or an acceleration of the elastomeric member. The delivery module is implemented in at least one of a memory or a processing device. The delivery module is configured to receive the electronic signal and to determine, based on the electronic signal, a movement profile of the elastomeric member. The output module is configured to produce at least one of an audio output, a visual output, or a wireless signal associated with the movement profile of the elastomeric member.

In some embodiments, the movement profile includes at least one of a current position of the elastomeric member, a rate of travel of the elastomeric member, a rate of delivery of the medicament from the medicament container, or a remaining amount of time to complete delivery of a dose of the medicament from the medicament container. In some embodiments, the sensing unit includes an infrared light emitter and an infrared light receiver.

In some embodiments, the sensing unit includes a plurality of light emitters and a plurality of detectors. Each of the plurality of detectors are configured to receive a light beam produced by a corresponding light emitter of the plurality of light emitters. In some embodiments, the medicament container extends from a first end portion to a second end portion. The plurality of light emitters and the plurality of detectors are spaced along a length of the medicament container between the first end portion and the second end portion.

In some embodiments, the electronic circuit system further includes a predictive module implemented in at least one of the memory or the processing device. The predictive module is configured to determine a remaining amount of time to complete delivery of a dose of the medicament based on the movement profile received over a time period. In some embodiments, the audio output, the visual output, and/or the wireless signal indicates the remaining amount of time to complete delivery of the dose of the medicament.

In some embodiments, a computer-implemented method includes emitting a first light beam from a first emitter, through a medicament container, and towards a first receiver. The medicament container is positioned between the first emitter and the first receiver. The medicament container contains a medicament and includes an elastomeric member that seals the medicament within the medicament container. The first receiver is configured to produce a first electronic signal associated with a magnitude of the first light beam. The method includes emitting a second light beam from a second emitter, through the medicament container, and towards a second receiver. The medicament container is positioned between the second emitter and the second receiver. The second receiver is configured to produce a second electronic signal associated with a magnitude of the second light signal. The method includes detecting at least one of the first electronic signal or the second electronic signal as the elastomeric member travels within the medicament container. The method includes determining a position of the elastomeric member within the medicament container based on a comparison between the first electronic signal and the second electronic signal. In some embodiments, the first emitter and the second emitter are configured to transmit at least one wavelength within an ultraviolet, a visible light, and/or an infrared light spectrum. In some embodiments, the first emitter and the second emitter are configured to transmit an infrared light beam.

In some embodiments, the method includes determining a rate of travel of the elastomeric member based on a time difference between when the first electronic signal is below a threshold and when the second electronic signal is below the threshold. In some embodiments, the method includes determining a rate of delivery of the medicament from the medicament container based on a time difference between when the first electronic signal is below a threshold and when the second electronic signal is below the threshold. In some embodiments, the method includes determining a remaining completion time to complete delivery of a dose of the medicament from the medicament container based on a time difference between when the first electronic signal is below a threshold and when the second electronic signal is below the threshold.

In some embodiments, an apparatus includes a housing, a carrier, a medicament container, and a delivery mechanism. The housing defines an opening placing a gas chamber in fluid communication with an external environment (e.g., the atmosphere) and the gas chamber is also configured to receive a pressurized gas to pressurize the gas chamber. The carrier has a proximal surface that defines a portion of the gas chamber. The medicament container is coupled to the carrier and has a distal end portion coupled to a delivery member. The medicament container contains a medicament and includes an elastomeric member that seals the medicament therein. The delivery mechanism is coupled to a proximal end portion of the medicament container and includes a flow restriction member for regulating a pressure supplied by the gas chamber to the elastomeric member. In some embodiments, the flow restriction member includes a flow restriction retainer and a flow restriction element disposed within the flow restriction retainer. The flow restriction retainer includes a radially extending flange configured to mount on the carrier. In some embodiments, the medicament container is a prefilled syringe with a drug or a biologic product. In some embodiments, the medicament has a viscosity of greater than or equal to 100 centipoise at room temperature. In some embodiments, the medicament includes high molecule weight compounds greater than 5 kDa.

In some embodiments, a method of delivering a dose of a composition includes placing a medical injector against a body. The medical injector includes a housing defining an internal volume, a container disposed within the housing, a needle coupled to the container, an elastomeric member disposed within the container, an actuating assembly including an energy storage member; and a gas vent assembly including a valve disposed between the internal volume of the housing and an exterior volume surrounding the housing, the valve being configured to selectively seal the vent opening. The container contains the dose of the composition within an internal volume of the container, and the dose of the composition has a delivered volume of at least 10 mL. The method includes actuating the medical injector such that the energy storage member produces a force within the internal volume of the housing applied on the container. The gas vent assembly regulates a portion of the force applied on the elastomeric member to move the elastomeric member within the container to deliver the dose of the composition from the container via the needle into the body over a delivery time greater than about 15 seconds and less than about 3 minutes.

In some embodiments, a method of delivering a dose of a composition includes actuating a medical injector such that an energy storage member produces a force via a compressed gas within an internal volume of a housing of the medical injector on a container containing a dose of the composition. The force causes the container to move within the housing to cause a needle to extend from the housing. The movement of the container compresses a retraction spring of the medical injector. The method also includes regulating, via a control assembly of the medical injector, a portion of the force applied on an elastomeric member of the container to cause a movement of the elastomeric member within the container to deliver an initial portion of the dose. A venting of the internal volume is initiated via a vent opening defined by the container. The vent opening is sized to maintain the force produced by the compressed gas on the container at a magnitude that is greater than a force applied by the retraction spring during a time to deliver a final portion the dose. The force produced by the compressed gas decreases to a magnitude that is less than the force applied by the retraction spring concurrent with the delivery of the final portion of the dose. Additionally, the method includes retracting the needle via a movement of the container within the housing in response to the force applied by the retraction spring.

As used herein, the terms "substance" or "medicament" includes any constituent of a therapeutic substance. A medicament can include such constituents regardless of their state of matter (e.g., solid, liquid or gas). Moreover, a medicament can include the multiple constituents that can be included in a therapeutic substance in a mixed state, in an unmixed state and/or in a partially mixed state. A medicament can include both the active constituents and inert constituents of a therapeutic substance. Accordingly, as used herein, a medicament can include non-active constituents such as water, colorant or the like.

The term "about" when used in connection with a referenced numeric indication means the referenced numeric indication plus or minus up to 10 percent of that referenced numeric indication. For example, "about 100" means from 90 to 110.

In a similar manner, term "substantially" when used in connection with, for example, a geometric relationship, a numerical value, and/or a range is intended to convey that the geometric relationship (or the structures described thereby), the number, and/or the range so defined is nominally the recited geometric relationship, number, and/or range. For example, two structures described herein as being "substantially parallel" is intended to convey that, although a parallel geometric relationship is desirable, some non-parallelism can occur in a "substantially parallel" arrangement. By way of another example, a structure defining a volume that is "substantially 0.50 milliliters (mL)" is intended to convey that, while the recited volume is desirable, some tolerances can occur when the volume is "substantially" the recited volume (e.g., 0.50 mL). Such tolerances can result from manufacturing tolerances, measurement tolerances, and/or other practical considerations (such as, for example, minute imperfections, age of a structure so defined, a pressure or a force exerted within a system, and/or the like). As described above, a suitable tolerance can be, for example, +10% of the stated geometric construction, numerical value, and/or range. Furthermore, although a numerical value modified by the term "substantially" can allow for and/or otherwise encompass a tolerance of the stated numerical value, it is not intended to exclude the exact numerical value stated.

As used herein, the term "set" can refer to multiple features or a singular feature with multiple parts. For example, when referring to set of walls, the set of walls can be considered as one wall with multiple portions, or the set of walls can be considered as multiple, distinct walls. Thus, a monolithically-constructed item can include a set of walls. Such a set of walls can include, for example, multiple portions that are either continuous or discontinuous from each other. A set of walls can also be fabricated from multiple items that are produced separately and are later joined together (e.g., via a weld, an adhesive, or any suitable method).

As used in this specification and the appended claims, the words "proximal" and "distal" refer to direction closer to and away from, respectively, an operator of the medical device. Thus, for example, the end of the medicament delivery device contacting the patient's body would be the distal end of the medicament delivery device, while the end opposite the distal end would be the proximal end of the medicament delivery device.

As used herein, the terms "stiffness" or "rigidity" relate to an object's resistance to deflection, deformation, and/or displacement produced by an applied force, and is generally understood to be the opposite of the object's "flexibility." For example, a gas release member with greater stiffness is more resistant to deflection, deformation and/or displacement when exposed to a force than a gas release member having a lower stiffness. Similarly stated, a gas release member having a higher stiffness can be characterized as being more rigid than a gas release member having a lower stiffness. Stiffness can be characterized in terms of the amount of force applied to the object and the resulting distance through which a first portion of the object deflects, deforms, and/or displaces with respect to a second portion of the object. When characterizing the stiffness of an object, the deflected distance may be measured as the deflection of a portion of the object different than the portion of the object to which the force is directly applied. Said another way, in some objects, the point of deflection is distinct from the point where force is applied.

Stiffness (and therefore, flexibility) is an extensive property of the object being described, and thus is dependent upon the material from which the object is formed as well as certain physical characteristics of the object (e.g., cross-sectional shape, length, boundary conditions, etc.). For example, the stiffness of an object can be increased or decreased by selectively including in the object a material having a desired modulus of elasticity, flexural modulus and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the stiffness of the object can be decreased, for example, by introducing into the object and/or constructing the object of a material having a relatively low modulus of elasticity.

The stiffness of an object can also be increased or decreased by changing a physical characteristic of the object, such as the shape or cross-sectional area of the object. For example, an object having a length and a cross-sectional area may have a greater stiffness than an object having an identical length but a smaller cross-sectional area. As another example, the stiffness of an object can be reduced by including one or more stress concentration risers (or discontinuous boundaries) that cause deformation to occur under a lower stress and/or at a particular location of the object. Thus, the stiffness (or flexibility) of the object can be decreased by decreasing and/or changing the shape of the object.

Thus, an object that deforms readily under small forces, such as, for example, a wire, a filament, a cord, or the like is said to be a flexible object.

The therapeutic compositions described herein can be included in any suitable medicament delivery device as described herein or in International Patent Publication No. WO2017/004345, entitled "Auto-Injectors for Administration of a Medicament Within a Prefilled Syringe," filed Jun. 30, 2016 ("the '4345 PCT"), International Patent Publication No. WO2020/140040, entitled "Devices and Methods for Delivery of Substances Within a Prefilled Syringe," filed Dec. 27, 2019 ("the '0040 PCT"), International Patent Publication No. WO2018/136413, entitled "Medicament Delivery Devices with Wireless Connectivity and Event Detection," filed Jan. 16, 2018 ("the '6413 PCT"), and/or WO2020/018433, entitled "Medicament Delivery Devices with Wireless Connectivity and Compliance Detection," filed Jul. 15, 2019 ("the '8433 PCT"), each of which is incorporated herein by reference in its entirety. For example, in some embodiments, a drug product is configured for administration by an untrained user (such a person accompanying the patient) (e.g., a dose of icatibant). Such drug products can include, for example, an auto-injector having a needle length and delivery profile (e.g., flow of the icatibant) sufficient to produce subcutaneous injection. In other embodiments, a drug product can include a therapeutic substance including of a monoclonal antibody. Such drug products can include, for example, an auto-injector having multiple prefilled syringe containers and that delivers the medicament from each of the syringes in one operation to deliver the desired dose. By including multiple syringes, such arrangements can allow for higher doses while still using a standard fill volume within the prefilled syringe.

In some embodiments, a gas-powered medicament delivery device can result in a compact device, in which the outer dimensions of the housing are not substantially larger than the length of the medicament container disposed therein. For example, as shown and described herein, in some embodiments, a medicament delivery device can be devoid of a mechanical linkage that exerts or transfers a force to an elastomeric member to expel a medicament from a medicament container therein. Similarly stated, in some embodiments, a medicament delivery device can be devoid of mechanical linkages (rams, rods) that transfer force to the elastomeric member. Rather, in some embodiments, the elastomeric member can exert a force onto a member (e.g., an expandable member) to provide control over the delivery. Such medicament delivery devices (or medicament delivery mechanisms) are considered to be "pistonless" systems. As one example, in a pistonless, gas-powered auto-injector, the force exerted by the gas can move the medicament container relative to the housing and similarly, can move the elastomeric member relative to (e.g., within) the medicament container. In some embodiments, by not including a movable mechanism, a piston, and/or the like, a height of the medical injector can be reduced relative to, for example, the height of a device that includes a rigid, single length piston.

For example, any of the medicament delivery devices described herein can include any suitable "pistonless" design, such as those described in the '4345 PCT, the '0040 PCT, or in International Patent Publication No. WO 2016/154427, entitled "DEVICES AND METHODS FOR DELIVERING A LYOPHILIZED MEDICAMENT," filed on Mar. 24, 2016, which is incorporated herein by reference in its entirety.

In some embodiments, the characteristics of the medicament, the medicament container and the needle are such that the force required to achieve the desired injection is not possible via manual injection. Accordingly, in some embodiments a device can include an energy storage member configured to produce the desired force (and/or pressure within the medicament container) to deliver the medicament. For example, in certain circumstances, the pressure of the medicament within a needle-based medicament container can be modeled by the Hagen-Poiseuille law, as indicated $$P = (8 * \mu * L * Q)/(\Pi * R^4) \qquad (1)$$

where P is the pressure of the medicament within the medicament container, $\mu$ is the viscosity of the medicament, L is the length of the needle (not shown), Q is the flow rate of the medicament through the needle, and R is the radius of the lumen defined by the needle. Because the pressure (and/or force) required to inject a high viscosity fluid through a small-bore needle is proportional to the inverse of the radius of the lumen of the needle to the fourth power, the pressure of the medicament within the medicament container necessary to achieve the desired flow rate can, at times, be relatively high. By including a gas-based energy storage member, the desired pressure can be achieved.

In some embodiments, the energy storage member can be configurable to include various amounts of stored energy without changing the size of the energy storage member. In such embodiments, therefore, a high force (e.g., to inject viscous medicaments) can be achieved in the same packaging that is used for lower viscosity medicaments. For example, in some embodiments, the energy storage member can be a compressed gas cylinder having any desired pressure (and thus, mass) of gas therein. Accordingly, the pressure and/or force can be achieved to complete the operations described herein, regardless of the medicament.

In such embodiments, the use of a non-mechanical energy storage member (e.g., gas, propellant, magnetic, electronic or the like) can produce a sufficiently high force to produce the desired pressure within the medicament container to produce the desired injection. For example, in such embodiments having a larger diameter, the amount of force needed to produce a desired internal pressure increases significantly. In some embodiments, any of the medicament delivery devices shown herein can include a gas-based energy storage system configured to produce a gas pressure (e.g., within the gas chamber) of between about 200 psi and about 2700 psi. In some embodiments, any of the injectors shown herein can include a gas-based energy storage system configured to produce a gas pressure of about 200 psi, 300 psi, 400 psi, 500 psi, 600 psi, 700 psi, 800 psi, 900 psi, 1100 psi, 1200 psi, 1300 psi, 1500 psi, 1700 psi, 1900 psi, 2100 psi, 2300 psi, 2500 psi, or 2700 psi. In some embodiments, any of the injectors shown herein can include a gas-based energy storage system configured to produce a gas pressure of between about 200 psi to 7000 psi. The gas pressure can be produced by any suitable mechanism, such as, for example, by puncturing a compressed gas container, releasing a propellant (e.g., hydrofluoroalkane), releasing a refrigerant (e.g., R134a), releasing a liquefied gas, triggering a chemical reaction, or the like.

FIG. 1 is a chart showing the delivery time for delivering 1 mL of a substance using a medicament delivery device of the types shown and described herein and in the '4335 PCT and the '0040 PCT as a function of both the gas pressure and the viscosity of the substance. As shown, the delivery time can be tailored to meet desired performance characteristics by adjusting the gas pressure within the device. For example, in some embodiments, any of the devices and drug products described herein can be used to perform a method of subcutaneous injection by limiting the gas pressure during the injection event. By limiting the gas pressure, the injection force (and therefore the momentum of the substance leaving the device) can be reduced to ensure that the substance is delivered subcutaneously and not intramuscularly. Control of the momentum of the substance leaving the device and the injection speed of the substance can also minimize pain to a patient, particularly when the substance is highly viscous (e.g., greater than about 100 centipoise at room temperature). By way of another example, in some embodiments, injection of medicaments or therapeutic substances including high molecule weight compounds (e.g., greater than about 5 kDa) may require an injection force less than a force required to overcome a spring-based actuation system of an autoinjector to prevent shearing and therefore damage to the medicament or therapeutic substance.

In some embodiments, the gas pressure can be controlled during the injection event by limiting the amount of pressurized gas within the compressed gas container. In other embodiments, the gas pressure can be controlled by selective movement of a gas release valve, such as the release valve 4345 described below, during a delivery (e.g., injection) event. Similarly stated, in some embodiments, any of the devices described herein (or in the 4345 PCT, the '0040 PCT, or the '6413 PCT) can include a valve and a mechanism that opens the valve by a predetermined amount during a delivery event. In yet other embodiments, any of the devices described herein (or in the '4345 PCT, the '0040 PCT, or the '6413 PCT) can include a porous valve member that allows some amount of pressure reduction during a delivery event.

FIGS. 2-5 are schematic illustrations of medicament delivery device 1000 according to an embodiment in a first configuration, a second configuration, a third configuration, and a fourth configuration, respectively. The medicament delivery device 1000 includes a housing 1100, a medicament container assembly 1200, an energy storage member 1400, a flow restriction member 1450, and a retraction member 1351. The housing 1100 defines a gas chamber 1139 that receives a pressurized gas from the energy storage member 1400. The gas chamber 1139 can be of any suitable size and shape, and can be, for example, a portion of the volume defined by the housing 1100 within which a portion of the medicament container assembly 1200 is disposed. The housing 1100 can be any suitable size, shape, or configuration and can be made of any suitable material. For example, in some embodiments, the housing 1100 is an assembly of multiple parts formed from a plastic material and defines a substantially rectangular shape when assembled. In other embodiments, the housing 1100 can have a substantially cylindrical shape.

The medicament container assembly 1200 has a medicament container body 1210 that defines a volume that contains (i.e., is filled with or partially filled with) a medicament. The distal end portion of the medicament container body 1210 includes a neck or opening through which the medicament can be delivered. In some embodiments, the medicament container assembly 1200 can include a delivery member 1216 coupled to the container body 1210 through which the medicament is delivered. For example, in some embodiments, the delivery member 1216 includes a needle, a nozzle, a mouthpiece, or the like. In some embodiments, the medicament container assembly 1200 can be a prefilled syringe having a needle staked thereto, of the types shown and described herein. In some embodiments, the medicament container assembly 1200 can include or be coupled to a carrier (not shown in FIGS. 2-5, but which can be similar to the carrier body 4360 described below) that moves the medicament container body 1210 within the housing 1100. In this manner, the carrier can facilitate moving the delivery member 1216 out of the housing 1100 in a deployed position, as described below. In some embodiments, one or more surfaces of the carrier can form at least a portion of a boundary of the gas chamber 1139. In some embodiments, the carrier can include one or more seals to fluidically isolate the gas chamber 1139.

The medicament container assembly 1200 includes an elastomeric member 1217 (i.e., a plunger) that seals the medicament within the container body 1210. The elastomeric member 1217 is configured to move within the container body to inject the medicament from the medicament container assembly 1200. The elastomeric member 1217 can be of any design or formulation suitable for contact with the medicament. For example, the elastomeric member 1217 can be formulated to minimize any reduction in the efficacy of the medicament that may result from contact (either direct or indirect) between the elastomeric member 1217 and the medicament. For example, in some embodiments, the elastomeric member 1217 can be formulated to minimize any leaching or out-gassing of compositions that may have an undesired effect on the medicament. In other embodiments, the elastomeric member 1217 can be formulated to maintain its chemical stability, flexibility and/or sealing properties when in contact (either direct or indirect)

with the medicament over a long period of time (e.g., for up to six months, one year, two years, five years or longer).

The medicament container assembly 1200 includes a proximal portion 1214 configured to translate within the housing 1100 to move the medicament container body 1210 between a first position and a second position as described herein. Although the medicament container assembly 1200 is shown as being disposed within the housing 1100 without a carrier, in other embodiments, the medicament container assembly 1200 can be disposed within or coupled to a carrier to facilitate movement within the housing 1100. The proximal portion 1214 of the medicament container assembly 1200, and the carrier if present), define a portion of a boundary of the gas chamber 1139. In this manner, when a pressurized gas is conveyed into the gas chamber 1139, the pressure therein will produce a force on the proximal portion 1214 to move the medicament container body 1210 (and the delivery member 1216) from the withdrawn position to the deployed position.

The energy storage member 1400 is disposed within the housing 1100, and is configured to convey the pressurized gas into the gas chamber 1139 to produce a force $F_1$ (see FIG. 2) to deploy the delivery member 1216 and to convey the contents of the medicament container assembly 1200 when the energy storage member 1400 is actuated. The energy storage member 1400 can be any suitable member or device that stores potential energy and, when actuated, produces the pressurized gas. For example, the energy storage member 1400 (and any of the energy storage members described herein) can be any of a device containing compressed gas, a device containing a vapor pressure-based propellant or the like.

The retraction member 1351 can be a retraction spring or any other energy accumulation member. In this manner, the retraction member 1351 is configured to move the medicament container assembly 1200 back towards a first position (e.g., withdrawn position) of the medicament container assembly 1200 after it has been deployed as described in further detail herein. In some embodiments, the retraction member 1351 can further be configured to maintain the medicament container assembly 1200 in the withdrawn position prior to gas pressure being supplied to the gas chamber 1139. Although shown as including a retraction member, in other embodiments, the medicament delivery device 1000 need not include a retraction member. For example, in some embodiments, the medicament delivery device 1000 can be configured to maintain the delivery member 1216 in the deployed position after delivery. In such embodiment, the medicament delivery device 1000 can include other suitable mechanisms for covering or shielding the delivery member (e.g., a cover that moves about the delivery member 1216 after delivery is completed).

Figure 2:
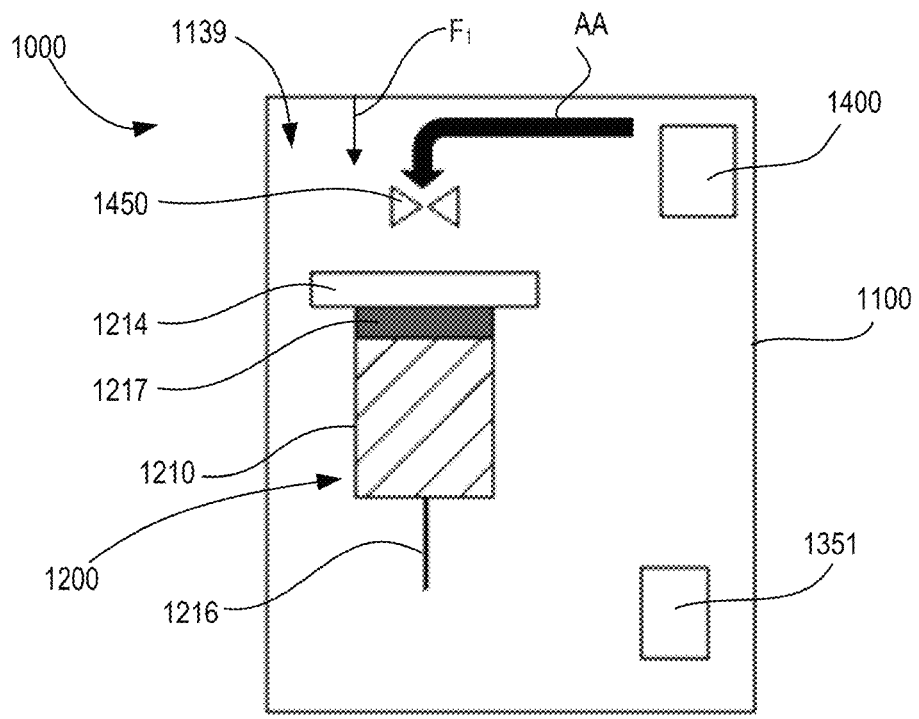
FIGS. 2-5 are schematic illustrations of a medicament delivery device according to an embodiment, in a first configuration, a second configuration, a third configuration, and a fourth configuration, respectively.

When the medicament delivery device 1000 is actuated, the energy storage member 1400 is activated and releases pressurized gas into the gas chamber 1139, as shown by the arrow AA. The released pressurized gas produces a force $F_1$ that moves the medicament container body 1210 together with the delivery member 1216 from a first position (e.g., withdrawn position), as shown in FIG. 2, to a second position (e.g., deployed position) in a first direction as indicated by the arrow BB in FIG. 3. As shown, the delivery member 1216 is disposed within the housing 1100 in the withdrawn position and the delivery member 1216 extends out of the housing 1100 in the deployed position.

Figure 3:
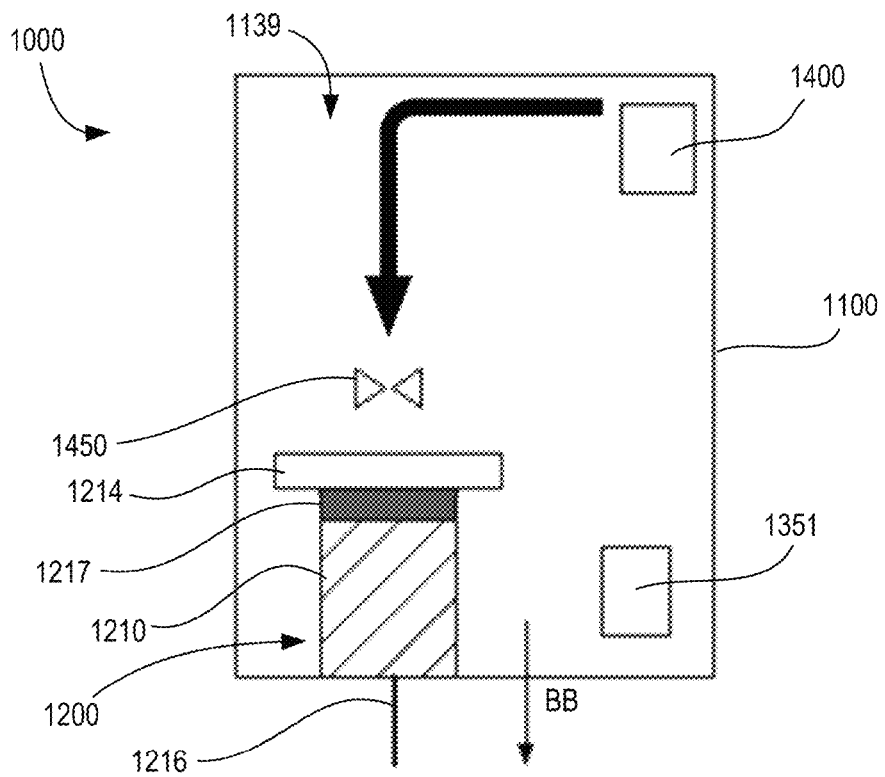
Figure 4:
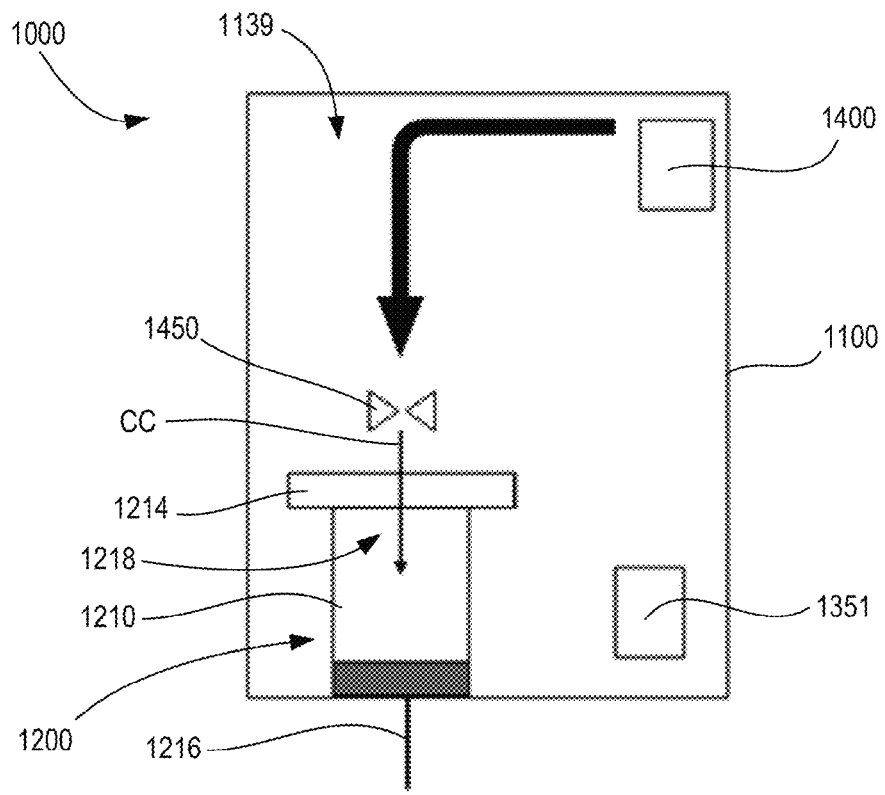

Once the medicament container body 1210 and the delivery member 1216 have been placed in the deployed position, the released pressurized gas travels through (or continues to travel through) the flow restriction member 1450 and into a medicament container gas chamber 1218 of the medicament container assembly 1200, as shown by the arrow CC in FIG. 4. The medicament container gas chamber 1218 is defined between the flow restriction member 1450 and the elastomeric member 1217. As the released pressurized gas passes through the flow restriction member 1450, the pressure builds up within the medicament container gas chamber 1218. After the pressure in the medicament container gas chamber 1218 overcomes resistance of the elastomeric member 1217 against an interior of the medicament container body 1210, the elastomeric member 1217 moves from a first elastomeric member position to a second elastomeric member position. As shown in FIGS. 3 and 4, the elastomeric member 1217 moves from the first elastomeric member position to the second elastomeric member position thereby expelling the medicament from within the medicament container body 1210.

By regulating the pressure build up within the medicament container gas chamber, via the flow restriction member 1450, full deployment of the medicament container body 1210 and the delivery member 1216 can be achieved prior to delivery of substantially any medicament from the medicament container body 1210. Furthermore, in embodiments where the medicament is highly viscous (i.e., having a viscosity greater than or equal to about 100 centipoise at room temperature) and/or where the medicament includes high molecular weight compounds greater than about 5 kDa, the flow rate of the medicament expelled from the medicament container body 1210 can be regulated. In other words, the force applied by the released pressurized gas in the medicament container gas chamber on the elastomeric member 1217 can be controlled and reduced by the flow restriction member 1450 (compared to the released gas pressure from the gas chamber 1139 being directly applied on the elastomeric member 1217). As a result, the regulated pressure through the flow restriction member 1450 allows controlled speed and movement of the elastomeric member 1217 through its travel stroke thereby preventing shearing of high molecular weight compounds in the medicament and reducing pain sensed by a patient.

The flow restriction member 1450 can be any suitable flow restriction member of the types shown and described herein. For example, in some embodiments, the flow restriction member 1450 can be included within a delivery control mechanism (not shown in FIGS. 2-5) that is coupled to the medicament container assembly 1200. In some embodiments, the flow restriction member 1450 can be at least partially within the container body 1210. Moreover, the flow restriction member 1450 can include any suitable structure for regulating the flow of pressurized gas into (and/or the pressure within) the medicament container gas chamber 1218. For example, the flow restriction member 1450 can include a porous material through which a portion of the pressurized gas can flow. In other embodiments, the flow restriction member 1450 can include a filter element, a diaphragm element, a single port orifice, a series of single port orifices, a sieve plate element, or an adjustable valve. In some embodiments, the flow restriction member 1450 includes a porous metal or porous ceramic material. The porous material provides multiple passageways through the flow restriction member 1450 thereby preventing clogs if any debris is present within the housing 1100. In some embodiments, the flow restriction member 1450 is calibrated with nitrogen gas ($N_2$) at 30 psig (inlet side) to atmosphere (outlet side) at standard temperature and pressure to have a flow rate of between about 0.5 to 3 standard cubic centimeter per minute (sccm). In some embodiments, the flow restriction member 1450 is calibrated with nitrogen gas ($N_2$) at 30 psig (inlet side) to atmosphere (outlet side) at standard temperature and pressure to have a flow rate of between about 0.75 and 1.5 standard cubic centimeter per minute (sccm). In some embodiments, the flow restriction member 1450 is calibrated with nitrogen gas ($N_2$) at 30 psig (inlet side) to atmosphere (outlet side) at standard temperature and pressure to have a flow rate of about 1 standard cubic centimeter per minute (sccm). As described herein, standard temperature is 60° F. (15.6° C.) and standard pressure is 14.696 psia (101.3 kPa).

Although the medicament delivery device 1000 is shown as including a flow restriction member 1450 that receives a flow of pressurized gas from the gas chamber 1139, in other embodiments, the medicament delivery device 1000 (and any of the medicament delivery devices herein) can define one or more gas flow paths such that the flow restriction member (and thus the medicament container gas chamber 1218) receive a flow of pressurized gas directly from the energy storage member 1400 and not via the gas chamber 1139 of the housing 1100. Similarly stated, although the gas flow path from the energy storage member 1400 to the gas chamber 1139 and the medicament container gas chamber 1218 are shown and described as being in series, in other embodiments, this gas flow path can be in parallel.

Figure 5:
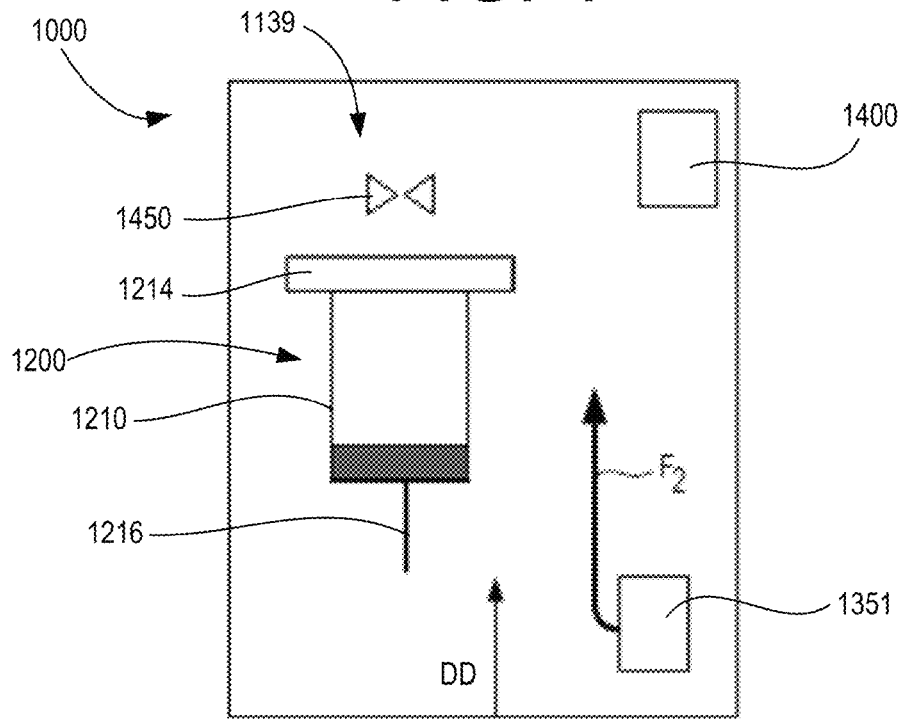

Once the elastomeric member 1217 has traveled from the first elastomeric member position to the second elastomeric member position to dispense a dose of the medicament, the retraction member 1351 can be activated to apply a force $F_2$ in a second direction indicated by the arrow DD in FIG. 5, opposite the first direction, to return the container body 1210 and the delivery member 1216 back towards the withdrawn position. In some embodiments, the retraction member 1351 produces a force $F_2$ greater than the force $F_1$ from the released pressurized gas in the gas chamber 1139. In some embodiments, the retraction member 1351 produces a force sufficient to move the medicament container body 1210 and the delivery member 1216 once the released pressurized gas has been moved out of the gas chamber 1139. For example, the released pressurized gas may be released from the gas chamber 1139 and moved to a second gas chamber within the housing 1100 such that the remaining force applied on the medicament container assembly 1200 in the first direction indicated by the arrow AA is less than the force $F_2$ applied by the retraction member 1351. Although the medicament delivery device 1000 is described as maintaining the released pressurized gas within the housing 1100, either by keeping the released pressurized gas in the gas chamber 1139 or moving a portion of the released pressurized gas to a second gas chamber within the housing 1100, in other embodiments, a medicament delivery device 1000 can include a gas release mechanism to vent the released pressurized gas to an external environment (i.e., an exterior environment external to the housing 1100).

FIGS. 6-9 are schematic illustrations of a medicament delivery device 1000' according to an embodiment in a first configuration, a second configuration, a third configuration, and a fourth configuration, respectively. The medicament delivery device 1000' includes a housing 1100', a medicament container assembly 1200', an energy storage member 1400', and a flow restriction member 1450', which are similar to the corresponding parts in the medicament delivery device 1000 described above. The housing 1100' defines a gas chamber 1139' that receives a pressurized gas from the energy storage member 1400'. The housing 1100' further defines an opening 1112' (see FIG. 9) extending through a wall of the housing 1100' to place the gas chamber 1139' in fluid communication with an external environment outside of the housing 1100'. The medicament delivery device 1000' further includes a gas release mechanism 1320' and a retraction member 1351' to return the medicament container assembly 1200' back towards a retracted (or withdrawn) position.

The retraction member 1351' can be a retraction spring or any other energy storage accumulation member. In this manner, the retraction member 1351' is configured to move the medicament container assembly 1200' back towards a first position (e.g., withdrawn position) of the medicament container assembly 1200' after it has been deployed. In some embodiments, the retraction member 1351' can further be configured to maintain the medicament container assembly 1200' in the withdrawn position prior to gas pressure is supplied to the gas chamber 1139'.

The medicament container assembly 1200 includes an elastomeric member 1217 (i.e., a plunger) that seals the medicament within the container body 1210. In some embodiments, the medicament container assembly 1200' can include a delivery member 1216' coupled to the container body 1210' through which the medicament is delivered. For example, in some embodiments, the delivery member 1216' includes a needle, a nozzle, a mouthpiece, or the like. In some embodiments, the medicament container assembly 1200' can be a prefilled syringe having a needle staked thereto, of the types shown and described herein. As the medicament container body 1210' moves from the withdrawn position to the deployed position, the delivery member 1216' is configured to extend out from the housing 1100' to dispense medicament to a user.

The energy storage member 1400' is disposed within the housing 1100, and is configured to convey the pressurized gas into the gas chamber 1139' to produce a force $F_1$ to deploy the delivery member 1216' and to convey the contents of the medicament container assembly 1200' when the energy storage member 1400 is actuated. The energy storage member 1400' can be similar to the energy storage member 1400 (or any of the energy storage members described herein). The flow restriction member 1450' can be similar to the flow restriction member 1450 (or any of the flow restriction members or delivery control mechanisms described herein) and can regulate the flow of the pressurized gas into the medicament container assembly 1200'. For example, in some embodiments, the flow restriction member 1450 can be at least partially within the container body 1210' or coupled to the container body 1210' via a delivery control mechanism housing. In some embodiments, the flow restriction member 1450' includes a porous metal or porous ceramic material for restricting flow through the flow restriction member 1450'. In some embodiments, the flow restriction member 1450' is calibrated with nitrogen gas ($N_2$) at 30 psig (inlet side) to atmosphere (outlet side) at standard temperature and pressure to have a flow rate of between about 0.5 to 3 standard cubic centimeter per minute (sccm). In some embodiments, the flow restriction member 1450' is calibrated with nitrogen gas ($N_2$) at 30 psig (inlet side) to atmosphere (outlet side) at standard temperature and pressure to have a flow rate of between about 0.75 and 1.5 standard cubic centimeter per minute (sccm). In some embodiments, the flow restriction member 1450' is calibrated with nitrogen gas ($N_2$) at 30 psig (inlet side) to atmosphere (outlet side) at standard temperature and pressure to have a flow rate of about 1 standard cubic centimeter per minute (sccm).

Figure 6:
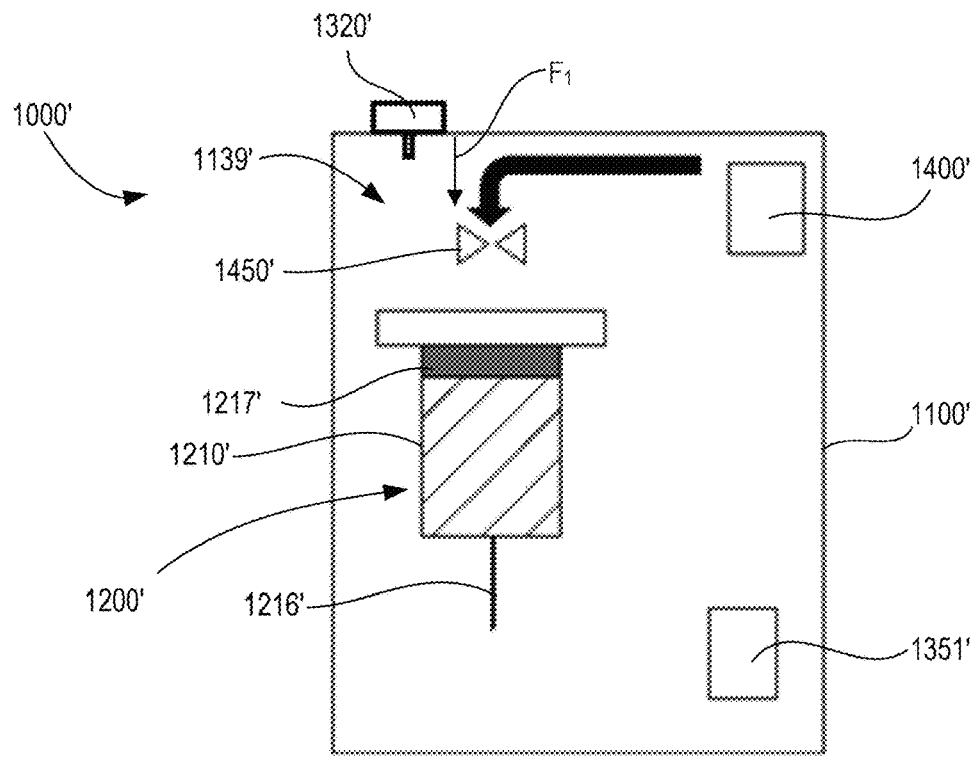
FIGS. 6-9 are schematic illustrations of a medicament delivery device according to an embodiment, in a first configuration, a second configuration, a third configuration, and a fourth configuration, respectively.
Figure 7:
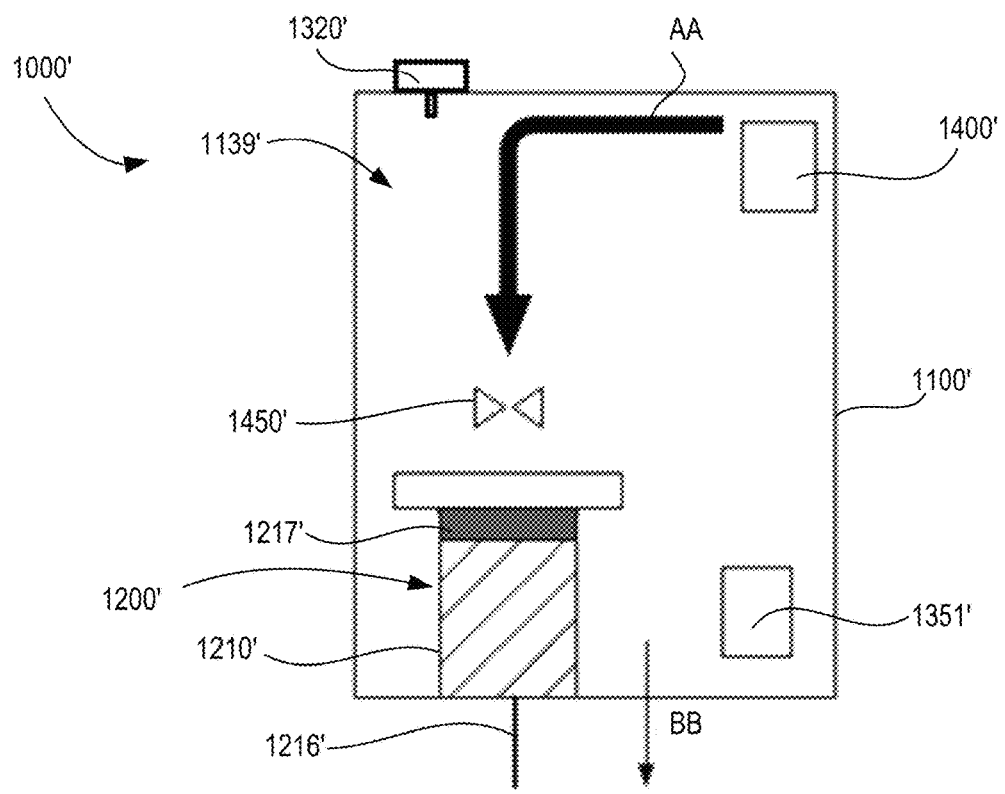

When the medicament delivery device 1000' is actuated, the energy storage member 1400' is activated and releases pressurized gas into the gas chamber 1139', as shown by the arrow A in FIG. 7. In this initial state as shown in FIG. 6, the gas release mechanism 1320' is in a closed position such that the opening 1112' of the housing 1100' is sealed and the gas chamber 1139' is isolated from the external environment outside of the housing 1100'. As the released pressurized gas fills the gas chamber 1139', pressure builds up and produces a first force $F_1$ that moves a medicament container body 1210' of the medicament container assembly 1200' from the first position (e.g., withdrawn position) to the second position (e.g., deployed position) in a first direction indicated by the arrow BB shown in FIG. 7.

Figure 8:
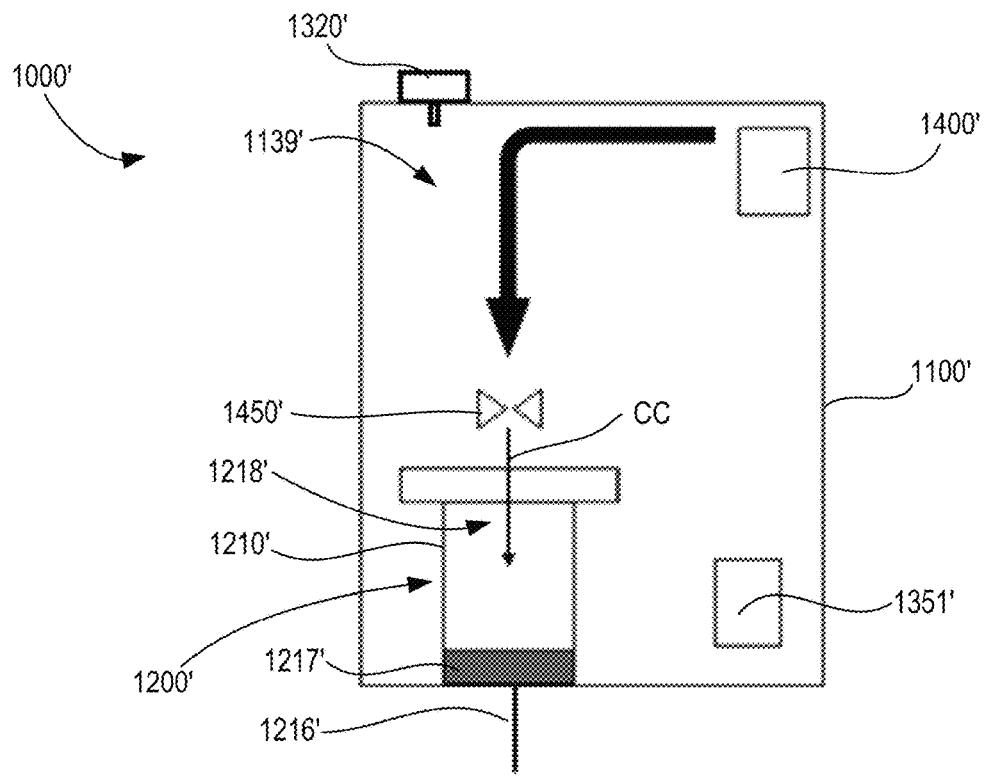
Figure 9:
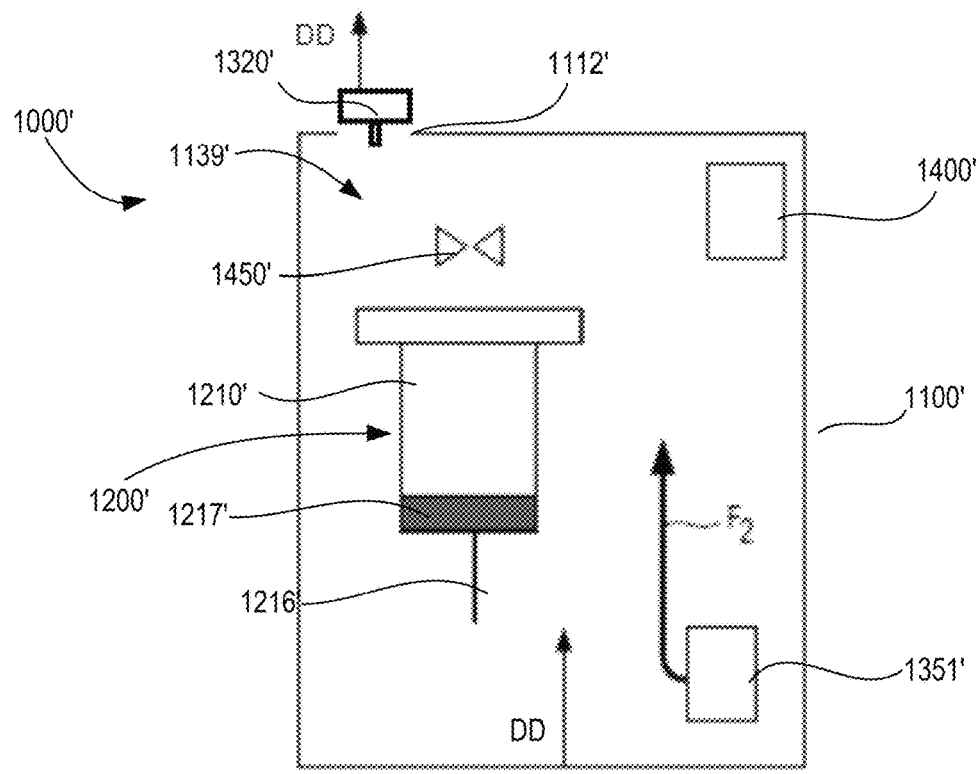

Once the medicament container body 1210' and the delivery member 1216' have been placed in the deployed position, the released pressurized gas travels through (or continues to travel through) the flow restriction member 1450' and into a medicament container gas chamber 1218' of the medicament container assembly 1200', as shown by the arrow CC in FIG. 8. The medicament container gas chamber 1218' is defined between the flow restriction member 1450' and the elastomeric member 1217'. As the released pressurized gas passes through the flow restriction member 1450' the pressure builds up within the medicament container gas chamber. After the pressure in the medicament container gas chamber 1218' is such that it overcomes resistance of the elastomeric member 1217' against an interior of the medicament container body 1210', the elastomeric member 1217' moves from a first elastomeric member position to a second elastomeric member position. As shown in FIGS. 7 and 8, the elastomeric member 1217 moves from the first elastomeric member position to the second elastomeric member position thereby expelling the medicament from within the medicament container body 1210'.

By regulating the pressure build up within the medicament container gas chamber 1218' via the flow restriction member 1450', full deployment of the medicament container body 1210' and the delivery member 1216' can be achieved prior to delivery of substantially any medicament from the medicament container body 1210'. Furthermore, in embodiments where the medicament is highly viscous (i.e., having a viscosity greater than or equal to about 100 centipoise at room temperature) and/or where the medicament includes high molecular weight compounds greater than about 5 kDa, the flow rate of the medicament expelled from the medicament container body 1210)' can be regulated. In other words, the force applied by the released pressurized gas on the elastomeric member 1217 can be controlled and reduced by the flow restriction member 1450' (compared to the released pressurized gas in the gas chamber 1139' being directly applied on the elastomeric member 1217'). As a result, the regulated pressure through the flow restriction member 1450' allows controlled movement and speed of the elastomeric member 1217' through its travel stroke thereby preventing shearing of high molecular weight compounds in the medicament and reducing pain sensed by a patient.

Once the elastomeric member 1217' has traveled from the first elastomeric member position to the second elastomeric member position to dispense a dose of the medicament, the gas release mechanism 1320' is actuated from a closed position to an open position to unseal the opening 1112' and to place the gas chamber 1139' in fluid communication with an external environment (e.g., ambient environment surrounding the medicament delivery device 1000'). In some embodiments, the gas release mechanism 1320 is operably coupled to the elastomeric member 1217' such that the gas release mechanism 1320' is placed in the open position as the elastomeric member 1217' reaches the end of its stroke at the second elastomeric member position. In some embodiments, the gas release mechanism 1320 is a manually operated valve that can be placed in the open position by a user. For example, in some embodiments, after the injection is completed, the user can manually depress a button or pull upwards on the gas release mechanism 1320'. In some embodiment, the gas release mechanism 1320' is operatively coupled to a controller that detects the end of the travel stroke of the elastomeric member 1217', and the gas release mechanism 1320' is configured to actuate to the open position in response to a signal from the controller.

After the gas chamber 1139' has been placed in fluid communication with the external environment, the released pressurized gas escapes and vents out of the opening 1112' thereby depressurizing the gas chamber 1139'. Additionally, the retraction member 1351' can be activated to move the medicament container body 1210' and the delivery member 1216' from the deployed position back to the withdrawn position. In particular, the retraction member 1351' produces a force $F_2$ in a second direction indicated by the arrow DD in FIG. 9, opposite the first direction, to return the container body 1210' and the delivery member 1216 back to the withdrawn position. The force $F_2$ applied by the retraction member 1351 is selected to sufficiently act against frictional forces between the medicament container assembly 1200' and the housing 1100', and/or to act against any released pressurized gas still remaining in the gas chamber 1139'.

In some embodiments, any of the medicament delivery devices shown and described herein can include a sensing unit that detects the movement and location of the elastomeric member and produces an output associated with a delivery rate (based on the detected movement) In some embodiments, the sensing unit can be included within an electronic circuit system that produces visual and/or audible outputs, such as any of the electronic circuit systems described in the '6413 PCT. In some embodiments, the sensing unit produces a wireless signal to communicate with an accessory device, a cellular device, a remote server, or remote network.

Figure 10:
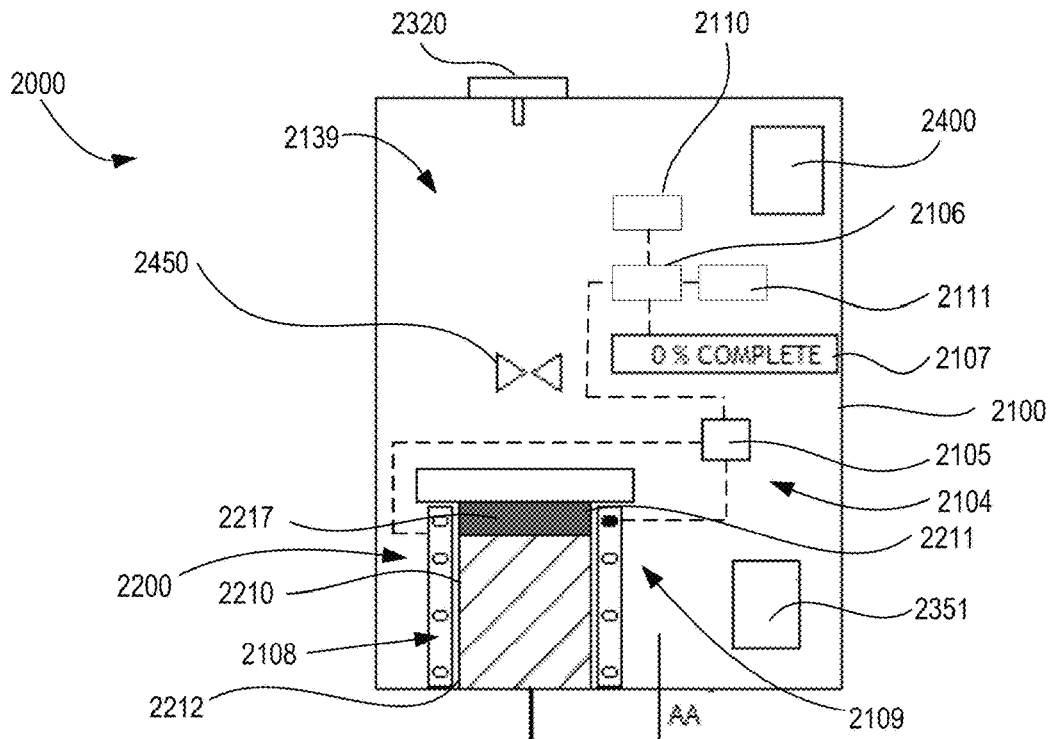
FIGS. 10-12 are schematic illustrations of a medicament delivery device according to an embodiment, in a first configuration, a second configuration, and a third configuration, respectively.
Figure 11:
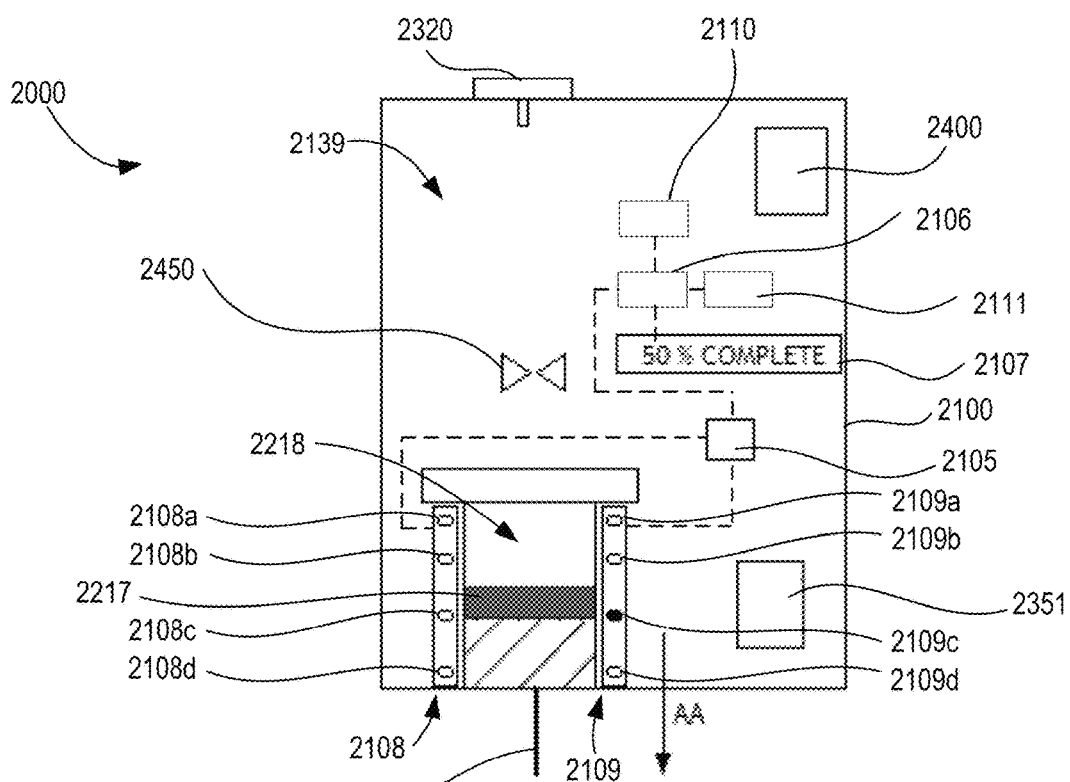
Figure 12:
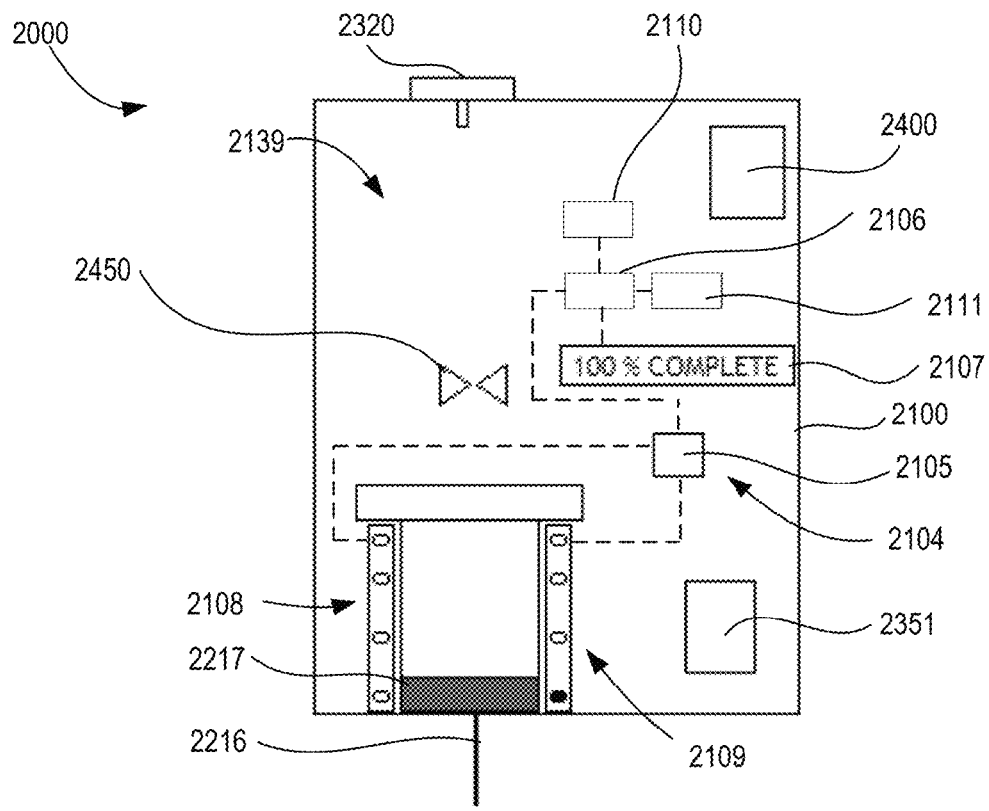

FIGS. 10-12 are schematic illustrations of a medicament delivery device 2000 according to an embodiment in a first configuration, a second configuration, a third configuration, respectively. The medicament delivery device 2000 includes a housing 2100, a medicament container assembly 2200, an energy storage member 2400, and a flow restriction member 2450, which are similar to the corresponding parts in the medicament delivery device 1000 described above. The medicament delivery device 2000 also includes an electronic circuit system 2104 coupled to the housing 2100. The electronic circuit system 2104 includes a sensing unit 2105, a delivery module 2106, and an output module 2107. The sensing unit 2105 includes an emitter 2108 and a receiver 2109 to detect the rate of medicament delivery, as described below.

The housing 2100 defines a gas chamber 2139 that receives a pressurized gas from the energy storage member 2400. The housing 2100 further includes an opening (not shown) extending through a wall of the housing 2100 to place the gas chamber 2139 in fluid communication with an external environment outside of the housing 2100. The medicament delivery device 2000 further includes a gas release mechanism 2320 and a retraction member 2351 configured to return the medicament container assembly 2200 back towards a withdrawn position after a dose of medicament has been dispensed. The gas release mechanism 2320 can be any suitable gas release mechanism described herein and the retraction member 2351 can be any suitable retraction member described herein.

The medicament container assembly 2200 has a medicament container body 2210 that defines a volume that contains (i.e., is filled with or partially filled with) a medicament. The medicament container body 2210 includes transparent or translucent walls configured to transmit light beams therethrough. In some embodiments, the medicament container body 2210 is made of glass or plastic. The distal end portion of the medicament container body 2210 includes a neck or opening through which the medicament can be delivered. In some embodiments, the medicament container assembly 2200 can include a delivery member 2216 coupled to the medicament container body 2210 through which the medicament is delivered. For example, in some embodiments, the delivery member 2216 includes a needle, a nozzle, a mouthpiece, or the like. In some embodiments, the medicament container assembly 2200 can be a prefilled syringe having a needle staked thereto, of the types shown and described herein.

The medicament container assembly 2200 includes an elastomeric member 2217 (i.e., a plunger) that seals the medicament within the medicament container body 2210. The elastomeric member 2217 is configured to move within the container body to inject the medicament from the medicament container assembly 2200. The elastomeric member 2217 can be of any design or formulation suitable for contact with the medicament as described herein.

The energy storage member 2400 is disposed within the housing 2100, and is configured to convey the pressurized gas into the gas chamber 2139 to produce a force to deploy the delivery member 2216 and to convey the contents of the medicament container assembly 2200 when the energy storage member 2400 is actuated. The energy storage member 2400 can be similar to the energy storage member 1400 (or any of the energy storage members described herein). The flow restriction member 2450 can be similar to the flow restriction member 1450 (or any of the flow restriction members or delivery control mechanisms described herein) and can regulate the flow of the pressurized gas into the medicament container assembly 2200.

When the medicament delivery device 2000 is actuated, the energy storage member 2400 is activated and releases pressurized gas into the gas chamber 2139. The released pressurized gas in the gas chamber 2139 causes the medicament container body 2210 and the delivery member 2216 to deploy such that at least a portion of the delivery member 2216 extends from the housing 2100. The released pressurized gas travels through (or continues to travel through) the flow restriction member 2450 and into a medicament container gas chamber 2218 of the medicament container assembly 2200. The medicament container gas chamber 2218 is defined between the flow restriction member 2450 and the elastomeric member 2217. As the released pressurized gas passes through the flow restriction member 2450, the pressure builds up within the medicament container gas chamber. After the pressure in the medicament container gas chamber 2218 is such that it overcomes resistance of the elastomeric member 2217 against an interior of the medicament container body 2210, the elastomeric member 2217 moves from a first elastomeric member position (FIG. 10) to a second elastomeric member (FIG. 12) position to dispense a dose of medicament from within the medicament container body 2210. As shown in FIG. 11, the elastomeric member may pass through one or more intermediate positions as it moves from the first elastomeric member position to the second elastomeric member position.

To detect a position of the elastomeric member 2217 within the medicament container body 2210, the medicament delivery device 2000 includes the sensing unit 2105 with the emitter 2108 and the receiver 2109. The emitter 2108 includes a set of emitter modules 2108a, 2108b, 2108c, 2108d which are operable to produce a light beam. The receiver 2109 includes a set of light receiving modules 2109a, 2109b, 2109c, 2109d which are operable to detect reception of the light beam. As shown in FIG. 10, the emitter 2108 and the receiver 2109 are positioned on opposite sides of the medicament container body 2210 when the medicament container body 2210 and the delivery member 2216 are in the deployed position (e.g., in a distal position relative to the housing and operable to dispense medicament to a user). In some embodiments, the medicament container assembly 2200 can include or be coupled to a carrier (not shown in FIGS. 10-12, but which can be similar to the carrier body 4360 described below) that moves the medicament container body 2210 within the housing 2100. In some embodiments, the emitter 2108 and the receiver 2109 can be coupled to (or within) the carrier. In some embodiments, the emitter 2108 and the receiver 2109 extend along either side of the medicament container body 2210 from a first end portion 2211 to a second end portion 2212 of the medicament container body 2210. In some embodiments, emitter modules 2108a, 2108b. 2108c, 2108d and the light receiving modules 2109a, 2109b, 2109c, 2109d are spaced along a length of the medicament container body 2210 between the first end portion 2211 and the second end portion 2212.

To detect a current position of the elastomeric member 2217, the plurality of emitter modules 2108a, 2108b, 2108c, 2108d are each activated to produce a light beam and the plurality of light receiving modules 2109a, 2109b, 2109c, 2109d detect whether (and/or the magnitude of) a light beam from a corresponding one of the plurality of emitter modules 2108a, 2108b, 2108c, 2108d is received. For example, as shown in FIG. 11, each of light receiving modules 2109a, 2109b, 2109c, 2109d are activated to produce a light beam and the light receiving modules receiving module 2109c produces a signal indicative that the light beam from the emitter module 2108e was not received (or that the magnitude of light received at the receiving module 2109c is below a predetermined threshold). In the alternative, it will be appreciated by one skilled in the art that the light receiving modules 2109a, 2109b, 2109d can be configured to produce a signal indicative of a light beam being received while the light receiving modules 2109c does not produce a signal. The sensing unit 2105 is configured to receive the signals from each of the light receiving modules 2109a, 2109b, 2109c, 2109d and to determine which of the light receiving modules 2109a, 2109b, 2109c, 2109d did not receive a light beam (or received an insufficient amount of light), which is indicative of the elastomeric member 2217 blocking the light transmission path. In some embodiments, instead of detecting the presence or absence of a signal representative of a light beam being received, the delivery module 2106 coupled to the sensing unit 2105 is configured to monitor a change in magnitude of the light received at the one or more light receiving modules 2109a, 2109b, 2109c, 2109d to determine a current location of the elastomeric member 2217. Because the emitters 2108 and light receiving modules 2109 are placed in pairs along the longitudinal axis of the medicament container assembly 2200, the position of the elastomeric member 2217 within the container body 2210 can be determined. In some embodiments, the emitter modules 2108a, 2108b. 2108c, 2108d are operable to transmit at least one wavelength within an ultraviolet, a visible light, or an infrared light spectrum and the light receiving modules 2109a, 2109b, 2109c, 2109d are operable to receive the at least one wavelength and to produce an electronic signal indicative of receiving the at least one wavelength or an electronic signal indicative of a magnitude of the at least one wavelength received. In some embodiments, the light receiving modules 2109a, 2109b, 2109c, 2109d are configured to transmit an infrared light beam. In some embodiments, the light receiving modules 2109a, 2109b, 2109c, 2109d are configured to transmit a light beam of a wavelength that does not adversely alter a medicament stored within the medicament container body 2210.

Specifically, the medicament delivery device 2000 further includes a delivery module 2106 coupled to the sensing unit 2105 to determine which of the light receiving modules 2109a, 2109b, 2109c, 2109d produced a signaled (e.g., received a light beam) and using that information determine a current position of the elastomeric member 2217 within the medicament container body 2210. In some embodiments, the delivery module 2106 is implemented in at least one of a memory or a processing device. Once the current position of the elastomeric member 2217 has been determined, the information can be stored in a memory module 2111 or be transmitted to an output module 2107 such as a display or a speaker. In some embodiments, the display is an LCD display configured to display text and/or graphical images. In some embodiments, the display is an array of LED lights configured to light up to indicate a current position of the elastomeric member 2217 or indicate an overall progress of the medicament delivery. For example, an array of 10 LED lights may be used and the first five LED lights may be lit up to indicate that 50% of the medicament delivery process has been completed. In some embodiments, the output module 2107 includes a speaker operable to produce one or more audible tones and/or verbal notification. For example, the output module 2107 can be configured to produce a first audible tone while medicament is being dispensed and a second audible tone when the dispensing has been completed. By way of another example, the output module 2107 can be configured to produce a verbal count down of the remaining time to completion and/or a current percentage of the medicament that has been delivered.

In some embodiments, the delivery module 2106 includes a predictive module 2110 to determine a movement profile of the elastomeric member 2217. The movement profile includes at least one of a current position of the elastomeric member, a rate of travel of the elastomeric member, a rate of delivery of the medicament from the medicament container body 2210, or a remaining amount of time to complete delivery of a dose of medicament. The predictive module 2110 is configured to calculate the rate of travel (e.g., travel velocity) of the elastomeric member 2217 based on a time difference between two light receiving modules 2109a, 2109b, 2109c, 2109d not receiving a light beam (or receiving an amount of light below a threshold) and a known distance between the two light receiving modules 2109a, 2109b, 2109c, 2109d. The predictive module 2110 is configured to calculate a rate of delivery of the medicament based on the rate of travel of the elastomeric member 2217 and a diameter of the medicament container body 2210. In some embodiments, the predictive module 2110 can determine one or more of an elapsed time of the medicament delivery process, an estimated remaining amount of time to completion of the medicament delivery process, or a remaining percentage of medicament remaining to be dispensed. In some embodiments, the predictive module 2110 is coupled to the memory module 2111 and is operable to retrieve stored values relating to a stored energy value of the energy storage member 2400, a resistance of the flow restriction member 2450, a stroke travel distance of the elastomeric member 2217 to complete delivery of a dose of medicament within the medicament container body 2210, and/or a total volume of medicament in a dose of medicament within the medicament container body 2210. In some embodiments, the delivery of the medicament may take longer than initially estimated and the predictive module 2110 is configured to update the remaining amount of time to completion or pause the remaining amount of time to completion until the elastomeric member 2217 reaches an anticipated position associated with the remaining amount of time to completion.

In some embodiments, the electronic circuit system 2104 is configured to determine a position of the elastomeric member within the medicament container body 2210 by performing a sequence of steps. The electronic circuit system 2104 is operable to control the emitter 2108 to emit a first light beam through a first emitter module of the emitter modules 2108a, 2108b, 2108c, 2108d through the medicament container body 2210 and towards a corresponding first receiver of the light receiving modules 2109a, 2109b, 2109c, 2109d. The first receiver is configured to produce a first electronic signal associated with a magnitude of the first light beam received. The electronic circuit system 2104 is operable to control the emitter 2108 to emit a second light beam through a second emitter module (different from the first emitter module) of the emitter modules 2108a, 2108b, 2108c, 2108d through the medicament container body 2210 and towards a corresponding second receiver (different from the first receiver) of the light receiving modules 2109a, 2109b, 2109c, 2109d. The second receiver is configured to produce a second electronic signal associated with a magnitude of the second light beam received. The electronic circuit system 2104 detects at least one of the first electronic signal or the second electronic signal and determines a position of the elastomeric member 2217 based on a comparison of the first electronic signal and the second electronic signal. In some embodiments, the electronic circuit system 2104 is operable to determine a rate of travel of the elastomeric member 2217, a rate of delivery of the medicament from the medicament container body 2210, and/or a remaining completion time to complete delivery of a dose of medicament from the medicament container body 2210 based on a time difference between when the first electronic signal is below a threshold and the second electronic signal is below a threshold.

Although the sensing unit 2105 is shown as including an emitter 2108 (with multiple light emitters) and a receiver 2109 (with multiple light receivers), in other embodiments, a sensing unit can include any suitable mechanism to detect the position of the elastomeric member within the medicament container body 2210 and produce an electronic signal associated with at least one of a position, a velocity, or an acceleration of the elastomeric member 2217 to detect the rate of medicament delivery. For example, in some embodiments any of the medicament delivery devices described herein can include a sensing unit that detects the position of the elastomeric member based on inductance. In such systems, the elastomeric member can include a ferromagnetic core and the sensor unit can include a coil of wire that detects movement of the elastomeric member. In other embodiments, any of the medicament delivery devices described herein can include a sensing unit that detects a change in refractivity of the contents (e.g., medicament, elastomeric member, or released pressurized gas) within the medicament container body 2210 in order to locate a current position of the elastomeric member.

As described herein, delivery of medicament that is highly viscous (i.e., having a viscosity greater than or equal to about 100 centipoise at room temperature) can be improved by regulating flow to ensure that the flow rate out of the delivery member is below a certain threshold to prevent shearing of high molecular weight compounds in the medicament and/or reduce pain sensed by a patient. In some embodiments, the flow rate of the medicament is less than about 0.2 mL/sec (or in some embodiments between 0.05 mL/sec and 0.01 mL/sec). As a result of the reduced flow rate, the medicament delivery process can take about 30 to 60 seconds, and in some instances about 60 to 120 seconds to complete. In some embodiments, a medicament delivery device can include two or more medicament containers, each having a delivery member through which the medicament therein can be delivered. Such embodiments can accommodate the delivery of viscous medicaments, delivery of large volumes of medicament (e.g., greater than 1 mL dose) by delivering portions of the overall dose in parallel, and/or delivery of two different medicaments together in parallel. Thus, the overall delivery time of a large dose of medicament and/or medicament that is highly viscous can be reduced through the use of two or more medicament containers operating to dispense in parallel.

FIGS. 13-16 are schematic illustrations of a medicament delivery device 3000 according to an embodiment in a first configuration, a second configuration, a third configuration, and a fourth configuration, respectively. The medicament delivery device 3000 includes a housing 3100, a first medicament container assembly 3200A, a first flow restriction member 3450A, a second medicament container assembly 3200B, a second flow restriction member 3450B, an energy storage member 3400, and a retraction member/retraction assembly 3351.

The housing 3100 defines a gas chamber 3139 that receives a pressurized gas from the energy storage member 3400. The gas chamber 3139 can be of any suitable size and shape, and can be, for example, a portion of the volume defined by the housing 3100 within which a portion of the medicament container is disposed. The housing 3100 can be any suitable size, shape, or configuration and can be made of any suitable material. For example, in some embodiments, the housing 3100 is an assembly of multiple parts formed from a plastic material and defines a substantially rectangular shape when assembled. In other embodiments, the housing 3100 can have a substantially cylindrical shape.

Each of the medicament container assemblies 3200A, 3200B has a respective medicament container body 3210A, 3210B. Each of the container bodies 3210A, 3210B defines a volume that contains (i.e., is filled with or partially filled with) a medicament. In some embodiments the medicament in each of the medicament container bodies 3210A, 3210B is the same medicament formulation and dosage. In some embodiments, the medicament is a different formulation in each of the medicament container body 3210A, 3210B and/or has a different dosage (e.g. different amount of medicament). Distal end portions of each of the medicament container bodies 3210A, 3210B each include a neck or opening through which the medicament can be delivered. In some embodiments, the medicament container assemblies 3200A, 3200B can each include a corresponding delivery member 3216A, 3216B coupled to the respective medicament container bodies 3210A, 3210B through which the medicament is delivered. For example, in some embodiments, delivery members 3216A, 3216B include a needle, a nozzle, a mouthpiece, or the like. In some embodiments, the medicament container assemblies 3200A, 3200B can be a prefilled syringe having a needle staked thereto, of the types shown and described herein. In some embodiments, the first medicament container body 3210A and the second medicament container body 3210B are positioned within the housing 3100 in a non-coaxial arrangement.

The first medicament container assembly 3200A includes a first elastomeric member 3217A (i.e., a plunger) that seals a first medicament within the first medicament container body 3210A. The first elastomeric member 3217A is configured to move within the first medicament container body 3210A to inject the first medicament from the first medicament container assembly 3200A. The second medicament container assembly 3200B includes a second elastomeric member 3217B (i.e., a plunger) that seals a second medicament within the second medicament container body 3210B. The second elastomeric member 3217B is configured to move within the second medicament container body 3210B to inject the second medicament from the second medicament container assembly 3200B. Each of the first elastomeric member 3217A and the second elastomeric member 3217B can be of any design or formulation as described herein.

The medicament container assemblies 3200A, 3200B each include a proximal end portion 3214A, 32214B configured to translate within the housing 3100 to move a corresponding medicament container assembly 3200A, 3200B between the first position and the second position. Although the first and second medicament container assemblies 3200A. 3200B are shown as being disposed within the housing 3100 without a carrier, in other embodiments, the medicament container assemblies 3200A, 3200B can be disposed within or coupled to a carrier to facilitate movement within the housing 3100. For example, in some embodiments, each of the container bodies 3210A, 3210B can be coupled to a separate carrier (not shown in FIGS. 13-16, but which can be similar to the carrier body 4360 described below) that moves each of the medicament container bodies 3210A, 3210B independently within the housing 3100. In other embodiments, each of the container bodies 3210A, 3210B can be coupled to a single carrier that moves both of the medicament container bodies 3210A, 3210B together within the housing 3100. The proximal portions 3214A, 3214B of the medicament container assemblies 3200A, 3200B (and the carrier if present), define a portion of a boundary of the gas chamber 3139. In this manner, when a pressurized gas is conveyed into the gas chamber 3139, the pressure therein will produce a force applied on the proximal portions 3214A, 3214B to move the medicament container bodies 3210A, 3210B simultaneously from the withdrawn position to the deployed position.

Figure 13:
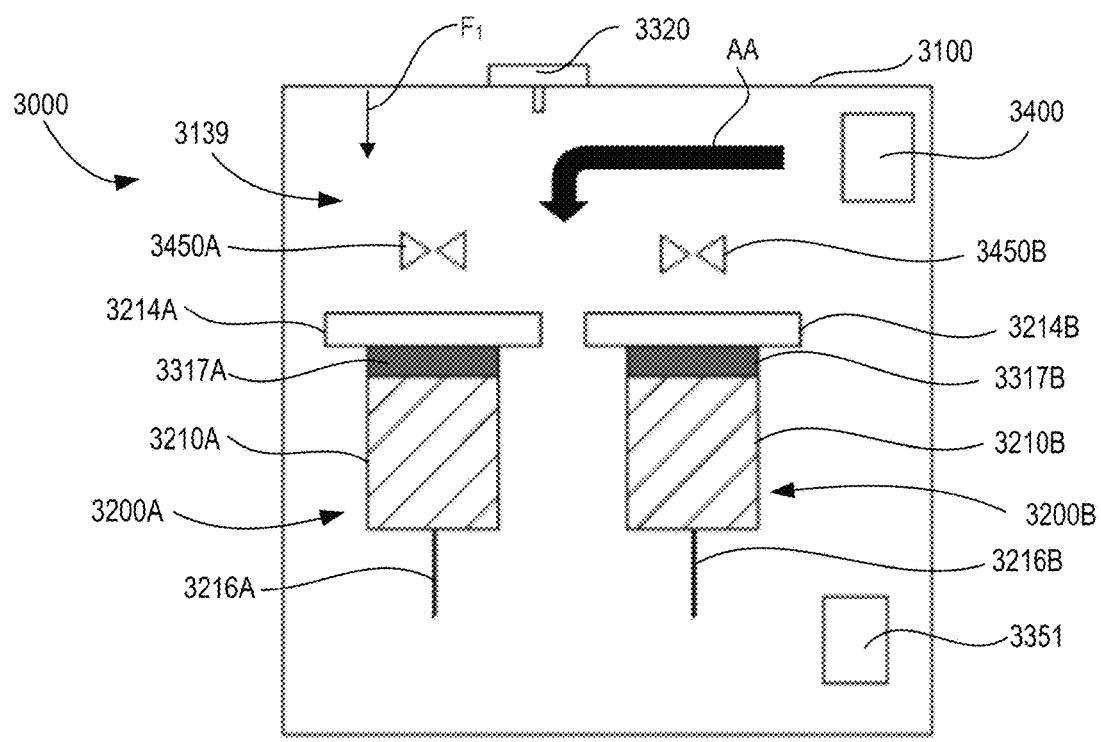
FIGS. 13-16 are schematic illustrations of a medicament delivery device according to an embodiment, in a first configuration, a second configuration, a third configuration, and a fourth configuration, respectively.

In particular, the energy storage member 3400 is disposed within the housing 3100, and is configured to convey the pressurized gas into the gas chamber 3139, as shown by the arrow AA in FIG. 13. The released pressurized gas produces a force $F_1$ to deploy the delivery members 3216A, 3216B and to convey the contents from each of the medicament container s 3210A, 3210B when the energy storage member 3400 is actuated. The energy storage member 3400 can be any suitable member or device as described herein.

The retraction assembly 3351 can be a retraction spring or any other energy accumulation member. In this manner, the retraction assembly 3351 is configured to move the first medicament container assembly 3200A and the second medicament container assembly 3200B back toward a first position (e.g., withdrawn position) after it has been deployed as described in further detail herein. In some embodiments, the retraction assembly 3351 may include a first retraction member and a second retraction member. The first retraction member can be coupled to the first medicament container assembly 3200A to maintain the first medicament container assembly 3200A in the withdrawn position prior to gas pressure being supplied to the gas chamber 3139 and to return the first medicament container assembly 3200A back to the withdrawn position after delivery of medicament as described below. The second retraction member can be coupled to the second medicament container assembly 3200B to maintain the second medicament container assembly 3200B in the withdrawn position prior to gas pressure being supplied to the gas chamber 3139 and to return the second medicament container assembly 3200B back to the withdrawn position after delivery of medicament as described below.

Once the medicament container bodies 3210A, 3210B and the delivery members 3216A, 3216B have been placed in the deployed position, the released pressurized gas then travels through (or continues to travel through) either (or both of) the first flow restriction member 3450A or the second flow restriction member 3450B. The release pressurized gas traveling through the first flow restriction member 3450A enters into a first medicament container gas chamber 3218A of the first medicament container assembly 3200A, as shown by the arrow CC1 in FIG. 15. The first medicament container gas chamber is defined between the first flow restriction member 3450A and the first elastomeric member 3217A. The release pressurized gas traveling through the second flow restriction member 3450B enters into a second medicament container gas chamber 3218B of the second medicament container assembly 3200B, as shown by the arrow CC2 in FIG. 15. The second medicament container gas chamber is defined between the second flow restriction member 3450B and the second elastomeric member 3217B.

Figure 14:
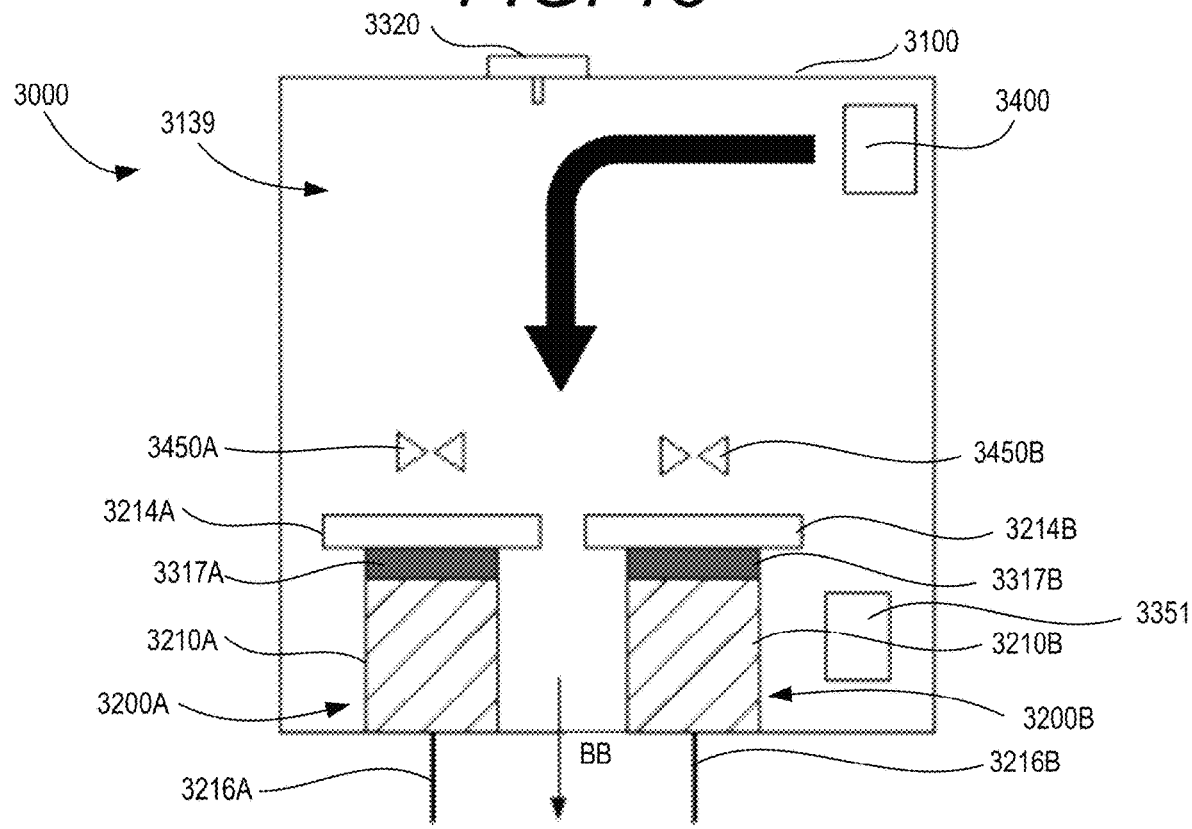
Figure 15:
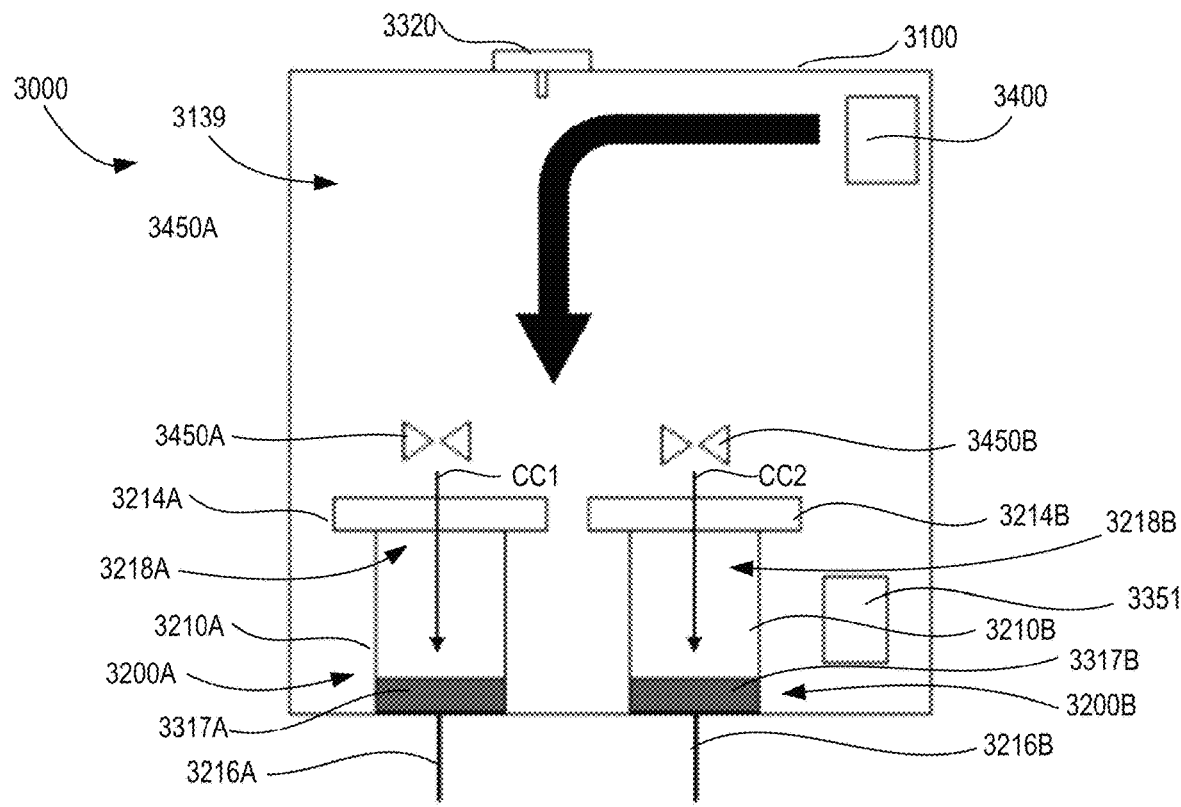

As the released pressurized gas builds up within the first medicament container gas chamber and the second medicament container gas chamber, respectively, the built up pressure overcomes resistance associated with the first elastomeric member 3217A and the second elastomeric member 3217B. As shown in FIGS. 14 and 15, the first elastomeric member 3217A moves from the first elastomeric member position to the second elastomeric member position within the first medicament container body 3210A to expel the first medicament, and the second elastomeric member 3217B moves from the first elastomeric member position to the second elastomeric member position within the second medicament container body 3210B to expel the second medicament.

By regulating the pressure build up within each of the first and second medicament container gas chambers via the flow restriction members 3450A, 3450B, full deployment of the first and second medicament container bodies 3210A, 3210B and the delivery members 3216A, 3216B can be achieved prior to delivery of substantially any medicament from either of the medicament container bodies 3210A, 3210B. Furthermore, in embodiments where the medicament is highly viscous (i.e., having a viscosity greater than or equal to about 100 centipoise at room temperature) and/or where the medicament includes high molecular weight compounds greater than about 5 kDa, the flow rate of the medicament expelled from the medicament container body 1210 can be regulated. In other words, the force applied by the released pressurized gas on the elastomeric members 3217A, 3217B can be controlled and reduced by the flow restriction members 3450A, 3450B, respectively. As a result, the regulated pressure through the flow restriction members 3450A, 3450B allow controlled movement and speed of the elastomeric members 3217A, 3217B through their respective travel strokes, thereby preventing shearing of high molecular weight compounds in the medicament and reducing pain sensed by a patient.

The flow restriction members 3450A, 3450B can be any suitable flow restriction member of the types shown and described herein. For example, in some embodiments, the flow restriction members can be included within a delivery control mechanism (not shown in FIGS. 13-16) that is coupled to each medicament container assembly 3200A, 3200B. In some embodiments, the flow restriction member can be at least partially within the container body. Moreover, the flow restriction members can include any suitable structure for regulating the flow of pressurized gas into (and/or the pressure within) the respective medicament container gas chamber. For example, the flow restriction members can include a porous material through which a portion of the pressurized gas can flow.

In some embodiments, the flow restriction members 3450A, 3450B can include a filter element, a diaphragm element, a single-port orifice, a series of single-port orifices, a multiple-port element, or an adjustable valve. In some embodiments, the flow restriction members 3450A, 3450B include a porous metal or porous ceramic material. The porous material provides multiple passageways through the flow restriction members 3450A, 3450B thereby preventing clogs if any debris is present within the housing 3100. In some embodiments, the flow restriction member 3450A, 3450B are each calibrated with nitrogen gas ($N_2$) at 30 psig (inlet side) to atmosphere (outlet side) at standard temperature and pressure to have a flow rate of between about 0.5 to 3 standard cubic centimeter per minute (sccm). In some embodiments, the flow restriction members 3450A, 3450B are each calibrated with nitrogen gas ($N_2$) at 30 psig (inlet side) to atmosphere (outlet side) at standard temperature and pressure to have a flow rate of between about 0.75 and 1.5 standard cubic centimeter per minute (sccm). In some embodiments, the flow restriction members 3450A, 3450B are each calibrated with nitrogen gas ($N_2$) at 30 psig (inlet side) to atmosphere (outlet side) at standard temperature and pressure to have a flow rate of about 1 standard cubic centimeter per minute (sccm).

Additionally, in some embodiments, the flow restrictor 3450A associated with the first medicament container assembly 3200A can be different from the flow restrictor 3450B associated with the second medicament container assembly 3200B For example, if the medicament in the first medicament container assembly 3200A is different (e.g. has a different viscosity) than the medicament in the second medicament container assembly 3200B, then the two flow restrictors may have different characteristics (e.g., nominal pore size, flow rating, etc.). In other embodiments, if the medicament in the first medicament container assembly 3200A is different (e.g., has a different viscosity) than the medicament in the second medicament container assembly 3200B, and it is desired to dispense the two medicament sequentially (e.g. dispense the second medicament after the completion of the first medicament), the second medicament container assembly 3200B can be provided with a flow restrictor 3450B while the first medicament container assembly 3200A is not provided with a Dow restrictor.

Figure 16:
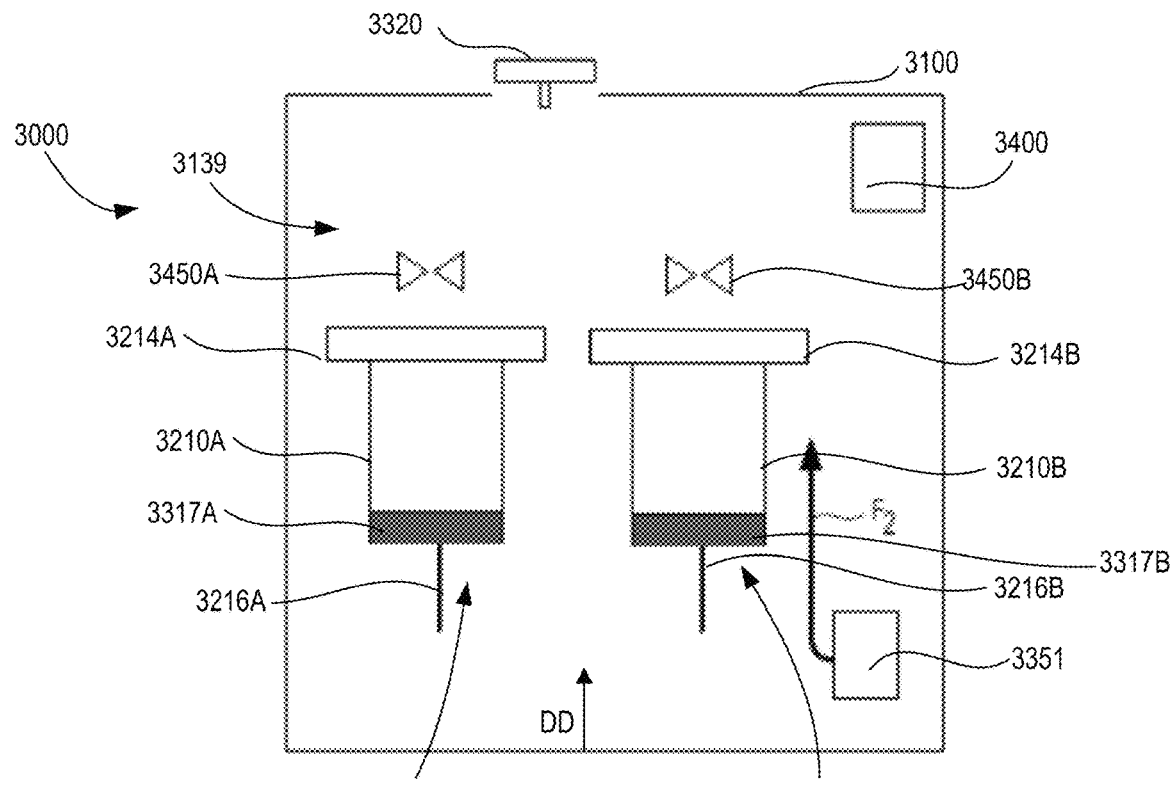

Once the elastomeric members 3217A, 3217B have traveled from their respective first elastomeric member position to the second elastomeric member position to dispense a dose of the medicament, the retraction member 3351 can be activated to apply a force $F_2$ in a second direction indicated by the arrow DD in FIG. 16, opposite the first direction, to return the medicament container bodies 3210A, 3210B and the delivery members 3216A, 3216B back towards the withdrawn position. In some embodiments, the retraction member 3351 produces a force $F_2$ greater than the force $F_1$ produced by the released pressurized gas in the gas chamber 3139. In some embodiments, the retraction member 3351 produces a force sufficient to move the medicament container bodies 3210A, 3210B and the delivery member 3216A, 3216B once the released pressurized gas has been moved out of the gas chamber 3139 via a valve portion 3320 coupled to the housing 3100.

In some embodiments, one or both of the elastomeric members 3217A, 3217B can be operatively coupled to a gas release mechanism (not shown in FIGS. 10-12, but which can be similar to the valve portion coupled to the rocker mechanism 6350, which may also be referenced as a rocker mechanism, described below with reference to FIGS. 58 and 59), and the gas release mechanism is configured to release pressurized gas from the gas chamber 3139 to a secondary chamber of the housing 3100 and/or to an external environment. In this manner, the force $F_1$ can be reduced to a point at which the force $F_2$ produced by the retraction member 3351 is greater than the force $F_1$, thereby allowing the medicament container bodies 3210A. 3210B and the delivery members 3216A, 3216B to be retracted.

In some embodiments, a medicament delivery can be an auto-injector having a pistonless delivery system in which the force exerted by the gas can move the medicament container relative to the housing and the elastomeric member relative to (e.g., within) the medicament container. For example, FIGS. 17-54 show a medical injector 4000 (also referred to as "auto-injector," "injector," or "device"), according to an embodiment. The medical injector 4000 is a gas-powered auto-injector configured to deliver a medicament contained within a prefilled syringe, as described herein. A discussion of the components of the medical injector 4000 will be followed by a discussion of the operation of the medical injector 4000. Certain aspects of the medical injector 4000 can be similar to or substantially the same to the medical injectors described in the '4345 PCT, the '0040 PCT, the '6413 PCT, U.S. patent application Ser. No. 13/357,935 (now U.S. Pat. No. 9,084,849) entitled, "MEDICAMENT DELIVERY DEVICES FOR ADMINISTRATION OF A MEDICAMENT WITHIN A PREFILLED SYRINGE," filed on Jan. 25, 2012 (referred to henceforth as the "'849 patent"), the disclosures of each of which are incorporated herein by reference in its entirety.

Figure 37:
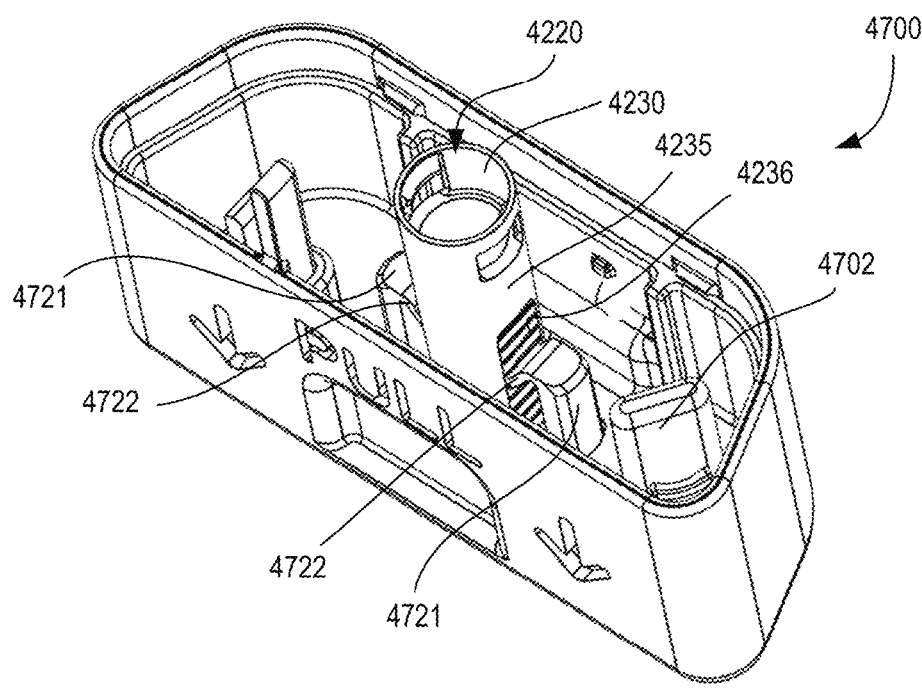
FIGS. 37 and 38 are perspective views of a safety lock of the medical injector shown in FIG. 17, with FIG. 37 showing the needle sheath assembly coupled to the safety lock.
Figure 38:
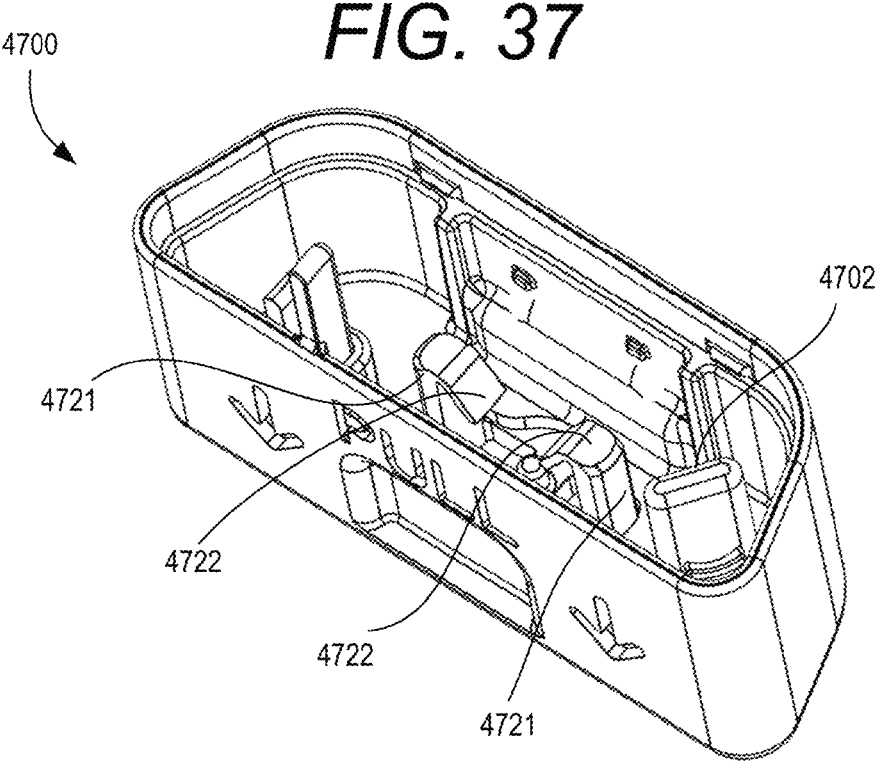

The medical injector 4000 includes a housing 4100 (see e.g., FIGS. 20 and 21), a system actuation assembly 4500 (see e.g., FIGS. 24 and 25), a medicament container assembly 4200 (see FIG. 34), a medicament delivery mechanism 4300 (see e.g., FIGS. 30-34), a base 4510 (or actuator, see FIGS. 39 and 40); and a safety lock 4700 (see FIGS. 37 and 38). As shown in FIGS. 18-21, the housing 4100 has a proximal end portion 4101 and a distal end portion 4102. The housing 4100 defines a first status indicator aperture 4130 and a second status indicator aperture 4160. The first status indicator aperture 4130 defined by the housing 4100 is located on a first side of the housing 4100, and the second status indicator aperture 4160 of the housing 4100 is located on a second side of the housing 4100. The status indicator apertures 4130, 4160 can allow a patient to monitor the status and/or contents of the medicament container assembly 4200, the carrier body 4360, and the medicament contained within the housing 4100. For example, by visually inspecting the status indicator apertures 4130, 4160, a patient can determine whether the medicament container assembly 4200 contains a medicament and/or whether the medicament has been dispensed.

Figure 17:
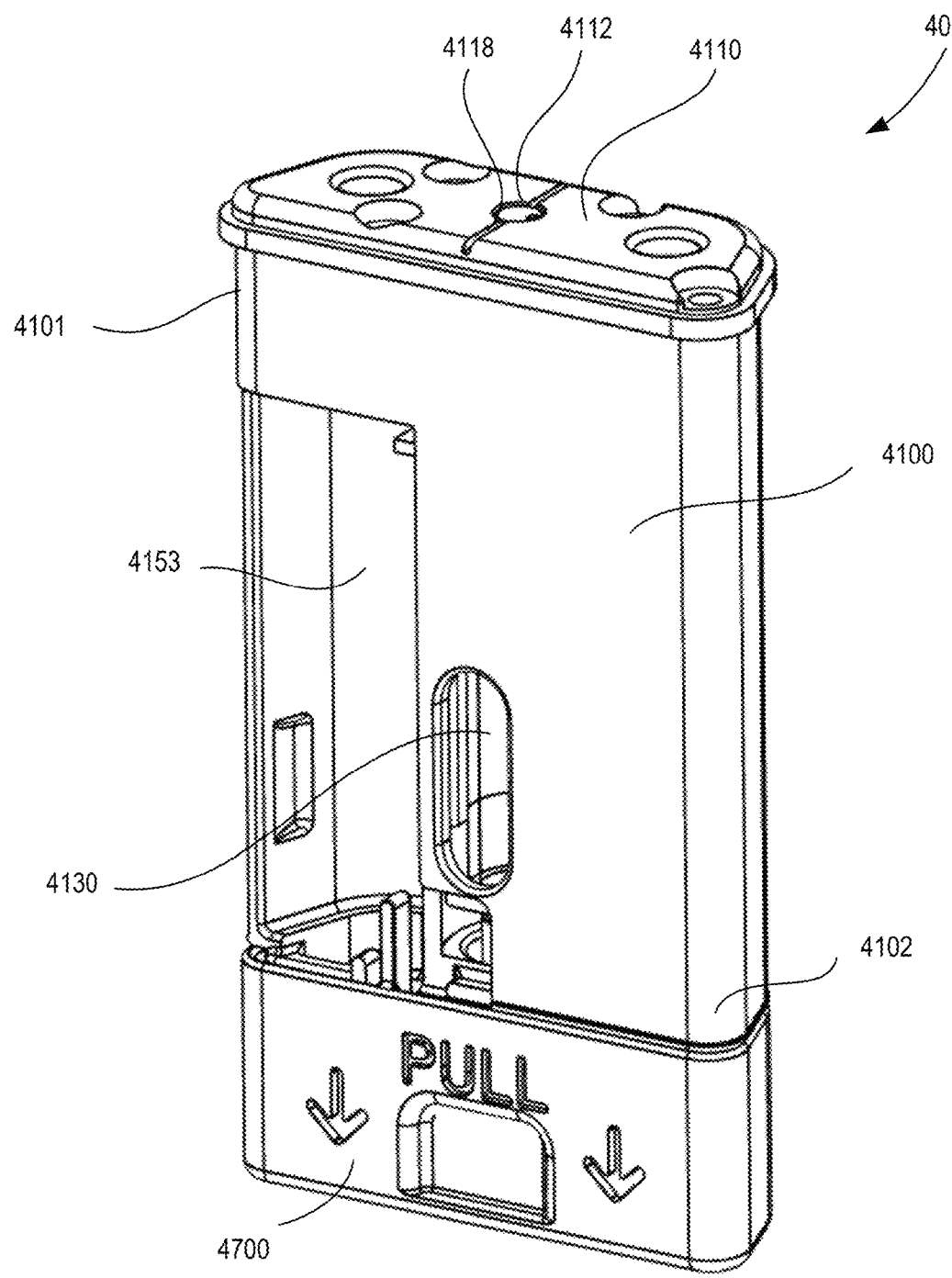
FIG. 17 is a front perspective view of a medical injector according to an embodiment, in a first configuration.
Figure 18:
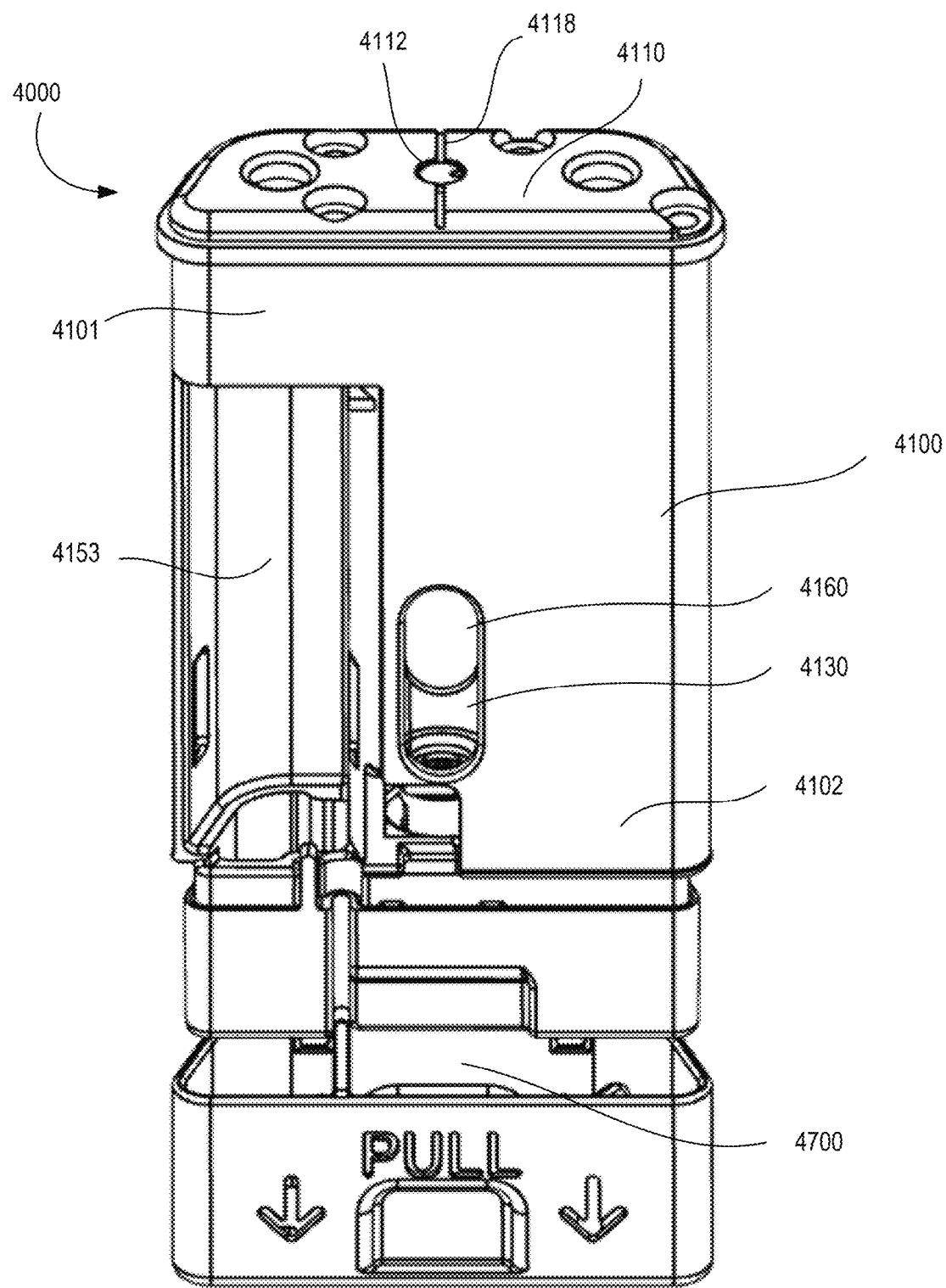
FIGS. 18 and 19 are front and rear perspective views, respectively, of the medical injector illustrated in FIG. 17, with the electronic circuit system hidden and the safety lock removed.
Figure 20:
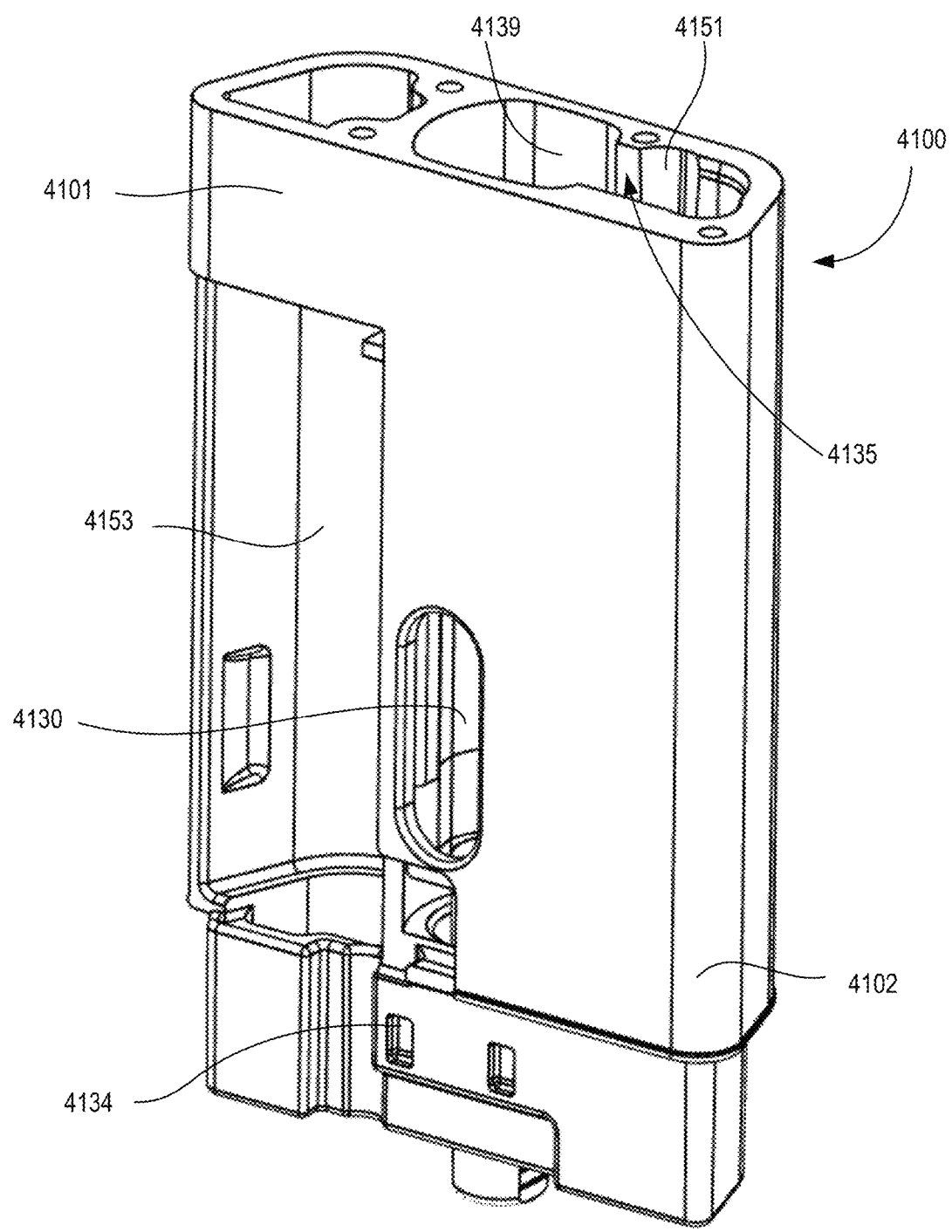
FIG. 20 is a perspective view of a housing of the medical injector illustrated in FIG. 17.

As shown in FIGS. 17, 18, and 20, the housing 4100 includes an electronic circuit system cavity 4153 that can house any of the electronics described herein, and/or any of the electronic circuit systems described in the '8433 PCT. Although the housing 4100 is shown with an electronic circuit system cavity 4153, in some embodiments, the medical injector 4000 need not include any electronics or the electronic circuit system cavity 4153. In some embodiments, the housing 4100 can include a label or indicia that mask or otherwise accentuates the status indicator apertures 4130, 4160 and/or the contents viewed therethrough. For example, in some embodiments, the housing 4100 can include a label (not shown) having border that surrounds at least a portion of the status indicator aperture 4130, the status indicator apertures 4160 (or both). In some embodiments, a label can include indicator colors that alert user (or assist a user in determining) whether the medicament is properly colored, whether a portion of the carrier body 4360 is visible through the window or the like.

Figure 21:
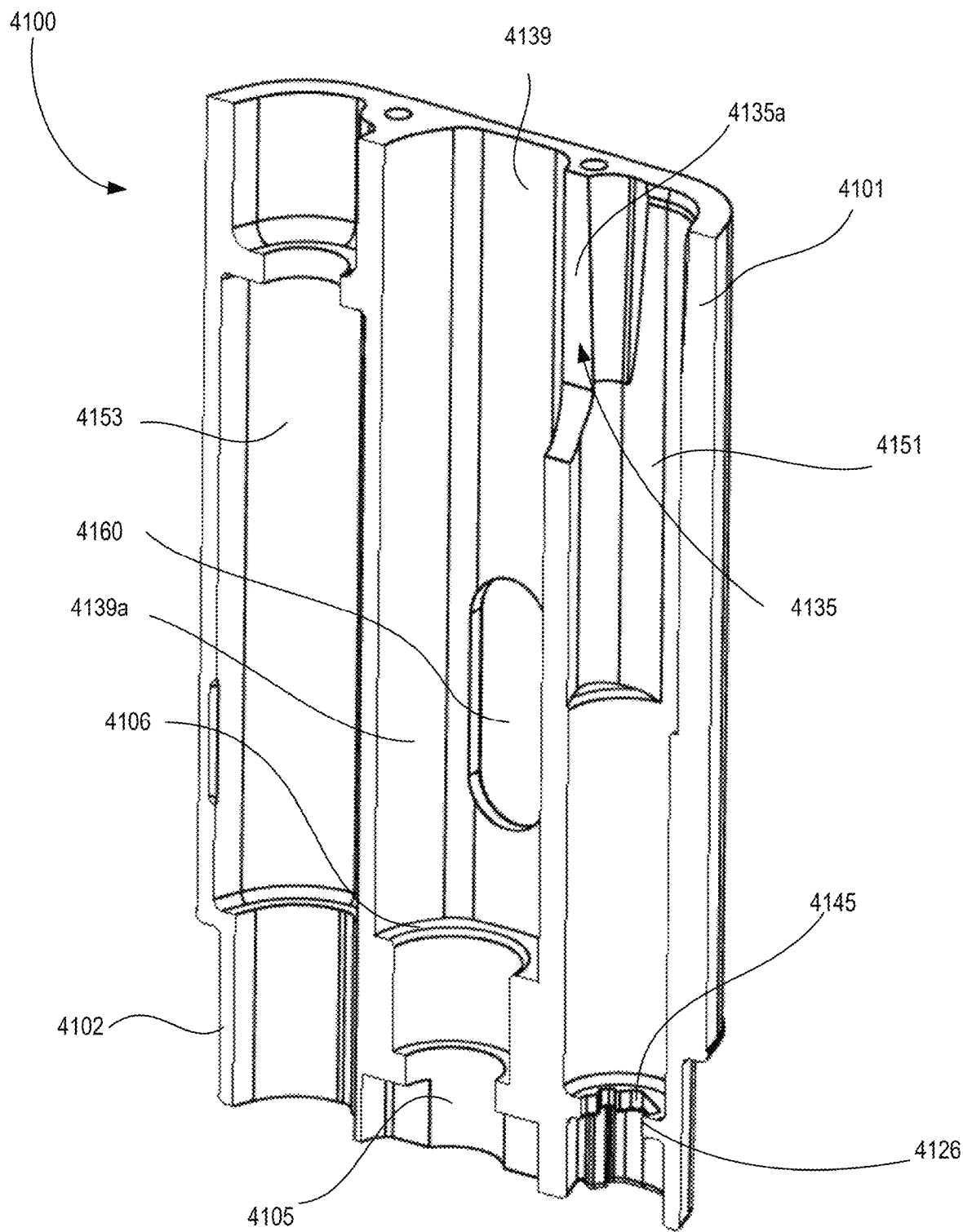
FIG. 21 is a cross-sectional view of the housing illustrated in FIG. 20.
Figure 24:
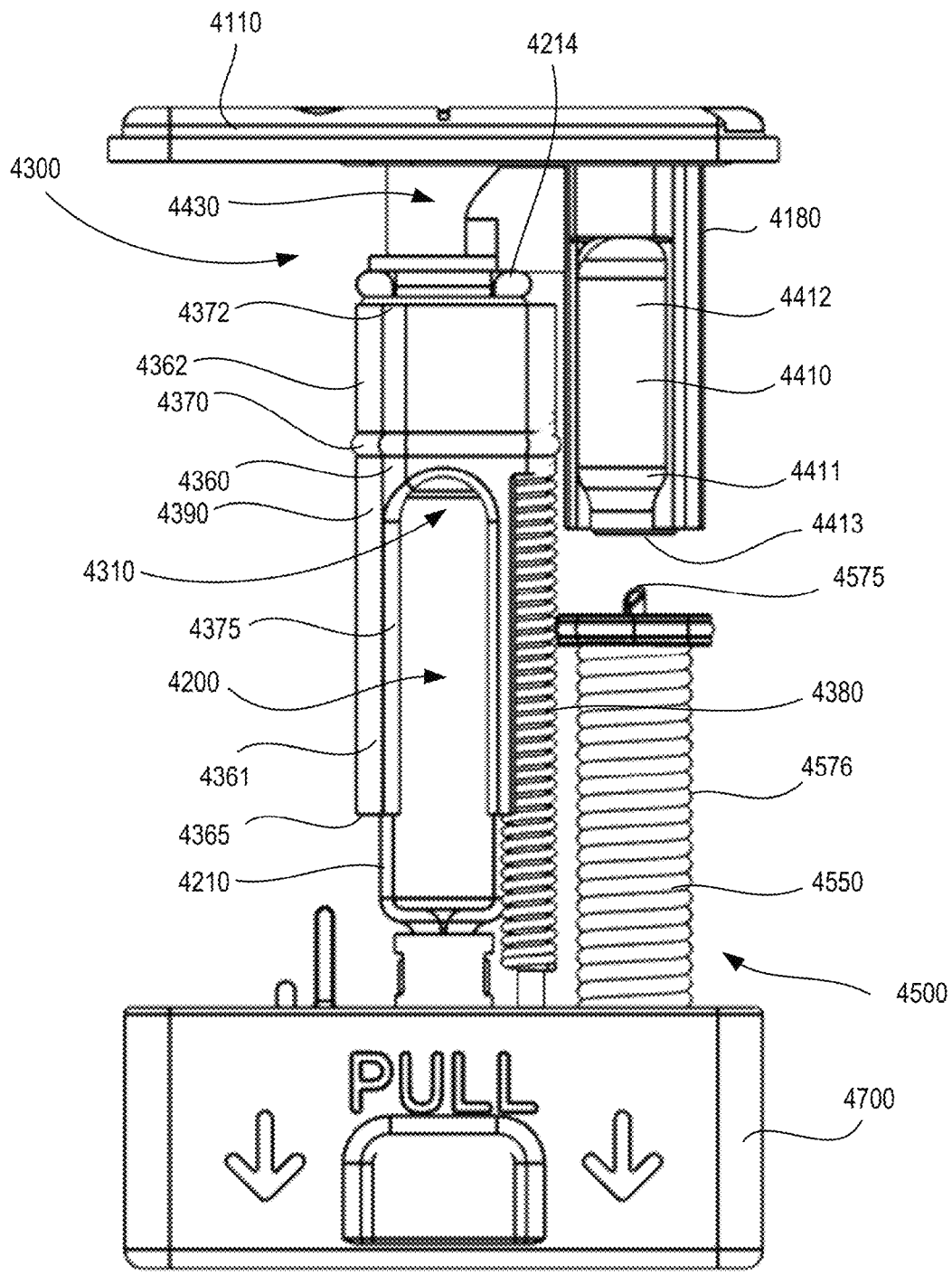
FIGS. 24 and 25 are front views of a medicament delivery mechanism of the medical injector shown in FIG. 17.
Figure 25:
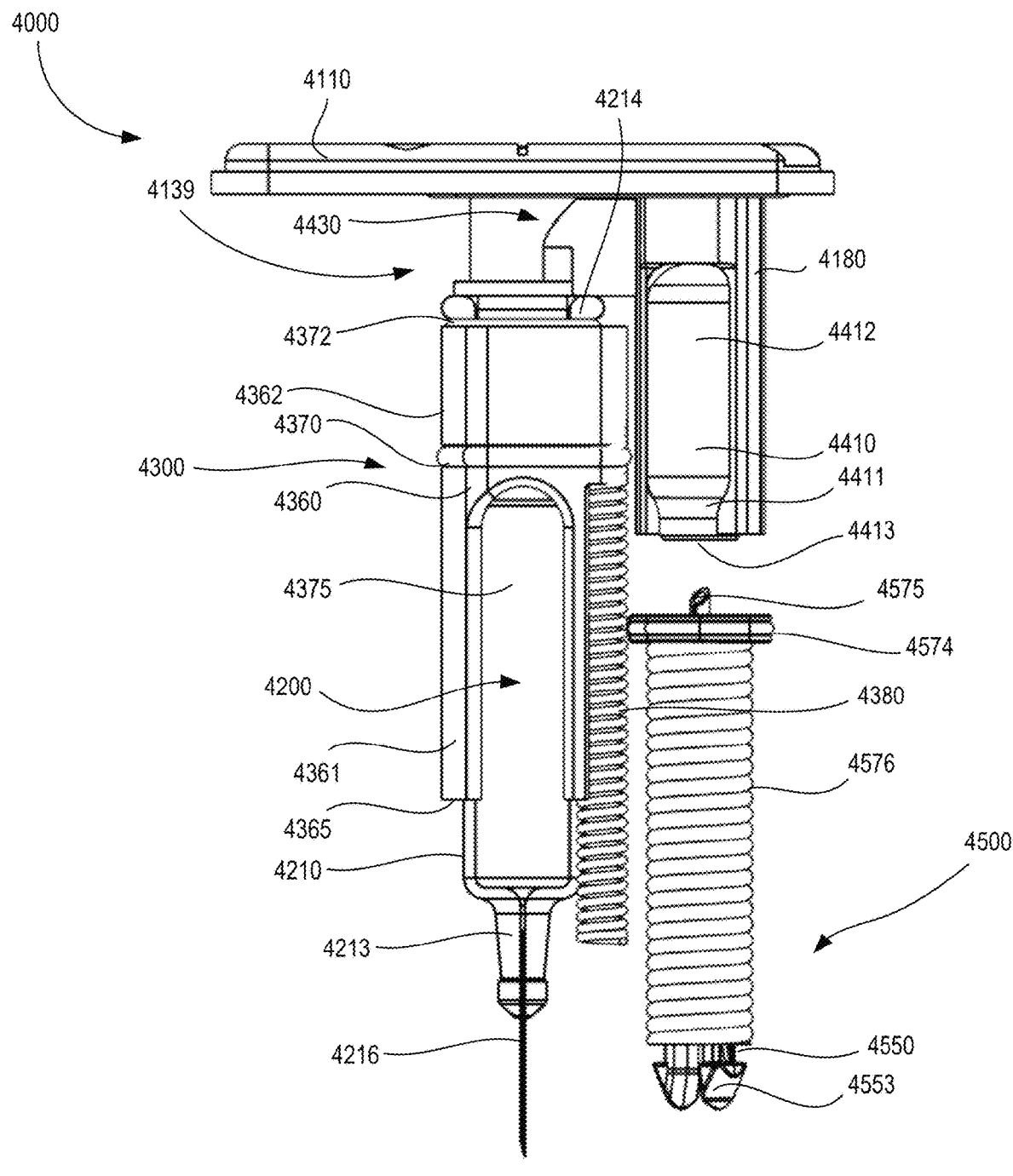
Figure 27:
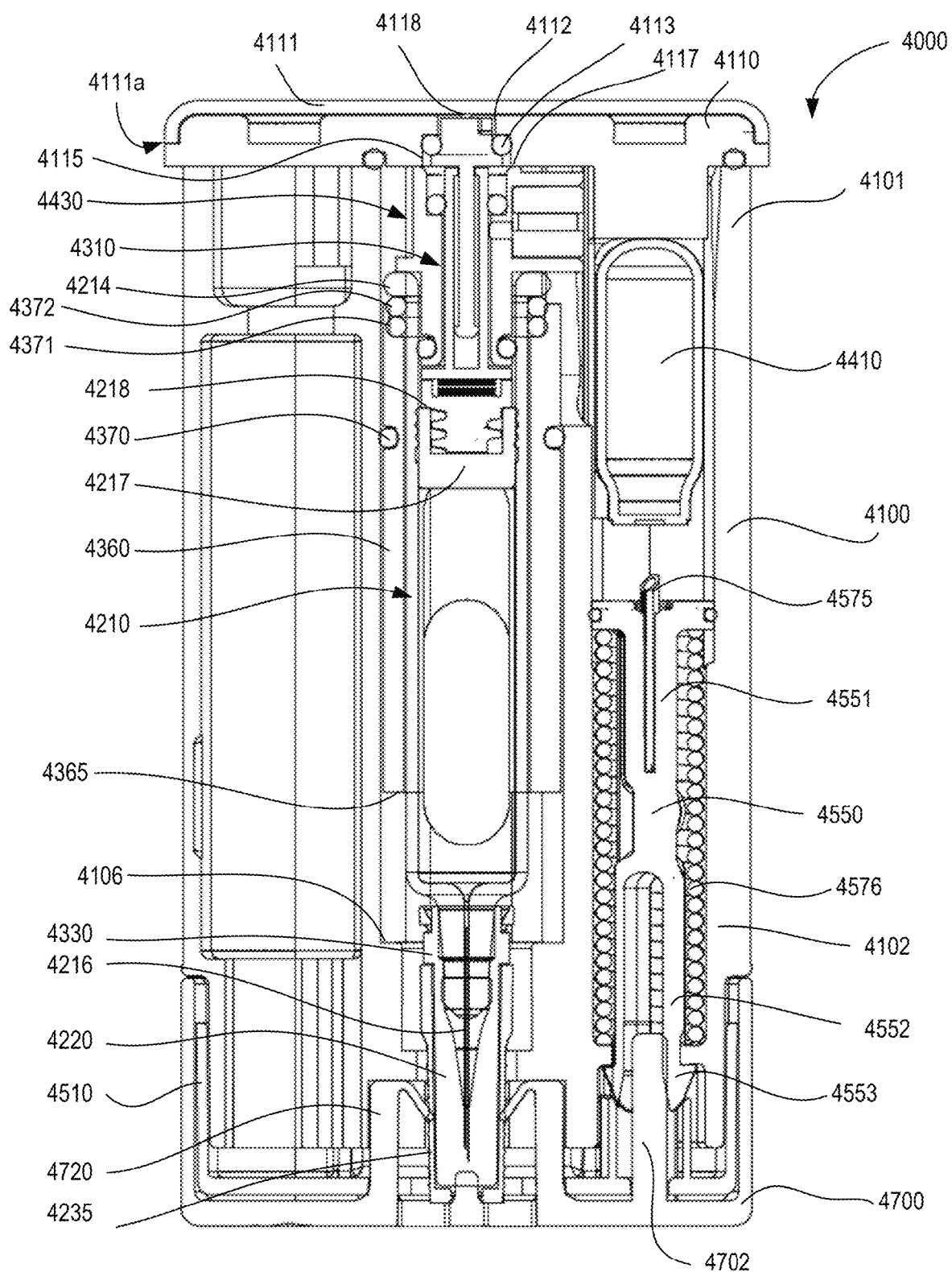
FIG. 27 is a front cross-sectional view of the medical injector shown in FIG. 17, in the first configuration.

As shown in FIGS. 20, 21 and 27, the housing 4100 defines a gas container cavity 4151 and a medicament cavity 4139. The gas container cavity 4151 is configured to receive the gas container 4410 and a portion of the system actuator assembly 4500 (e.g., a release member 4550 and the spring 4576, as shown in FIGS. 24 and 25). The proximal end portion of the gas container cavity 4151 is configured to receive the gas container retention member 4180 of a proximal cap 4110 of the housing 4100, as described in further detail herein. The gas container cavity 4151 is in fluid communication with the medicament cavity 4139 via a gas passageway 4135 defined in the housing 4100, as described in further detail herein.

The medicament cavity 4139 is configured to receive the medicament container assembly 4200 and at least a portion of the medicament delivery mechanism 4300. In particular, as described below; the medicament delivery mechanism 4300 includes a carrier assembly 4390 (see e.g., FIGS. 24, 25 and 30-33) and a gas vent assembly 4310 see e.g., FIGS. 22, 23, and 27A, 35 and 36A-36C) movably disposed in the medicament cavity 4139. The medicament cavity 4139 is in fluid communication with a region outside the housing 4100 via a needle aperture 4105 and also a vent opening 4112.

Figure 22:
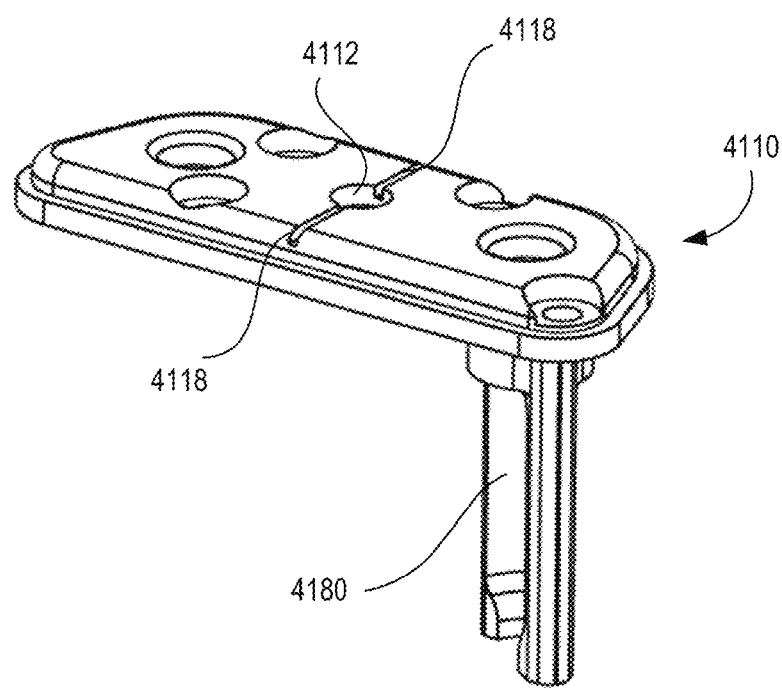
FIGS. 22 and 23 are a perspective view and a cross-sectional view, respectively, of a proximal cap of the medical injector illustrated in FIG. 17.
Figure 23:
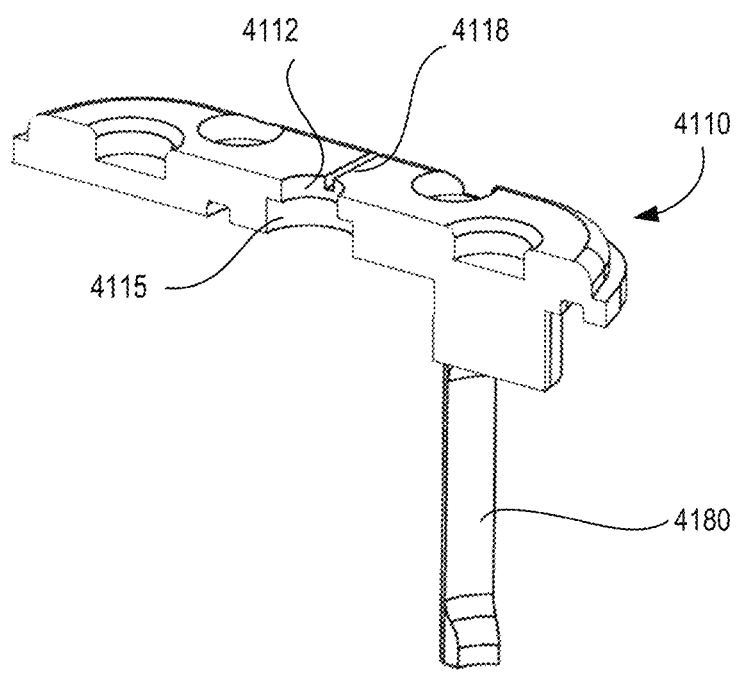
Figure 27A:
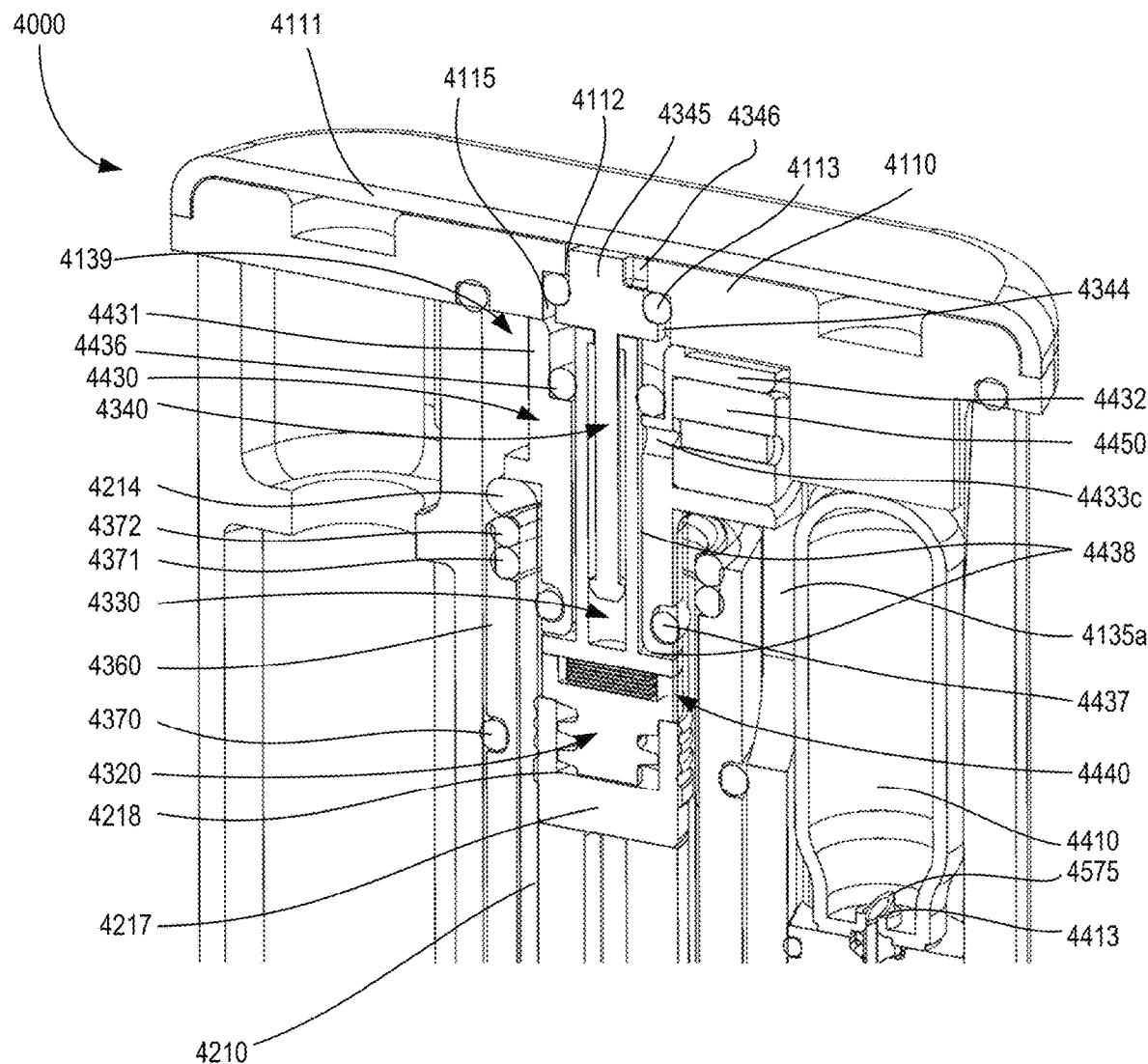
FIG. 27A is an enlarged cross-sectional view of a portion of the medical injector shown in FIG. 27, in the first configuration.

The proximal end portion 4101 of the housing 4100 includes a proximal cap 4110 (see e.g., FIGS. 22, 23, and 27A). The proximal cap 4110 includes a gas container retention member 4180 configured to receive and/or retain a gas container 4410 that contains a pressurized gas, as shown in FIGS. 22-25. When the medical injector 4000 is actuated, pressurized gas from the gas container 4410 is conveyed from the gas container cavity 4151 to the medicament cavity 4139 via the gas passageway 4135 of the housing 4100. Said another way, the gas passageway 4135 places the gas container cavity 4151 in fluid communication with the medicament cavity 4139. Thus, the proximal portion of the medicament cavity 4139 can be referred to as a housing gas chamber. Similarly stated, the proximal portion of the medicament cavity 4139 is a volume within which a pressurized gas is conveyed to move the carrier body 4360 and to serve as a pressurized gas reservoir used to inject the medicament, as described herein.

The proximal cap 4110 also includes a cap cover 4111 coupled to a proximal end portion of the proximal cap 4110 while retaining a gap 4111*a* between the proximal end portion of the proximal cap 4110 and the cap cover 4111. The cap cover 4111 prevents the vent opening 4112 from direct external contact and prevents clogging from external debris. The proximal cap 4110 also includes an O-ring 4113 and defines the vent opening 4112. The vent opening 4112 provides the passageway through which pressurized gas is conveyed from the medicament cavity 4139 (or housing gas chamber portion of the medicament cavity 4139) to a volume outside of the medical injector 4000. As shown in FIGS. 22 and 23, the proximal end portion of the proximal cap 4110 defines vent channels 4118 extending laterally away from the vent opening 4112. Together with the gap 4111*a*, the vent channels 4118 form multiple vent passageways that allow pressurized gas from within the medicament cavity 4139 to escape out to the volume outside the medical injector 4000. In this manner, the force produced by the pressurized gas on the medicament delivery mechanism 4300 and/or the medicament container assembly 4200 can be reduced to allow needle retraction after the injection is completed. As shown in FIG. 27A, the O-ring 4113, in conjunction with the valve portion 4345 of the gas vent assembly 4310, selectively seals the vent opening 4112 during needle insertion and delivery of the medicament.

Although the vent opening 4112 is shown as being defined by the proximal cap 4110, and being in a proximal surface thereof, in other embodiments, the vent opening 4112 (and any of the vent openings described herein) can be defined within any suitable portion of the proximal cap or side wall. For example, in some embodiments, the vent opening 4112 (and any of the vent openings described herein) can be defined by the proximal cap 4110, but can have a centerline that is nonparallel to a longitudinal axis of the medical injector 4000. Said another way, in some embodiments, the vent opening 4112 (and any of the vent openings described herein) can open towards a side of the medical injector, rather than opening towards the proximal end, as shown. In other embodiments, the vent opening 4112 (and any of the vent openings described herein) can be defined by any wall and/or surface of the housing 4100.

The proximal cap 4110 includes a guide wall 4115 within which the third (or proximal) member 4340) of the gas vent assembly 4310 moves. Specifically, the guide wall 4115 defines an inner cylindrical wall surface within which a guide surface 4344 of the first member 4340) (see e.g., FIGS. 27A and 35) slide during operation. The proximal cap 4110 also includes an end surface 4117 against which a portion of a delivery control mechanism (also referred to as a flow restriction assembly) rests when the medical injector 4000 is in its first configuration (i.e., the "storage" state).

As shown in FIG. 21, the distal end portion 4102 of the housing 4100 includes a shoulder portion 4106 with a contact surface and defines a needle aperture 4105. The distal end portion 4102 also includes base rail grooves 4114 and base retention recesses 4134 (see FIGS. 19 and 20). The shoulder portion 4106 is configured to contact a corresponding surface 4365 of the carrier body 4360 (see e.g., FIGS. 21, 32, 41 and 44) when the needle 4216 has been inserted a desired distance. In this manner the shoulder 4106 can act as an "end stop" or insertion limiting mechanism. The needle aperture 4105 is the opening through which the needle 4216 is disposed when the medical injector 4000 is actuated, as described in further detail herein.

Figure 27B:
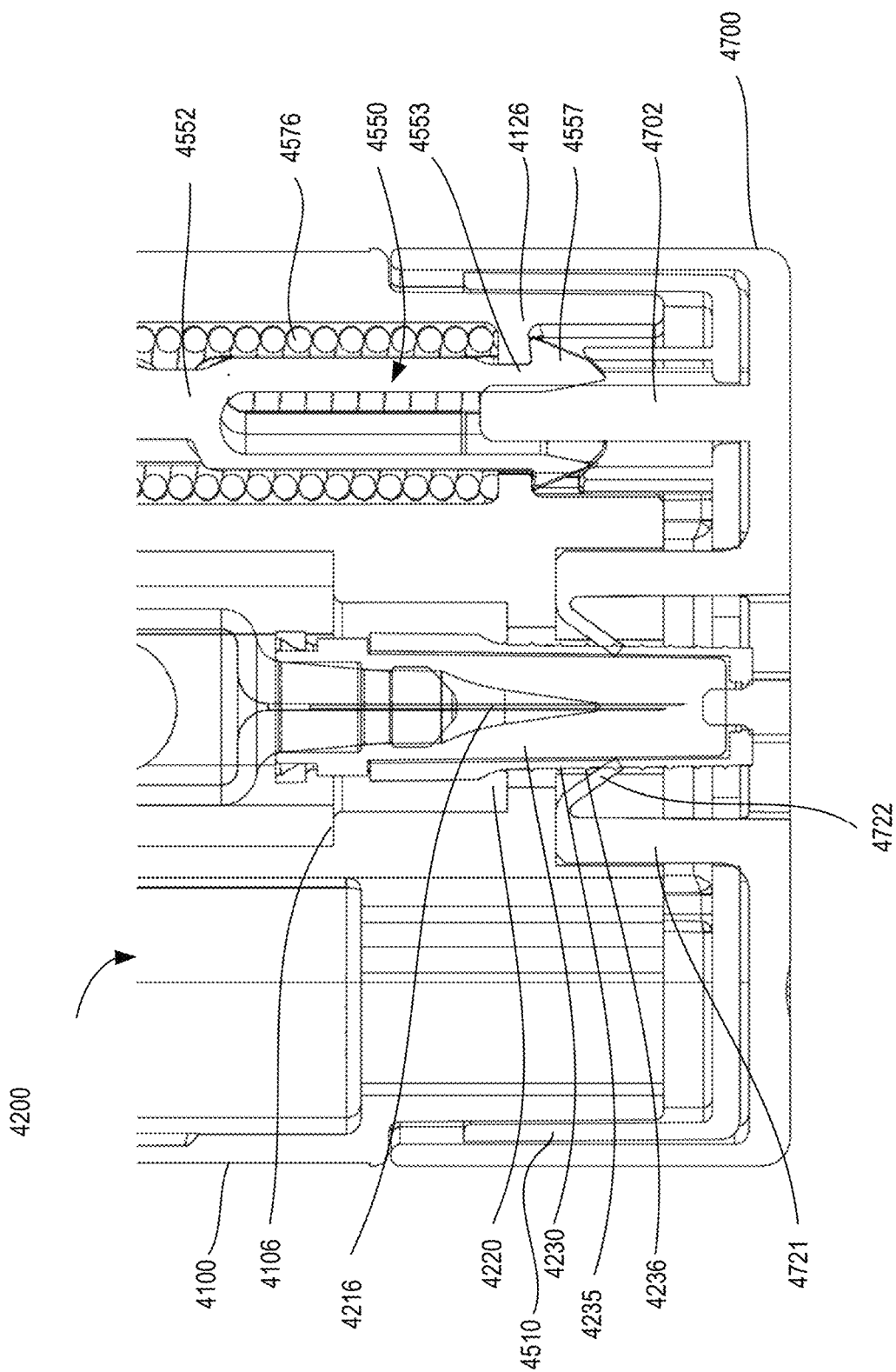
FIG. 27B is an enlarged cross-sectional view of a portion of the medical injector shown in FIG. 27, in the first configuration.

The distal end portion 4102 of the housing also includes a release member contact surface 4126 and defines the release member aperture. As shown in FIG. 27B, the release member aperture 4145 receives a distal end portion 4552 of a release member 4550, such that the extensions 4553 of the release member 4550 engage with the release member contact surface 4126 to prevent activation of the medical injector 4000. The safety lock 4700, its components and functions are described in more detail below.

The distal base retention recesses 4134 (see FIG. 20) are configured to receive the base connection knobs 4518 of the actuator 4510 (also referred to herein as "base 4510," see e.g., FIGS. 39 and 40) when the base 4510 is in a first position relative to the housing 4100 . . . . The distal base retention recesses 4134 include an elongated groove extending from a proximal to distal direction to allow the base connection knobs 4518 to move and translate within the elongated groove. This allows the base retention recesses 4134 to receive the base connection knobs 4518 such that the base 4510 can move proximally relative to the housing 4100 in a first position and can move distally relative to the housing 4100 in a second position. In some embodiments, the base retention recesses 4134 can include ratcheting teeth members that engage the base connection knobs 4518 to prevent the base 4510 from moving back in the distal direction.

Figure 19:
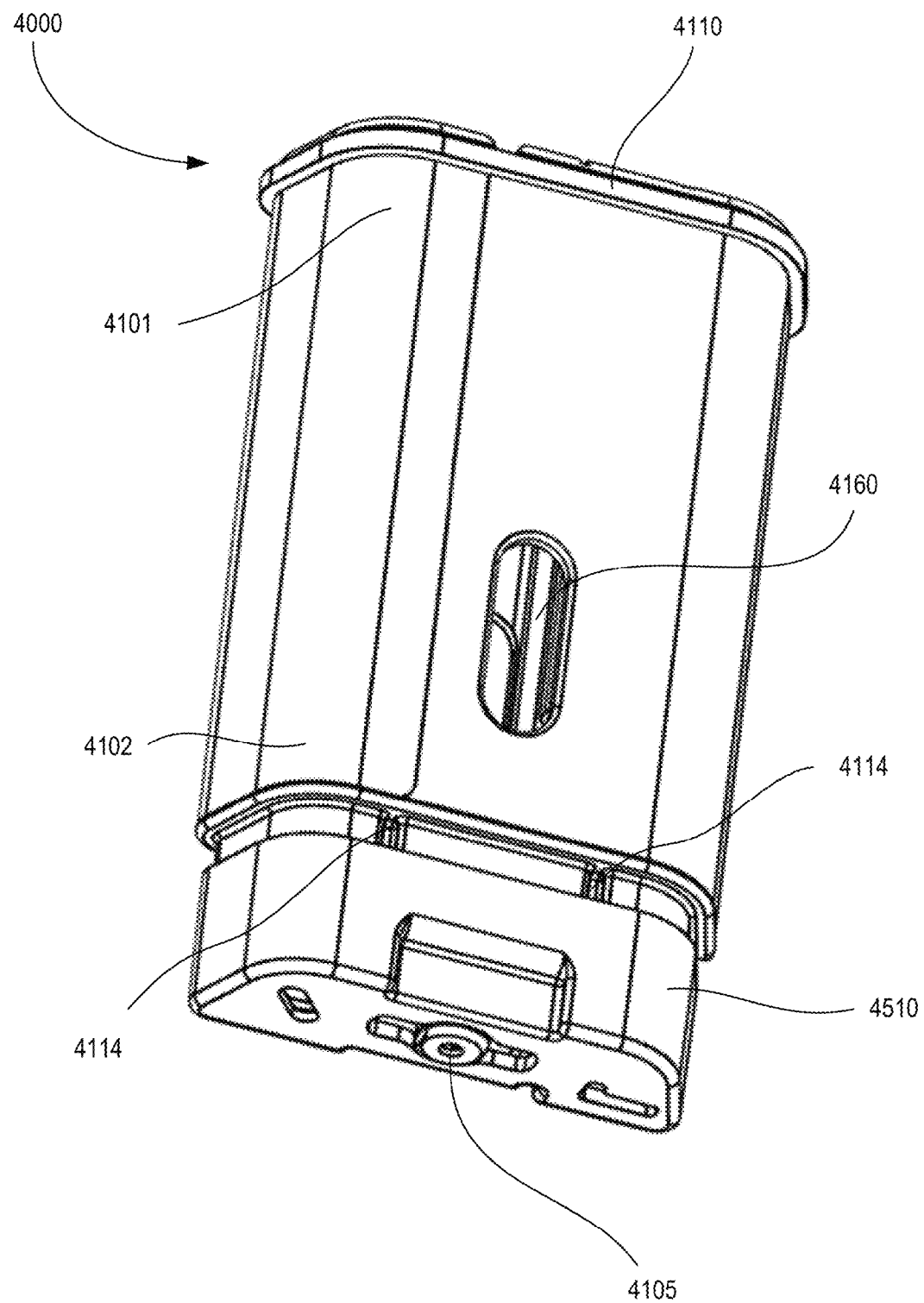
Figure 39:
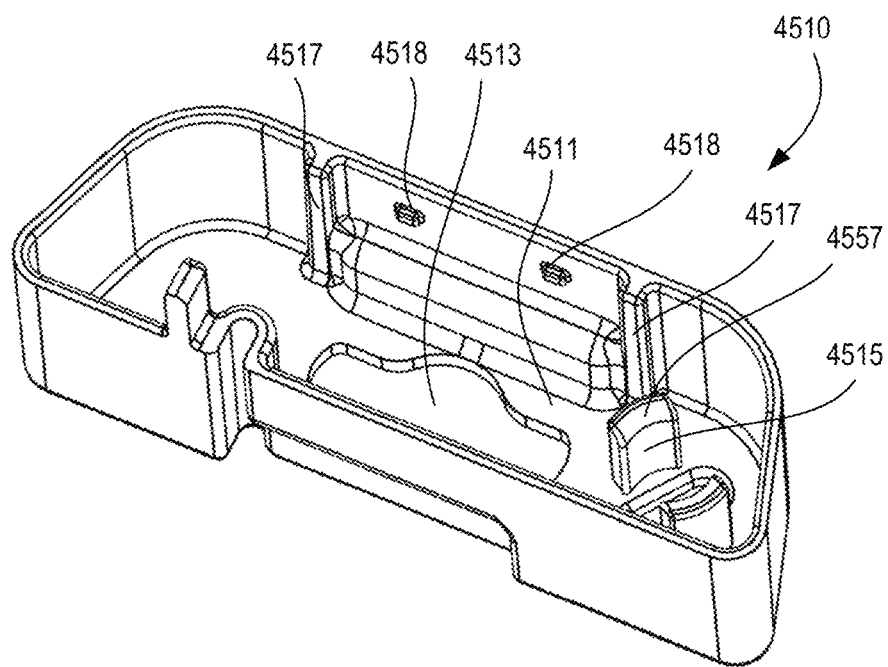
FIGS. 39 and 40 are perspective views of a system actuator of the medical injector shown in FIG. 17.
Figure 40:
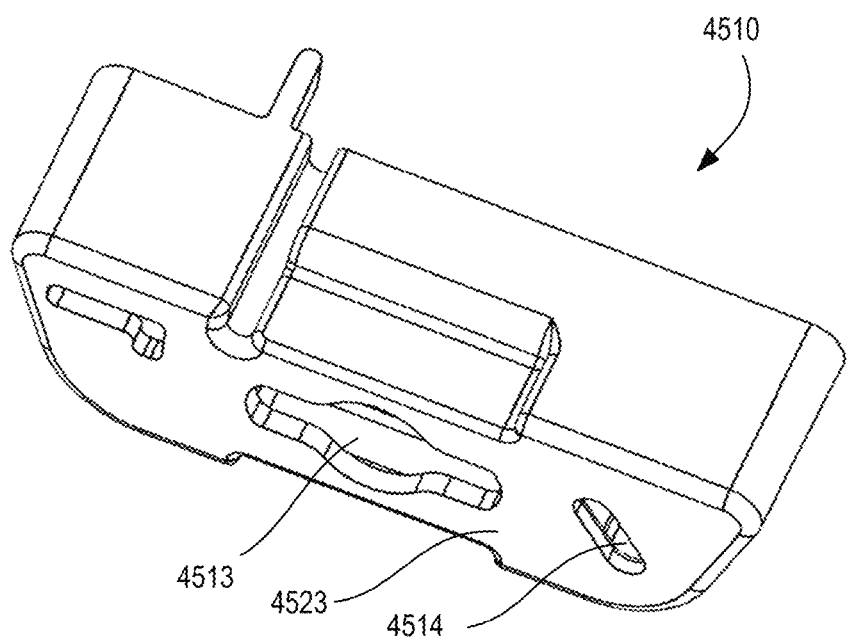

The base rail grooves 4114 receive the guide members 4517 of the base 4510 (see FIGS. 19, 39 and 40). The guide members 4517 of the base 4510 and the base rail grooves 4114 of the housing 4100 engage each other in a way that allows the guide members 4517 of the base 4510 to slide in a proximal and/or distal direction within the base rail grooves 4114 while limiting lateral movement of the guide members 4517. This arrangement allows the base 4510 to move in a proximal and/or distal direction with respect to the housing 4100 but prevents the base 4510 from moving in a lateral direction with respect to the housing 4100.

Figure 34:
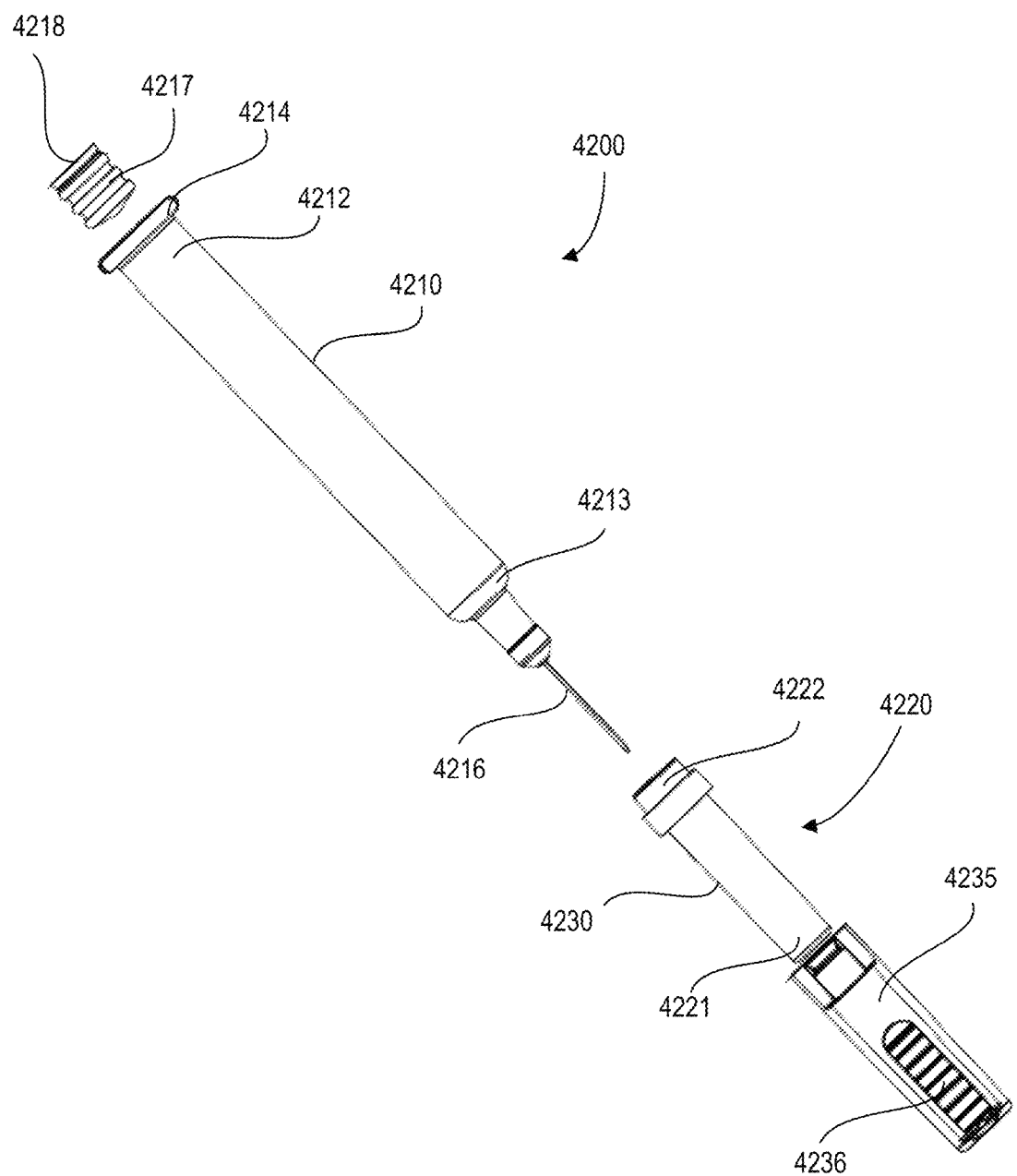
FIG. 34 is an exploded view of a medicament container assembly of the medical injector shown in FIG. 27.

FIGS. 24 and 25 provide an overview of the medicament container assembly 4200, the system actuator assembly 4500, the medicament delivery mechanism 4300, and the flow restriction assembly 4430 (which functions as a delivery control mechanism) of the medical injector 4000. Referring to FIG. 34, the medicament container assembly 4200 has a container body 4210 with a distal end portion 4213 and a proximal end portion 4212. The container body 4210 defines a volume that contains (i.e., is filled with or partially filled with) a medicament. The distal end portion 4213 of the medicament container assembly 4200 includes a neck that is coupled to the needle 4216, as described below. The proximal end portion 4212 of the medicament container assembly 4200 includes an elastomeric member 4217 (i.e., a plunger) that seals the medicament within the container body 4210. The elastomeric member 4217 is configured to move within the container body to inject the medicament from the medicament container assembly 4200.

More particularly, as shown in FIG. 27A, the elastomeric member 4217 includes a proximal end portion 4212 and is coupled to the distal member 4320 of the gas venting assembly 4310. In this manner, as described below, when the pressurized gas is conveyed into the medicament cavity 4139 (or "housing gas chamber"), the pressurized gas flows through the flow restriction assembly 4430 and the gas venting assembly and into a medicament container gas chamber located above the elastomeric member 4217 (i.e., bounded between the flow restriction assembly 4430, elastomeric member 4217 and an interior of the medicament container body 4210). The pressure in the medicament container gas chamber exerts a force on the proximal surface 4218 to move the elastomeric member 4217 within the container body 4210 (i.e., to expel the medicament therefrom). Further, because the elastomeric member 4217 is coupled to the gas venting assembly 4310, movement of the elastomeric member 4217 within the container body 4210 produces movement of at least a portion of the distal member 4320. Similarly stated, when the elastomeric member 4217 is exposed to a force (e.g., produced by the pressurized gas within the medicament container gas chamber 4440 acting directly on the proximal surface 4218), movement of the elastomeric member 4217 exerts a force on the distal member 4320. Specifically, distal movement of the elastomeric member 4217 can produce a tensile force on the distal member 4320.

The distal member 4320 can be coupled to the elastomeric member 4217 in any suitable manner. For example, as shown, the proximal surface 4218 receives and/or couples to a protrusion 4323 of the distal member 4320 of the gas venting assembly 4310. In some embodiments, the distal member 4320 includes a threaded portion and proximal end portion 4212 includes a corresponding threaded portion to receive the distal member 4320. In some embodiments, the threaded portion of the distal member 4320 is a self-tapping threaded portion. In other embodiments, the distal member 4320 can be threadedly coupled to the elastomeric member 4217. In yet other embodiments, the distal member 4320 can be bonded to the elastomeric member 4217 via an adhesive, a weld process, or the like.

The elastomeric member 4217 can be of any design or formulation suitable for contact with the medicament. For example, the elastomeric member 4217 can be formulated to minimize any reduction in the efficacy of the medicament that may result from contact (either direct or indirect) between the elastomeric member 4217 and the medicament. For example, in some embodiments, the elastomeric member 4217 can be formulated to minimize any leaching or out-gassing of compositions that may have an undesired effect on the medicament. In other embodiments, the elastomeric member 4217 can be formulated to maintain its chemical stability, flexibility and/or sealing properties when in contact (either direct or indirect) with the medicament over a long period of time (e.g., for up to six months, one year, two years, five years or longer).

In some embodiments, the elastomeric member 4217 can be constructed from multiple different materials. For example, in some embodiments, at least a portion of the elastomeric member 4217 can be coated. Such coatings can include, for example, polydimethylsiloxane. In some embodiments, at least a portion of the elastomeric member 4217 can be coated with polydimethylsiloxane in an amount of between approximately 0.02 mg/cm$^2$ and approximately 0.80 mg/cm$^2$.

The proximal end portion 4212 of the container body 4210 includes a flange 4214 configured to be disposed within a portion of the carrier body 4360, as described in further detail herein. The flange 4214 can be of any suitable size and/or shape. Although shown as substantially circumscribing the container body 4210, in other embodiments, the flange 4214 can only partially circumscribe the container body 4210.

The medicament container assembly 4200 can have any suitable size (e.g., length and/or diameter) and can contain any suitable volume of the medicament. In some embodiments, the medicament container assembly 4200 (and any of the medicament container assemblies described herein) can be a prefilled (or prefillable) syringe, such as those manufactured by Becton Dickinson, Gerresheimer, Ompi Pharma or others. For example, in some embodiments, the medicament container assembly 4200 (and any of the medicament container assemblies described herein) can be a Becton Dickinson "BD Hypak Physiolis" prefillable syringe containing any of the medicaments described herein. The medical injector 4000 can be configured to inject any suitable dosage such as, for example, a dose of up to 4 mL of any of the medicaments described herein. In other embodiments, the medical injector 4000 can be configured to inject a dose of up to 2 mL, 3 mL, 4 mL, 5 mL, or more of any of the medicaments described herein.

The container body 4210 can be constructed from glass and can be fitted and/or coupled to any suitable needle. For example, in some embodiments, the container body 4210) can be coupled to a needle having any suitable size. Any of the medicament container assemblies and/or prefilled syringes described herein can be coupled to a needle having a gauge size of 21 gauge, 22 gauge, 23 gauge, 24 gauge, 25 gauge, 26 gauge, 27 gauge, 28 gauge, 29 gauge, 30 gauge, or 31 gauge. Any of the medicament container assemblies and/or prefilled syringes described herein can be coupled to a needle having any suitable length, such as, for example, a length of about 0.2 inches, about 0.27 inches, about 0.38 inches, about 0.5 inches, about 0.63 inches, about 0.75 inches, or more. In some embodiments, for example, any of the medicament containers and/or prefilled syringes described herein can be coupled to a 29 gauge, needle having a length of approximately 0.5 inches.

As shown in FIG. 34, the medicament container assembly 4200 includes a needle sheath assembly 4220, that includes a sheath body 4230 and a sheath cover 4235. The needle sheath assembly 4220 includes a distal end portion 4221 and a proximal end portion 4222. The sheath body 4230) defines a bore that receives the needle 4216 and/or a distal end portion of the 4213 of the medicament container body 4210. The inner portion of the sheath body 4230 defines a friction fit with the distal end portion 4213 of the medicament container body 4210. In this manner, the needle sheath assembly 4220 can protect the user from the needle 4216 and/or can keep the needle 4216 sterile before the user actuates the medical injector 4000.

The sheath cover 4235 is disposed about (and surrounds) the sheath body 4230. The sheath cover 4235 includes a series of ribs 4236 that engage the tabs 4722 of the safety lock 4700 (see e.g., FIGS. 27, 27B, 34, 37 and 38). Specifically, the distal end portion of the sheath assembly 4220 is configured to be inserted into a space defined between the tabs 4722 of the engagement members 4721 of the safety lock 4700. The tabs 4722 are angled and/or bent towards the distal direction to allow the distal end portion of the sheath assembly 4220 to move between the engagement members 4721 in a distal direction, but not in a proximal direction. Similarly stated, the tabs 4722 include an edge that contacts the ribs 4236 of the sheath cover 4235 to prevent the safety lock 4700 from moving in a distal direction relative to the needle sheath 4220). In this manner, the needle sheath assembly 4220 is removed from the needle 4216 when the safety lock 4700 is moved in a distal direction with respect to the housing 4100.

Figure 41:
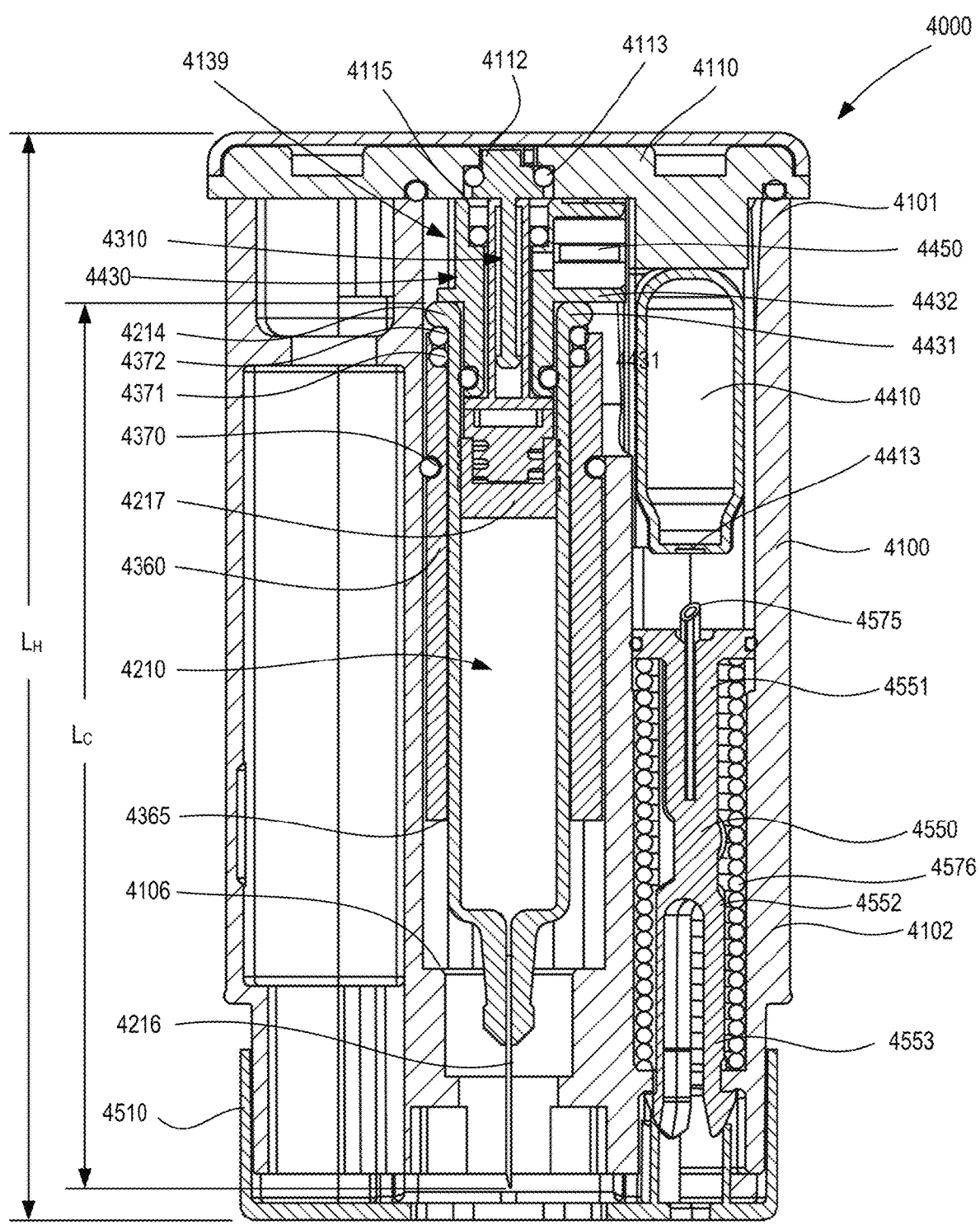
FIG. 41 is a front cross-sectional view of the medical injector shown in FIG. 17, in a second configuration (safety lock removed).

As shown in FIG. 41, the delivery mechanism 4300 includes a gas vent assembly 4310 (also referred to as an expandable assembly) but does not rely on a piston or rigid member to move the elastomeric member 4217 within the container body 4210 to inject the medicament. Rather, the elastomeric member 4217 is moved by the force produced by the pressurized gas within the gas chamber (or medicament cavity 4139). Accordingly, the stroke length and/or the dosage amount can be set by the expanded length of the gas vent assembly 4310. In this manner, the length of the medicament container assembly 4200 and the length of the gas vent assembly 4310 can be configured such the desired dosage amount is delivered. Moreover, because the gas vent assembly 4310 moves from a collapsed to an expanded configuration, the medicament delivery mechanism 4300 can fit within the same housing 4100 regardless of the fill volume, the delivery volume and/or the ratio of the fill volume to the delivery volume. In this manner, the same housing and production tooling can be used to produce devices having various dosages of the medicament. For example, in a first embodiment (e.g., having a fill volume to delivery volume ratio of 0.4), the medicament container has a first length and the second movable member has a first length. In a second embodiment (e.g., having a fill volume to delivery volume ratio of 0.6), the medicament container has a second length shorter than the first length, and the second movable member has a second length longer than the first length. In this manner, the stroke of the device of the second embodiment is longer than that of the device of the first embodiment, thereby allowing a greater dosage. The medicament container of the device of the second embodiment, however, is shorter than the medicament container of the device of the first embodiment, thereby allowing the components of both embodiments to be disposed within the same housing and/or a housing having the same length.

In some embodiments, the medical injector 4000 is configured such that a ratio of the housing length $L_H$ to the container length $L_C$ (which includes the needle extending from the end of the container body) is less than about 1.5. In other embodiments, the medical injector 4000 is configured such that a ratio of the housing length Lu to the container length $L_C$ is less than about 1.25. In yet other embodiments, the medical injector 4000 is configured such that a ratio of the housing length $L_H$ to the container length $L_C$ is less than about 1.1.

In some embodiments, the medical injector 4000 is configured such that a ratio of the housing length $L_H$ to a sum of the container length $L_C$, the carrier distance, and the stroke is less than about 1.1. In other embodiments, the medical injector 4000 is configured such that a ratio of the housing length $L_H$ to a sum of the container length $L_C$, the carrier distance, and the stroke is less than about 1.0. In yet other embodiments, the medical injector 4000 is configured such that a ratio of the housing length $L_H$ to a sum of the container length $L_C$, the carrier distance, and the stroke is less than about 0.9.

Figure 45:
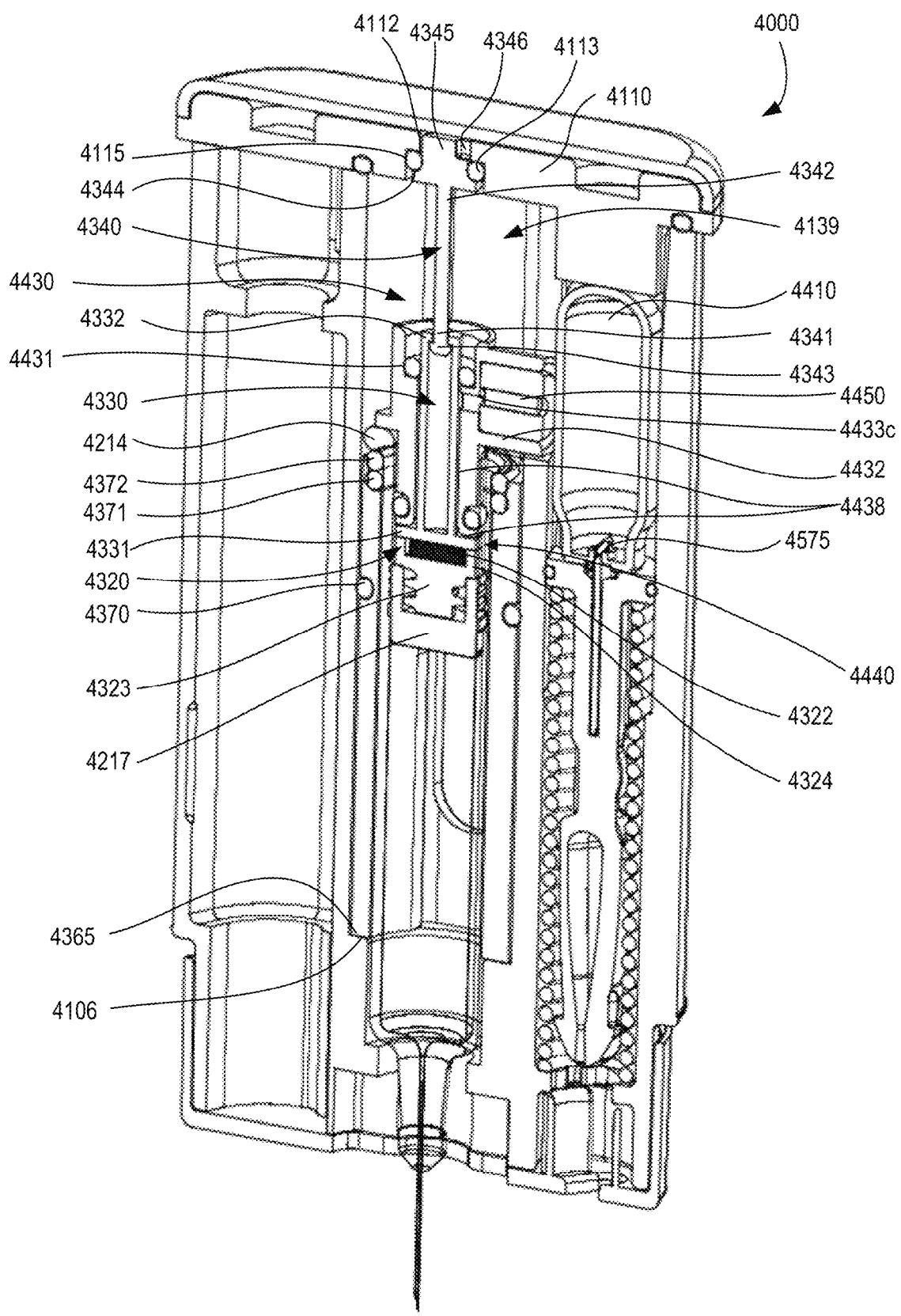
FIG. 45 is an enlarged cross-sectional view of the medical injector shown in FIG. 17, in the fourth configuration (needle inserted).

As shown in FIGS. 24, 25, and 45, the system actuator assembly 4500 includes the base 4510, a release member 4550 and a spring 4576. FIG. 25 shows certain internal components of the medical injector 4000 without the base 4510 and the safety lock 4700 so that the release member 4550 can be more clearly shown. The release member 4550 has a proximal end portion 4551 and a distal end portion 4552, and is movably disposed within the distal end portion of the gas container cavity 4151. The proximal end portion of the release member 4550 includes a sealing member 4574 and a puncturer 4575. The sealing member 4574 is configured to engage the sidewall of the housing 4100 defining the gas container cavity 4151 such that the proximal end portion of the gas container cavity 4151 is fluidically isolated from the distal end portion of the gas container cavity 4151. In this manner, when gas is released from the gas container 4410, the gas contained in the proximal end portion of the gas container cavity 4151 is unable to enter the distal end portion of the gas container cavity 4151. The puncturer 4575 of the release member 4550 is configured to contact and puncture a frangible seal 4413 on the gas container 4410 when the release member 4550 moves proximally within the gas container cavity 4151.

Figure 42:
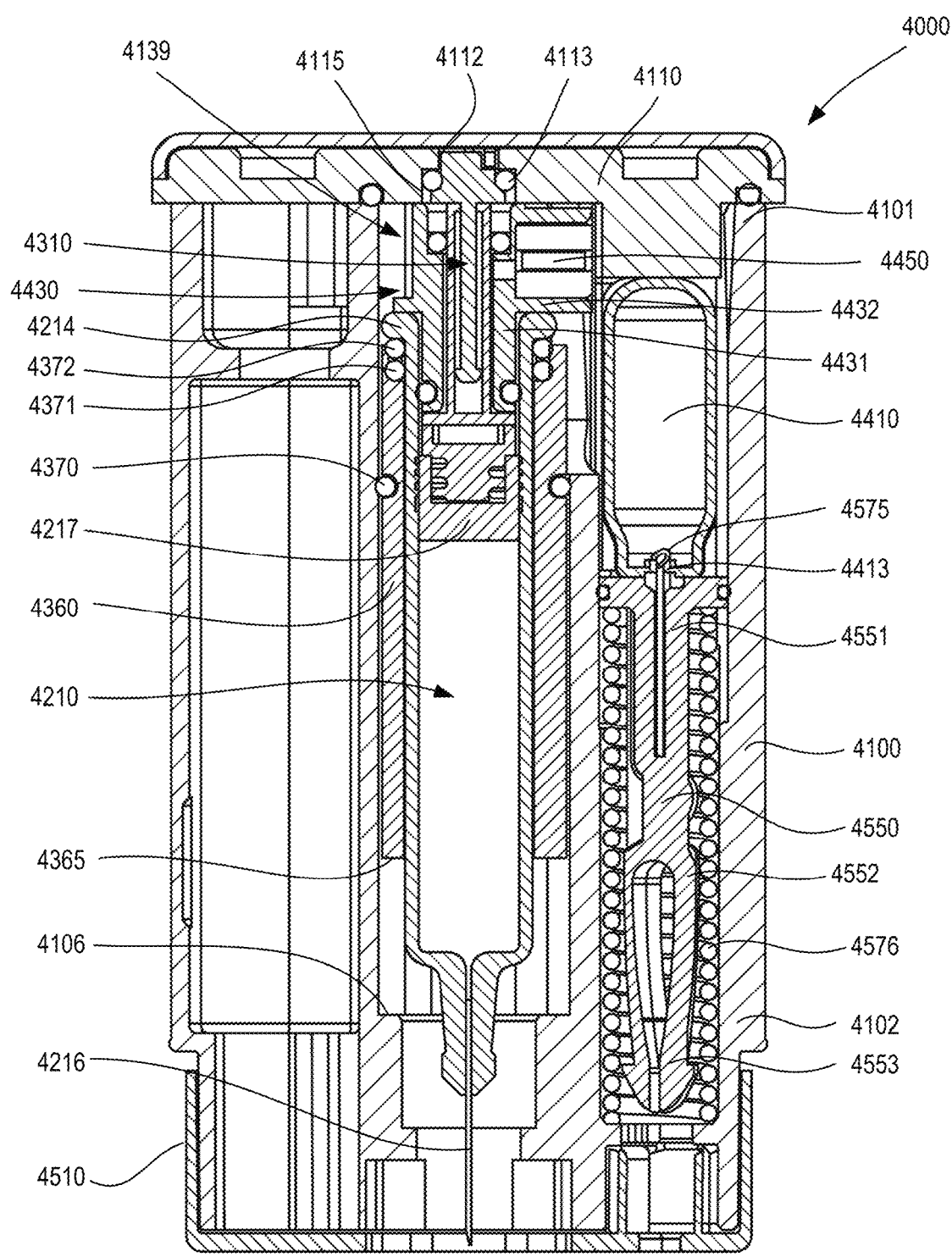
FIG. 42 is a front cross-sectional view of the medical injector shown in FIG. 17, in a third configuration (actuated).

The distal end portion 4552 of the release member 4550 includes extensions 4553. The extensions 4553 have projections that include tapered surfaces and engagement surfaces. Further, the extensions 4553 define an opening between the adjacent extensions 4553. The engagement surfaces are configured to extend through the release member aperture and contact the release member contact surface of the housing 4100, as shown in FIG. 42. In this manner, the engagement surfaces limit proximal movement of the release member 4550.

The opening defined by the extensions 4553 is configured to receive the safety lock protrusion 4702 of the safety lock 4700 (see e.g., FIGS. 27 and 27B) when the safety lock 4700 is coupled to the housing 4100 and/or the base 4510. The safety lock protrusion 4702 is configured to prevent the extensions 4553 from moving closer to each other. Said another way, the safety lock protrusion 4702 is configured to ensure that the extensions 4553 remain spaced apart and the engagement surfaces remain in contact with the release member contact surface of the housing 4100. In some embodiments, for example, the release member 4550 and/or the extensions 4553 can be constructed from any suitable material configured to withstand deformation that may occur when exposed to a load over an extended period of time.

The tapered surfaces of the extensions 4553 are configured to contact corresponding tapered surfaces 4557 of the base 4510 when the base 4510 is moved proximally relative to the housing 4100. Accordingly, when the base 4510 is moved proximally relative to the housing 4100, the extensions 4553 are moved together by the tapered surfaces. The inward movement of the extensions 4553 causes the release member 4550 to disengage the release member contact surface 4126 of the housing 4100, thereby allowing the release member 4550 to be moved proximally along its longitudinal axis as the spring 4576 expands (see FIG. 45).

The gas container 4410 includes a distal end portion 4411 and a proximal end portion 4412, and is configured to contain and/or produce a pressurized gas. The distal end portion 4411 of the gas container 4410 contains a frangible seal 4413 configured to break when the puncturer 4575 of the release member 4550 contacts the frangible seal 4413. The gas container retention member 4180 of the proximal cap 4110 of the housing 4100 is configured to receive and/or retain the proximal end portion 4412 of the gas container 4410. Said another way, the position of the gas container 4410 within the gas container cavity 4151 is maintained by the gas container retention member 4180. As shown in FIGS. 24 and 25, the length of the gas container retention member 4180 and the length of the release member 4550 collectively determine the distance between the puncturer 4575 and the frangible seal 4413 when the medical injector 4000 is in the storage configuration. Accordingly, this distance, which is the distance through which the puncturer 4575 travels when the medical injector 4000 is actuated, can be adjusted by changing the length of the gas container retention member 4180 and/or the length of the release member 4550. In some embodiments, the actuation time and/or the force exerted by the puncturer 4575 on the frangible seal 4413 can be adjusted by changing the distance between the puncturer 4575 and the frangible seal 4413.

As shown in generally in FIG. 24, the medicament delivery mechanism 4300 includes a carrier assembly 4390, a flow restriction assembly 4430 (also referred to as a delivery control mechanism), and a gas vent assembly 4310. The carrier assembly 4390 and the gas vent assembly 4310 are each movably disposed within the medicament cavity 4139 of the housing 4100. As shown in FIGS. 30-34, the carrier assembly 4390 includes a carrier body 4360 and a retraction spring 4380. The carrier body 4360 includes a distal end portion 4361 and a proximal end portion 4362. The proximal end portion 4362 of the carrier body 4360 defines an opening within which the medicament container body 4210 is disposed. The proximal end portion 4362 also includes a proximal surface 4376, forms a portion of the boundary of the housing gas chamber (i.e., the portion of the medicament cavity 4139 within which the pressurized gas flows in a first phase of expansion when the medicament container body 4210 is actuated within the housing 4100). In this manner, the pressurized gas produces a force on the proximal surface 4376, which moves the carrier assembly 4390 distally within the housing 4100.

An inner surface of the proximal end portion 4362 defines a groove within which a first O-ring 4371 and a second O-ring 4372 are disposed. The first O-ring 4371 and the second O-ring 4372 are disposed between a top surface of the carrier body 4360 and the flange 4214 of the medicament container body 4210. In this manner, the first O-ring 4371 and the second O-ring 4372 form a substantially fluid-tight seal. Accordingly, when pressurized gas flows into the proximal portion of the medicament cavity 4139 (i.e., the housing gas chamber), the area between the inner surface of the carrier body 4360 and the medicament container body 4210 is sealed. The first O-ring 4371 and the second O-ring 4372 also dampen any impact on the flange 4214.

An outer surface of the carrier body 4360 defines an O-ring groove and includes an outer O-ring 4370). The outer surface is configured to slide against sidewalls 4139a within the medicament cavity 4139 (see FIG. 21), and the O-ring 4370 and an inner surface of the housing 4100 define a form a substantially fluid-tight seal. Accordingly, when pressurized gas flows into the proximal portion of the medicament cavity 4139, the area between the outer surface of the carrier body 4360 and the inner surface of the housing 4100 is sealed. The outer O-ring 4370 is in a fixed location relative to each of the inner O-rings 4371, 4372. In other embodiments, however, a carrier assembly can include components that move relative to each other such that an outer seal member moves relative to an inner seal member.

The distal end portion 4361 of the carrier body 4360 has an open end. Thus, as shown in FIGS. 30-33, the distal end portion 4213 of the medicament container body 4210 extends beyond the carrier body 4360. Additionally, the distal end portion 4361 of the carrier body 4360 includes two extensions (or "legs") that collectively define an opening 4375. This opening is configured to align with the status apertures 4130, 4160 of the housing to allow viewing of the medicament within the medicament container assembly, the elastomeric member 4217 or the like. The distal end portion 4361 also includes an end surface 4365 configured to contact the shoulder portion 4106 of the housing 4100 (see e.g., FIG. 44) when the needle 4216 has been inserted a desired distance.

Figure 32:
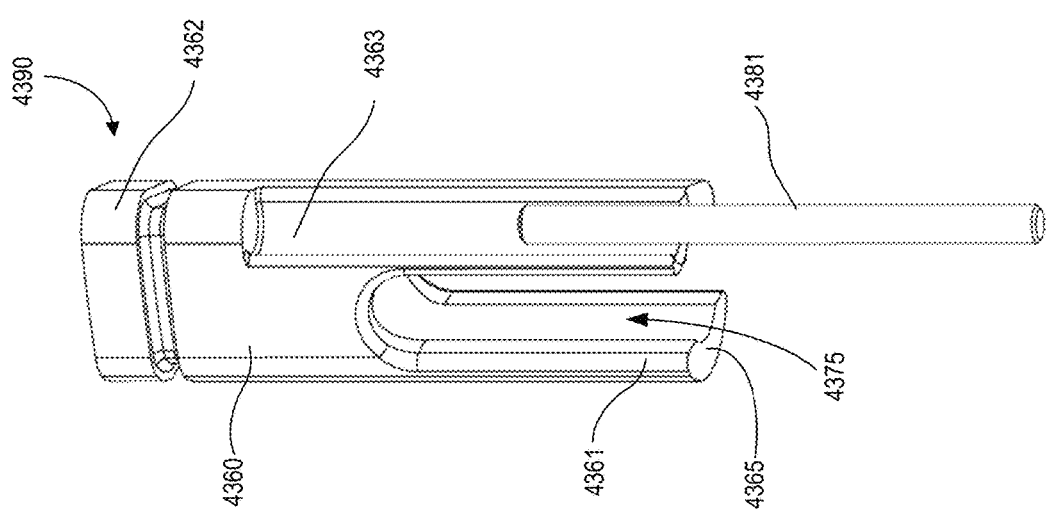
FIG. 32 is a perspective view of the carrier assembly of the medical injector shown in FIG. 27.

The retraction spring 4380 is disposed within a spring pocket 4363 defined by the outer surface of the carrier body 4360, as shown in FIG. 32. The retraction spring 4380 is disposed about a spring pin 4381 that limits buckling or other lateral movement of the retraction spring 4380 during use. The delivery control mechanism 4430 (also referred to as the flow restriction assembly) is configured to regulate the pressure applied on the elastomeric member 4217 to control the rate in which the elastomeric member 4217 moves within the medicament container body 4210. In this manner, the flow rate at which the medicament is dispensed out of the medicament container body 4210 via the needle 4216 as the elastomeric member 4217 moves through its travel stroke can be controlled. Control of the flow rate of medicament leaving the device can minimize pain or discomfort, particularly when the medicament is highly viscous (e.g., greater than about 100 centipoise at room temperature). Additionally, where the medicament includes high molecule weight compounds (e.g., greater than about 5 kDa), reduced injection force less than a force required to overcome the retraction spring 4380 prevents shearing and therefore damage to the medicament or therapeutic substance.

Figure 28:
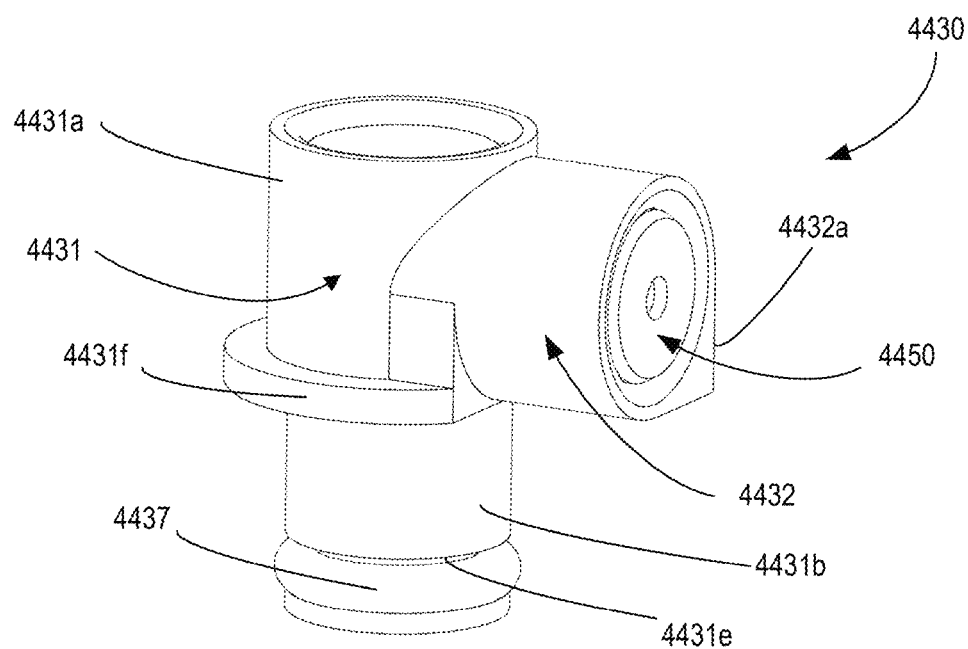
FIGS. 28 and 28A are a perspective view (FIG. 28) and a cross-sectional view (FIG. 28A) of a delivery control mechanism of the medical injector shown in FIG. 27.
Figure 28A:
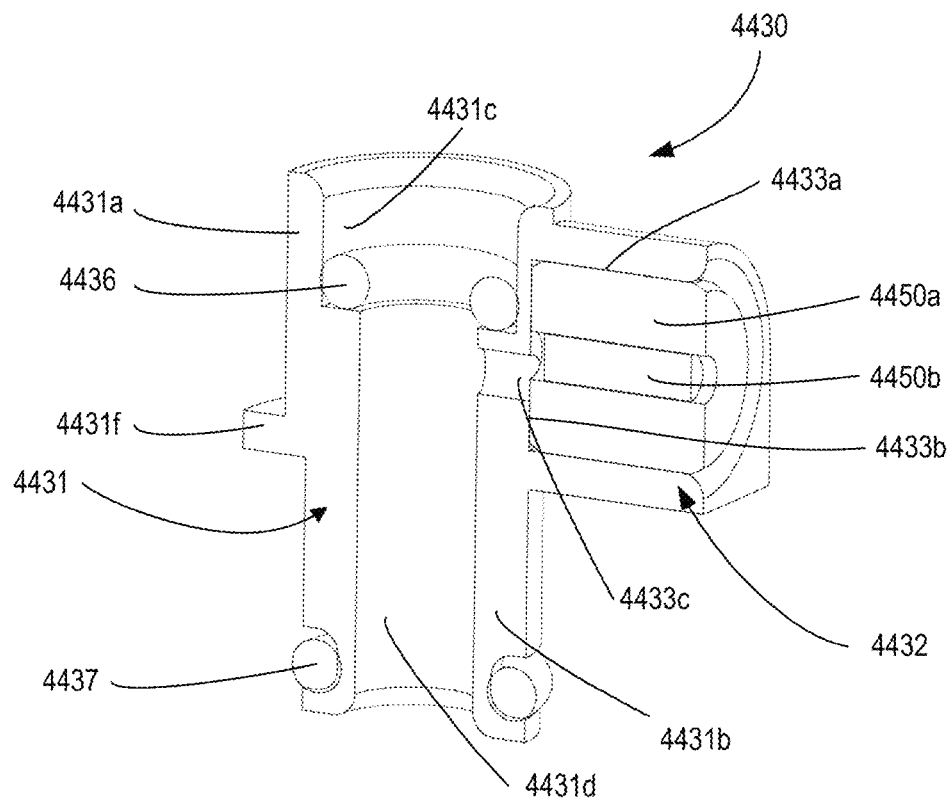
Figure 29:
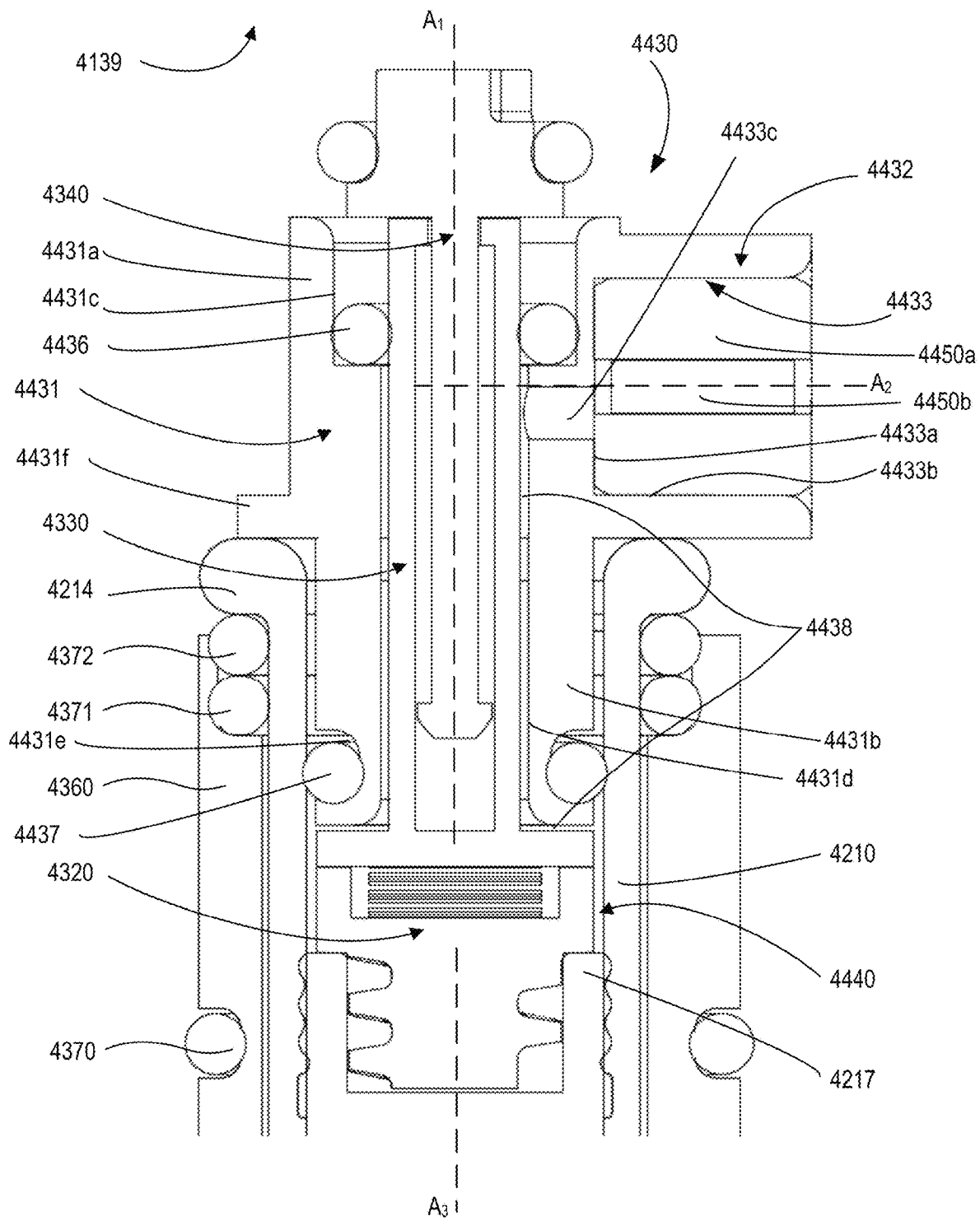
FIG. 29 is a cross-sectional view of the delivery control mechanism shown in FIGS. 28 and 28A within the proximal end portion of the medicament container.
Figures 30, 31:
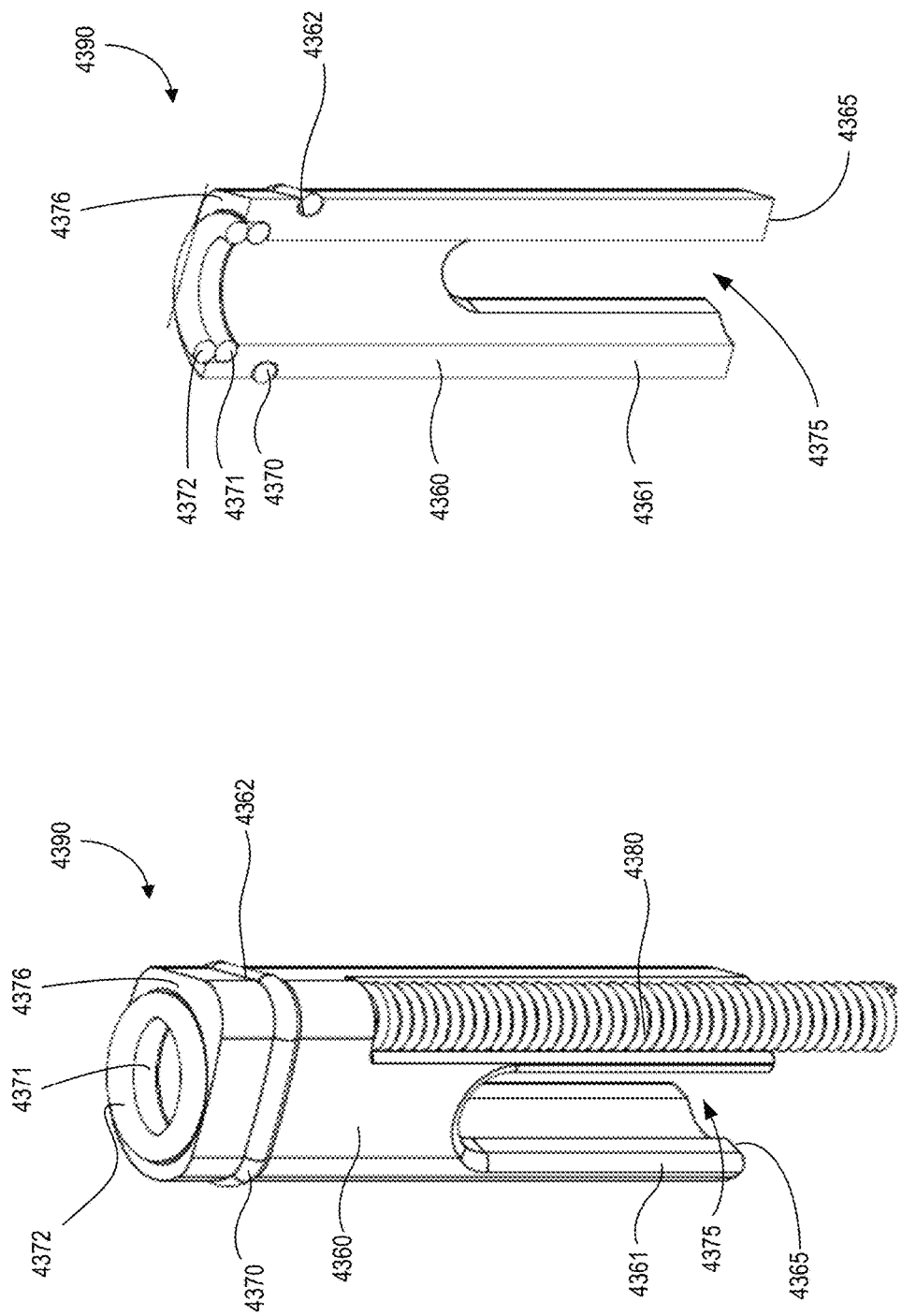
FIGS. 30 and 31 are a perspective view and a cross-sectional view, respectively, of a carrier assembly of the medical injector shown in FIG. 27.
Figure 33:
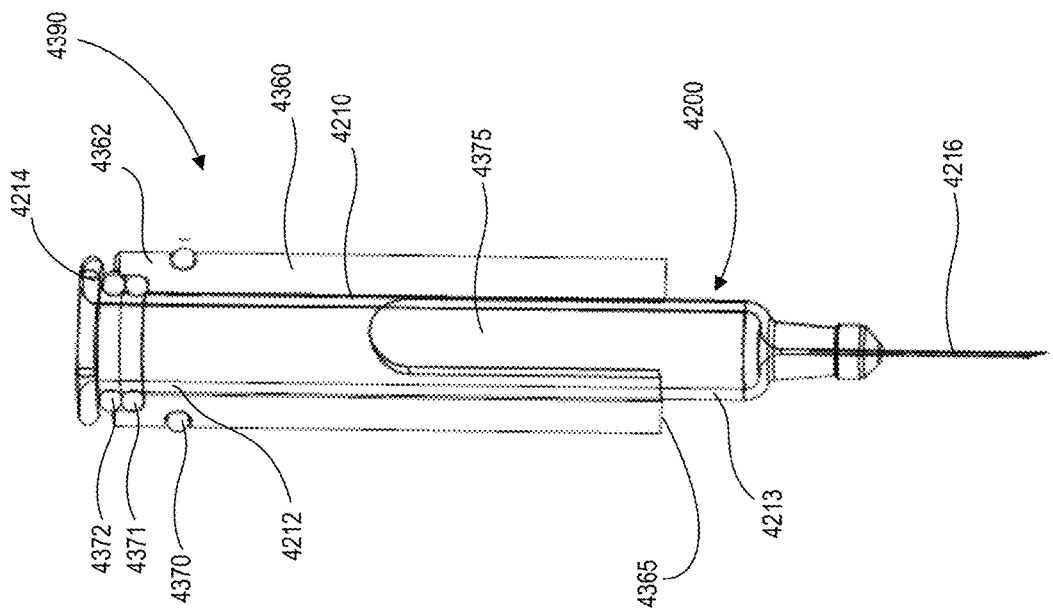
FIG. 33 is a cross-sectional view of the carrier assembly and a medicament container of the medical injector shown in FIG. 27.

As shown in FIGS. 28, 28A, and 29, the delivery control mechanism 4430 includes a first body portion 4431 and a second body portion 4432. The second body portion 4432 extends from the first body portion 4431. The second body portion 4432 includes a flow restriction retainer 4433 configured to support at least a portion of a flow restriction member 4450. As shown in FIG. 28A, the flow restriction retainer 4433 includes a cylindrical inner surface 4433a and an end surface 4433b. The end surface 4433b defines a through-hole 4433c extending into an interior portion of the first body portion 4431. In this manner, the interior of the first body portion 4431 is in fluid communication with the second body portion 4432. Although the through-hole 4433c is shown as being non-coaxial with a center of the flow restriction member 4450, in some embodiments, the through-hole 4433c is co-axial with the flow restriction member 4450. In some embodiments, at least a portion of a flow restriction element 4450b of the flow restriction member 4450 overlaps with a portion through-hole 4433c. In some embodiments, at least 50% of the flow restriction element 4450b overlaps with the through-hole 4433c. In some embodiments, the flow restriction member 4450 is press fit or threaded into the flow restriction retainer 4433.

The flow restriction member 4450) includes a sleeve member 4450a and a flow restriction element 4450b, and the flow restriction element 4450b is supported within the sleeve member 4450a. In some embodiments, the sleeve member 4450a is a metal sleeve. In some embodiments, the metal sleeve is made of stainless steel or brass. In some embodiments, the flow restriction element 4450b is a porous material. In some embodiments, the porous material is sintered porous metal. In some embodiments, the flow restriction element 4450b is calibrated with nitrogen gas ($N_2$) at 30 psig (inlet side) to atmosphere (outlet side) at standard temperature and pressure to have a flow rate of between 0.5 to 3 standard cubic centimeter per minute (sccm). In some embodiments, the flow restriction member 4450b is calibrated with nitrogen gas ($N_2$) at 30 psig (inlet side) to atmosphere (outlet side) at standard temperature and pressure to have a flow rate of between about 0.75 and 1.5 standard cubic centimeter per minute (sccm). In some embodiments, the flow restriction member 4450b is calibrated with nitrogen gas ($N_2$) at 30 psig (inlet side) to atmosphere (outlet side) at standard temperature and pressure to have a flow rate of about 1 standard cubic centimeter per minute (sccm). As described herein, standard temperature is 60° F. (15.6° C.) and standard pressure is 14.696 psia (101.3 kPa).

In some embodiments, the compressed gas supplied by the gas container 4410 is an argon gas and the flow restriction element 4450b has a flow rate rating of about 0.75 and 1.5 sccm based on the nitrogen gas calibration described above. In some embodiments, the compressed gas supplied by the gas container 4410 is an argon gas and the flow restriction element 4450b has a flow rate rating of about 1 sccm based on the nitrogen gas calibration described above. In some embodiments, the compressed gas in the gas container 4410 has a molecular weight greater than the molecular weight of argon. For example, in some embodiments, the compressed gas supplied by the gas container 4410 is R134a (Tetrafluoroethane) and the flow restriction element 4450b has a flow rate rating of about 10 to 100 sccm based on the nitrogen gas calibration described above. In some embodiments, the compressed gas supplied by the gas container 4410 is R134a (Tetrafluoroethane) and the flow restriction element 4450b has a flow rate rating of about 20 to 40 sccm based on the nitrogen gas calibration described above.

In some embodiments, the flow rate of the medicament can be reduced to less than 0.2 mL/sec (or in some embodiments between 0.05 mL/sec and 0.01 mL/sec) using gas pressure that is initially supplied to medicament cavity 4139 and through the flow restriction member 4450. The lower injection forces and/or slower delivery (compared with pressures supplied directly from the medicament cavity 4139 to the elastomeric member) can produce laminar flow of the medicament through the needle, prevent shearing of high molecular weight compounds in the medicament, and/or reduce pain sensed by a patient particularly if the medicament being delivered is very high viscosity (e.g., greater than about 100 centipoise at room temperature). In some embodiments, a screen or mesh protective member can be provided on a proximal side of the flow restriction member 4450 to prevent any particulate or debris from clogging the flow restriction element 4450b during operation.

The first body portion 4431 includes a proximal end portion 4431a and a distal end portion 4431b. The proximal end portion 4431a includes a first inner cylindrical surface 4431c and the first inner cylindrical surface 4431c is configured to support an O-ring 4436, which in turn contacts a portion of the gas vent assembly 4310 to seal an interior of the first body portion 4431 from housing gas chamber portion of the medicament cavity 4139 as described in further detail herein.

The distal end portion 4431b extends into a proximal end portion of the medicament container body 4210. The distal end portion 4431b also includes a second inner cylindrical surface 4431d and an outer cylindrical groove 4431e configured to support an O-ring 4437, which in turn contacts and seals against an interior wall of the medicament container body 4210. The first inner cylindrical surface 4431c and the second inner cylindrical surface 4431d define a bore extending from the proximal end portion 4431a to the distal end portion 4431b. The bore permits the gas vent assembly 4310 to extend into and through the first body portion 4431. A portion of the bore further defines a gas passageway between the second body portion 4432 and a medicament body gas chamber 4440 as described in detail below. As shown in FIG. 28A, an inner diameter of the first inner cylindrical surface 4431c is larger than the inner diameter of the second inner cylindrical surface 4431d. The first body portion 4431 further includes a flange portion 4431f extending radially from an outer surface of the first body portion 4431. The flange portion 4431f is configured to mount onto the flange 4214 of the medicament container body 4210 or onto a proximal end portion of the carrier body 4360.

As shown in FIG. 29, the first body portion 4431 defines a first axis $A_1$, the second body portion 4432 defines a second axis $A_2$, and the first axis is non-parallel with the second axis. In some embodiments, the first axis $A_1$ and the second axis $A_2$ are perpendicular to one another. In other embodiments, the first axis and the second axis define an acute angle therebetween. In some embodiments, the medicament container body 4210 defines a third axis $A_3$, and the first axis of the first body portion 4431 is parallel with the third axis $A_3$. In some embodiments, the second body portion 4432 includes a guide surface 4432a (see FIG. 28A) to contact a wall or guide member 4135a of the housing 4100 (see FIG. 21) to prevent rotation of the delivery control mechanism 4430 about the first axis $A_1$ during operation.

The gas vent assembly 4310 is configured to expand and/or change configurations during operation of the medical injector 4000, and selectively produces a pathway through which pressurized gas escapes the medicament cavity 4139 after delivery of the medicament. By releasing or removing the force from the carrier body 4360, the delivery control mechanism 4430) and/or the medicament container assembly 4200, the retraction spring 4380 can move the carrier body 4360 proximally to retract the needle 4216. Notably, the gas vent assembly 4310 does not exert a distal force on the elastomeric member 4217, but rather, is carried distally by the elastomeric member 4217 during delivery of the medicament. Thus, this arrangement is considered a "pistonless" delivery system, because the force for insertion and medicament delivery is provided via the pressurized gas acting either directly upon the medicament container assembly 4200 (e.g., the proximal surface 4218 of the elastomeric member 4217), the delivery control mechanism 4430 (e.g., the first body portion 4431 and the second body portion 4432 of the delivery control mechanism extending out of the medicament container body 4210), and/or the carrier assembly 4390 (e.g., the proximal surface 4376 of the carrier body 4360), or indirectly through gas pressure supplied from the medicament cavity 4139 through the delivery control mechanism 4430 via the flow restriction member as described herein.

As shown in FIGS. 35, 36A, 36B, and 36C, the gas vent assembly 4310 includes a first (or distal) member 4320, a second (or central) member 4330 and a third (or proximal) member 4340). These components are nested together such that the gas vent assembly 4310 can be transitioned from a collapsed configuration (FIGS. 27, 27A and 42) to an expanded configuration (FIGS. 47 and 48, just prior to complete delivery of medicament), and a series of partially expanded configurations therebetween (see e.g., FIG. 44). The gas vent assembly 4310 reaches the expanded configuration just prior to a complete dose of medicament being delivered. Once the gas vent assembly 4310 has been placed in the expanded configuration, the elastomeric member 4217 continues to travel a final distance to deliver the remaining amount from the complete dose, which in turn pulls on the valve portion 4345 to at least partially unseat it from the opening 4112. Stated in a different manner, the length of the gas vent assembly 4310 in the expanded configuration is selected to expand and reach the expanded configuration before the end of travel of the elastomeric member 4217 continues. When the gas vent assembly 4310 is in the expanded configuration and continues to travel with the elastomeric member 4217 the final distance to finish delivery of the complete dose (FIGS. 50 and 51, after delivery of the medicament is complete), the opening 4112, the O-ring 4113 and the passageway 4346 collectively allow the pressurized gas from the housing gas chamber of the medicament cavity 4139 to escape the medicament cavity 4139, such that needle retraction can occur.

The first member 4320 includes a proximal end portion 4322 and a distal end portion 4321. The distal end portion 4321 includes a protrusion 4323 configured to matingly engage the elastomeric member 4217. In this manner, movement of the elastomeric member 4217 distally causes movement of first member 4320 distally. In some embodiments, the protrusion 4323 is a threaded portion that matingly engages the elastomeric member 4217. The proximal end portion 4322 includes a pair of retention walls 4324 configured to engage a corresponding distal end surface 4333 of the second (or central) member 4330. In some embodiments, the pair of retention walls 4324 each include a pin or tab that loosely couples the proximal end portion 4322 of the first member 4320 to the distal end surface 4333 of the second member 4330) to assist in assembly of the device, but separates once pressure is applied on the elastomeric member 4217 in a distal direction. The proximal end portion 4322 further includes a flexible expansion member 4325 that is fixed at a first end 4325a to the proximal end portion 4322 of the first member 4320 and is fixed at a second end 4325b to the distal end surface 4333 of the second member 4330. During the second phase of expansion (i.e., movement of the elastomeric member 4217 as the device transitions from the fourth configuration to the fifth configuration) the elastomeric member 4217 is moved distally within the medicament container body 4210. As the elastomeric member 4217 is moved, the first end 4325a and the second end 4325b move away from each other as the flexible expansion member 4325 expands. As shown in FIGS. 35 and 36A-36C, the flexible expansion member 4325 is collapsed down with an accordion fold. In some embodiments, the flexible expansion member 4325 is a filament or a band. In some embodiments, the flexible expansion member 4325 is over-molded with a plastic material. In some embodiments, the flexible expansion member 4325 is a cable that is initially coiled or spooled between the proximal end portion 4322 of the first member 4320) and the distal end surface 4333 of the second member 4330).

The second member 4330) includes a distal end portion 4331 and a proximal end portion 4332. The distal end portion 4331 includes the distal end surface 4333 that engages the first member 4320. The second member 4330 includes a sidewall 4334 extending from the distal end portion 4331 to the proximal end portion 4332. The proximal end portion 4332 includes a shoulder portion 4335 extending towards a center of the second member 4330) and the shoulder portion 4335 defines an opening 4336. The distal end portion 4331, the proximal end portion 4332, and the sidewall 4334 define an internal volume 4337.

Figure 35:
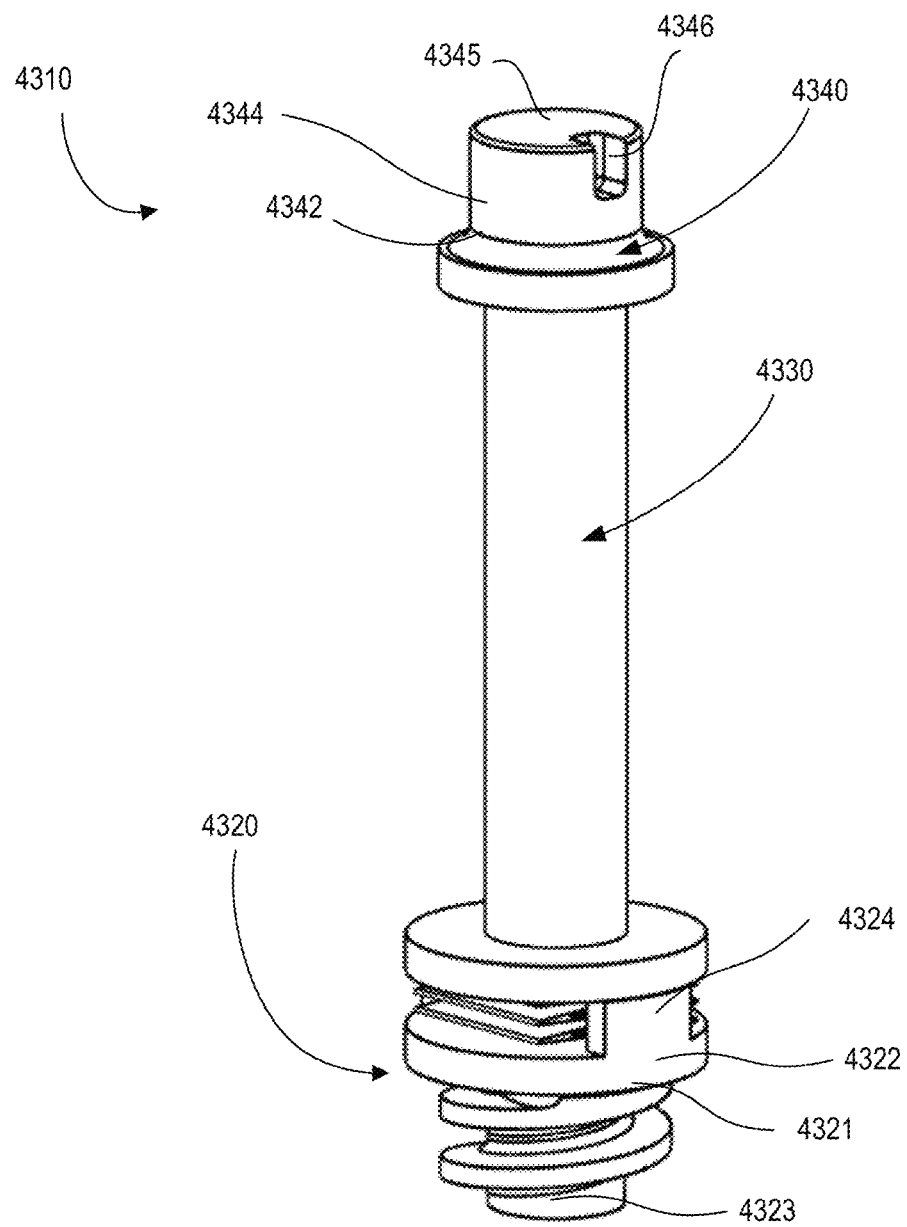
FIG. 35 is a perspective view of a gas vent assembly of the medical injector shown in FIG. 27.
Figure 36:
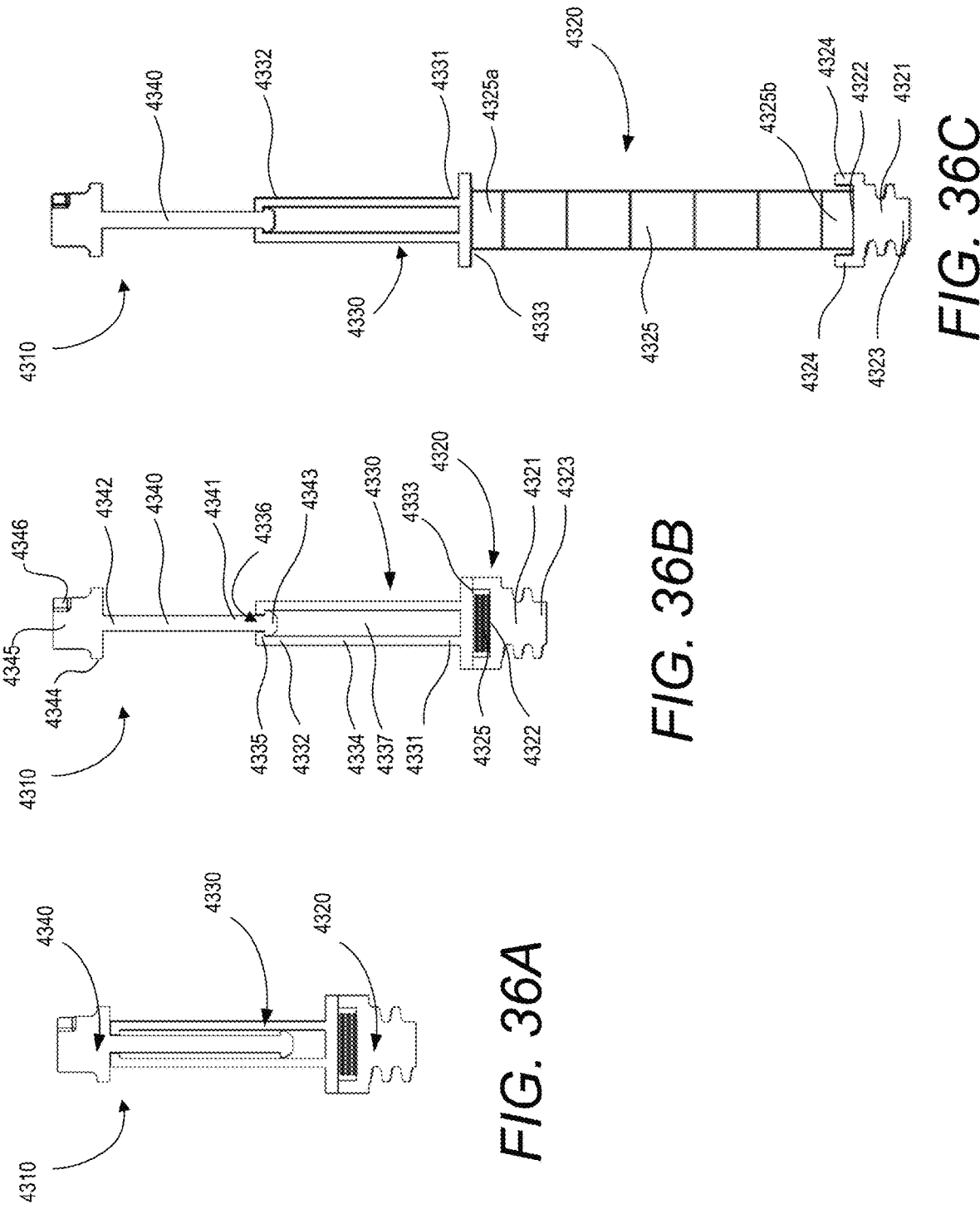
FIGS. 36A, 36B and 36C are cross-sectional views of the gas vent assembly of FIG. 35, in a first configuration, a second configuration, and a third configuration, respectively

The third member 4340) includes a distal end portion 4341 and a proximal end portion 4342. The distal end portion 4341 extends through opening 4336 of the second member 4330. The distal end portion 4341 includes a distal protrusion 4343 configured to travel within the internal volume 4337 and to engage the shoulder portion 4335 of the second member 4320 when the second member 4320 is extended away from the third member 4340. In this manner, distal protrusion 4343 limits movement of the second member 4340 as it extends away from the third member 4340) during the first phase of expansion as described herein. The proximal end portion 4342 includes a guide surface 4344 and a valve portion 4345. The guide surface 4344 engages the O-ring 4113 and slides within the guide wall 4115 of the proximal cap 4110 (FIG. 27A). The valve portion 4345 defines a passageway 4346 that bypasses the O-ring 4113 when the valve portion 4345 is placed in an open configuration (see FIGS. 53 and 54). As shown in FIG. 35, the passageway 4346 is a recessed portion extending into the proximal end portion 4342.

As shown in FIGS. 27, 37, and 38, the safety lock 4700 includes a safety lock protrusion 4702 and an engagement portion 4720. As described above, when the safety lock 4700 is in a first (locked) position, the safety lock protrusion 4702 is configured to be disposed in the opening defined by the extensions 4553 of the release member 4550. Accordingly, the safety lock protrusion 4702 is configured to prevent the extensions 4553 from moving closer to each other, thereby preventing proximal movement of the release member 4550) and/or delivery of the medicament.

The engagement portion 4720 of the safety lock 4700 includes engagement members 4721 that extend in a proximal direction. The engagement members 4721 have tabs 4722 that extend from a surface of the engagement members. The tabs 4722 engage the ribs 4236 of the sheath cover 4235 to limit relative movement between the safety lock 4700 and the needle sheath assembly 4220, as described above. In this manner, the needle sheath assembly 4220 can protect the user from the needle 4216 and/or can keep the needle 4216 sterile before the user actuates the medical injector 4000, and the needle sheath assembly 4220 can be removed from about the needle 4216 when the safety lock 4700 is removed.

The outer surface of the safety lock 4700 include a grip portion (recessed finger grips) and indicia thereon. The recessed finger grips provides an area for the user to grip and/or remove the safety lock 4700 from about the housing 4100. The indicia provide instruction on how to remove the safety lock 4700. In some embodiments, for example, indicia can indicate the direction the user should pull the safety lock 4700 to remove the safety lock 4700.

FIGS. 39 and 40 show the base (or actuator) 4510 of the medical injector 4000. The base 4510 includes a proximal (or inner) surface 4511, a distal (or outer) surface 4523 and base connection knobs 4518. The distal surface 4523 is disposed against a target surface (not shown) during use of the injector 4000. As described below, the housing 4100 is moved distally relative to the base 4510 and/or the distal surface 4523, thereby causing the base 4510 to move proximally relative to the housing 4100 to actuate the medical injector 4000. The base 4510 defines a needle aperture 4513 and a safety lock protrusion aperture 4514. The needle aperture 4513 is configured to receive the needle 4216 when the medical injector 4000 is actuated. The safety lock protrusion aperture 4514 of the base 4510 receives the safety lock protrusion 4702 of the safety lock 4700 when the safety lock 4700 is coupled to the housing 4100 and/or the base 4510.

The proximal surface 4511 of the base 4510 includes guide members 4517 and protrusions 4515. The guide members 4517 of the base 4510 engage and/or slide within the base rail grooves 4114 of the housing 4100, as described above. The protrusions 4515 of the base 4510 engage the tapered surfaces of the extensions 4553 of the release member 4550. As described in further detail herein, when the safety lock 4700 is removed and the base 4510 is moved in a proximal direction with respect to the housing 4100, the protrusions 4515 of the base 4510 are configured to move the extensions 4553 of the release member 4550) closer to each other, actuating the medicament delivery mechanism 4300. In some embodiments, the base connection knobs 4518 engage the base retention recesses 4134 in a way that allows proximal movement of the base 4510 but limits distal movement of the base 4510.

Figure 26:
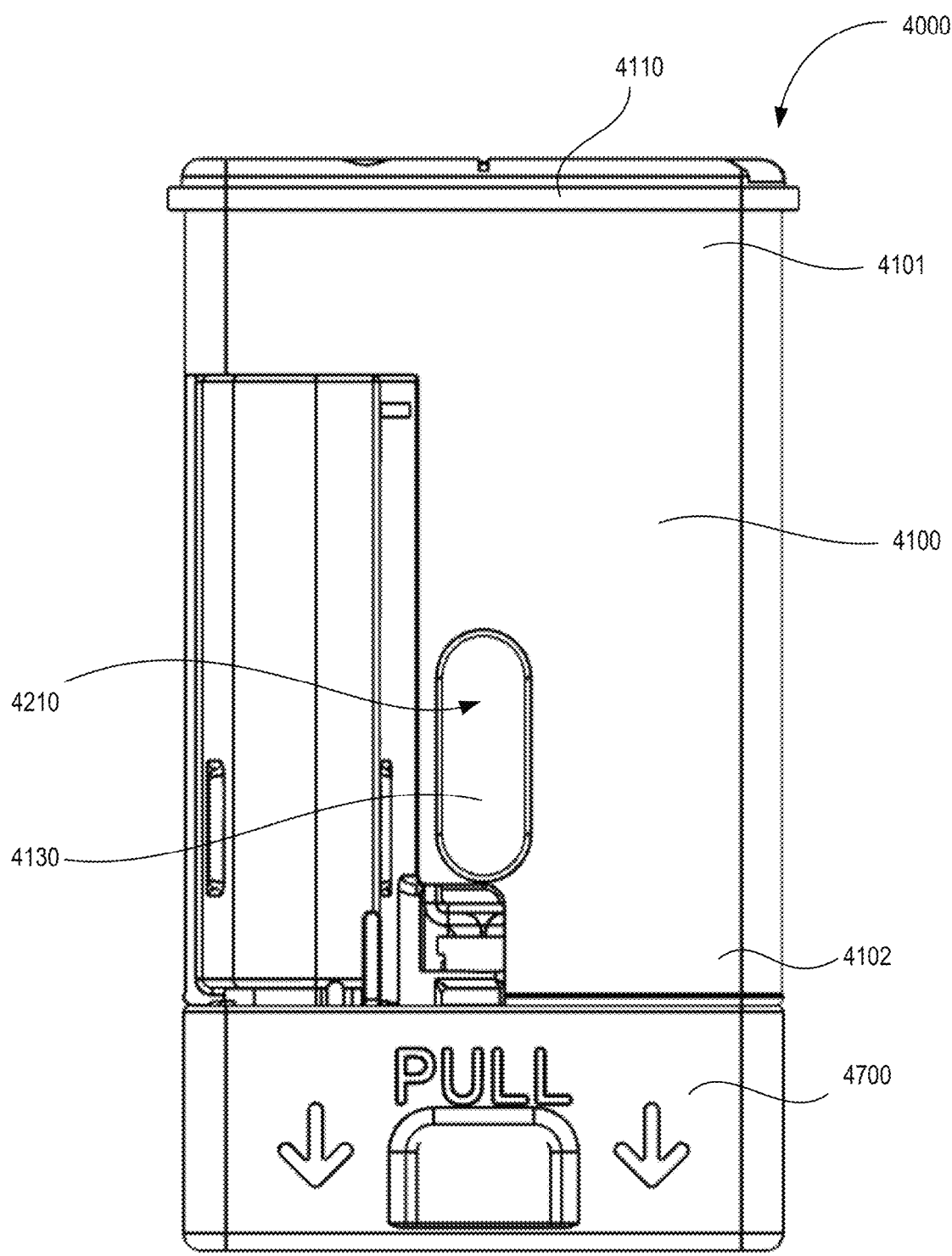
FIG. 26 is a front view of the medical injector shown in FIG. 17, in the first configuration.

The medical injector 4000 can be moved from the first configuration (FIGS. 26 and 27) to a second configuration (FIG. 42) by moving the safety lock 4700 from a first position to a second position. The safety lock 4700 is moved from a first position to a second position by moving and/or removing the safety lock 4700 distally with respect to the housing 4100. When the safety lock 4700 is moved from the first position to the second position, the safety lock protrusion 4702 is removed from between the extensions 4553 of the release member 4550), thereby enabling the medicament delivery mechanism 4300. As shown in FIG. 26, prior to actuation, a portion of the medicament container assembly 4200 can be viewed via the status aperture 4130. Specifically, the medicament container body 4210 and the contents therein (e.g., the medicament) can be viewed. As described above, in some embodiments, the housing 4100 can include a label or other indicia providing a color strip (against which the medicament can be compared), instructions for viewing or the like. Although not shown in FIG. 26, in some embodiments, a portion of the elastomeric member 4217 is visible via the status aperture 4130.

After the safety lock 4700 is moved from the first position to the second position, the medical injector 4000 can be moved from the second configuration (FIG. 42) to a third configuration (FIG. 43) by moving the base 4510 from a first position to a second position. Similarly stated, the medical injector 4000 can be actuated by the system actuator assembly 4500 by moving the base 4510 proximally relative to the housing 4100. The base 4510 is moved from its first position to its second position by placing the medical injector 4000 against the body of the patient and moving the base 4510 with respect to the housing 4100. Specifically, as described above the base includes a "contact portion" (i.e., the distal surface 4523) that can be placed against and/or in contact with the target location. Moving the base 4510 from the first position to the second position causes the base 4510 to engage the extensions 4553 of the release member 4550, thereby moving the extensions 4553 together. The inward movement of the extensions 4553 causes engagement surface of the release member 4550 to become disengaged from the housing 4100, thereby allowing the release member 4550 to be moved proximally along its longitudinal axis as the spring 4576 expands.

Figure 43:
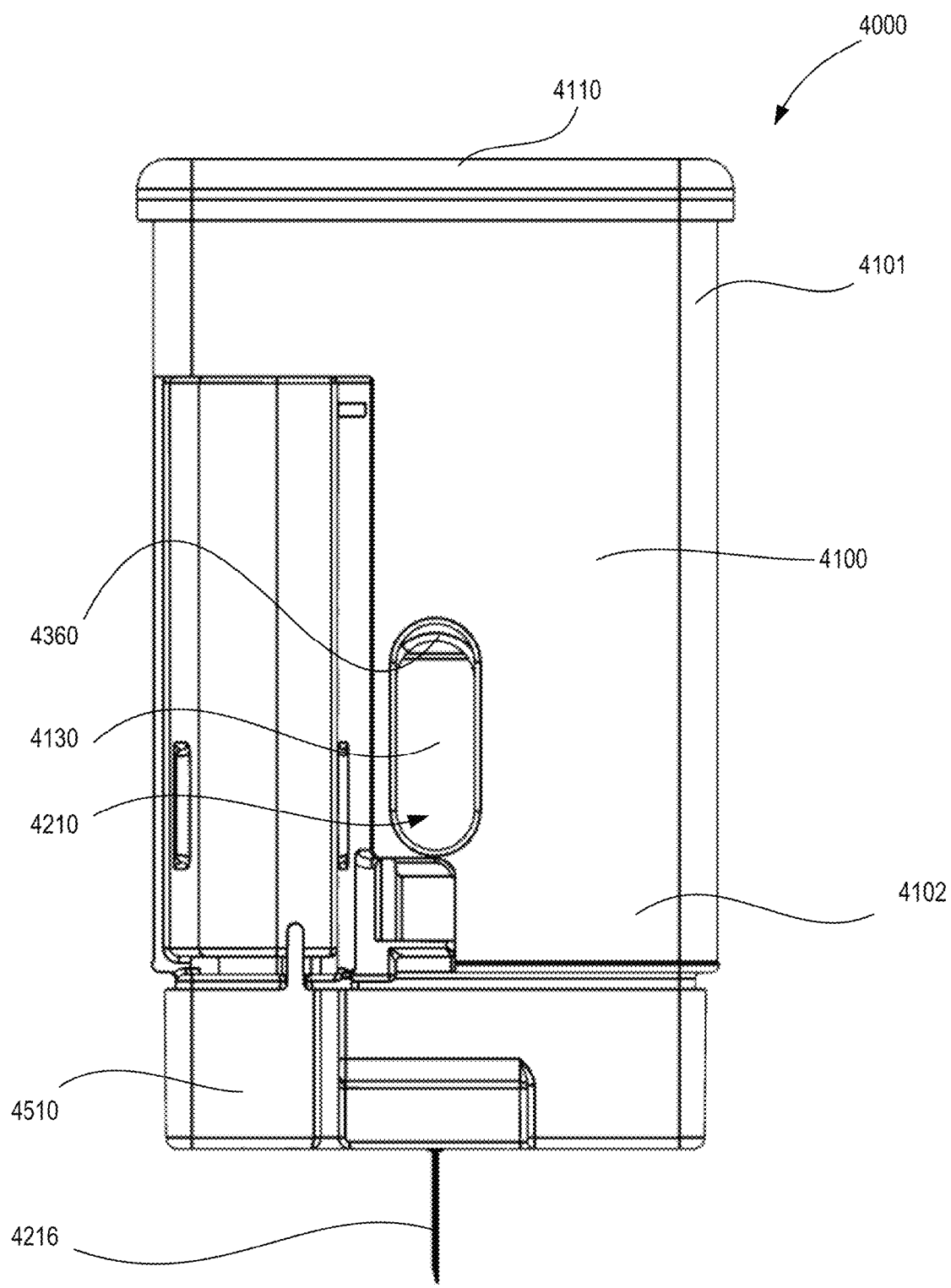
FIG. 43 is a front view of the medical injector shown in FIG. 17, in a fourth configuration (needle inserted).
Figure 44:
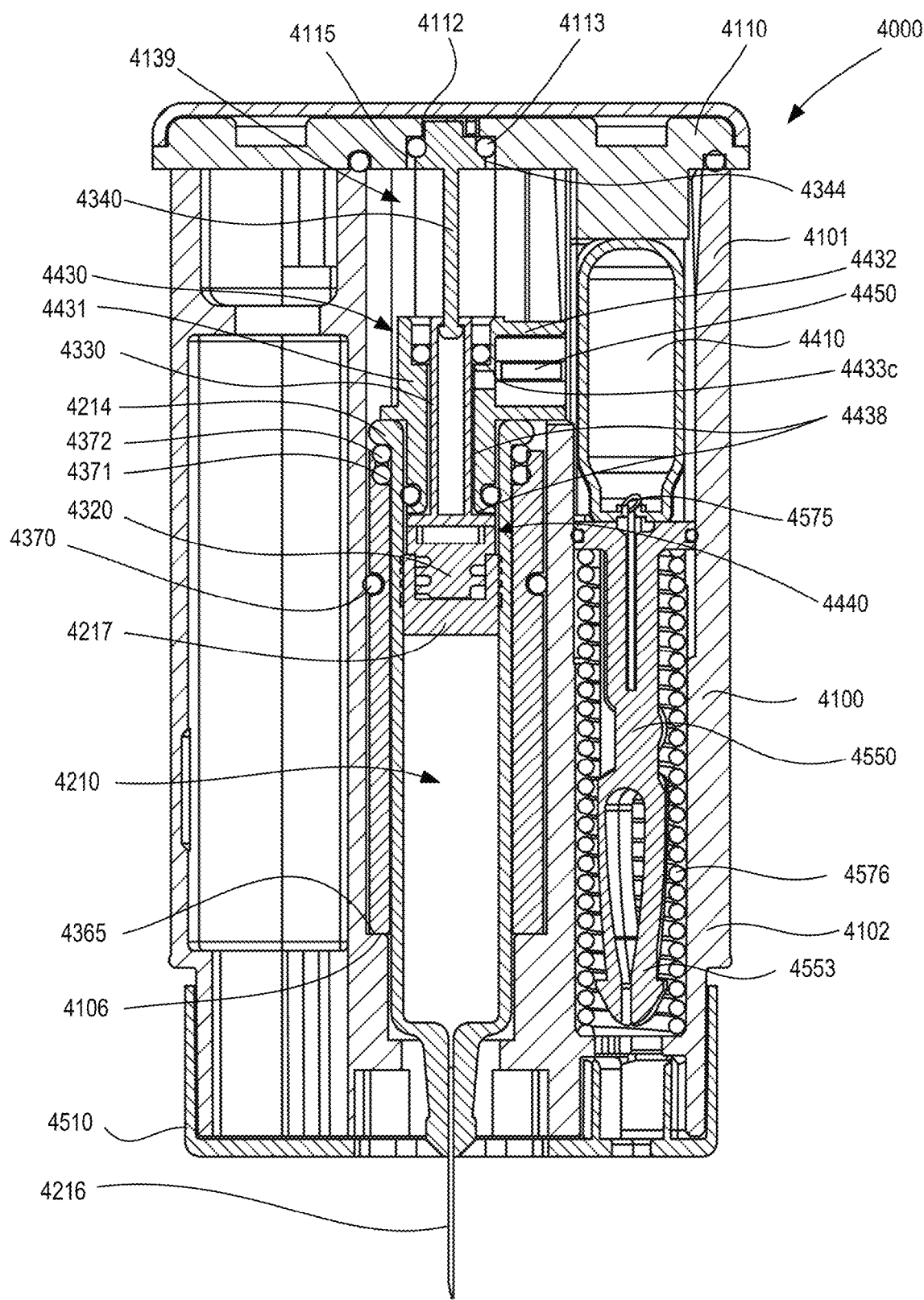
FIG. 44 is a front cross-sectional view of the medical injector shown in FIG. 17, in the fourth configuration (needle inserted).

When the base 4510 is moved from the first position to the second position, the system actuator assembly 4500 actuates the medicament delivery mechanism 4300, thereby placing the medical injector 4000 in its fourth configuration (i.e., the needle insertion configuration), as shown in FIGS. 43-45. More particularly, when the medical injector 4000 is in its fourth configuration, the puncturer 4575 of the release member 4550 is in contact with and/or disposed through the frangible seal 4413 of the gas container 4410.

After the frangible seal 4413 has been punctured, an actuating portion of a compressed gas flows from the gas container 4410, via the gas passageway 4135 and into the medicament cavity 4139 to begin a first phase of expansion (i.e., movement of the carrier assembly 4390 as the device transitions from the third configuration to the fourth configuration). The gas applies gas pressure to flange 4214 of the medicament container, the delivery control mechanism 4430 and/or the top surface of the carrier body 4360. Because the seals 4371, 4372 of the medicament container assembly 4200, the outer seal 4370 of the carrier assembly 4390, and the seals of the delivery control mechanism 4430 maintain the medicament cavity 4139 fluidically isolated from the exterior of the device, the gas pressure exerts a force to move the carrier assembly 4390 distally within the medicament cavity 4139, as shown in FIGS. 44 and 45. The medicament container body 4210 and delivery control mechanism 4430 also move distally together with the carrier assembly 4390. In this manner, the movement of the needle 4216 in a distal direction causes the distal end portion of the needle 4216 to exit the housing 4100 and enter the body of a patient prior to administering the medicament. In some embodiments, the gas container 4410 can contain a pressurized gas at about 1000 psi prior to the frangible seal 4413 being punctured. Once the frangible seal 4413 has been punctured, the pressurized gas is released into the medicament cavity 4139 is pressurized to about 500 psi at the start of the third configuration (i.e., prior to gas vent assembly 4310 and the carrier assembly 4390 actuating). In some embodiments, the compressed gas supplied by the gas container 4410 is an argon gas. In some embodiments the compressed gas supplied by the gas container 4410 is a refrigerant such as R134a.

As shown in FIGS. 44 and 45, when the device moves from the third configuration to the fourth configuration, the gas vent assembly 4310 expands from its collapsed configuration (FIGS. 36A and 42) to a partially expanded configuration. Notably, in the partially expanded configuration, gas pressure within the medicament cavity 4139 acts on an underside of the proximal end portion 4342 and the valve portion 4345 is maintained in a sealed position within the opening 4112 and the O-ring 4113. Thus, the medicament cavity 4139 is maintained in fluidic isolation.

When the needle 4216 has extended by a desired distance, the distal surface 4365 of the carrier body 4360 contacts the shoulder portion 4106 of the housing 4100 to limit further distal movement of the carrier assembly 4390 within the housing 4100. When the distal movement of the carrier assembly 4390 is prevented, the first phase of expansion is complete. The gas within the medicament cavity 4139 (i.e., the housing gas chamber) continues to travel through the delivery control mechanism 4430 to apply gas pressure to the elastomeric member 4217 to begin a second phase of expansion. During the first phase of expansion, the flow restriction provided by the delivery control mechanism 4430 prevents movement of the elastomeric member 4217 prior to the carrier body 4360 contacting the shoulder portion 4106. In some embodiments, the flow delivery control mechanism 4430 can permit gas to pass through the flow restriction member 4450 but not build enough pressure to move the elastomeric member 4217 during the first phase of expansion. In some embodiments, the pressurized gas in the medicament cavity 4139 drops to about 90-100 psi at the end of the fourth configuration (i.e., when the housing 4100 and shoulder portions 4106 limits the carrier assembly 4390 from any further distal movement).

As generally shown in FIG. 27A, the gas from the medicament cavity 4139 passes through and is regulated by the flow restriction member 4450. The gas passing through the flow restriction member 4450 travels through the through-hole 4433c and along an interior passage 4438 between the second inner cylindrical surface 4431d and sidewall 4334 of the second member 4330. The interior passage 4438 between the second member 4330) and the first body portion 4431 defines an annulus-shaped passageway. In some embodiments, the second member 4330 and/or the first body portion 4431 can include one or more dimple or bumper portions extending along the axis $A_1$ to maintain separation between the second member 4330) and/or the first body portion 4431 and to the prevent interior passage 4438 (see FIG. 29) from being sealed or restricted. In some embodiments, a surface of the distal end portion 4331 facing the first body portion 4431 includes one or more grooves or ridges. In some embodiments, a surface of the distal end portion 4331 facing the first body portion 4431 includes a textured surface.

Figure 47:
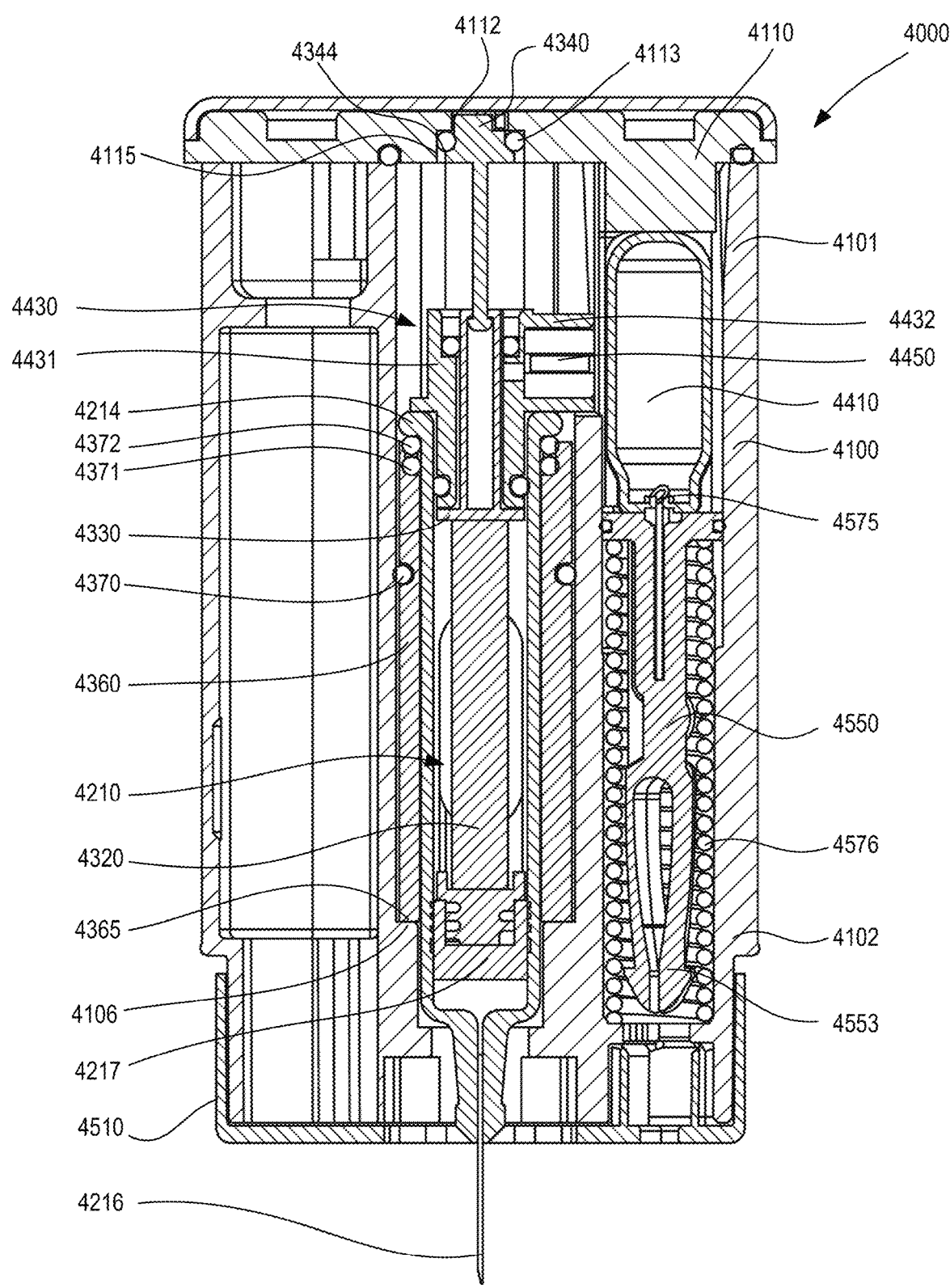
FIG. 47 is a front cross-sectional view of the medical injector shown in FIG. 17, in the fifth configuration (medicament delivered).
Figure 48:
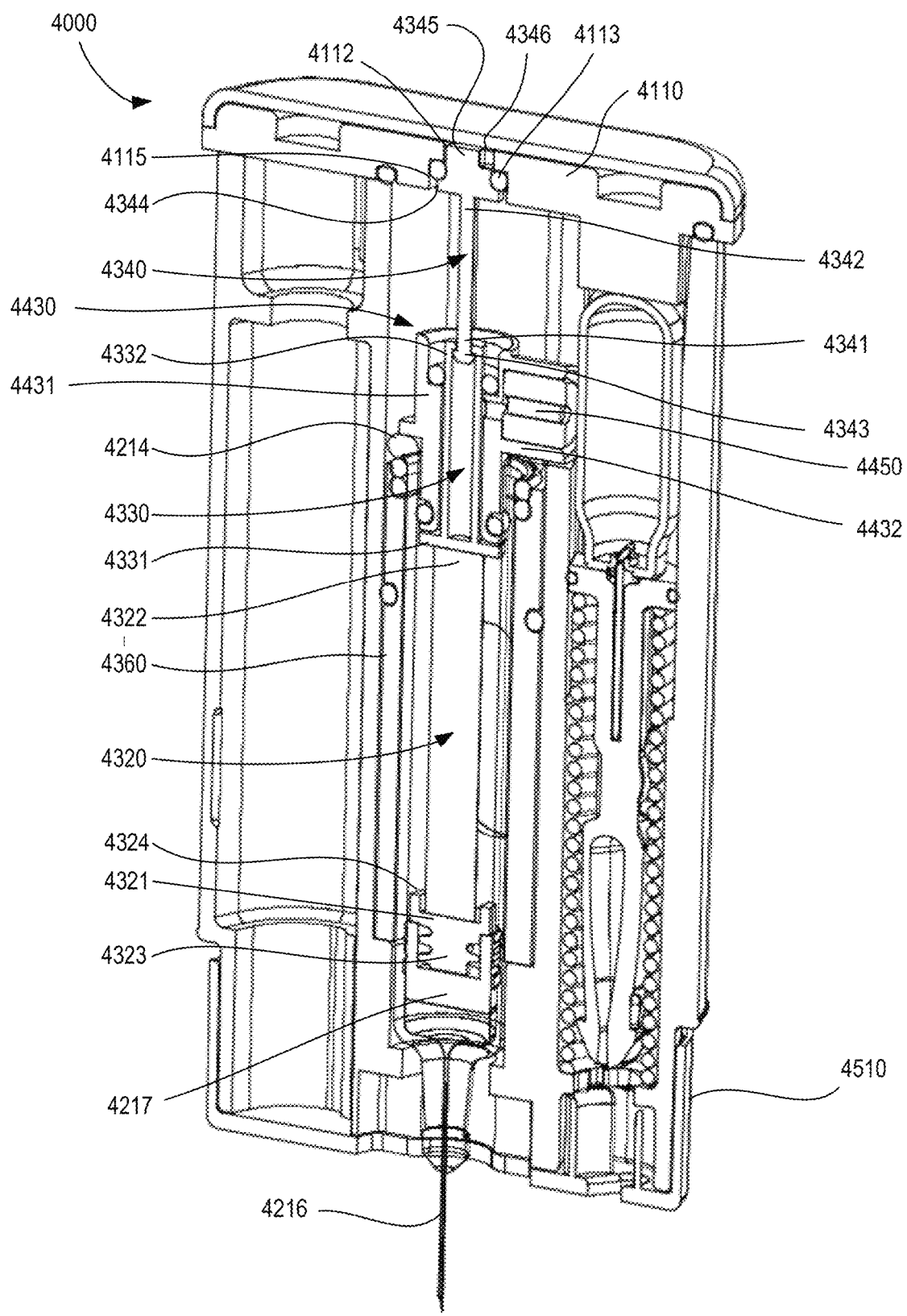
FIG. 48 is a perspective cross-sectional view of the medical injector shown in FIG. 17, in the fifth configuration (medicament delivered).
Figure 49:
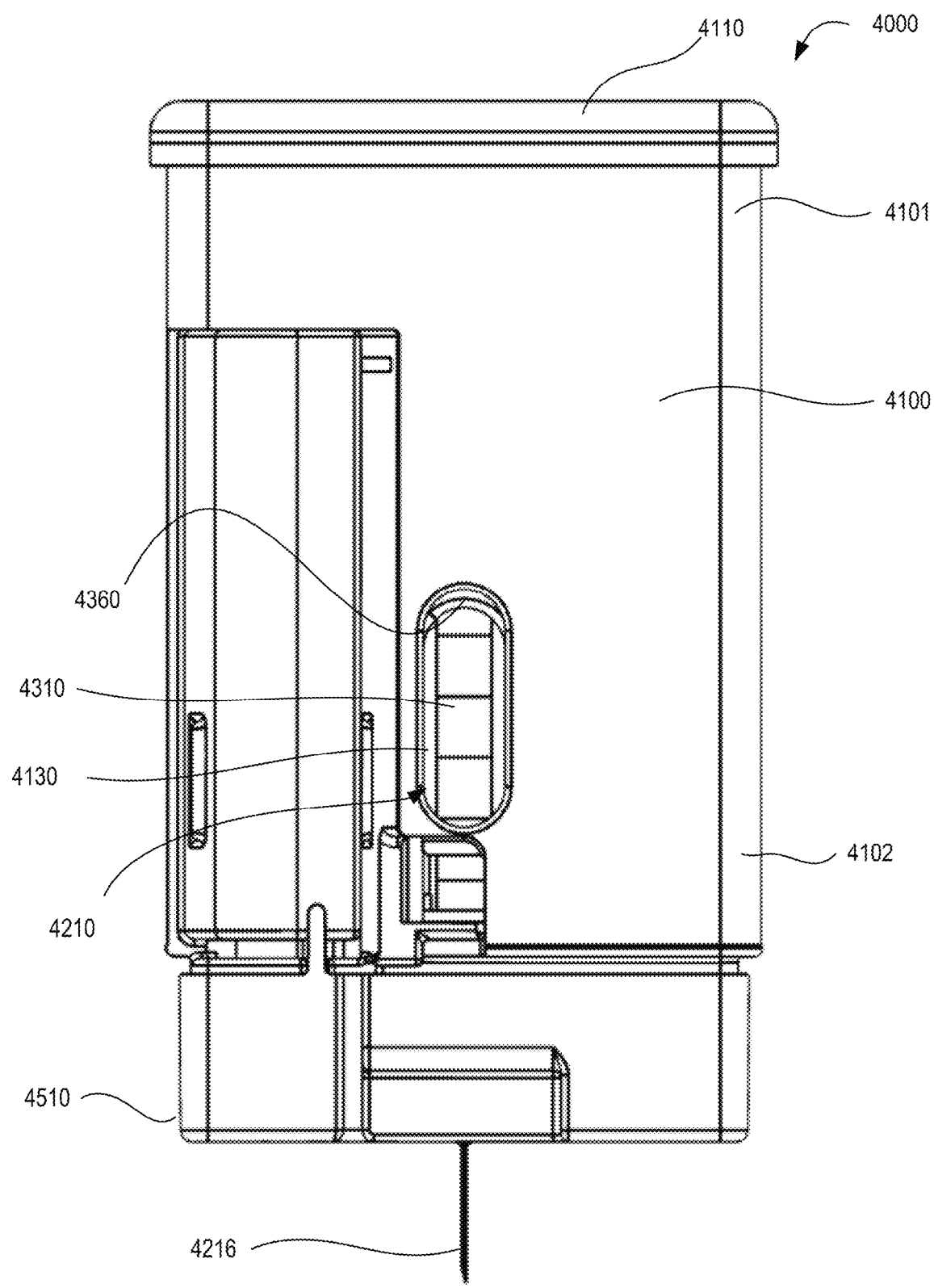
FIG. 49 is a front view of the medical injector shown in FIG. 17, in a sixth configuration (housing gas chamber vented).
Figure 50:
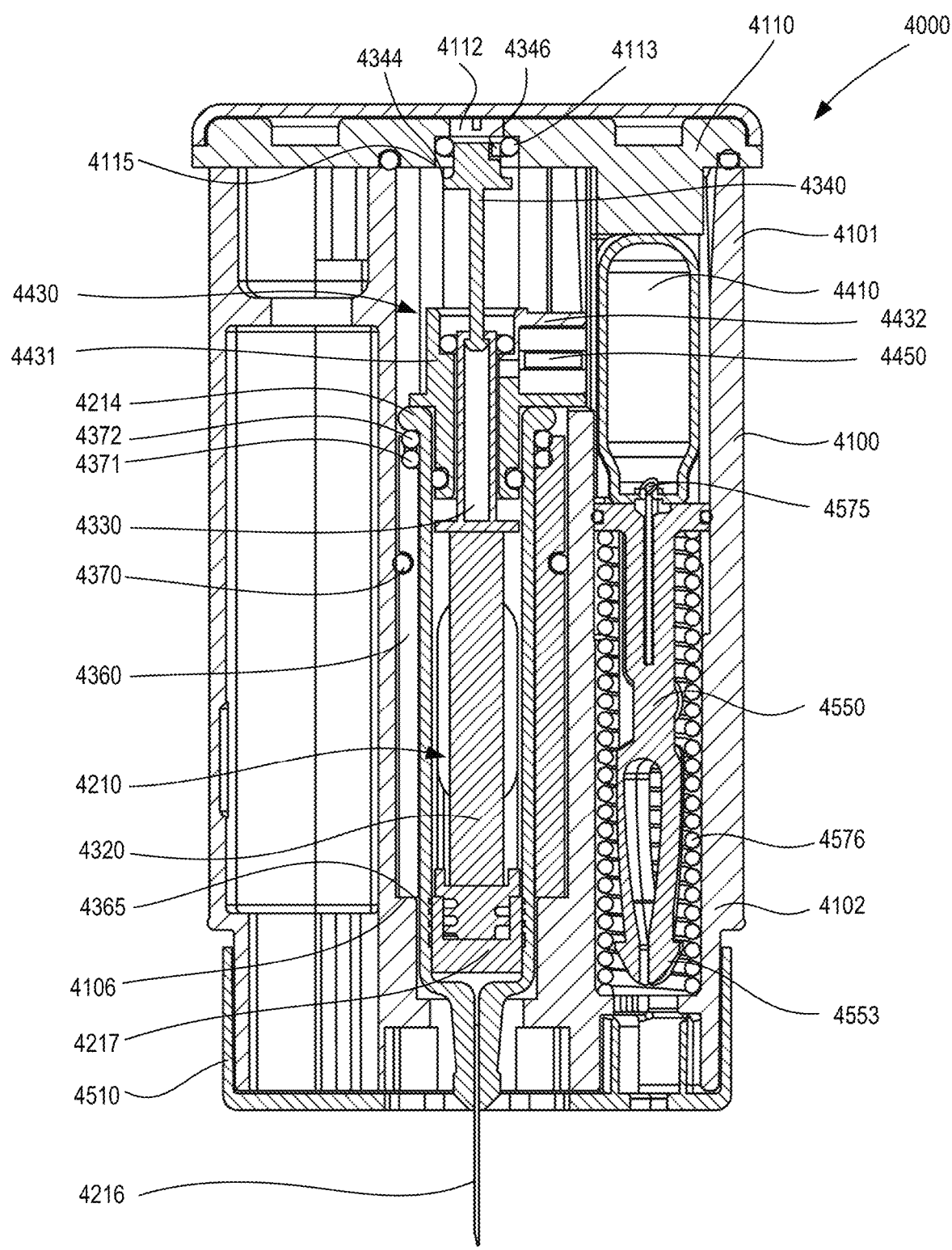
FIG. 50 is a front cross-sectional view of the medical injector shown in FIG. 17, in the sixth configuration (housing gas chamber vented).
Figure 51:
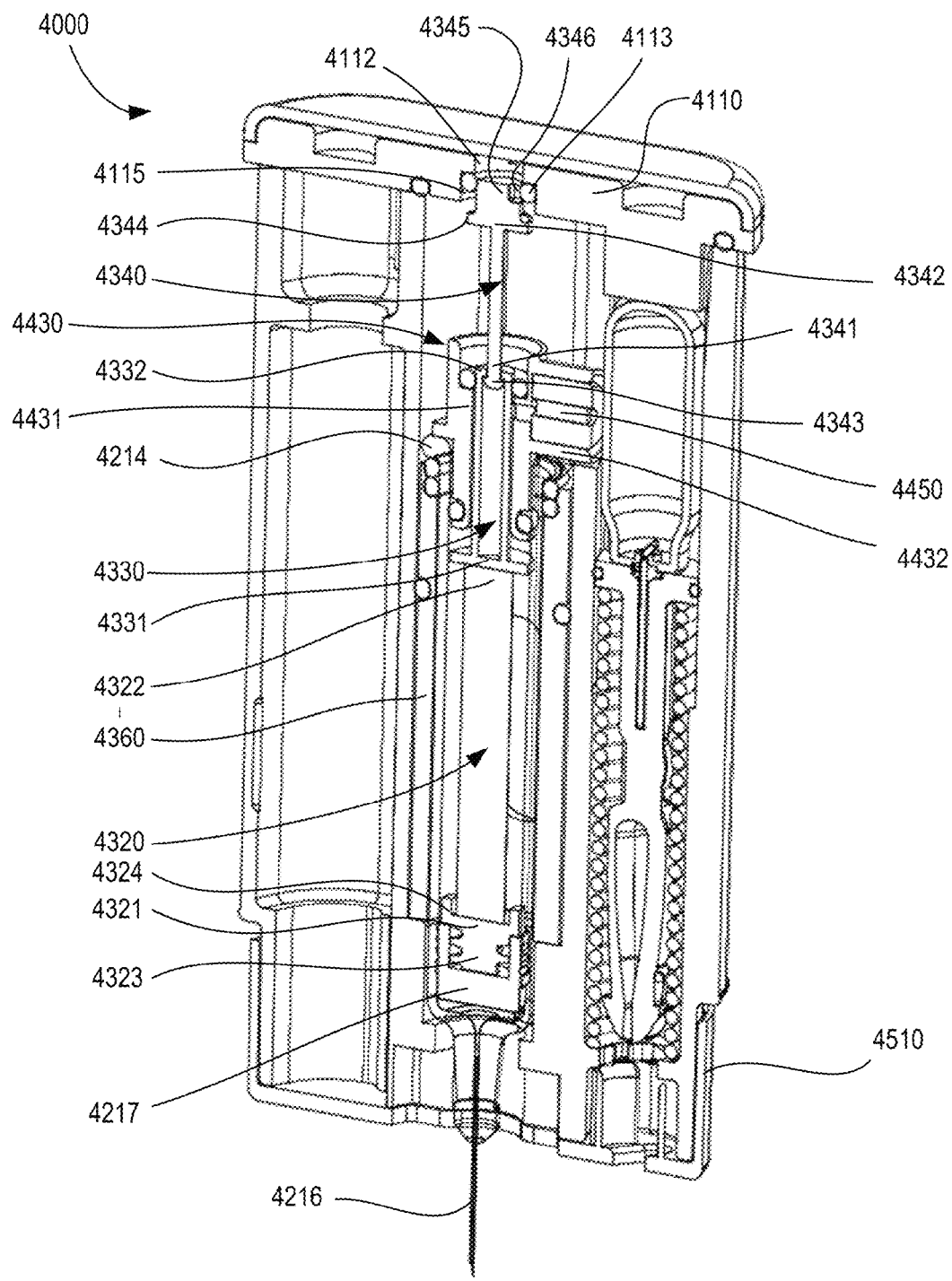
FIG. 51 is a perspective cross-sectional view of the medical injector shown in FIG. 17, in the sixth configuration (housing gas chamber vented).

After passing through the interior passage 4438, the gas enters a medicament body gas chamber 4440 sealed between a distal side of the O-ring 4437 and a proximal side of the elastomeric member 4217. This causes the elastomeric member 4217 (and therefore the first member 4320 of the gas vent assembly 4310) to move in the distal direction within the medicament container body 4210. Distal movement of the elastomeric member 4217 generates a pressure upon the medicament contained within the medicament container assembly 4200, thereby allowing at least a portion of the medicament to flow out of the medicament container assembly 4200 via the needle 4216. The medicament is delivered to a body of a user via the medicament delivery path defined by the medicament container assembly 4200 and the needle 4216. As the elastomeric member 4217 travels to dispense medicament, the gas vent assembly 4310 expands from the partially expanded configuration to a fully expanded configuration and the medical injector is in its fifth configuration (FIGS. 47 and 48). In some embodiments, the medicament body gas chamber 4440 is pressurized to about 10 to 20 psi to begin actuation the elastomeric member 4217.

Figure 46:
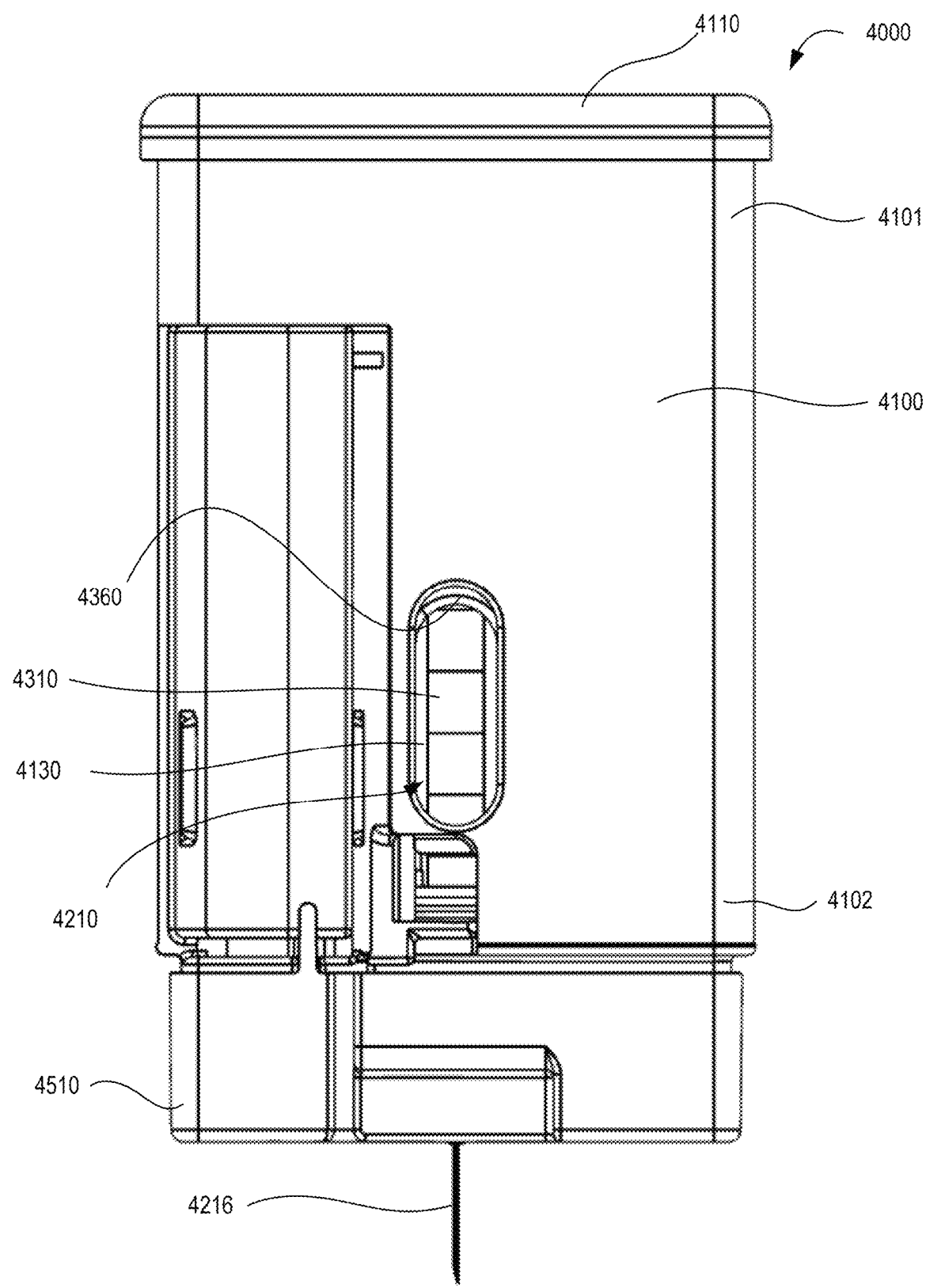
FIG. 46 is a front view of the medical injector shown in FIG. 17, in a fifth configuration (medicament delivered).

As shown in FIG. 46, when the medical injector 4000 is in its fifth configuration and/or is transitioning to its sixth configuration, a portion of the medicament container assembly 4200, a portion of the carrier body 4360, and a portion of the gas vent assembly 4310 can be viewed via the status aperture 4130. As described above, in some embodiments, the housing 4100 can include a label or other indicia providing a color strip to assist the user in identifying the carrier, providing instructions for viewing, or the like. Although not shown in FIG. 11, in some embodiments, a portion of the elastomeric member 4217 is visible via the status aperture 4130 when the medical injector 4000 is in its fifth configuration or in its sixth configuration to indicate that the delivery of medicament is nearing completion or has completed.

As shown in FIGS. 47 and 48, as the elastomeric member 4217 moves distally, the gas vent assembly 4310 moves together with the elastomeric member 4217 in its fully expanded configuration. Once the gas vent assembly 4310 is in the fully expanded configuration and begins to pull on the valve portion 4345, the medical injection 4000 is in its sixth configuration. In this sixth configuration, the elastomeric member 4217 continues to move a predetermined distance within the medicament container body 4210 (corresponding to a remainder of the desired dose), the valve portion 4345 is moved from within the opening 4112 thereby allowing the pressurized gas contained within the housing gas chamber (i.e., the volume within the medicament cavity 4139 between the proximal end of the housing 4100 and the surface of the carrier body 4360) to escape via the passageway 4346 and the opening 4112. More specifically, the pressure applied by the gas in the medicament body gas chamber 4440) on the elastomeric member 4217 is greater than the pressure applied by the gas on the underside of the proximal end portion 4342 and the frictional forces acting on the guide surface 4344. In some embodiments, the medicament body gas chamber 4440 is pressurized to about 30-50 psi to actuate the valve portion 4345.

Figure 53:
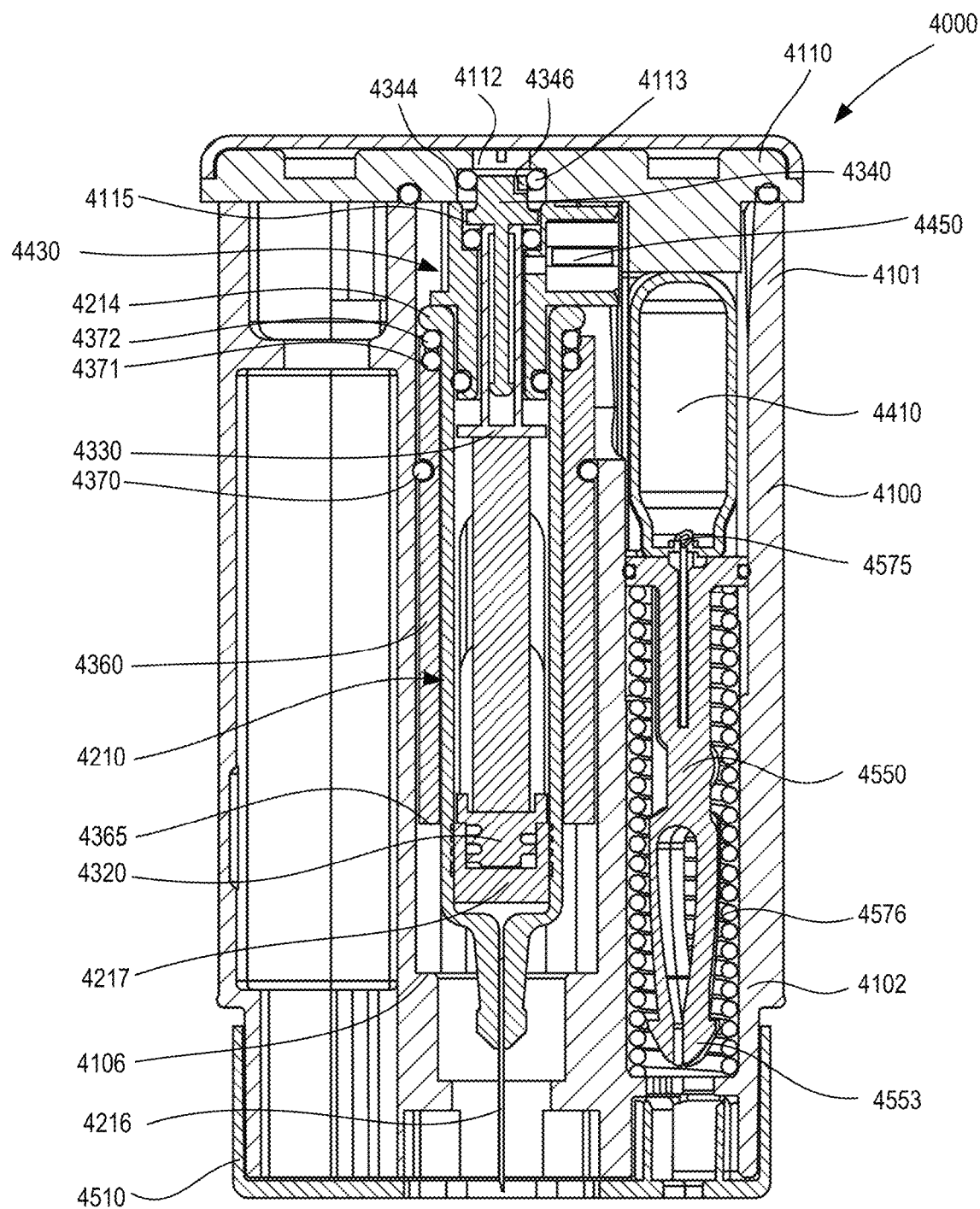
FIG. 53 is a front cross-sectional view of the medical injector shown in FIG. 17, in a seventh configuration (needle retracted).
Figure 54:
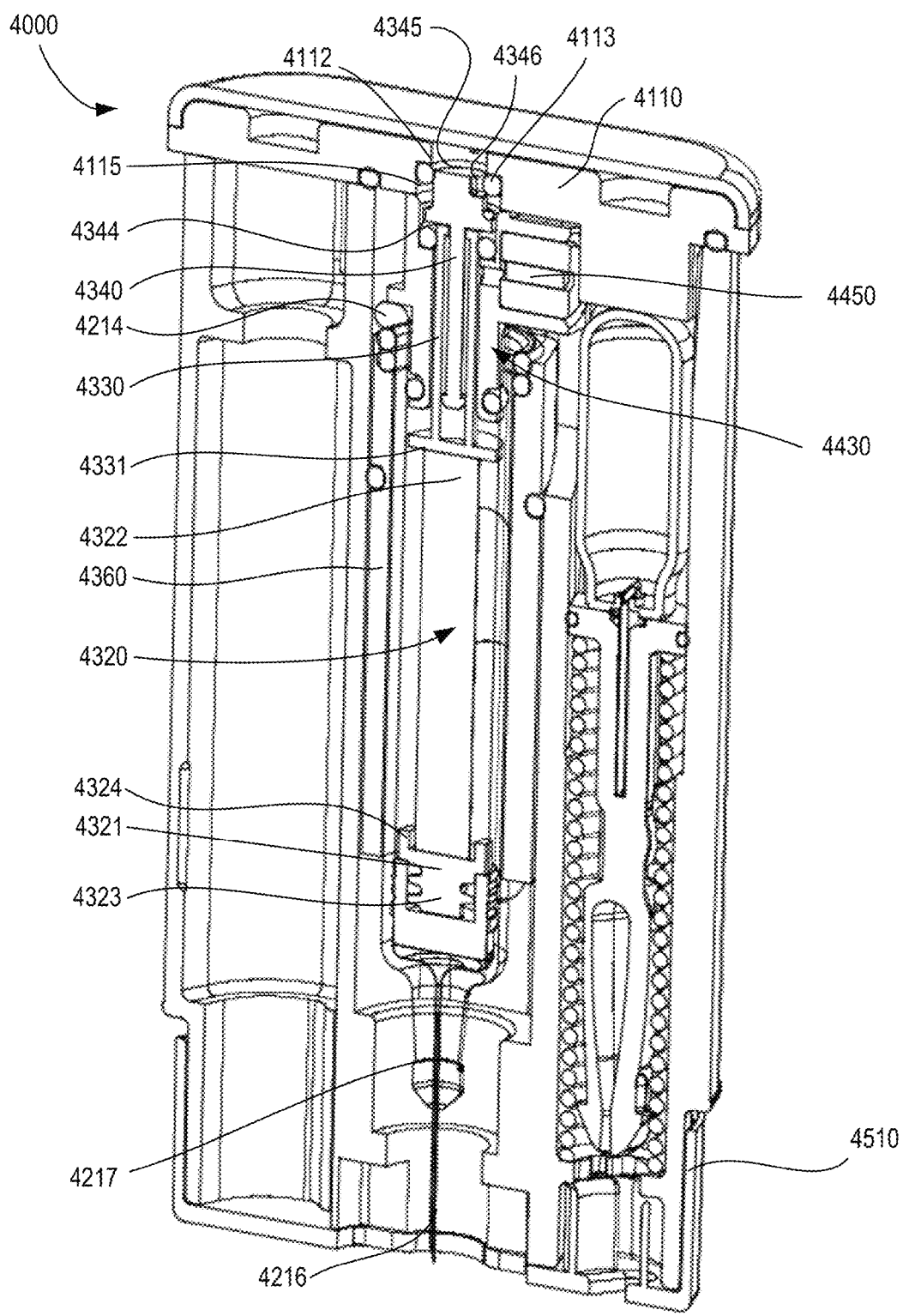
FIG. 54 is a perspective cross-sectional view of the medical injector shown in FIG. 17, in the seventh configuration (needle retracted).

After the gas pressure within the medicament cavity 4139 decreases below a certain level, the force exerted by the retraction spring 4380 on the carrier body 4360 is sufficient to cause the carrier body 4360 to move proximally within the housing 4100 (i.e., to retract). This places the medical injector in its seventh configuration (FIGS. 53 and 54). As shown in FIGS. 27A, 28A, 53 and 54, an inner diameter of the first inner cylindrical surface 4431c is greater than an outer diameter of the guide surface 4344. In this manner, as the carrier assembly 4390, the gas vent assembly 4310, and the flow restriction assembly 4430 move back towards the proximal end of the housing 4100, the first body portion 4431 bypasses the guide surface 4344 to prevent the valve portion 4345 from contact and closing back on the opening 4112.

Figure 52:
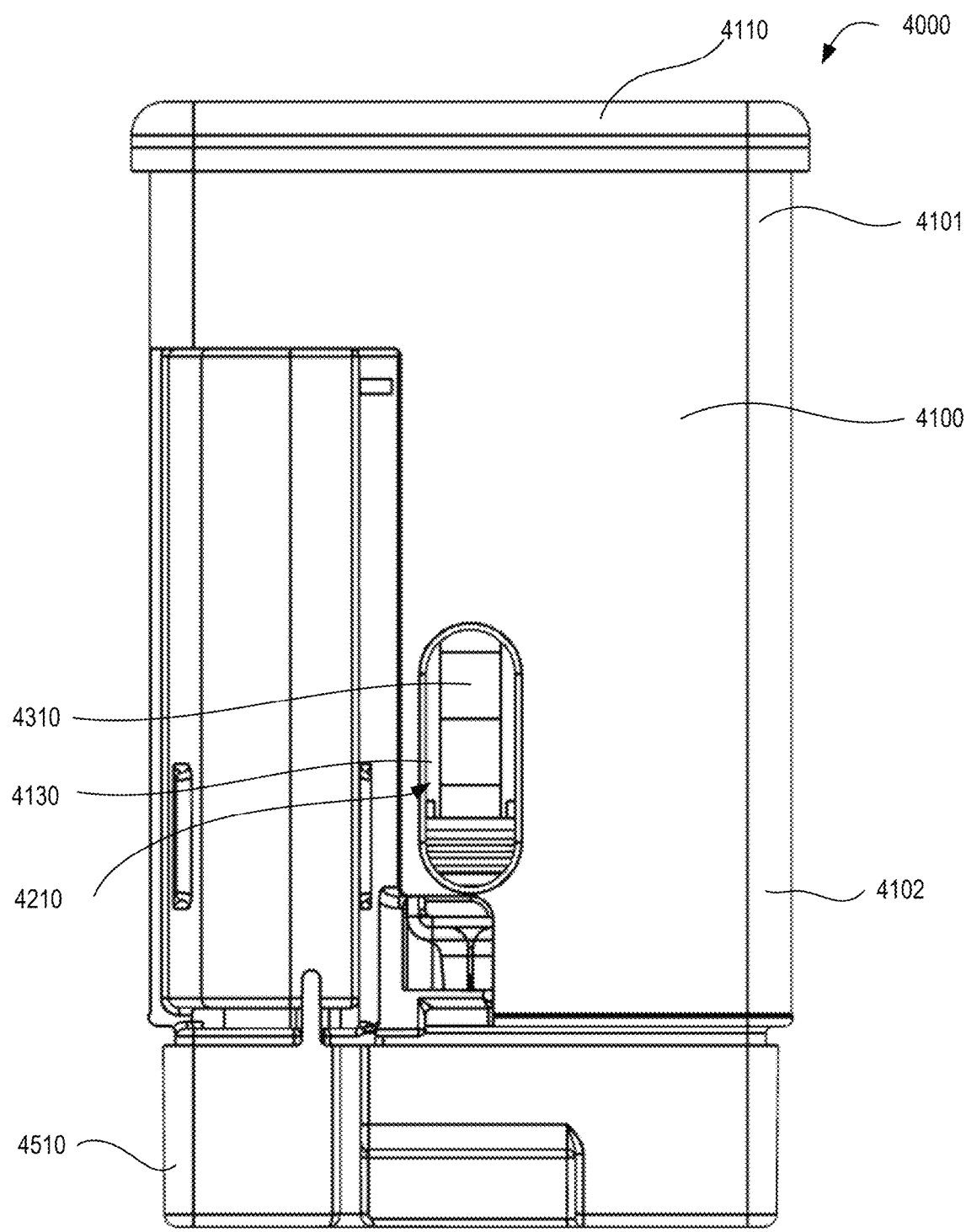
FIG. 52 is a front view of the medical injector shown in FIG. 17, in a seventh configuration (needle retracted).

As shown in FIG. 52, when the medical injector 4000 is in its seventh configuration, a portion of the medicament container assembly 4200 can be viewed via the status aperture 4130. Specifically, as shown, the medicament container body 4210 and a portion of the elastomeric member 4217 are visible via the status aperture 4130. As described above, in some embodiments, the housing 4100 can include a label or other indicia providing a color strip to assist the user in identifying the elastomeric member, providing instructions for viewing, or the like. Although not shown in FIG. 52, in some embodiments, a portion of the carrier body 4360 is visible via the status aperture 4130 when the medical injector 4000 is in its seventh configuration.

As described above, the medicament delivery mechanism 4300 is considered to be a "pistonless" system. With a pistonless gas-powered auto-injector, the force exerted by the gas can move the medicament container relative to the housing and similarly, can move the elastomeric member 4217 relative to (e.g., within) the medicament container body 4210. In some embodiments, by not including a movable mechanism, a piston, and/or the like, a height of the medical injector 4000 can be reduced relative to, for example, the height of a device that includes a rigid, single length piston.

Figure 55:
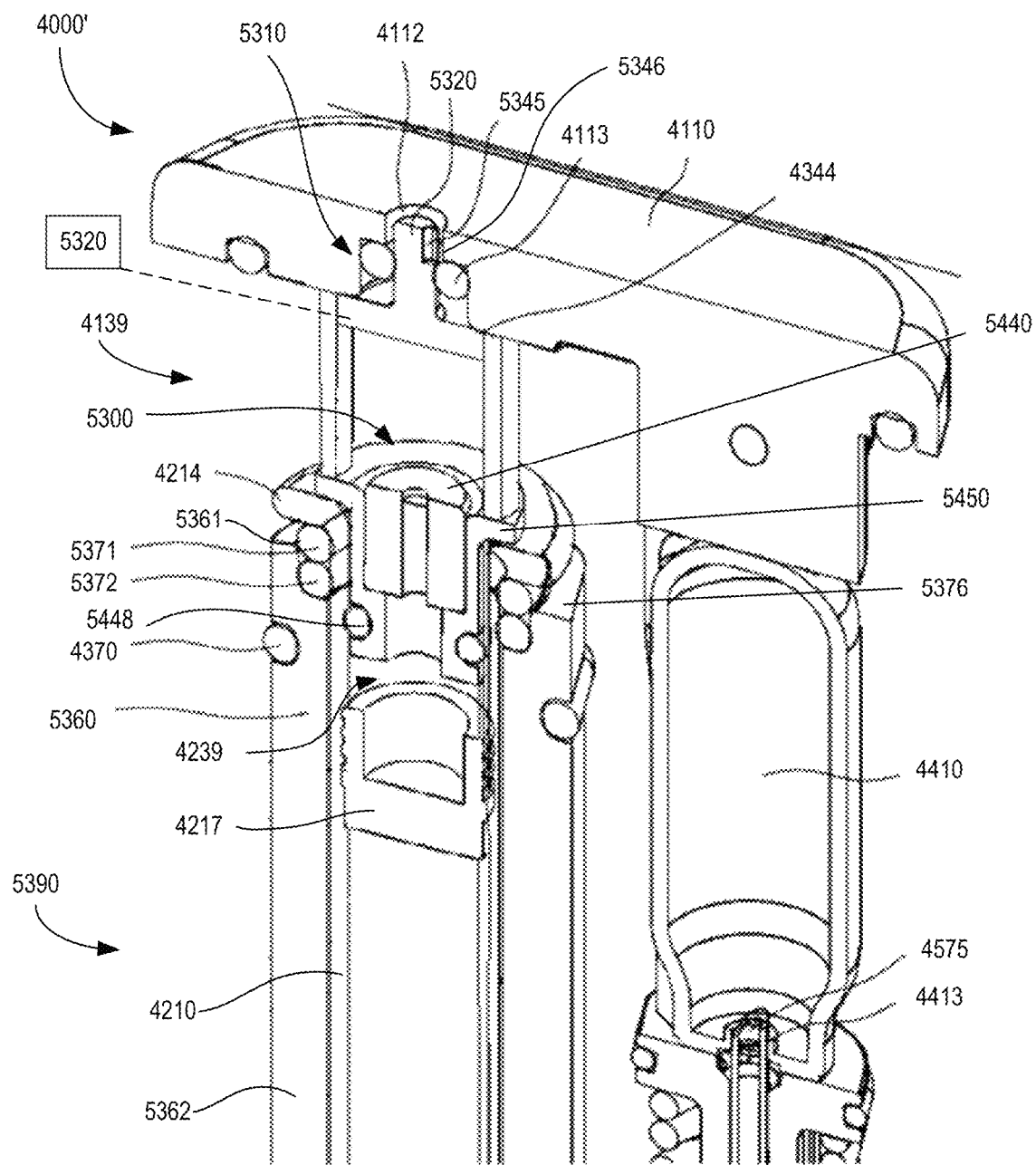
FIG. 55 is a cross-sectional view of a portion of a medical injector according to an embodiment.

Although the medical injector 4000 is shown as including a gas vent assembly 4310 that releases the pressurized gas in response to the elastomeric member 4217 reaching a pre-determined position, in other embodiments, a medical injector can include any suitable mechanism for releasing the pressurized gas. For example, FIG. 55 shows a medical injector 4000' where the medicament delivery mechanism 4300 described above is replaced with a medicament delivery mechanism 5300 as detailed below. The medicament delivery mechanism 5300 includes a carrier assembly 5390 and a gas vent assembly 5310. The gas vent assembly 5310 includes a valve actuator 5320 and a valve portion 5345. The valve actuator 5320 is coupled to the valve portion 5345 and is operable to seal the opening 4112 during storage through the medicament delivery process, and to allow the gas to escape at the end of the injection such that needle 4216 retraction can occur. In some embodiments, the valve actuator 5320 is configured to detect lift off or separation of the base 4510 from the patient after injection. In some embodiments, the medical injector 4000' can include an electronic circuit system, such as one described in relation to the medicament delivery device 2000 above, to detect a location of the elastomeric member and/or detect completion of medicament delivery. In some embodiments, the medical injector 4000', and any of the devices described herein, can include an electronic circuit system described in '8433 PCT.

Once detection of completion has occurred, the valve actuator 5320 actuates the valve portion 5345 to an open position to vent the high pressure gas from the medicament cavity 4139, thereby allowing the needle 4216 to retract by the force of a retraction spring, as described above. In some embodiments, the valve actuator 5320 can be an be an electronically controlled actuator that actuates the valve portion 5345 based on input received from the electronic circuit system described above. In some embodiments, the valve actuator 5320 can be an electronically controlled actuator with one or more sensors to detect lift off of the base 4510 and/or a completion of delivery of a desired dose of medicament. In other embodiments, the valve actuator 5320 is mechanically coupled to the base 4510 such that after the medical injector is actuated subsequent movement of the base 4510 in a distal direction (e.g., that may occur when the user removes the injector from the target location) causes the valve actuator 5320 to actuate the valve portion 5345. In yet other embodiments, the valve actuator 5320 is a manually operated valve. In this manner, a user can depress, pull, slide, or rotate the valve actuator 5320 to the open position. As described herein, the user can detect completion by looking through a status indicator (such as the status indicator 4130) described herein) and/or after receiving an audible or visual alert (such as from output module 2107 described herein).

The carrier assembly 5390 and the gas vent assembly 5310 are each movably disposed within the medicament cavity 4139 of the housing 4100. The carrier assembly 5390 includes a carrier body 5360 and a retraction spring (not shown). The carrier body 5360 includes a proximal end portion 5361 and a distal end portion 5362. The proximal end portion 5361 of the carrier body 5360 defines an opening within which the medicament container body 4210 is disposed. The proximal end portion 5361 also includes a proximal surface 5376, forms a portion of the boundary of the gas chamber (i.e., the portion of the medicament cavity 4139 in which the pressurized gas flows). In this manner, the pressurized gas produces a force on the proximal surface 5376, which moves the carrier assembly 5390 distally within the housing 4100.

In some embodiments, an inner surface of the proximal end portion 5361 defines a groove within which a first O-ring 5371 and a second O-ring 5372 are disposed. The first O-ring 5371 and the second O-ring 5372 are disposed between a top surface of the carrier body 5360 and the flange 4214 of the medicament container body 4210. In this manner, the first O-ring 5371 and the second O-ring 5372 form a substantially fluid-tight seal. Accordingly, when pressurized gas flows into the proximal portion of the medicament cavity 4139 (i.e., the gas chamber), the area between the inner surface of the carrier body 5360 and the medicament container body 4210 is sealed. The first O-ring 5371 and the second O-ring 5372 can also dampen any impact on the flange 4214.

In some embodiments, the medicament delivery mechanism 5300 includes a flow restriction member 5430. The flow restriction member 5430 is inserted into the proximal end portion 4212 of the medicament container assembly 4200, and a medicament control cavity 4239 can be defined within the medicament container assembly 4200 between the flow restriction member 5430 and the elastomeric member 4217. As shown, the flow restriction member 5430 includes a flow restriction retainer 5440 and a flow restriction element 5450, the flow restriction element 5450 being retained at least partially within the flow restriction retainer 5440.

Figure 56:
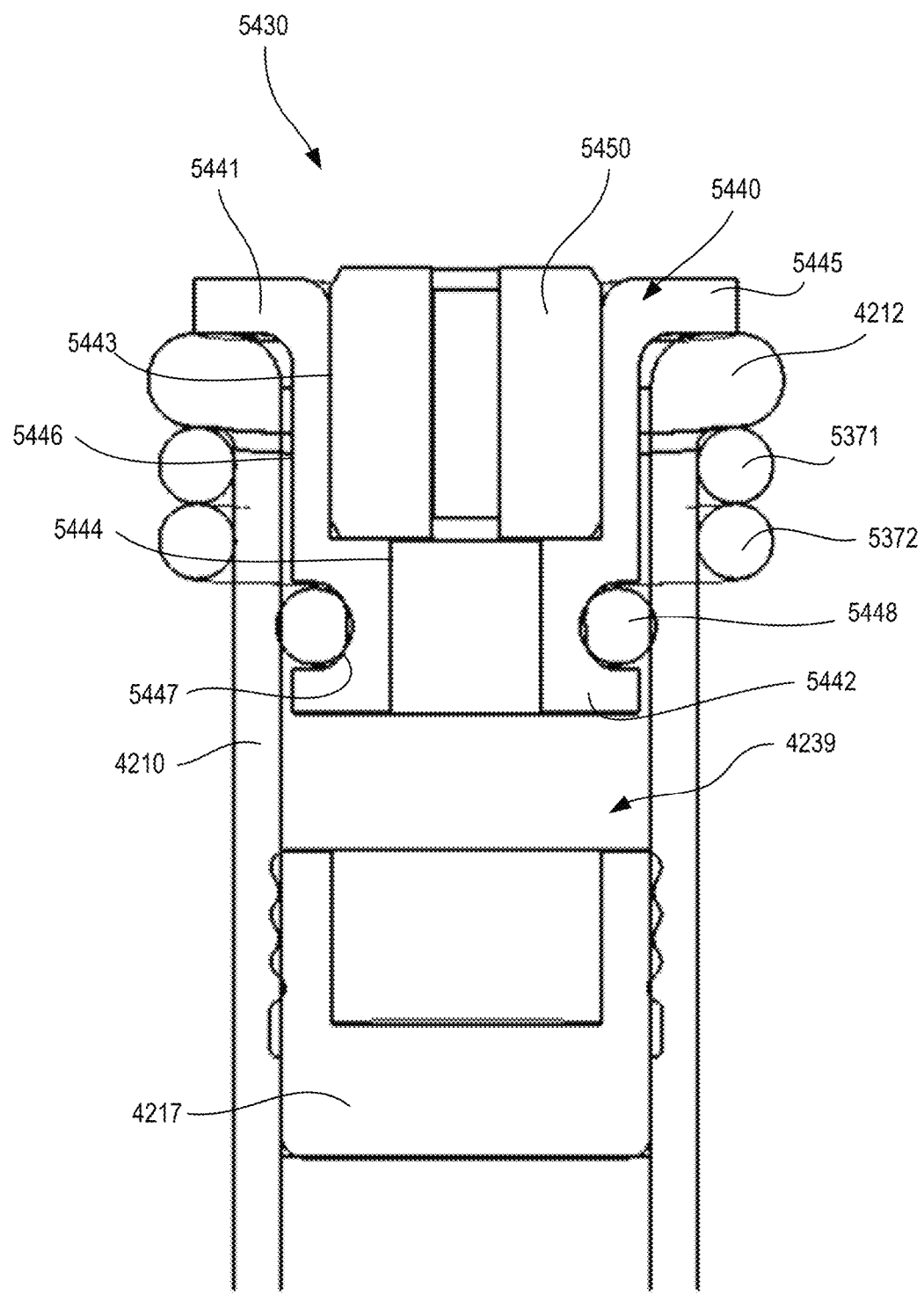
FIG. 56 is an enlarged cross-sectional view of the medical injector shown in FIG. 55.
Figure 57:
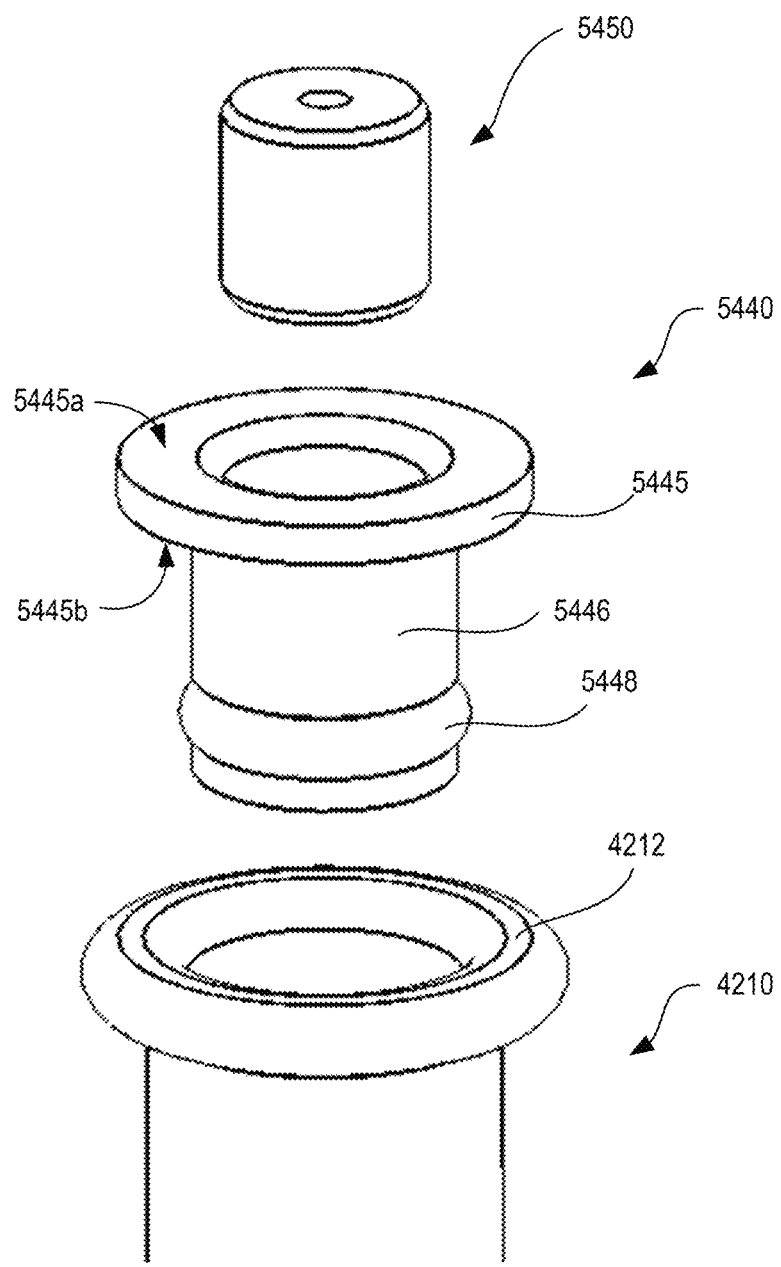
FIG. 57 is an enlarged exploded view of a flow restriction member of the medical injector shown in FIG. 55.

As shown in FIGS. 56 and 57, the flow restriction retainer 5440) includes a proximal end portion 5441 and a distal end portion 5442. The flow restriction retainer 5440 includes a first internal cylindrical portion 5443 and a second internal cylindrical portion 5444, a diameter of the first internal cylindrical portion 5443 being greater than a diameter of the second internal cylindrical portion 5444. The first and second internal cylindrical portions extend parallel to a longitudinal axis of the flow restriction retainer 5440 between the proximal end portion and the distal end portion. In some embodiments, the proximal end portion of the flow restriction retainer 5440 includes a flange portion 5445 extending radially away from the longitudinal axis of the flow restriction retainer 5440. The flange portion 5445 includes at least a top surface 5445*a* and a bottom surface 5445*b*, the top surface 5445*a* being configured to abut against a guide wall 4115 of the proximal cap 4110 (described above) and the bottom surface 5445*b* operable to mount on and abut against a proximal end of the carrier body 5360 to prevent the flow restriction retainer 5440 from migrating relative to the carrier body 5360.

The flow restriction retainer 5440 includes an outer circumferential surface 5446 extending between the proximal end portion 5441 and the distal end portion 5442. The outer circumferential surface 5446 of the flow restriction retainer 5440) is configured to be inserted into the medicament container body 4210 as shown in FIG. 56. In some embodiments, the outer circumferential surface 5446 may include a groove 5447 for securing a seal or O-rings 5448 to prevent pressurized gas from bypassing the flow restriction element 5450) between the outer circumferential surface of the flow restriction retainer 5440) and the carrier body 5360.

In some embodiments, the flow restriction element 5450) can be a filter element, a diaphragm element, a single port orifice, a series of single port orifices, a sieve plate element, an adjustable valve, a single port valve, multi-port valve, or porous member to allow for reduction of pressure during a delivery event. For example, the size of the port(s) or the porosity of the flow restriction element 5450 can be selected to enable gas pressure to be built up in the medicament cavity 4139 and/or the gas chamber to deploy the needle 4216 prior to actuating the elastomeric member 4217. The size of the port(s) or the porosity of the flow restriction element 5450) can also be selected to control a travel speed of the elastomeric member 4217 and therefore the flow rate of the medicament being injected into a patient. In particular, the flow restriction element 5450 can enable the medicament delivery mechanism 5300 to rapidly deploy the needle 4216 via high pressure gas supplied by the gas container 4410 to medicament cavity 4139, but then regulate and reduce the pressure supplied to the medicament control cavity 4239. By limiting the pressure supplied from the medicament cavity 4139 to the medicament control cavity 4239 via the flow restriction element 5450, thereby promoting a slow and gradual build-up of pressure within the medicament control cavity 4239, actuation of the elastomeric member 4217 can be controlled allowing for lower injection forces and/or slower delivery of medicament.

In some embodiments, the flow rate of the medicament can be reduced to less than 0.2 mL/sec (or in some embodiments between 0.05 mL/sec and 0.01 mL/sec) using gas pressure that is initially supplied to medicament cavity 4139 and through the flow restriction element 5450). The lower injection forces and/or slower delivery (compared with pressures supplied directly from the medicament cavity 4139 to the elastomeric member) can produce laminar flow of the medicament through the needle, prevent shearing of high molecular weight compounds in the medicament, and/or reduce pain sensed by a patient particularly if the medicament being delivered is very high viscosity (e.g., greater than about 100 centipoise at room temperature). In some embodiments, a screen or mesh protective member can be provided on a proximal side of the flow restriction element 5450 to prevent any particulate or debris from clogging the flow restriction element 5450) during operation. In some embodiments, the flow restriction element 5450) includes a porous metal or porous ceramic material. The porous material provides multiple passageways through the flow restriction element 5450 thereby preventing clogs if any debris is present within the housing 4100. In some embodiments, the flow restriction element 5450 is calibrated with nitrogen gas ($N_2$) at 30 psig (inlet side) to atmosphere (outlet side) at standard temperature and pressure to have a flow rate of between about 0.5 to 3 standard cubic centimeter per minute (sccm). In some embodiments, the flow restriction member 5450) is calibrated with nitrogen gas ($N_2$) at 30 psig (inlet side) to atmosphere (outlet side) at standard temperature and pressure to have a flow rate of between about 0.75 and 1.5 standard cubic centimeter per minute (sccm). In some embodiments, the flow restriction member 5450 is calibrated with nitrogen gas ($N_2$) at 30 psig (inlet side) to atmosphere (outlet side) at standard temperature and pressure to have a flow rate of about 1 standard cubic centimeter per minute (sccm).

In some embodiments, the compressed gas supplied by the gas container 4410) is an argon gas and the flow restriction member 5450 has a flow rate rating of about 0.75 and 1.5 sccm based on the nitrogen gas calibration described above. In some embodiments, the compressed gas supplied by the gas container 4410 is an argon gas and the flow restriction member 5450) has a flow rate rating of about 1 sccm based on the nitrogen gas calibration described above. In some embodiments, the compressed gas in the gas container 4410 has a molecular weight greater than the molecular weight of argon. For example, in some embodiments, the compressed gas supplied by the gas container 4410 is R134a (Tetrafluoroethane) and the flow restriction member 5450 has a flow rate rating of about 10 to 100 sccm based on the nitrogen gas calibration described above. In some embodiments, the compressed gas supplied by the gas container 4410 is R134a (Tetrafluoroethane) and the flow restriction member 5450) has a flow rate rating of about 20 to 40 sccm based on the nitrogen gas calibration described above.

As with the medical injector 4000, the medical injector 4000' can be moved from the first configuration (i.e., the "storage" state) to the second configuration by moving the safety lock 4700, as described above. From the second configuration (see e.g., FIG. 41), the medical injector 4000' can be moved from the second configuration to the third configuration (see e.g., FIG. 42) by moving the base 4510 from the first position to the second position. By moving the base 4510 from the first position to the second position, the system actuator assembly 4500 actuates the medicament delivery mechanism 5300 to place the medical injector 4000' in a fourth configuration (i.e., the needle insertion configuration). As the base 4510 is moved from the first position to the second position, the system actuator assembly 4500 actuates the medicament delivery mechanism 5300, thereby placing the medical injector 4000' in the fourth configuration (i.e., the needle insertion configuration), as shown in FIG. 44.

In particular, as shown in FIG. 55, when the medical injector 4000' is in the fourth configuration, the puncturer 4575 of the release member 4550) is in contact with and/or disposed through the frangible seal 4413 of the gas container 4410. After the frangible seal 4413 has been punctured, an actuating portion of a compressed gas flows from the gas container 4410, via the gas passageway and into the medicament cavity 4139. The gas applies gas pressure to the flange 4214 of the medicament container and/or the proximal surface 5376 of the carrier body 5360. Because the seals 5371, 5372 and the outer seal 4370) maintain the medicament cavity 4139 fluidically isolated from the exterior of the device, the gas pressure exerts a force to move the carrier assembly 5390 distally within the medicament cavity 4139, as shown in FIGS. 55-57. In this manner, the movement of the needle 4216 in a distal direction causes the distal end portion of the needle 4216 to exit the housing 4100 and enter the body of a patient prior to administering the medicament.

As the compressed gas flows from the gas container 4410 into the medicament cavity 4139 and applies pressure on the flange 4214 of the medicament container and/or the proximal surface 5376 to extend the needle 4216, a portion of the compressed gas passes through flow restriction member 5430. When the needle 4216 has extended by a desired distance, a distal surface of the carrier body 5360 contacts the shoulder portion 4106 of the housing 4100 to limit further distal movement of the carrier assembly 5390 within the housing 4100. While the distal movement of the carrier assembly 5390 is prevented, the gas within the medicament cavity 4139 (i.e., the gas chamber) continues to pass through the flow restriction element 5450) to the medicament control cavity 4239.

As gas pressure builds up in the medicament control cavity 4239 and overcomes frictional forces of the elastomeric member 4217 against the medicament container body 4210, the elastomeric member 4217 begins to move in the distal direction within the medicament container body 4210. Distal movement of the elastomeric member 4217 generates a pressure upon the medicament contained within the medicament container assembly 4200, thereby allowing at least a portion of the medicament to flow out of the medicament container assembly 4200 via the needle 4216. The medicament is delivered to a body of a user via the medicament delivery path defined by the medicament container assembly 4200 and the needle 4216. At the end of injection, the medical injector is in its fifth configuration.

In some embodiments, the flow restriction element 5450) is sized and configured to prevent movement of the elastomeric member 4217 while the needle 4216 is being extended from the housing 4100. Once the needle 4216 is fully extended, the flow restriction element 5450) is configured to permit a sufficient build-up of pressure within the medicament control cavity 4239 to permit movement of the elastomeric member 4217. In some embodiments, the gas pressure within the medicament control cavity 4239 remains lower than a gas pressure of the medicament cavity 4139 throughout the medicament injection process.

After the elastomeric member 4217 has moved a predetermined distance within the medicament container body 4210) (corresponding to the desired dose) to place the medical injector in the sixth configuration, or after the base 4510 has been lifted from the injection site, the valve portion 5345 is moved from within the opening 4112 thereby allowing the pressurized gas contained within the gas chamber (i.e., the volume within the medicament cavity 4139 between the proximal end of the housing 4100 and the surface of the carrier body 5360) to escape via the valve portion 5345 and the opening 4112. After the gas pressure within the medicament cavity 4139 decreases below a certain level, the force exerted by the retraction spring on the carrier body 5360 is sufficient to cause the carrier body 5360 to move proximally within the housing 4100 (i.e., to retract). This places the medical injector in its seventh configuration (FIG. 53).

Figure 58:
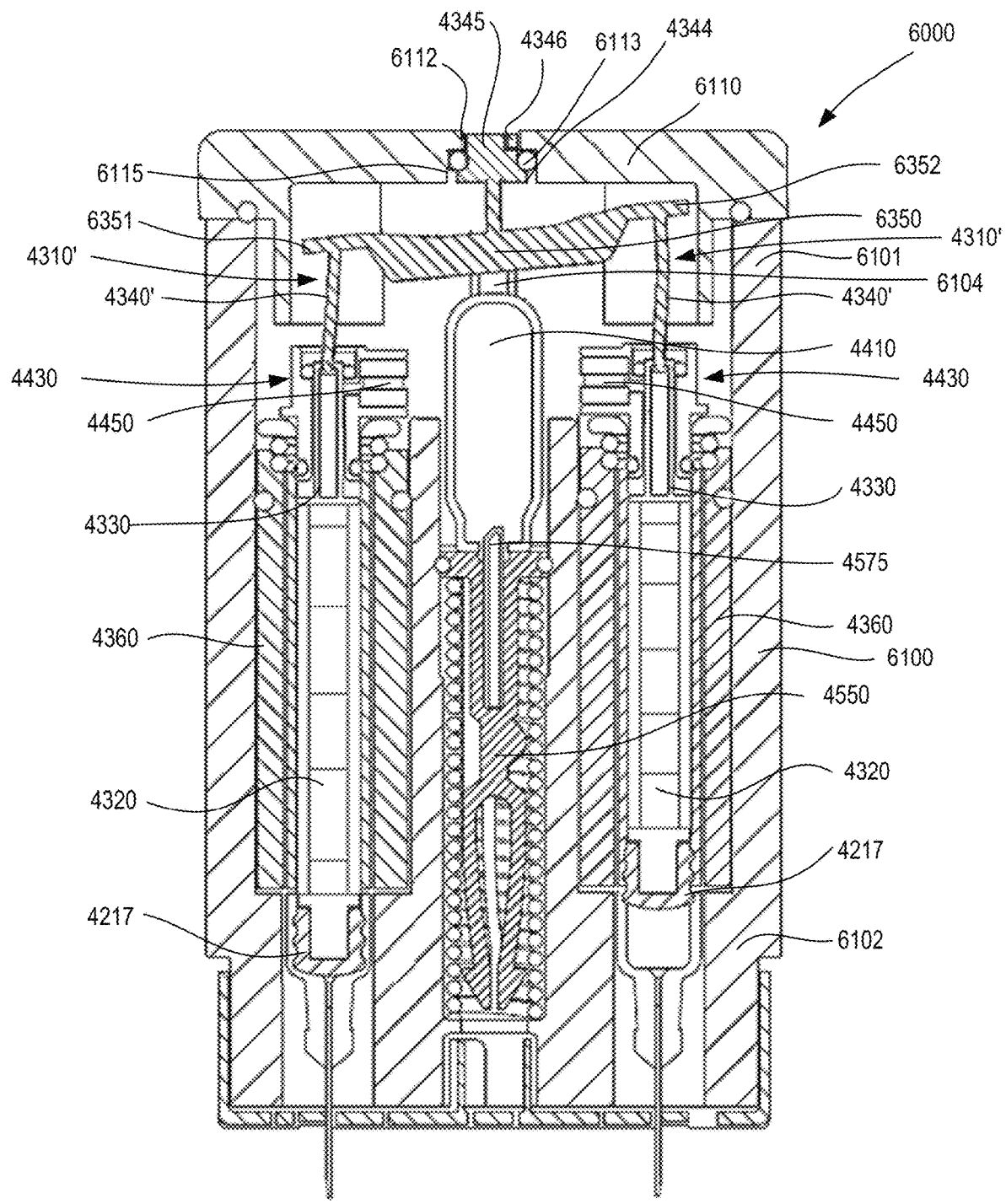
FIG. 58 is a front cross-sectional view of a medical injector according to an embodiment, in a first configuration.
Figure 59:
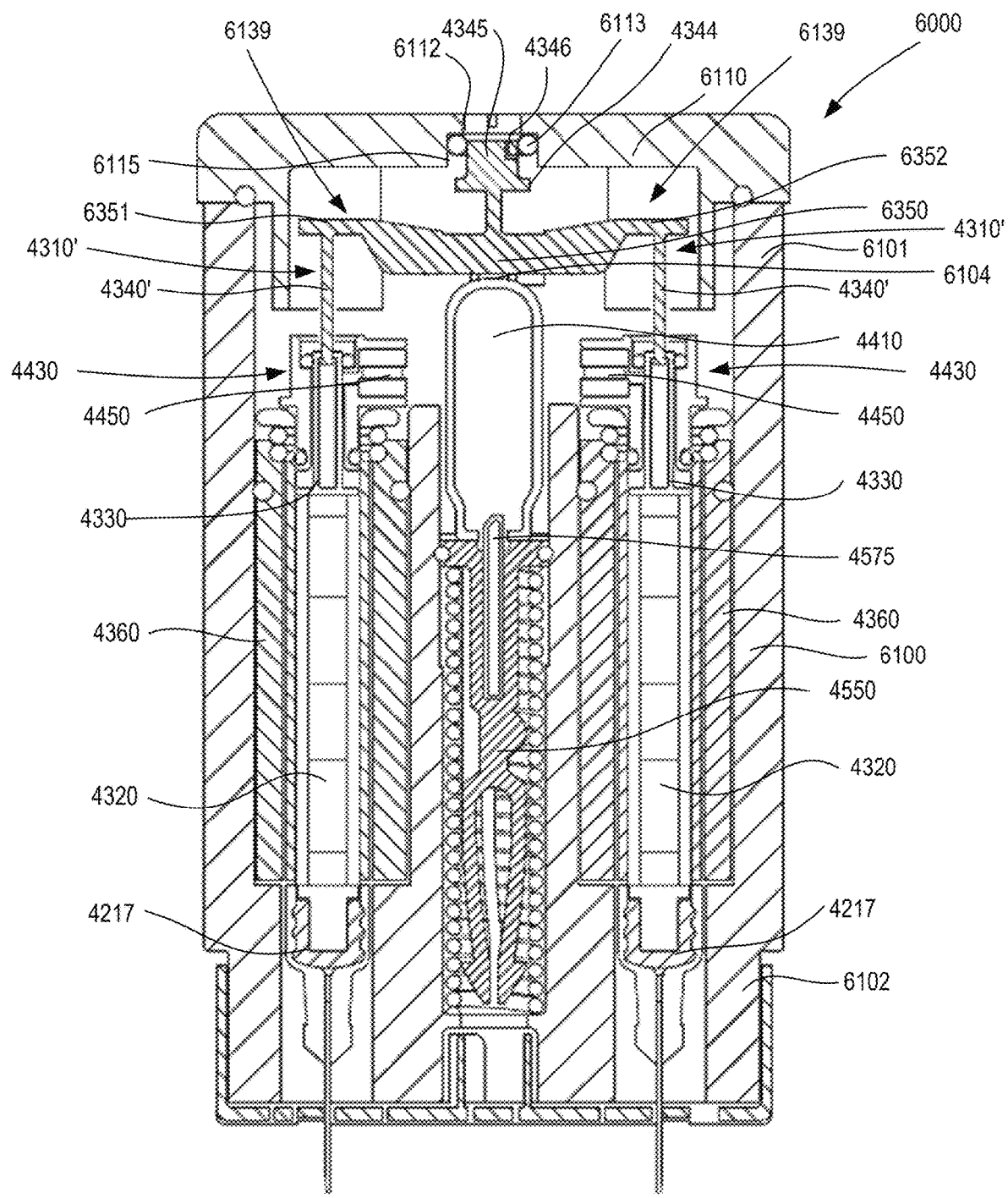
FIG. 59 is a front cross-sectional view of the medical injector of FIG. 58 in a second configuration.

Although the medical injector 4000 is shown as including a single medicament container assembly 4200, in other embodiments, a medical injector can include two or more medicament container assemblies to deliver a large dose (e.g., >1 mL dose) of medicament, or to deliver two separate formulations of medicament, as described above with reference to the medicament delivery device 3000. For example, FIGS. 58 and 59 show a medical injector 6000 with a housing 6100 that replaces the housing 4100. The corresponding components in the medical injector 6000 that are similar to those provided in the medical injector 4000 are identified by the same reference numerals. The housing 6100 includes a proximal end portion 6101, a distal end portion 6102, and a medicament cavity 6139 sized to accommodate two medicament delivery mechanisms 4300, two carrier assemblies 4390, and two delivery control mechanisms 4430. Additionally, the third member 4340 of the gas vent assembly 4310 is modified to be coupled to a combined actuation member 6350 (also referred to as a rocker mechanism) to form a modified gas vent assembly 4310' including a modified third member 4340).

The housing 6100 includes a proximal cap 6110 with a vent opening 6112 that is in fluid communication with a region outside the housing 6100. The proximal cap 6110 further includes a guide wall 6115 within which an O-ring 6113 and the valve portion 4345 is seated when the valve portion 4345 is in a closed configuration. Like the medical injector 4000, the medicament delivery mechanisms 4300 of the medical injector 6000 are each coupled to a delivery control mechanism 4430 to regulate the flow rate of the medicament being dispensed, as described herein. To prevent premature venting of the medicament cavity 6139 and retraction in instances where the first medicament container has completed dispensing medicament, but the second medicament container has not, each of the gas vent assemblies 4310' are coupled to combined actuation member 6350. The combined actuation member 6350) requires both gas vent assemblies 4310' to each move a predetermined distance before the combined actuation member 6350) actuates the valve portion 4345.

Comparing FIG. 36B and FIG. 59, the combined actuation member 6350) is an intermediate member coupled between the distal portion 4341 and the valve portion 4345 of the third (proximal) member 4340) shown in FIG. 36B. The combined actuation member 6350 includes a first arm portion 6351 and a second arm portion 6352. The first arm portion 6351 is coupled to the third member 4340)' associated with the first gas vent assembly 4310'. The second arm portion 6352 is coupled to the third member 4340)' associated with the second gas vent assembly 4310'. In this manner, the combined actuation member 6350) is configured to actuate the valve portion 4345 to an open position only when both sets of the gas vent assemblies 4310 are fully expanded and both of elastomeric members 4217 have completed their entire travel stroke. Stated in a different manner, the combined actuation member 6350 is operable to actuate the valve portion 4345 once force is applied on both the first arm portion 6351 and the second arm portion 6352 as a result of both sets of the medicament delivery mechanisms 4300 transitioning to the sixth configuration, as described above.

A center of the combined actuation member 6350 includes a guide member (not shown) configured to interact with a guide rail or groove 6104 of the housing 6100. The guide member enables the combined actuation member 6350 to rotate (e.g., similar to a see-saw) when force is applied unevenly to the first arm portion 6351 and to the second arm portion 6352. The combined actuation member 6350 translates axially along the guide rail or groove 6104 when force input is received from both the first arm portion 6351 and the second arm portion 6352. Once both sets of the medicament delivery mechanisms 4300 transition to the sixth configuration as described herein, sufficient force is applied through the combined actuation member 6350 to unseat the valve portion 4345 to place the medicament cavity 6139 in fluid communication with an external environment. Retraction of the carrier assemblies 4390) and the medicament delivery mechanisms 4300 can be performed in the same manner as described above for the medical injector 4000. In some embodiments, the guide member is a pin member or a rounded protrusion. In some embodiments, the guide member is a guide rail or groove to translate along a fix guide pin or guide protrusion of the housing 6100.

Although FIGS. 58 and 59 depict the same flow restriction member 4450) installed in each of the delivery control mechanisms 4430, in some embodiments, different flow restriction members can be used to vary the gas pressure applied to each respective medicament container gas chamber 4440. For example, in some embodiments, a different dosage and/or formulation of medicament may be supplied to each of the medicament container bodies 4210) and the flow restriction properties can be adjusted to regulate the flow rate desired for each of the medicaments to prevent damage to the medicaments and/or to minimize discomfort to the patient.

In some embodiments, the flow restriction member 4450 includes a porous material. In some embodiments, the porous material is sintered porous metal. In some embodiments, the flow restriction member 4450 is calibrated with nitrogen gas ($N_2$) at 30 psig (inlet side) to atmosphere (outlet side) at standard temperature and pressure to have a flow rate of between about 0.5 to 3 standard cubic centimeter per minute (sccm). In some embodiments, the flow restriction member 4450 is calibrated with nitrogen gas ($N_2$) at 30 psig (inlet side) to atmosphere (outlet side) at standard temperature and pressure to have a flow rate of between about 0.75 and 1.5 standard cubic centimeter per minute (sccm). In some embodiments, the flow restriction member 4450 is calibrated with nitrogen gas ($N_2$) at 30 psig (inlet side) to atmosphere (outlet side) at standard temperature and pressure to have a flow rate of about 1 standard cubic centimeter per minute (sccm).

In some embodiments, the compressed gas supplied by the gas container 4410) is an argon gas and the flow restriction member 4450 has a flow rate rating of about 0.75 and 1.5 sccm based on the nitrogen gas calibration described above. In some embodiments, the compressed gas supplied by the gas container 4410 is an argon gas and the flow restriction member 4450) has a flow rate rating of about 1 sccm based on the nitrogen gas calibration described above. In some embodiments, the compressed gas in the gas container 4410 has a molecular weight greater than the molecular weight of argon. For example, in some embodiments, the compressed gas supplied by the gas container 4410 is R134a (Tetrafluoroethane) and the flow restriction member 4450 has a flow rate rating of about 10 to 100 sccm based on the nitrogen gas calibration described above. In some embodiments, the compressed gas supplied by the gas container 4410 is R134a (Tetrafluoroethane) and the flow restriction member 4450 has a flow rate rating of about 20 to 40 sccm based on the nitrogen gas calibration described above.

In some embodiments, the flow rate of the medicament can be reduced to less than 0.2 mL/sec (or in some embodiments between 0.05 mL/sec and 0.01 mL/sec) using gas pressure that is initially supplied to medicament cavity 6139 and through the flow restriction member 4450). The lower injection forces and/or slower delivery (compared with pressures supplied directly from the medicament cavity 6139 to the elastomeric member) can produce laminar flow of the medicament through the needle, prevent shearing of high molecular weight compounds in the medicament, and/ or reduce pain sensed by a patient particularly if the medicament being delivered is very high viscosity (e.g., greater than about 100 centipoise at room temperature). In some embodiments, a screen or mesh protective member can be provided on a proximal side of the flow restriction member 4450 to prevent any particulate or debris from clogging the flow restriction element 4450b during operation.

Figure 60:
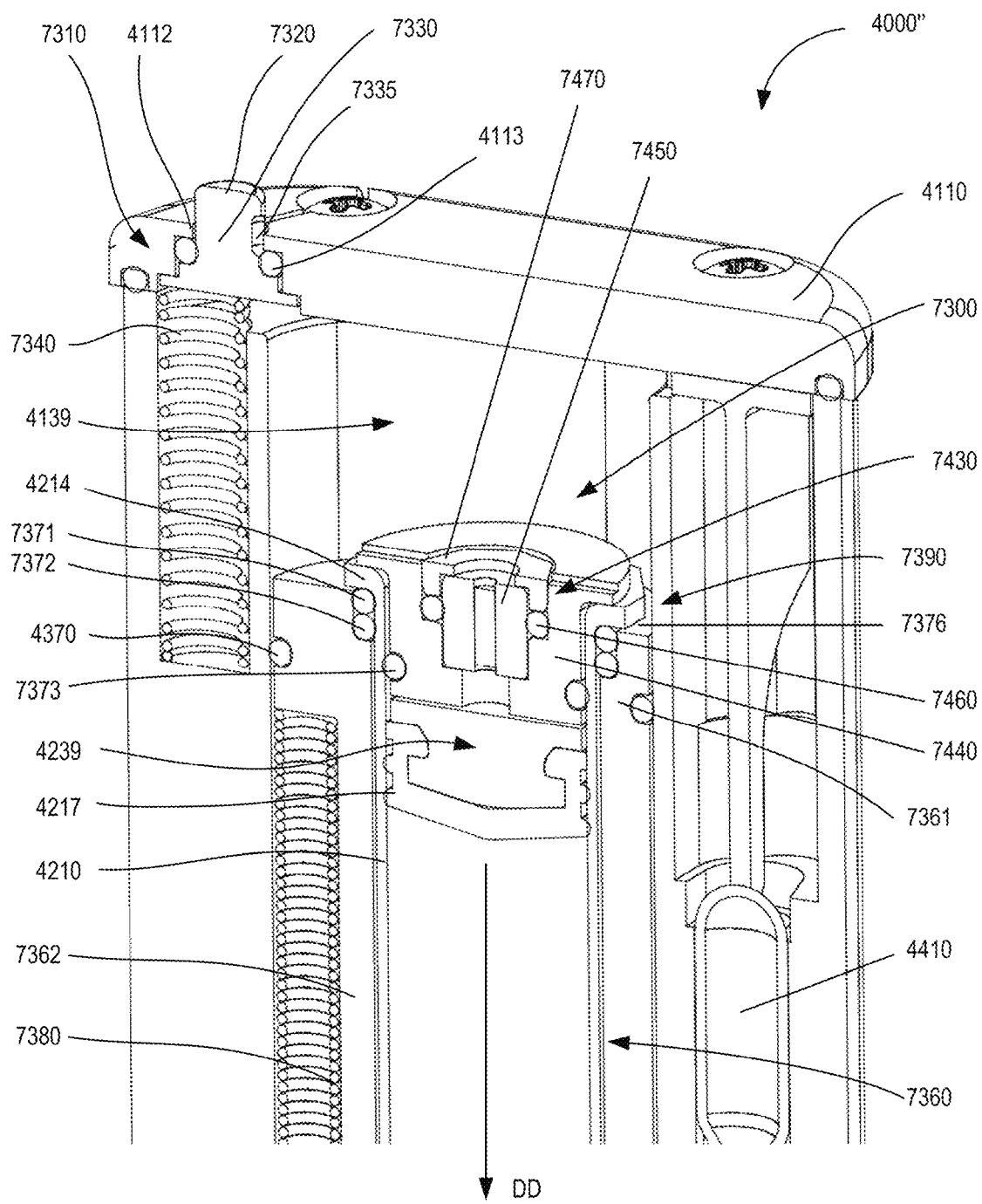
FIG. 60 is a cross-sectional view of a portion of a medical injector according to an embodiment.

Although the medical injector 4000 is shown as including a gas vent assembly 4310 that releases the pressurized gas in response to the elastomeric member 4217 reaching a predetermined position, in other embodiments, a medical injector can include any suitable mechanism for releasing the pressurized gas. For example, FIG. 60 shows a medical injector 4000" where the medicament delivery mechanism 4300 described above is replaced with a medicament delivery mechanism 7300 (also referred to as a control assembly) and a gas vent assembly 7310 as detailed below. The medicament delivery mechanism 7300 includes a carrier assembly 7390 and the gas valve assembly 7310 (also referred to as a vent valve assembly). The gas valve assembly 7310 includes a valve actuator 7320, a valve member 7330, and a valve spring member 7340. The valve member 7330 includes a valve passageway 7335 that is sealed against the opening 4112 in a first position (e.g., during storage through the medicament delivery process), and separated from the opening 4112 in a second position to let the gas within the medical injector 4000" escape to the outside environment (e.g., at the end of the injection such that needle 4216 retraction can occur). The valve spring member 7340 applies a force on the valve member 7330 and presses the valve member 7330 against the proximal cap 4110 to maintain or return the valve member 7330 back to the first position.

The valve actuator 7320 extends beyond a surface of the proximal cap 4110 and is configured to be depressed by an operator, against the force of the valve spring member 7340, to move the valve member 7330 from the first position (i.e., closed position) to the second position (i.e., open position). When the operator releases the valve actuator 7320 (i.e., when the operator is no longer pressing on the valve actuator 7320), the force of the valve spring member 7340) moves the valve member 7330 from the second position to the first position. Although the valve actuator 7320 is shown as a push button in FIG. 60, in some embodiments, the valve actuator 7320 can be configured as a push, slide, or rotatable switch or lever. In some embodiments, the medical injector 4000" can include an electronic circuit system, such as one described in relation to the medicament delivery device 2000 above, to detect a location of the elastomeric member and/or detect completion of medicament delivery. In some embodiments, the medical injector 4000", and any of the devices described herein, can include an electronic circuit system described in '8433 PCT.

As described herein, the operator can detect completion by looking through a status indicator (such as the status indicator 4130 described herein) and/or after receiving an audible or visual alert (such as from output module 2107 described herein). Once completion of delivery has been detected, the operator can depress the valve actuator 7320 to actuate the valve member 7330 from the first position to the second position, thereby causing high pressure gas to vent out of the medicament cavity 4139 and into the atmosphere/ external environment. As the high pressure gas is vented, the needle 4216 retracts due to the force applied by the retraction spring 7380, as described generally above. Although the valve member 7330 is shown and described as returning to the first position (i.e., closed position) when the user removes force from the valve actuator 7320, in other embodiments, the gas vent assembly 4310 can include a latch or hysteresis mechanism (not shown) to maintain the valve member 7330 in the second position (i.e., opened position) after gas release has started. In this manner, the gas vent assembly can ensure full exhaustion of gas from the device.

The carrier assembly 7390 and the gas valve assembly 7310 are each movably disposed within the medicament cavity 4139 of the housing 4100. The carrier assembly 7390 includes a carrier body 7360 and a retraction spring 7380. The carrier body 7360 includes a proximal end portion 7361 and a distal end portion 7362. The proximal end portion 7361 of the carrier body 7360 defines an opening within which the medicament container body 4210 is disposed. The proximal end portion 7361 also includes a proximal surface 7376, which forms a portion of the boundary of the gas chamber (i.e., the portion of the medicament cavity 4139 within which the pressurized gas flows). In this manner, the pressurized gas produces a force on the proximal surface 7376, which moves the carrier assembly 7390 distally within the housing 4100.

In some embodiments, an inner surface of the proximal end portion 7361 defines a groove within which a first O-ring 7371 and a second O-ring 7372 are disposed. The first O-ring 7371 and the second O-ring 7372 are disposed between a top surface of the carrier body 7360 and the flange 4214 of the medicament container body 4210. In this manner, the first O-ring 7371 and the second O-ring 7372 form a substantially fluid-tight seal. Accordingly, when pressurized gas flows into the proximal portion of the medicament cavity 4139 (i.e., the gas chamber), the area between the inner surface of the carrier body 7360 and the medicament container body 4210 is sealed. The first O-ring 7371 and the second O-ring 7372 can also dampen any impact on the flange 4214.

In this embodiment, the medicament delivery mechanism 7300 includes a flow restriction member 7430. The flow restriction member 7430 is inserted into the proximal end portion 4212 of the medicament container assembly 4200, and a medicament control cavity 4239 can be defined within the medicament container assembly 4200 between the flow restriction member 7430) and the elastomeric member 4217. As shown, the flow restriction member 7430) includes a flow restriction retainer 7440), a flow restriction element 7450), a flow restriction seal member 7460), and a flow restriction cap 7470. The flow restriction element 7450 is at least partially inserted within the flow restriction retainer 7440. The flow restriction seal member 7460 is disposed between the flow restriction element 7450) and the flow restriction retainer 7440 to prevent pressurized gas from bypassing the flow restriction element 7450 as the pressurized gas travels from the medicament cavity 4139 to the medicament control cavity 4239. The flow restriction cap 7470 is at least partially inserted within the flow restriction retainer 7440. The flow restriction element 7450) and the flow restriction seal member 7460) are disposed between the flow restriction retainer 7440) and the flow restriction retainer 7440) to prevent the flow restriction element 7450) and the flow restriction seal member 7460 from moving relative to the flow restriction retainer 7440). In some embodiments, the flow restriction cap 7470) is press fit into the flow restriction retainer 7440.

In some embodiments the flow restriction cap 7470 threaded into, welded onto, or bonded with the flow restriction retainer 7440).

Figure 61:
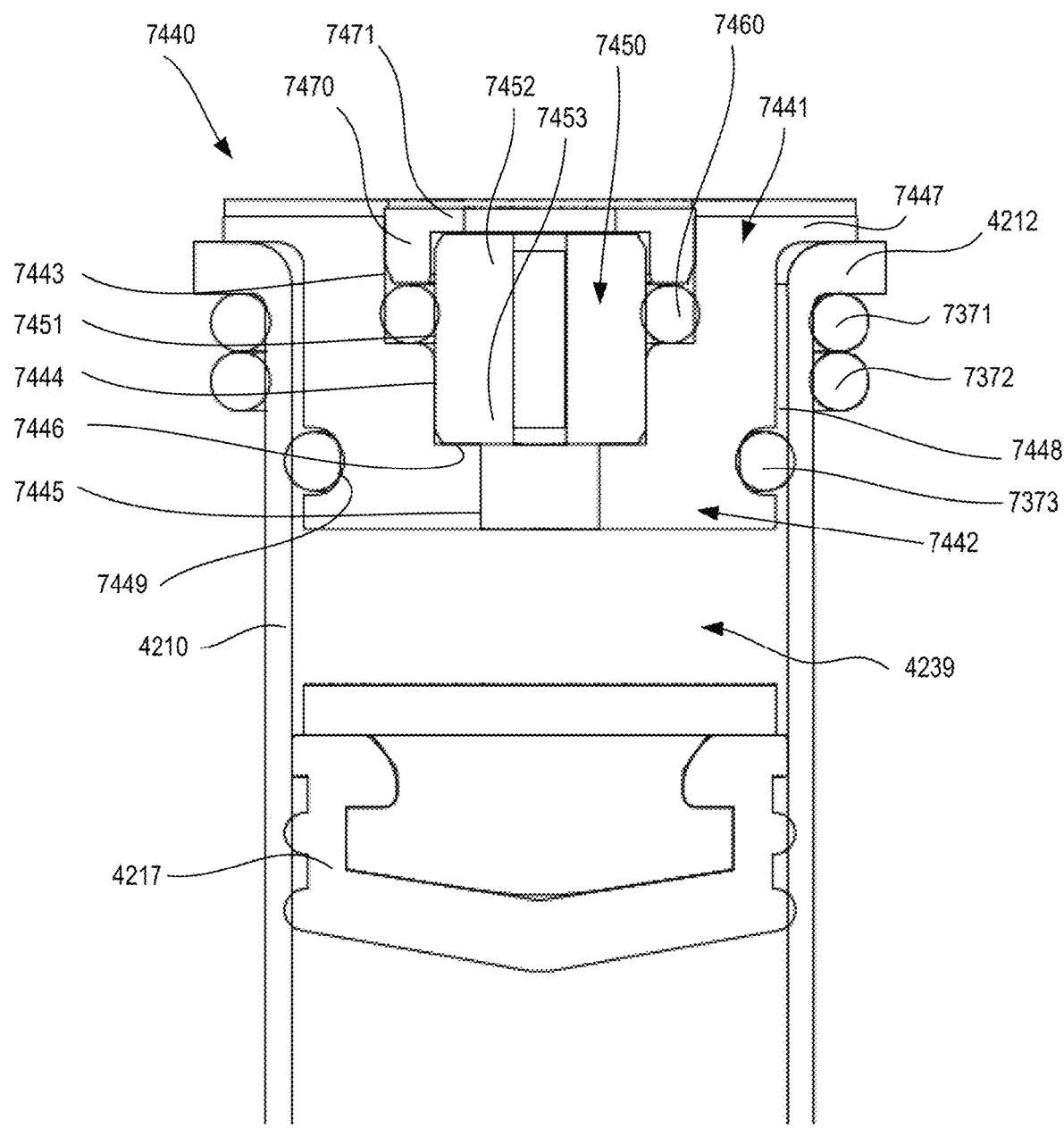
FIG. 61 is an enlarged cross-sectional view of the medical injector shown in FIG. 60.
Figure 62:
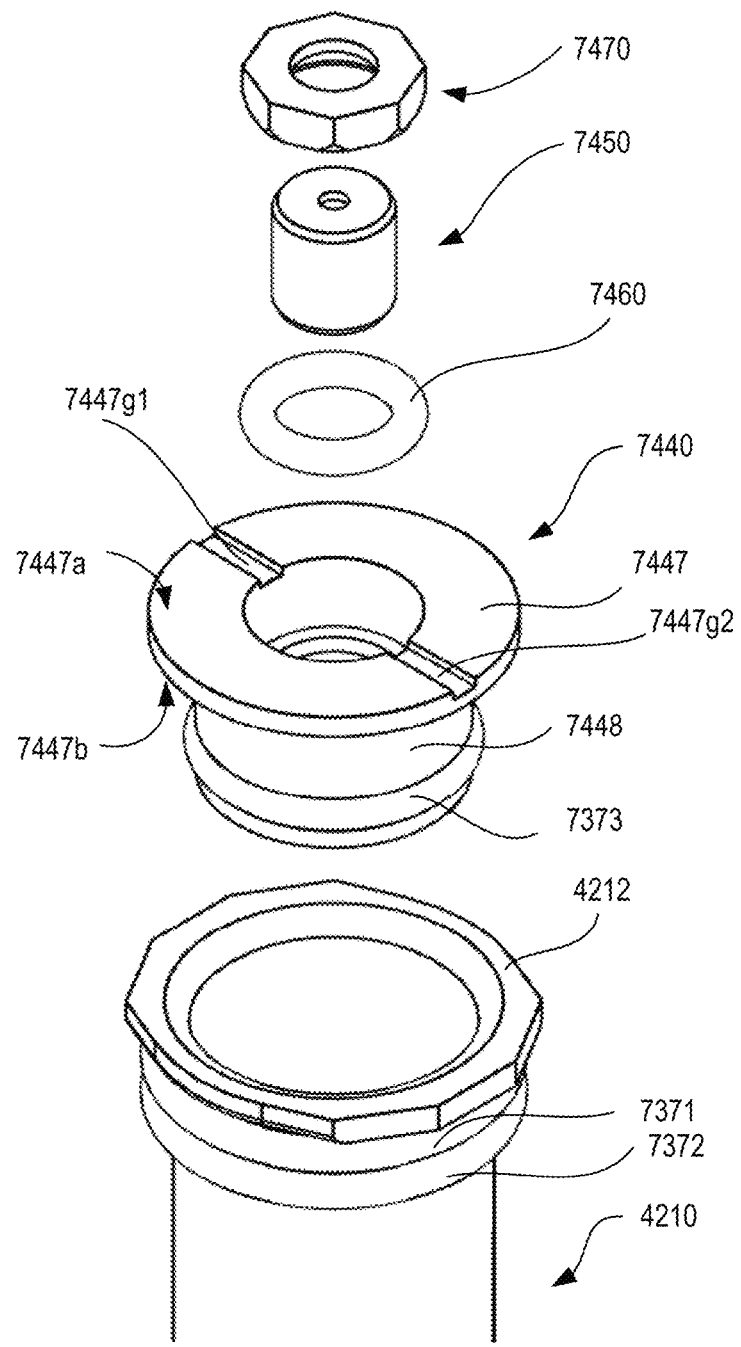
FIG. 62 is an enlarged exploded view of a flow restriction member of the medical injector shown in FIG. 60.

As shown in FIGS. 61 and 62, the flow restriction retainer 7440) includes a proximal end portion 7441 and a distal end portion 7442. The flow restriction retainer 7440) includes a first internal cylindrical surface 7443, a second internal cylindrical surface 7444, and a third internal cylindrical surface 7445. A diameter of the first internal cylindrical surface 7443 is greater than a diameter of the second internal cylindrical surface 7444, and the second internal cylindrical surface 7444 is greater than a diameter of the third internal cylindrical surface 7445. The first, second, and third internal cylindrical surfaces 7443, 7444, 7445 extend parallel to a longitudinal axis of the flow restriction retainer 7440 between the proximal end portion 7441 and the distal end portion 7442.

As shown in FIG. 61, both an outer surface of the flow restriction cap 7470) and an outer surface of the flow restriction seal member 7460 abut against the first internal cylindrical surface 7443 of the flow restriction retainer 7440. Both an inner surface of the flow restriction cap 7470) and an inner surface of the flow restriction seal member 7460 abut against an outer surface of the flow restriction element 7450. The outer surface 7451 of the flow restriction element 7450 also abuts against the second internal cylindrical surface 7444 of the flow restriction retainer 7440. The flow restriction cap 7470 includes a flange portion 7471 extending radially inward. A proximal end portion 7452 of the flow restriction element 7450) abuts against the flange portion 7471 of the flow restriction cap 7470. The flow restriction retainer 7440) includes a platform portion 7446 extending radially from the second internal cylindrical surface 7444 to the third internal cylindrical surface 7445. A distal end portion 7453 of the flow restriction element 7450 abuts against the platform portion 7446.

The proximal end portion 7441 of the flow restriction retainer 7440 includes a flange portion 7447 extending radially away from the longitudinal axis of the flow restriction retainer 7440. The flange portion 7447 includes a top surface 7447a and a bottom surface 7447b. The top surface 7447a is configured to abut against a guide wall 4115 of the proximal cap 4110 (described above) and the bottom surface 7447b is operable to mount on and abut against the proximal end portion 4212 of the medicament container assembly 4200 to prevent the flow restriction retainer 7440 from moving or shifting relative to the medicament container assembly 4200. The flange portion 7447 includes a first groove portion 7447g1 and a second groove portion 7447g2 extending into the top surface 7447a to provide an air gap between the flow restriction retainer 7440 and the guide wall 4115 (when the flow restriction retain 7440 is positioned to abut against the guide wall 4115). The bottom surface 7447b is configured to mount on and abut against one or more of the proximal end portion 4212 of the medicament container assembly 4200 or a proximal end of the carrier body 7360.

The flow restriction retainer 7440 includes an outer circumferential surface 7448 extending between the proximal end portion 7441 and the distal end portion 7442. The outer circumferential surface 7448 of the flow restriction retainer 7440 is configured to be inserted into the medicament container body 4210 as shown in FIG. 61. The outer circumferential surface 7448 includes a groove 7449 for securing a seal or O-rings 7373 to prevent pressurized gas from bypassing the flow restriction element 7450 between the outer circumferential surface of the flow restriction retainer 7440 and the carrier body 7360.

In some embodiments, the flow restriction element 7450 can be a filter element, a diaphragm element, a single port orifice, a series of single port orifices, a sieve plate element, an adjustable valve, a single port valve, multi-port valve, or porous member to allow for reduction of pressure during a delivery event. For example, the size of the port(s) or the porosity of the flow restriction element 7450 can be selected to enable gas pressure to be built up in the medicament cavity 4139 and/or the gas chamber to deploy the needle 4216 prior to actuating the elastomeric member 4217. The size of the port(s) or the porosity of the flow restriction element 7450) can also be selected to control a travel speed of the elastomeric member 4217 and therefore the flow rate of a composition or medicament being injected into a patient. In particular, the flow restriction element 7450 can enable the medicament delivery mechanism 7300 to rapidly deploy the needle 4216 via high pressure gas supplied by the gas container 4410 to medicament cavity 4139, but then regulate and reduce the pressure supplied to the medicament control cavity 4239. By limiting the pressure supplied from the medicament cavity 4139 to the medicament control cavity 4239 via the flow restriction element 7450, thereby promoting a slow and gradual build-up of pressure within the medicament control cavity 4239, actuation of the elastomeric member 4217 can be controlled allowing for lower injection forces, more consistent delivery rate through the entire injection process, and/or slower delivery of medicament.

In some embodiments, the flow rate of the composition or medicament can be reduced to less than 0.2 mL/sec (or in some embodiments between about 0.05 mL/sec and about 0.1 mL/sec, or between about 0.01 mL/sec and about 0.05 mL/sec) using gas pressure that is initially supplied to medicament cavity 4139 and through the flow restriction element 7450. The lower injection forces and/or slower delivery (compared with pressures supplied directly from the medicament cavity 4139 to the elastomeric member) can produce laminar flow of the medicament through the needle, limit shearing of high molecular weight compounds in the medicament, and/or reduce pain sensed by a patient particularly if the medicament being delivered is very high in viscosity (e.g., greater than about 100 centipoise at room temperature). In some embodiments, the dose of composition includes immunoglobulin. In some embodiments, the dose of composition includes 120 mg/mL of immunoglobulin (IgG). In some embodiments, the dose of composition has a viscosity is between about 4 centipoise and about 200 centipoise. In some embodiments, the dose of composition has a viscosity of about 5 centipoise. In some embodiments, the flow rate of the composition or medicament can be controlled such that a first 20% of the delivered volume of the composition is dispensed over a first time duration, and a last 20% of the delivered volume of the composition is dispensed over a second time duration. The second time duration is less than 2 times the first time duration. In other words, the flow restriction element 7450 is configured to limit or moderate delivery of the composition such that the first 20% of the delivered volume is not delivered more than two times faster than the last 20% of the delivered volume. In some embodiments, the elapsed time to dispense the last 20% of the delivered volume is between about one to two times the elapsed time to dispense the first 20% of the delivered volume. For example, if the elapsed time to dispense the first 20% of the delivered volume is about 15 seconds, the elapsed time to dispense the last 20% of the delivered volume is between about 15 seconds to about 30 seconds. In some embodiments, the elapsed time to dispense the last 20% of the delivered volume is between about 100% to about 195% of the elapsed time to dispense the first 20% of the delivered volume.

In some embodiments, the flow restriction element 7450 is configured to control delivery of about 5 mL to 30 mL of the composition or medicament through the needle 4216 over a period of about 30 seconds to 3 minutes. In some embodiments, the flow restriction element 7450 is configured to control delivery of about 5 mL of the composition or medicament through the needle 4216 over a period of about 45 seconds to 75 seconds. In some embodiments, the flow restriction element 7450) is configured to control delivery of about 10 mL of the composition or medicament through the needle 4216 over a period greater than about 15 seconds and less than about 3 minutes. In some embodiments, the composition or medicament to be delivered by the medical injector 4000" includes a viscosity between about 4 centipoise and 200 centipoise. In some embodiments, the composition or medicament to be delivered by the medical injector 4000" includes a viscosity of about 5 centipoise.

In some embodiments, a screen or mesh protective member can be provided on a proximal side of the flow restriction element 7450 to prevent any particulate or debris from clogging the flow restriction element 7450 during operation. In some embodiments, the flow restriction element 7450) includes a porous metal or porous ceramic material. The porous material provides multiple passageways through the flow restriction element 7450 thereby preventing clogs if any debris is present within the housing 4100. In some embodiments, the flow restriction element 7450 is calibrated with nitrogen gas ($N_2$) at 30 psig (inlet side) to atmosphere (outlet side) at standard temperature and pressure to have a flow rate of between about 0.5 to 5 standard cubic centimeter per minute (sccm). In some embodiments, the flow restriction element 7450 is calibrated with nitrogen gas ($N_2$) at 30 psig (inlet side) to atmosphere (outlet side) at standard temperature and pressure to have a flow rate of between about 1 to 3 standard cubic centimeter per minute (sccm). In some embodiments, the compressed gas supplied by the gas container 4410 is an argon gas and the flow restriction member 7450) has a flow rate rating of about 1.5 and 2.5 sccm based on the nitrogen gas calibration described above. In some embodiments, the compressed gas supplied by the gas container 4410 is an argon gas and the flow restriction member 7450 has a flow rate rating of about 2 sccm based on the nitrogen gas calibration described above.

In some embodiments, the compressed gas in the gas container 4410 has a molecular weight greater than the molecular weight of argon. For example, in some embodiments, the compressed gas supplied by the gas container 4410 is R134a (Tetrafluoroethane) and the flow restriction member 7450 has a flow rate rating of about 10 to 100 sccm based on the nitrogen gas calibration described above. In some embodiments, the compressed gas supplied by the gas container 4410 is R134a (Tetrafluoroethane) and the flow restriction member 7450) has a flow rate rating of about 20 to 40 sccm based on the nitrogen gas calibration described above.

Figure 63:
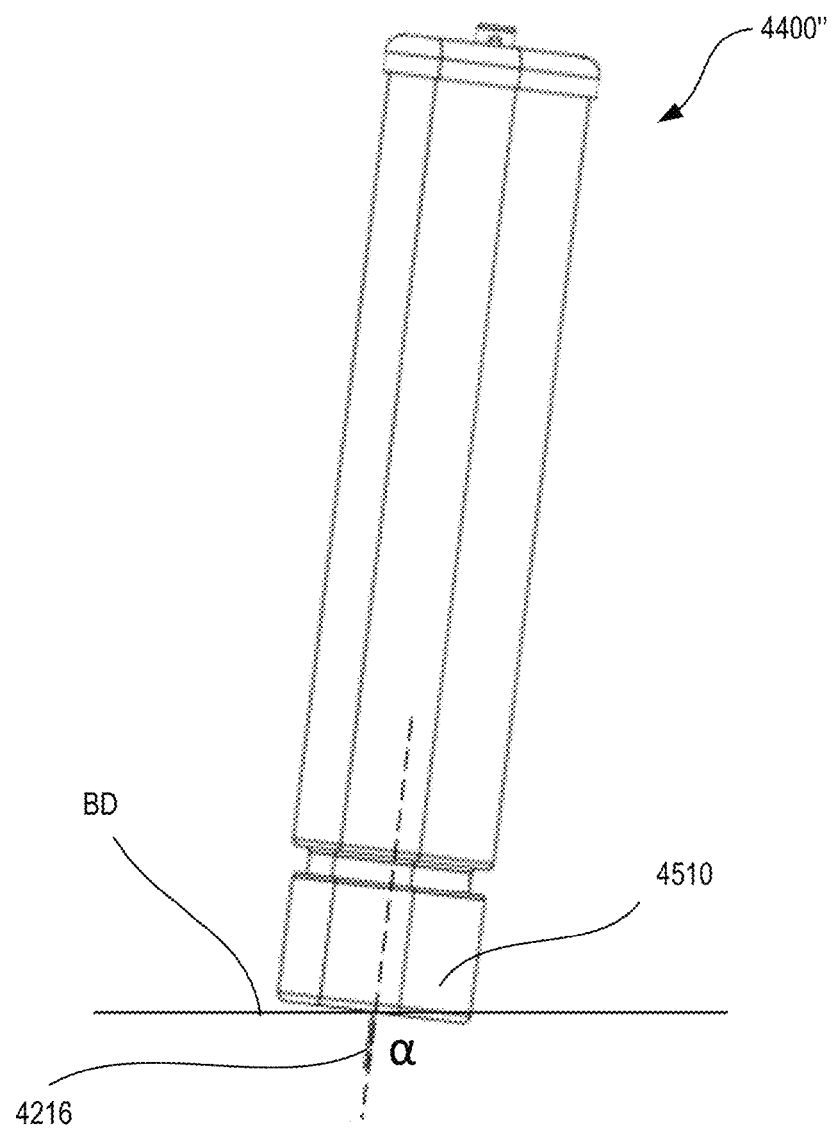
FIG. 63 is a side view of the medical injector shown in FIG. 60 being applied against a surface of a body.

As with the medical injector 4000, the medical injector 4000" can be moved from the first configuration (i.e., the "storage" state) to the second configuration by moving the safety lock 4700, as described above. From the second configuration (see e.g., FIG. 41), the medical injector 4000" can be moved from the second configuration to the third configuration (see e.g., FIG. 42) by moving the base 4510 from the first position to the second position. In some embodiments, as shown in FIG. 63, the base 4510 of the medical injector 4000" can be placed against the body such that the needle 4216 is oriented at the angle α of between about 75 degrees to 105 degrees relative to a surface of the body BD where the needle 4216 is inserted, and such that about 5 ml to about 30 mL of composition can be dispensed into the body while the needle 4216 is at the angle α. As the base 4510 moves from the first position to the second position, the system actuator assembly 4500 actuates the medicament delivery mechanism 7300 to place the medical injector 4000" in a fourth configuration (i.e., the needle insertion configuration). As the base 4510 is moved from the first position to the second position, the system actuator assembly 4500 actuates the medicament delivery mechanism 7300, thereby placing the medical injector 4000" in the fourth configuration (i.e., the needle insertion configuration), as shown in FIGS. 44 and 63. In some embodiments, the needle 4216 is a 21 to 27 gauge needle. In some embodiments, the needle 4216 is a 23 or 25 gauge needle. In some embodiments, a length of needle extended from a surface of the base 4510 is between about 5/8 inches (1.95 cm) to about 1 inch (2.54 cm). In some embodiments, the needle 4216 is configured to deliver a dose of composition subcutaneously.

In particular, as shown in FIG. 60, when the medical injector for the 4000" is in the fourth configuration, the puncturer 4575 of the release member 4550 is in contact with and/or disposed through the frangible seal 4413 of the gas container 4410. After the frangible seal 4413 has been punctured, an actuating portion of a compressed gas flows from the gas container 4410, via the gas passageway and into the medicament cavity 4139. The gas applies gas pressure to the flange 4214 of the medicament container and/or the proximal surface 7376 of the carrier body 7360. Because the seals 7371, 7372, 7373 and the outer seal 4370) maintain the medicament cavity 4139 fluidically isolated from the exterior of the device, the gas pressure exerts a force to move the carrier assembly 7390 distally within the medicament cavity 4139 (see e.g., FIGS. 42 and 44). In this manner, the movement of the needle 4216 in a distal direction causes the distal end portion of the needle 4216 to exit the housing 4100 and enter the body of a patient prior to administering the medicament.

As the compressed gas flows from the gas container 4410 into the medicament cavity 4139 and applies pressure on the flange 4214 of the medicament container and/or the proximal surface 7376 of the carrier body 7360 to extend the needle 4216, a portion of the compressed gas passes through the flow restriction member 7430. When the needle 4216 has extended by a desired distance, a distal surface of the carrier body 7360 contacts the shoulder portion 4106 of the housing 4100 to limit further distal movement of the carrier assembly 7390 within the housing 4100. While the distal movement of the carrier assembly 7390 is prevented, the gas within the medicament cavity 4139 (i.e., the gas chamber) continues to pass through the flow restriction element 7450 to the medicament control cavity 4239.

As gas pressure builds up in the medicament control cavity 4239 and overcomes frictional forces of the elastomeric member 4217 against the medicament container body 4210 (e.g., at about 7 psig (48.26 kPa)), the elastomeric member 4217 begins to move in the distal direction within the medicament container body 4210, as shown by the arrow DD in FIG. 60. Distal movement of the elastomeric member 4217 generates a pressure upon the composition or medicament contained within the medicament container assembly 4200, thereby allowing at least a portion of the composition or medicament to flow out of the medicament container assembly 4200 via the needle 4216. The composition or medicament is delivered to a body of a user via the medicament delivery path defined by the medicament container assembly 4200 and the needle 4216. At the end of injection, the medical injector is in its fifth configuration (see e.g., FIG. 47). In some embodiments, a dose or volume of the composition or medicament delivered as the elastomeric member 4217 travels through its entire stroke is at least 10 mL. In some embodiments, the dose or volume of the composition or medicament delivered is between about 10 mL and 30 mL.

In some embodiments, the flow restriction element 7450 is sized and configured to prevent movement of the elastomeric member 4217 while the needle 4216 is in the process of extending from the base 4510 of the housing 4100. Once the needle 4216 is fully extended, the flow restriction element 7450 is configured to permit a sufficient build-up of pressure within the medicament control cavity 4239 to permit movement of the elastomeric member 4217. In some embodiments, the gas pressure within the medicament control cavity 4239 remains lower than a gas pressure of the medicament cavity 4139 throughout the medicament injection process. In some embodiments, the flow restriction element 7450 limits the gas pressure within the medicament control cavity 4239 to below about 50 psi (344.7 kPa).

After the elastomeric member 4217 has moved a predetermined distance within the medicament container body 4210 (corresponding to the desired dose) to place the medical injector in the sixth configuration, the operator can depress the valve actuator 7320 to move the valve member 7330 from the first position to the second position, as described herein. Movement of the valve member 7330 from the first position to the second position allows the pressurized gas contained within the gas chamber (i.e., the volume within the medicament cavity 4139 between the proximal end of the housing 4100 and the surface of the carrier body 7360) to escape via the passageway 7345 and the opening 4112. After the gas pressure within the medicament cavity 4139 decreases below a certain level, the force exerted by the retraction spring on the carrier body 7360 is sufficient to cause the carrier body 7360 to move proximally within the housing 4100 (i.e., to retract). This places the medical injector in its seventh configuration (see e.g., FIG. 53) where the needle is needle 4216 is retracted back into the housing 4100 and the medical injector 4000" can be safely handled and/or disposed of.

FIG. 64 is a chart showing delivery times and pressures for delivering 10 mL of a composition or medicament using the medical injector 4000" as measured on a bench test. The 10 mL composition delivered using the medical injector 4000" has a viscosity of about 5 centipoise. The needle 4216 of the medical injector 4000" is a 23 gauge needle that is 1 inch (2.54 cm) in length. The gas container 4410 of the medical injector 4000" includes about 180 mg of argon gas prior to being punctured and released from the gas container 4410. The composition within the control assembly 7300 (also referred to as medicament delivery mechanism) of the medical injector 4000" limits gas pressure entering into the medicament control cavity 4239, allowing the elastomeric member 4217 to move at a more controlled speed compared with mechanical systems or pressurized gas systems without flow restriction element 7450, particularly when a large dose of composition or medicament is being delivered (i.e., greater than about 5 mL). As shown in the chart, the delivery time of the composition or medicament can be tailored such that the entire 10 mL is dispensed over a period of about 1 minute, 45 seconds to about 2 minutes, 15 seconds. In other words, delivery of the entire 10 mL is completed after about 1 minute, 45 seconds to about 2 minutes, 15 seconds from when injection of the composition through the needle 4216 begins. By limiting the gas pressure, the injection force (and therefore the momentum of the substance leaving the device) can be reduced to ensure that a large volume of the composition or medicament can be delivered subcutaneously without seeping back out from the target surface. The control of the momentum of the substance leaving the device and the injection speed of the substance can also minimize pain to a patient, and/or to prevent shearing and damage of medicament or therapeutic substance, particularly when the medicaments or therapeutic substances include high molecule weight compounds (e.g., greater than about 5 kDa).

As shown in the chart in FIG. 64, the initial pressure within the medicament cavity 4139 is about 100 psi. The final pressure in the medicament cavity 4139 after the entire 10 mL of composition has been delivered is generally above 80 psi. Additionally, as shown in the chart, the average elapsed time for delivering a first 20% of the composition is about 17 seconds, the average elapsed time for delivering a second 20% of the composition is about 19 seconds, the average elapsed time for delivering a third 20% of the composition is about 21 seconds, the average elapsed time for delivering a fourth 20% of the composition is 25 seconds, the average elapsed time for delivering a fifth and final 20% of the composition is about 31 seconds. As shown in the chart, the flow restriction element 7450 (and/or the control assembly 7300) is configured to limit and moderate delivery of the composition such that the first 20% of the delivered volume is not delivered more than two times faster than the last 20% of the delivered volume. In other words, the first 20% of the delivered volume is delivered less than two times faster than the last 20% of the delivered volume (i.e. about 17 seconds versus about 31 seconds). In some embodiments, the elapsed time to dispense the last 20% of the delivered volume is between about one to two times the elapsed time to dispense the first 20% of the delivered volume. For example, if the elapsed time to dispense the first 20% of the delivered volume is about 15 seconds, the elapsed time to dispense the last 20% of the delivered volume is between about 15 seconds to about 30 seconds. In some embodiments, the elapsed time to dispense the last 20% of the delivered volume is between about 100% to about 195% of the elapsed time to dispense the first 20% of the delivered volume.

Figure 65:
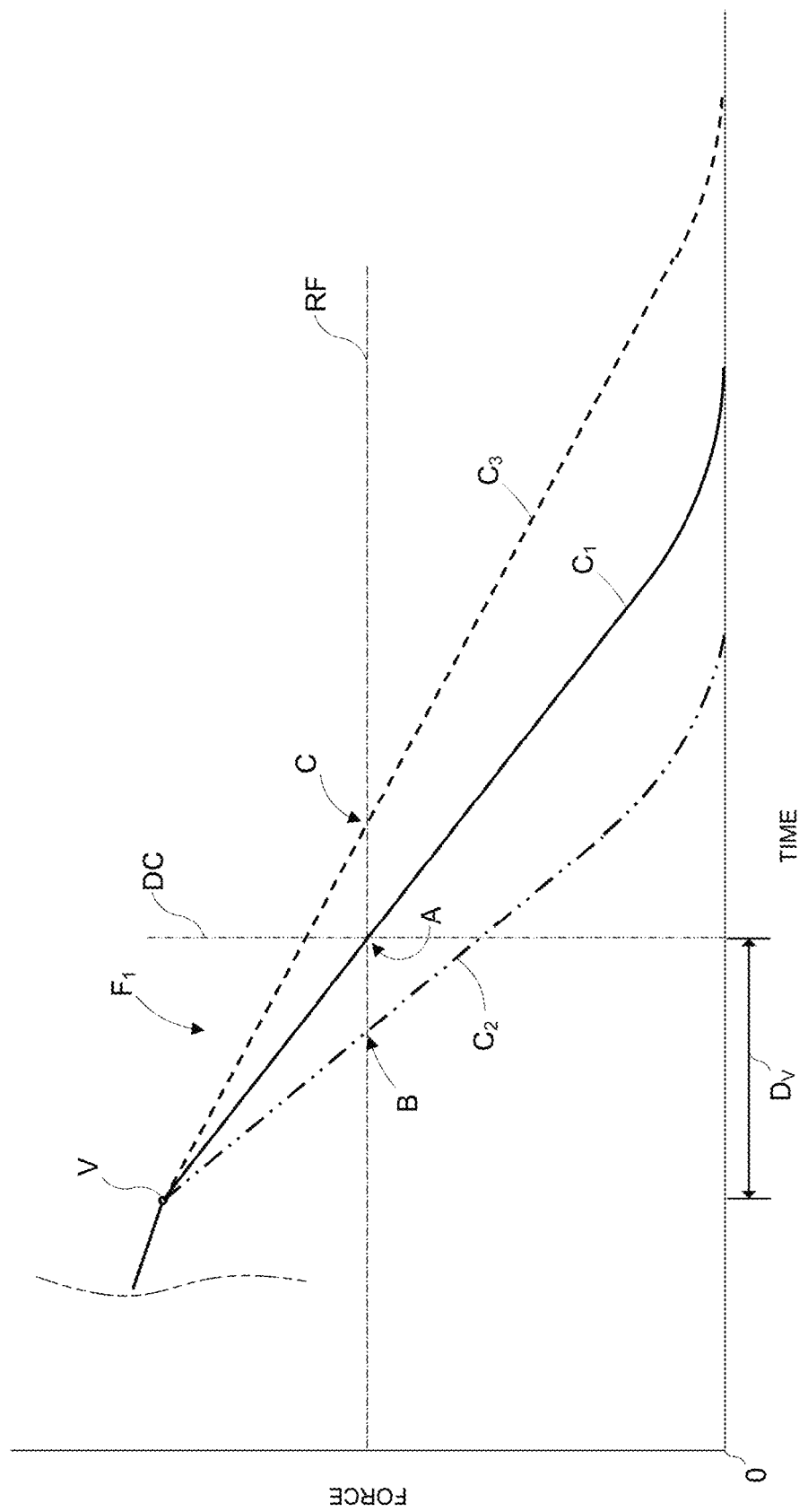
FIG. 65 is a graphical depiction of the impact of venting on the force generated by a compressed gas during the delivery of the dose via the medical injector according to an embodiment.
Figure 66:
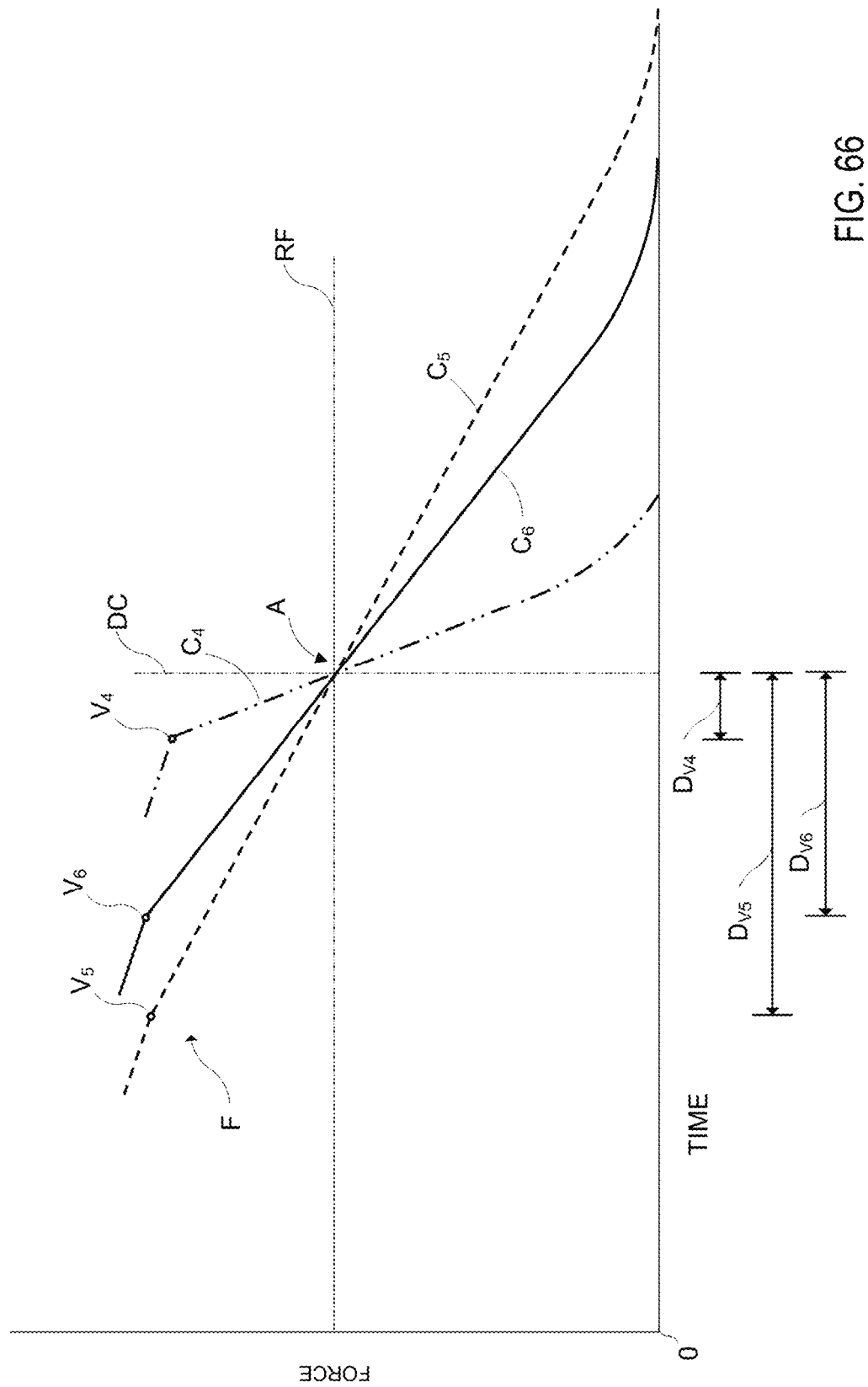
FIG. 66 is a graphical depiction of the impact of tuning of a vent assembly on the force generated by a compressed gas during the delivery of the dose via the medical injector according to an embodiment.

In addition to including a control assembly (e.g., the flow restriction assembly 4430, the flow restriction member 5430, or the control assembly 7300) to regulate a portion of the force to control the movement of the elastomeric member, in some embodiments, any of the medical injectors described herein can include a gas vent assembly (e.g. the gas vent assembly 4310, the gas vent assembly 5310, or the gas vent assembly 7310) that is configured to regulate a portion of the force to control movement of the elastomeric member. In some embodiments, any of the gas vent assemblies can be configured to regulate the pressure within towards the end of the delivery event in a manner that produces the desired retraction timing (at the end of delivery) while also maintaining the delivery rate within the desired range. FIG. 65 is a graphical depiction of the impact of venting on the force generated by a pressurized gas during the delivery of the dose via any of the medical injectors (e.g., a medicament injector) described herein, such as medical injector 4000, the medical injector 4000", medical injector 6000, or medical injector 8000 as described herein, while FIG. 66 is a graphical depiction of the impact of the tuning of the gas vent assembly on the force generated by the pressurized gas. As described, in some embodiments, the gas pressure within the internal volume of the medical injector is vented to the exterior volume surrounding the medical injector via a gas vent assembly, such as gas vent assembly 4310, 5310, or gas valve assembly 7310, after a specified period following the actuation of the medical injector.

In some embodiments, the rate of venting, with the corresponding reduction in the force generated by the compressed gas, is calibrated to ensure delivery of the final portion of the dose accurately and within a desired time period (e.g., so that the first portion of the delivered volume is delivered less than two times faster than the final portion of the delivered volume) prior to retracting the needle. However, as depicted in FIG. 65 and FIG. 66, it may be desirable that concurrent with the completion of the delivery of the final portion, the force generated by the pressurized gas within the gas chamber be less than a retraction force applied by the retraction spring. In other words, the force of the compressed gas is maintained at a magnitude that is greater than the retraction force until the time at which the final portion is completely delivered. In some embodiments, the force of the pressurized gas falls below the retraction force concurrent with the completion of the delivery of the final portion, which will initiate needle retraction substantially concurrent with the end of the delivery event. In some additional embodiments, the force of the compressed gas falls below the retraction force after the completion of the delivery of the final portion. However, it should be appreciated that maintaining the force of the compressed gas at a magnitude that is greater than the retraction force beyond the completion of the delivery of the final portion may result in the undesirable maintaining of the needle in the body of patient for longer than is required to deliver the dose. It should also be appreciated that venting the compressed gas too quickly may be undesirable in that it may permit the force of the compressed gas to fall below the retraction force prior to the final portion being completely delivered. In addition to the timing of when the venting starts, the rate of venting can also impact the timing and accuracy of delivery of the final portion of the dose.

For example, as depicted in FIGS. 65 and 66, in some embodiments the medical injector is actuated such that an energy storage member produces a force ($F_1$) via a compressed gas within an internal volume of the housing of the medical injector. The force ($F_1$) is produced on a container containing a dose of the composition. The force ($F_1$) causes the container to move within the housing to cause a needle to extend from the housing. The movement of the container also compresses a retraction spring (e.g., the retraction spring 4380) of the medical injector. In some embodiments, as described herein, a control assembly (e.g., medicament delivery mechanism 4300, 5300 and/or control assembly 7300) is utilized to regulate the portion of the force ($F_1$) applied to an elastomeric member of the container to cause a movement of the elastomeric member within the container to deliver an initial portion of the dose.

In some embodiments, the venting of the internal volume is initiated (as depicted by points V, $V_4$, $V_5$, and $V_6$) to facilitate a ramped reduction of the force ($F_1$) of the compressed gas within the internal volume. The venting is accomplished via the gas vent assembly and/or a vent opening defined by the housing (e.g., vent opening 4112, 6112). In some embodiments, the venting is initiated via the actuation of a valve of the gas vent assembly. The actuation may be accomplished via the structure of the medical injector and/or by manually actuating a valve actuator of the gas vent assembly. The gas vent assembly is configured (e.g., the vent opening is sized and/or shaped) to maintain the force ($F_1$) produced by the compressed gas on the container at a magnitude that is greater than the force applied by the retraction spring (e.g., force $F_2$, a retraction force (RF)) during a time to deliver the final portion of the dose. In other words, the gas vent assembly is tuned such that the force ($F_1$) of the compressed gas remains greater than the retraction force (RF) during the period of time required to complete the delivery of the final portion of the dose. (the completion of the delivery of the final portion of the dose is depicted by line DC). In some embodiments, the venting duration ($D_V$) commences with the actuating (at point V, $V_4$, $V_5$, or $V_6$) of a valve of the gas vent assembly and may culminate with the delivery of the final portion of the dose (line DC) (e.g., at point A). It should be appreciated that the venting duration ($D_V$) may correspond to the desired time to deliver the final portion of the dose and may, therefore, be determined based on the delivery properties of the composition.

As depicted in FIG. 66, in some embodiments, the gas vent assembly, including the vent opening size and/or movement of a valve body within the opening, and/or the instant at which the venting is initiated (points $V_4$, $V_5$, or $V_6$) may be configured so that the force ($F_1$) produced by the compressed gas decreases to a magnitude that is less than the force applied by the retraction spring (e.g., retraction force (RF)) concurrent with the conclusion of the delivery of the final portion of the dose. For example, the gas vent assembly is configured (e.g., tuned) by selecting the vent opening size, the vent opening shape, the valve body size, and/or the valve body shape to achieve a desired rate of decrease of the force ($F_1$) within the internal volume. The desired rate of decrease of the force ($F_1$) may, for example, be based on the desired delivery properties of the composition, characteristics of pressurized gas, and/or environmental parameters. For example, in some embodiments, the vent opening is configured (e.g., sized) to establish a venting duration ($D_V$) of at least 0.5 seconds and less than 1.5 seconds. In some additional embodiments, the vent opening is sized to establish a venting duration ($D_V$) of at least 5 seconds and less than or equal to 15 seconds.

Three different gas vent assembly configurations are represented in FIG. 66 to illustrate the impact of the gas vent assembly on the dose delivery. A first configuration is illustrated by curve $C_4$. As depicted, curve $C_4$ is representative of a relatively high rate of venting that establishes a relatively brief venting duration ($D_{V4}$) following venting initiation (point $V_4$). Such a configuration may facilitate a rapid reduction of the force ($F_1$). However, ensuring the magnitude of the force ($F_1$) remains greater than the retraction force until delivery of the final portion of the dose (line DC) may require an accurate venting initiation (point $V_4$). A second configuration is illustrated by curve $C_5$. As depicted, curve $C_5$ is representative of a relatively low rate of venting that establishes a relatively extended venting duration ($D_{V5}$) following venting initiation (point $V_5$). Such a configuration may facilitate a gradual reduction of the force ($F_1$), thus facilitating delivery of the final portion of the dose (line DC). The slower rate of venting (relative to curve $C_4$ or curve $C_6$) may allow for more variability in the initiation of the venting but may also cause a much slower rate of delivery. In other words, in some embodiments, the gradual reduction of the force may result in a reduction in the flow rate of the composition. A third configuration is illustrated by curve $C_6$. As depicted, curve $F_6$ is representative of a rate of venting that falls between the rate of venting of the first configuration and the rate of venting of the second configuration and establishes a venting duration ($D_{V6}$) following venting initiation (point $V_6$). While three configurations are depicted in FIG. 66, it should be appreciated that additional configurations (e.g., tunings) are possible based on the desired rate of decrease of the force ($F_1$). It should further be appreciated that each configuration of the gas vent assembly may be desirable under different delivery properties of the composition.

Referring again to FIG. 65, in some embodiments, the gas vent assembly, is configured so that the force ($F_1$) produced by the compressed gas decreases to a magnitude that is less than the force applied by the retraction spring (e.g., retraction force (RF)) concurrent with the delivery of the final portion of the dose. Such a configuration is represented in FIG. 65 by curve $C_1$, with point A being the concurrent, or substantially concurrent, intersection of the decreasing force ($F_1$), the retraction force (RF), and the completion of the delivery of the final portion of the dose (line DC). Once the force ($F_1$) of the compressed gas decreases to a magnitude that is less than the retraction force (RF), the needle of the medical injector is retracted via a movement of the container within the housing in response to the force applied by the retraction spring (e.g., in response to the retraction force (RF)).

As further depicted in FIG. 65, curve $C_2$ and curve $C_3$ illustrate the effects of an alternatively configured (e.g., sized) gas vent assemblies and/or vent openings relative to a common time of venting initiation (point V). Curve $C_2$ illustrates a rate of decrease of the force ($F_1$) (due to a higher rate of venting of the compressed gas) that is greater than that of curve $C_1$ (e.g., this level of performance could be achieved by having a larger vent opening than that used in connection with the curve $C_1$. Although this can produce a very fast venting with a rapid, well-defined end of delivery, small variability in the time at which venting is initiated can result in undesired changes in the amount of dose delivered. As such, in certain instances the magnitude of the force ($F_1$) decreases below the magnitude of the retraction force (RF) (at point B) prior to the completion of the delivery of the final portion of the dose. Accordingly, the venting of the compressed gas at a higher rate may result in the incomplete delivery of the desired dose, which may be undesirable. In contrast, curve $C_3$ illustrates a rate of decrease of the force ($F_1$) (due to restricted/limited venting of the compressed gas) that is less than may be desired based on the required delivery time of the final portion of the dose. As such, the magnitude of the force ($F_1$) remains greater than the magnitude of the retraction force (RF) (until point C) after the completion of the delivery of the final portion of the dose. Accordingly, the venting of the compressed gas at a restricted/limited rate may result in delaying the retraction of the needle, which may be undesirable.

Figure 67:
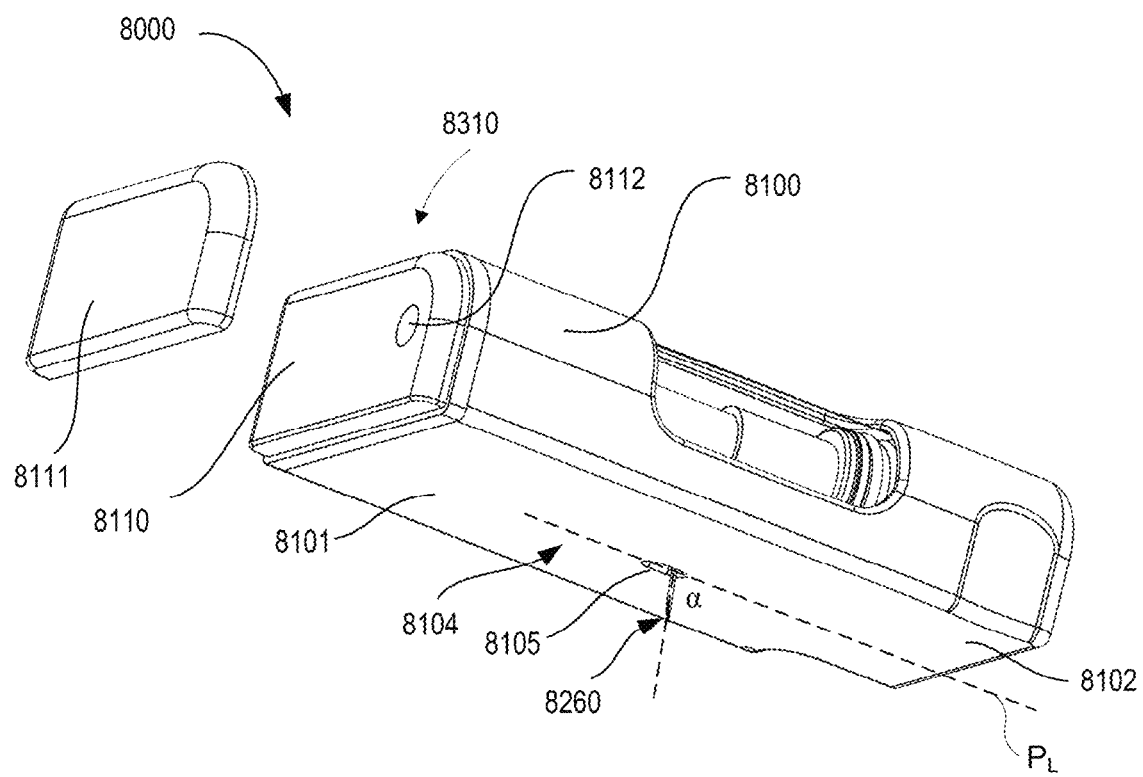
FIG. 67 is a perspective view of an embodiment of the medical injector configured as a wearable delivery device.

FIG. 67 is a perspective view of an embodiment of the medical injector, such as medical injector 4000 or medical injector 6000, configured as a wearable delivery device 8000. The wearable delivery device 8000 (also referred to as a medical injector) includes a housing 8100, a needle assembly (not shown), a medicament delivery mechanism (not shown), and system actuation assembly (not shown), which may be similar to the corresponding parts in the medical injector 4000 or medical injector 6000 described above. The wearable delivery device 8000 further includes a medicament container assembly (not shown) configured to actuate within the housing 8100, and a gas vent assembly 8310 configured to retract the needle assembly at the end of delivery.

The housing 8100 has a first (or proximal) end portion 8101 and a second (or distal) end portion 8102. The housing 2100 includes a bottom portion 8104 extending between the proximal end portion 8101 and a distal end portion 8102. The bottom portion 8104 includes a contact surface for contacting a body surface of a patient. The bottom portion 8104 includes a needle aperture 8105 configured to allow a needle 8260 of the needle assembly to pass through during operation.

In some embodiments, the bottom portion 8104 is configured as an attachment surface. The attachment surface is configured to maintain the position of the wearable delivery device 8000 in position against a portion of the body of the patient absent a manually applied pressure from the user. In some embodiments, the bottom portion 8104 is secured against the portion of the body via an adhesive surface, a strap, a band, a sleeve, and/or a bandage. For example, in some embodiments, the bottom portion 8104 (e.g., the attachment surface) includes an adhesive material for temporarily securing the bottom portion 8104 to the body surface of the patient. In some embodiments, the contact surface may be provided with an adhesive patch or material to further secure the bottom portion 8104 of the housing 8100 to the body surface of a patient. In some embodiments, the adhesive patch or material may include a protective film or backing that may be removed by the patient prior to securing the bottom portion 8104 onto the body surface of the patient. In some embodiments, the protective film is coupled to a needle aperture cover or guard such that removal of the protective film from the adhesive patch also removes the cover or guard from the needle aperture. In some embodiments, a portion of the protective film is attached securely to the activation input member to prevent actuation of the activation input member until the protective film is removed from the bottom portion 8104.

The first (or proximal) end portion 8101 of the housing 8100 includes a housing cap 8110 and a cap cover 8111. In some embodiments, the housing cap 8110 is configured to retain a gas container retention member (not shown) within a gas container cavity (not shown). When the wearable delivery device 8000 is actuated, pressurized gas from the gas container (not shown) is conveyed from the gas container cavity to the medicament cavity (not shown) and to the delivery mechanism cavity (not shown) via the gas passageway (not shown) of the housing 8100. Thus, the pressurized gas from the gas container is conveyed from the gas container cavity to the delivery mechanism cavity to move the insertion member and the needle 8260. In some embodiments, the pressurized gas from the gas container is conveyed from the gas container cavity to a proximal portion of the medicament cavity to actuate the medicament container assembly. The proximal portion of the medicament cavity also serves as a pressurized gas reservoir used to inject the medicament, as described herein.

In some embodiments, the housing cap 8110 includes a vent opening 8112 selectively placed in fluid communication with the gas passageway within the housing 8100. The housing cap 8110 also includes a cap cover 8111 coupled to a proximal end portion of the housing cap 8110 while retaining a gap between the proximal end portion of the housing cap 8110 and the cap cover 8111. The cap cover 8111 prevents the vent opening 8112 from direct external contact and prevents clogging from external debris. The vent opening 8112 provides the passageway through which pressurized gas is conveyed from gas passageway (including from within the medicament cavity and the delivery mechanism cavity) to a volume outside of the wearable delivery device 8000. The vent opening 8112 and the gap between the housing cap 8110 and the cap cover 8111 allows pressurized gas from within the medicament cavity to escape out to the volume outside the wearable delivery device 8000. In this manner, the force produced by the pressurized gas on the medicament delivery mechanism and/or the medicament container assembly (via the delivery control assembly) can be reduced to allow needle retraction after the injection is completed.

Although the vent opening 8112 is shown as being defined by the housing cap 8110, and being in a proximal surface thereof, in other embodiments, the vent opening 8112 (and any of the vent openings described herein) can be defined within any suitable portion of the housing cap or side wall. For example, in some embodiments, the vent opening 8112 (and any of the vent openings described herein) can be defined by the housing cap 8110 but can have a centerline that is nonparallel to a longitudinal axis of the wearable delivery device 8000. Said another way, in some embodiments, the vent opening 8112 (and any of the vent openings described herein) can open towards a side of the medical injector, rather than opening towards the proximal end, as shown. In other embodiments, the vent opening 8112 (and any of the vent openings described herein) can be defined by any wall and/or surface of the housing 8100.

When the wearable delivery device 8000 is actuated, pressurized gas flows into the housing gas chamber and within the delivery mechanism cavity. In this manner, the pressurized gas produces a force on the proximal surface, which moves the insertion member distally within the housing 8100. When the pressurized gas produces a force on the proximal surface, the force from the pressurized gas is high enough such that the insertion member overcomes a force applied by the retraction spring. As a result, the insertion member moves distally within the delivery mechanism cavity of the housing 8100. As the insertion member moves distally, the needle assembly is rotated about a rotational axis (not shown). In some embodiments, the needle assembly is rotated about the rotational axis by about 5 degrees to about 45 degrees while the needle 8260 is moved from the retracted orientation to the deployed orientation. In some embodiments, the needle assembly is rotated about the rotational axis by about 10 degrees to about 30 degrees. In some embodiments, the needle 8260 extends at a nonorthogonal angle relative to a plane of the bottom portion 8104 of the housing 8100. In some embodiments, the needle 8260 extends at an angle ($\alpha$) of between about 80 degrees to about 88 degrees relative to the plane of the bottom portion 8104. In some embodiments, the needle 8260 extends at an angle ($\alpha$) of between about 75 degrees to about 87 degrees relative to the plane of the bottom portion 8104. Said another way, in some embodiments, when deployed, the needle 8260 extends at an angle ($\alpha$) of between 75 degrees and 88 degrees relative to a longitudinal plane ($P_L$) of the wearable delivery device 8000.

Figure 68:
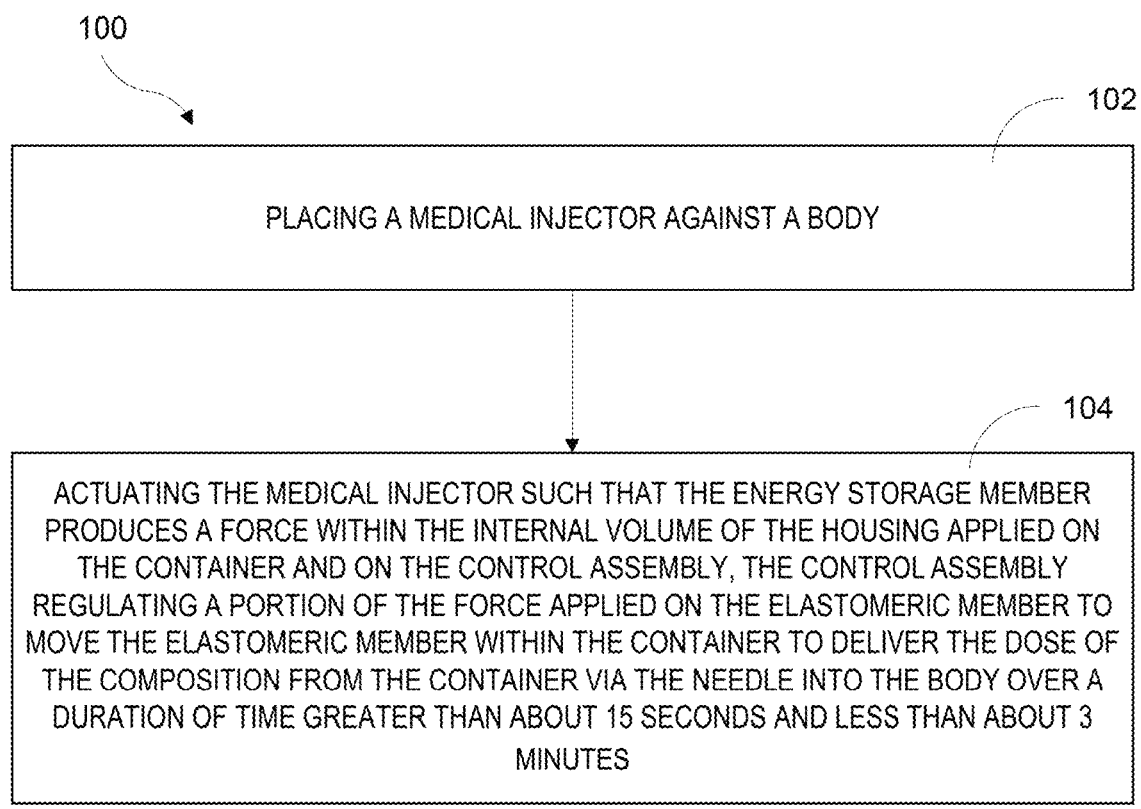
FIG. 68 is a flow chart of a method for delivering a dose of a composition according to an embodiment.

FIG. 68 is a flow chart of a method 100 for delivering a dose of a composition according to an embodiment. The method 100 may, in some embodiments, be performed via a medical injector (e.g., a medicament injector), such as medical injector 4000, medical injector 6000, and wearable delivery device 8000 as described herein. However, it should be appreciated that in various embodiments, aspects of the method 100 may be accomplished via additional embodiments of the medical injector or components thereof. Accordingly, the method 100 may be implemented on any suitable device as described herein. Those of ordinary skill in the art, using the disclosures provided herein, will understand that various steps of the method 100 or any of the other methods disclosed herein may be adapted, modified, rearranged, performed simultaneously, or modified in various ways without deviating from the scope of the present disclosure.

As shown at (102), the method 100 includes placing a medical injector against a body (e.g., a body of the patient). The medical injector includes a housing defining an internal volume and a container disposed within the housing. The container contains the dose of the composition within an internal volume of the container. The dose of the composition has a delivered volume of at least 10 mL. The medical injector also includes a needle configured to be coupled to the container, an elastomeric member disposed within the container, an actuating assembly including an energy storage member, and a control assembly disposed between the internal volume of the housing and the internal volume of the container. As shown at (104), the method also includes actuating the medical injector such that the energy storage member produces a force within the internal volume of the housing applied on the container and on the control assembly. The control assembly regulates the portion of the force that is applied on the elastomeric member to move the elastomeric member within the container to deliver the dose of the composition from the container via the needle into the body over a duration of time greater than about 15 seconds and less than about 3 minutes.

Figure 69:
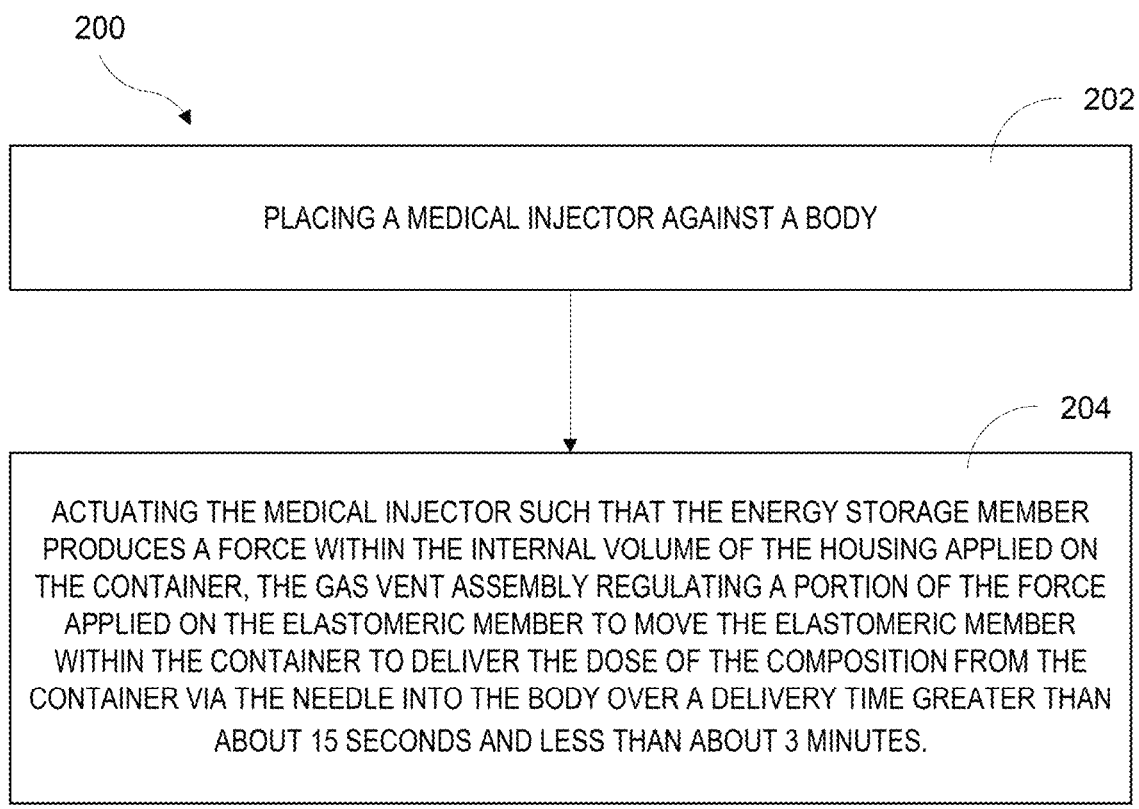
FIG. 69 is a flow chart of a method for delivering a dose of a composition according to an embodiment.

FIG. 69 is a flow chart of a method 200 for delivering a dose of a composition according to an embodiment. The method 200 may, in some embodiments, be performed via a medical injector (e.g., a medicament injector), such as medical injector 4000, medical injector 6000, and wearable delivery device 8000 as described herein. However, it should be appreciated that in various embodiments, aspects of the method 200 may be accomplished via additional embodiments of the medical injector or components thereof. Accordingly, the method 200 may be implemented on any suitable device as described herein. Those of ordinary skill in the art, using the disclosures provided herein, will understand that various steps of the method 200 or any of the other methods disclosed herein may be adapted, modified, rearranged, performed simultaneously, or modified in various ways without deviating from the scope of the present disclosure.

As shown at (202), the method 200 includes placing a medical injector against a body (e.g., a body of the patient). The medical injector includes a housing defining an internal volume and a vent opening. The medical injector also includes a container disposed within the housing. The container contains the dose of the composition within an internal volume of the container. The dose of the composition has a delivered volume of at least 10 mL. Additionally, the medical injector includes a needle configured to be coupled to the container, an elastomeric member disposed within the container, an actuating assembly including an energy storage member. Further, the medical injector includes a gas vent assembly. The gas vent assembly includes a valve disposed between the internal volume of the housing and an exterior volume surrounding the housing. The valve is configured to selectively seal the vent opening. As shown at (104), the method also includes actuating the medical injector such that the energy storage member produces a force within the internal volume of the housing applied on the container. The gas vent assembly regulates the portion of the force that is applied on the elastomeric member to move the elastomeric member within the container to deliver the dose of the composition from the container via the needle into the body over a delivery time greater than about 15 seconds and less than about 3 minutes.

Figure 70:
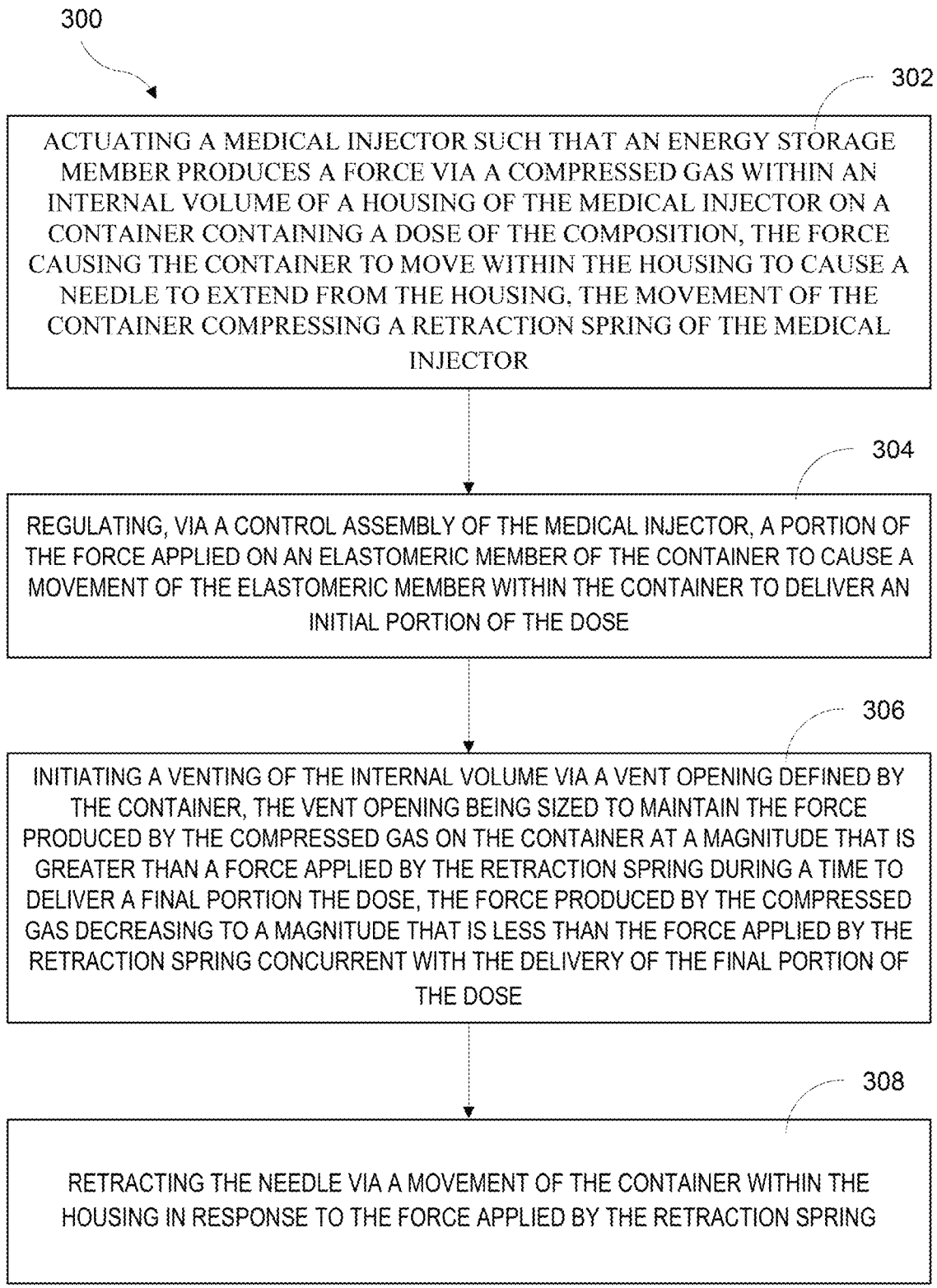
FIG. 70 is a flow chart of a method for delivering a dose of a composition according to an embodiment.

FIG. 70 is a flow chart of a method 300 for delivering a dose of a composition according to an embodiment. The method 300 may, in some embodiments, be performed via a medical injector (e.g., a medicament injector), such as medical injector 4000, medical injector 6000, and wearable delivery device 8000 as described herein. However, it should be appreciated that in various embodiments, aspects of the method 300 may be accomplished via additional embodiments of the medical injector or components thereof. Accordingly, the method 300 may be implemented on any suitable device as described herein. Those of ordinary skill in the art, using the disclosures provided herein, will understand that various steps of the method 300 or any of the other methods disclosed herein may be adapted, modified, rearranged, performed simultaneously, or modified in various ways without deviating from the scope of the present disclosure.

As shown at (302), the method 300 includes actuating a medical injector such that an energy storage member produces a force via a compressed gas within an internal volume of a housing of the medical injector on a container containing a dose of the composition. The force causes the container to move within the housing to cause a needle to extend from the housing. The movement of the container also compresses a retraction spring of the medical injector. As shown at (304), the method 300 includes regulating, via a control assembly of the medical injector, a portion of the force applied on an elastomeric member of the container to cause a movement of the elastomeric member within the container to deliver an initial portion of the dose. As shown at (306), the method 300 includes initiating a venting of the internal volume via a vent opening defined by the container. The vent opening is sized to maintain the force produced by the compressed gas on the container at a magnitude that is greater than a force applied by the retraction spring during a time to deliver a final portion the dose. The force produced by the compressed gas decreases to a magnitude that is less than the force applied by the retraction spring concurrent with the delivery of the final portion of the dose. Additionally, as shown at (308), the method 300 includes retracting the needle via a movement of the container within the housing in response to the force applied by the retraction spring.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, in some embodiments, a medicament delivery device can include two or more medicament containers, each having a delivery member through which the medicament therein can be delivered. Such embodiments can accommodate the delivery of viscous medicaments and/or large volumes of medicament (e.g., >1 mL dose) by delivering portions of the overall dose in parallel. Specifically, as discussed above with respect to Eq. 1, the needle length (L) and the needle gauge (identified as the radius R of the needle lumen) can have a profound impact on the pressure needed to deliver a desired volume of medicament therethrough. Thus, by using a "parallel delivery" device of the types shown and described herein, delivery of viscous medicaments, such as certain large or macromolecular injectables that include carbohydrate-derived formulations, lipids, nucleic acids, hyaluronidase, proteins/peptides (e.g. monoclonal antibodies) and other biotechnologically-derived medicaments, can be facilitated. Any of the gas venting mechanisms, electronic circuit systems, or other components described herein can be included in a dual container device of the types shown and described in the 4345 PCT or the '0040 PCT.

For example, any of the elastomeric members described herein can be constructed from any suitable material or combination of different materials. For example, in some embodiments, at least a portion of any of the elastomeric members described herein can be coated. Such coatings can include, for example, polydimethylsiloxane. In some embodiments, at least a portion of any of the elastomeric members described herein can be coated with polydimethylsiloxane in an amount of between approximately 0.02 mg/cm$^2$ and approximately 0.80 mg/cm$^2$.

Any of the medicament container assemblies described herein can have any suitable size (e.g., length and/or diameter) and can contain any suitable volume of the medicament. In some embodiments, any of the medicament container assemblies described herein can be a prefilled (or prefillable) syringe, such as those manufactured by Becton Dickinson, Gerresheimer, Ompi Pharma or others. For example, in some embodiments, the medicament container assembly 4200 (and any of the medicament container assemblies described herein) can be a Becton Dickinson "BD Hypak Physiolis" prefillable syringe containing any of the medicaments described herein. Moreover, any of the medicament delivery devices and/or medical injectors described herein can be configured to inject any suitable dosage such as, for example, a dose of up to 1 mL of any of the medicaments described herein. In other embodiments, any of the medicament delivery devices and/or medical injectors described herein can be configured to inject a dose of up to 2 mL, 3 mL, 4 mL, 5 mL, or more of any of the medicaments described herein.

Any of the container bodies described herein can be constructed from glass, and can be fitted and/or coupled to any suitable needle. For example, in some embodiments, any of the container bodies described herein (including the container body 4210) can be coupled to a needle having any suitable size. Any of the medicament container assemblies and/or prefilled syringes described herein can be coupled to a needle having a gauge size of 21 gauge, 22 gauge, 23 gauge, 24 gauge, 25 gauge, 26 gauge, 27 gauge, 28 gauge, 29 gauge, 30 gauge, or 31 gauge. Any of the medicament container assemblies and/or prefilled syringes described herein can be coupled to a needle having any suitable length, such as, for example, a length of about 0.2 inches, about 0.27 inches, about 0.38 inches, about 0.5 inches, about 0.63 inches, about 0.75 inches, or more. In some embodiments, any of the medicament containers and/or prefilled syringes described herein can be coupled to a 29 gauge needle having a length of approximately 0.5 inches. Moreover, any of the medicament containers and/or prefilled syringes described herein can include a staked needle at the distal end thereof.

Although the medical injectors are shown and described as being used in connection with prefilled syringes, in other embodiments, the delivery control assembly can be used with any suitable containers. For example, the delivery control assembly can be used with ampoules, vials, or the like.

For example, any of the medical injectors shown and described herein can include a base (or distal actuator)

having a mechanism for cooling the surface of the target injection site. By cooling the target injection site, patient comfort during an injection operation can be improved. Such cooling mechanisms can include, for example, an electronic cooler (e.g., a thermo-electric cooler) that is triggered upon removal of a safety guard, a chemical or spray that is emitted by the base upon removal of the safety guard, or any other suitable mechanism.

Any of the medical injectors shown and described herein can include a base (or distal actuator) having a mechanism for expanding, stretching or otherwise pulling taut a patient's skin at or near an injection site. In other embodiments, the base (or distal actuator) of any of the injectors described herein can include a mechanism that increases the surface area of the base (or distal actuator) against the injection site. For example, in some embodiments a base can include a series of grips, protrusions, microneedles, or the like that can grip the skin and expand to stretch the surface prior to actuation and/or injection or allow for a large surface area of contact against the skin for added stability for injectate administration. In other embodiments, a base can include a series of grips, protrusions, microneedles, or the like that can grip the skin and pinch the surface together prior to actuation and/or injection. Such a base can include a dome or other structure to pinch certain portions of the anatomy, such as, for example, the abdomen.

Although the medical injectors shown and described above include a delivery mechanism (e.g., 4300) including the release of a pressurized gas, in other embodiments, a medicament delivery device can include any suitable method of delivery of a medicament disposed within. For example, in some embodiments, any of the devices described herein can include a mechanical energy storage (e.g. spring, gears, racks, pinions, pulleys, or the like) member, rather than a compressed gas container. In other embodiments, any of the devices described herein can include any other suitable energy storage member (e.g., magnetic, electrical, propellant based, chemical reaction based, or the like).

While the medical injectors herein are described as being "pistonless" gas-powered auto-injectors, in other embodiments, any of the medical injectors can include any suitable energy storage member configured to produce a force directly on a medicament container and/or a carrier (as described, for example, in the '849 patent). For example, in some embodiments, a medical injector can include one or more bias members, springs, and/or any other suitable mechanical drives (as described above) configured to exert a force on one or more medicament containers. By way of example, a medical injector can include a first spring configured to produce a force on a first medicament container and a second spring configured to produce a force, substantially equal to the force produced by the first spring, on a second medicament container. Moreover, the first spring and the second spring can be actuated substantially concurrently and/or via the same actuation event such that the first spring and second spring move the first medicament container and the second medicament container substantially concurrently.

Although particular injection events, mechanisms, devices, and/or components have been described herein, it is to be understood that they have been presented by way of example and not limitation. That is to say, an auto-injector can include more than one medicament container and can be configured to deliver at least one dose of a medicament to a patient in response any suitable actuation event and/or the like.

Any of the devices and/or medicament containers shown and described herein can be constructed from any suitable material. Such materials include glass, plastic (including thermoplastics such as cyclic olefin copolymers), or any other material used in the manufacture of prefilled syringes containing medications.

Any of the devices and/or medicament containers shown and described herein can contain and/or deliver a wide array of large or macromolecular injectables that include carbohydrate-derived formulations, lipids, nucleic acids, nucleic acids, hyaluronidase, proteins/peptides (e.g. monoclonal antibodies) and other biotechnologically-derived medicaments. For example, anti-tumor necrosis factor agents such as infliximab, etanercept, adalimumab, golimumab, natalizumab, vedolizumab, and certolizumab can be administered using the described auto-injector heroin, Other macromolecular injectable medications that can be administered using the device and/or medicament containers shown and described herein include viscous medicaments that target pro-inflammatory cytokines (e.g. IL-1, IL-2, IL-4, IL-5, IL-6, IL-12. IL-13, IL-23, IL-17, IL-21, IL-23A, and associated receptors) including dupilumab, sarilumab, mepolizumab, benralizumab, reslizumab, lebrikizumab, ustekinumab, anrunkinzumab, bertilimumab, tralokinumab, and risankizumab. Large anti-adhesion molecules to treat a variety of diseases may be administered using the device and/or medicament containers shown and described herein including etrolizumab and vatelizumab. Still other large and viscous monoclonal antibodies that may be administered using the device and/or medicament containers shown and described herein include tezepelumab, anifrolumab, omalizumab, and proprotein convertase subtilisin kexin type 9 (PCSK9) inhibitors including alirocumab and evolocumab.

Any of the devices and/or medicament containers shown and described herein can include any suitable medicament or therapeutic agent. In some embodiments, the medicament contained within any of the medicament containers shown herein can be a vaccine, such as, for example, an influenza vaccine, a hepatitis vaccine, a *haemophilus* influenza Type B (HiB) vaccine, a measles vaccine, a mumps vaccine, a rubella vaccine, or combination vaccine (e.g. measles, mumps and rubella, quadrivalent, or hexavalent vaccines), a polio vaccine, a human papilloma virus (HPV) vaccine, a tetanus vaccine, a diphtheria vaccine, a pertussis vaccine, a bubonic plague vaccine, a yellow fever vaccine, a cholera vaccine, a malaria vaccine, a smallpox vaccine, a pneumococcal vaccine, a rotavirus vaccine, a varicella vaccine, a dengue fever vaccine, a rabies vaccine and/or a meningococcus vaccine. In other embodiments, the medicament contained within any of the medicament containers shown herein can be a catecholamine, such as epinephrine. In other embodiments, the medicament contained within any of the medicament containers shown herein can be an opioid receptor antagonist, such as naloxone, including any of the naloxone formulations described in U.S. Pat. No. 8,627,816, entitled "Medicament Delivery Device for Administration of Opioid Antagonists Including Formulation for Naloxone," filed on Feb. 28, 2011. In yet other embodiments, the medicament contained within any of the medicament containers shown herein can include peptide hormones such as insulin and glucagon; human growth hormone (HGH); sumatriptan; a corticosteroid such as dexamethasone; ondansetron; an opioid agonist receptor modulators such as fentanyl; a partial agonist opioid receptor modulators such as buprenorphine; a mixed agonist/antagonist opioid receptor modulator such as nalbuphine; a benzodiazepine such as diazepam, midazolam or lorazepam; erythropoiesis-stimulating agents (ESA) such as darbepoetin alfa; immunoglobulins including dual-variable domain immunoglobulins; interferons; anti-tumor; granulocyte colony-stimulating factor (GCSF) such as pegfilgrastim; icatibant; and other therapies suitable for injection in mammals. In yet other embodiments, the medicament contained within any of the medicament containers shown herein can be a placebo substance (i.e., a substance with no active ingredients), such as water.

The medicament containers and/or medicament delivery devices disclosed herein can contain any suitable amount of any medicament. For example, in some embodiments, a medicament delivery device as shown herein can be a single-dose device containing an amount of medicament to be delivered of approximately 0.4 mg, 0.8 mg, 1 mg, 1.6 mg or 2 mg. As described above, the fill volume can be such that the ratio of the delivery volume to the fill volume is any suitable value (e.g., 0.4, 0.6 or the like). In some embodiments, an electronic circuit system can include "configuration switch" that, when actuated during the assembly of the delivery device, can select an electronic output corresponding to the dose contained within the medicament container.

In some embodiments, a medical injector can include two prefilled syringes, each containing up to 1 mL of medicament (or more), and each having a needle. Such devices (e.g., "dual container devices") are shown and described in the '4345 PCT, which is incorporated by reference herein. Upon actuation of the device (as described above), a single energy storage member (e.g., a compressed gas container) can release energy to move the two containers within the housing in substantially the same operation to inject the two needles. The force produced by the energy storage member can further inject the medicament from each container. In such embodiments, the two containers can include either the same medicament or two different medicaments. For example, a dual container device can be filled with and/or used to inject methotrexate (from one container) and tocilizumab (in the other container) for the treatment of rheumatoid arthritis. In some embodiments, a dual container device can be filled with and/or used to inject tocilizumab and methotrexate for the treatment of rheumatoid arthritis, adalimumab and methotrexate for the treatment of psoriasis or rheumatoid arthritis, etanercept and methotrexate for the treatment of psoriatic arthritis, belimumab and rituximab for the treatment of Primary Sjogren's Syndrome, lanreotide autogel and pegvisomant for the treatment of acromegaly, narlaprevir and ritonavir for the treatment of chronic hepatitis C, alemtuzumab and rituximab for the treatment of chronic lymphocytic leukemia, pertuzumab and trastuzumab for the treatment of HER2-Positive early breast cancer, long-acting insulin glargine and fast-acting insulin lispro for the treatment of Type 2 diabetes, pramlintide and insulin for the treatment of Type 1 diabetes, insulin glargine and insulin lispro for the treatment of Type 1 diabetes, mosunetuzumab and atezolizumab for the treatment of neoplasm, nivolumab and tumor-infiltrating lymphocytes with interleukin-2 for the treatment of metastatic melanoma, pertuzumab and trastuzumab for the treatment of HER2 positive early breast cancer, ocrelizumab and recombinant human hyaluronidase for the treatment of multiple sclerosis, daratumumab recombinant human hyaluronidase for the treatment of multiple myeloma, nivolumab and recombinant human hyaluronidase for the treatment of metastatic tumors, and insulin lispro and recombinant human hyaluronidase for the treatment of diabetes mellitus.

Any of the medicament containers described herein can include any suitable elastomeric member and/or plunger. For example, an elastomeric member can be formulated to be compatible with the medicament contained within a medicament container. Moreover, a medicament container can include any number of elastomeric members. For example, in some embodiments, a medicament container can include a dry portion of a medicament and a fluid portion of the medicament, configured to be mixed before injection. The piston portion of the medicament delivery mechanism can be configured to engage multiple elastomeric members associated with the portions of the medicament. In this manner, multiple elastomeric members can be engaged to mix the dry portion with the fluid portion of the medicament before the completion of an injection event. In some embodiments, for example, any of the devices shown and described herein can include a mixing actuator similar to the mixing actuators shown and described in U.S. Pat. No. 9,173,999, entitled "Devices and Methods for Delivering Medicaments from a Multi-Chamber Container," filed Jan. 25, 2012, which is incorporated herein by reference in its entirety.

Although the injectors described herein have been shown and described as including mechanisms for needle retraction, in other embodiments any of the injectors shown and described herein can include a needle shield that extends distally after the injection to cover the exposed needle. Such a design may be used, for example, in a "pistonless" design as discussed above. For example, in some embodiments, a base of a medical injector (e.g. the base 4510) can be (or include) an extending portion that, upon completion of the injection, extends distally to cover the needle. In some such embodiments, the gas vent assembly can divert all or a portion of the pressurized gas to a volume within the housing such that the diverted gas exerts a force on the base (or a portion of the base) to cause the base (or portion of the base) to extend distally to cover the needle. In other such embodiments, a spring, biasing member, or retraction member can propel the base (or portion of the base) distally.

Although the gas vent assembly 4310 is shown and described herein as moving a valve portion relative to a seal to selectively place an internal gas chamber in fluid communication with an external volume, in other embodiments, any of the gas vent assemblies disclosed herein can be operable to vent all or a portion of the pressurized gas to a second region within the housing. Further, any of the gas vent assemblies disclosed herein can include any suitable valve arrangement. For example, in some embodiments a gas vent assembly and/or a portion a housing can include a tear-through seal that is punctured or torn when a portion of a medicament carrier or a portion of an elastomeric member moves past a specific point during a delivery event. In other embodiments, a gas vent assembly and/or a portion of a housing can include a movable valve member (e.g., a poppet, ball, or the like) that is moved to release pressure when a portion of a medicament carrier or a portion of an elastomeric member moves past a specific point during a delivery event.

Although various embodiments have been described as having particular features and/or combinations of components, other embodiments are possible having a combination of any features and/or components from any of embodiments where appropriate. For example, any of the devices shown and described herein can include an electronic circuit system as described herein.

What is claimed is:

1. A method of delivering a dose of a composition, comprising:

actuating a medical injector via a system actuation assembly such that an energy storage member produces a force via a compressed gas within an internal volume of a housing of the medical injector on a container containing a dose of the composition, the force causing the container to move within the housing to cause a needle to extend from the housing, the movement of the container compressing a retraction spring of the medical injector;

regulating, via a control assembly positioned within the housing, a portion of the force applied on an elastomeric member to cause a movement of the elastomeric member within the container to deliver an initial portion of the dose;

initiating a venting of the internal volume via a vent opening defined by the housing, the vent opening being sized to maintain the force produced by the compressed gas acting on the container at a magnitude that is greater than a force applied to the container by the retraction spring during a time to deliver a final portion of the dose, the force produced by the compressed gas decreasing to a magnitude that is less than the force applied by the retraction spring concurrent with the delivery of the final portion of the dose; and retracting the needle via a movement of the container within the housing in response to the force applied by the retraction spring.

2. The method of claim 1, wherein:
the control assembly includes a gas vent assembly;
the gas vent assembly includes a valve configured to selectively place the internal volume of the housing in fluid communication with an exterior volume surrounding the housing; and
initiating the venting of the internal volume includes actuating the valve.

3. The method of claim 2, wherein:
the gas vent assembly includes a valve actuator; and
actuating the valve includes manually actuating the valve actuator.

4. The method of claim 2, wherein:
the vent opening is sized to establish a venting duration of at least 0.5 seconds and less than 1.5 seconds; and
the venting duration commences with the actuation of the valve of the gas vent assembly and culminating with the delivery of the final portion of the dose.

5. The method of claim 2, wherein:
the vent opening is sized to establish a venting duration of at least 5 seconds and less than or equal to 15 seconds; and
the venting duration commences with the actuation of the valve of the gas vent assembly and culminating with the delivery of the final portion of the dose.

6. The method of claim 1, wherein:
the control assembly regulates the portion of the force to cause a first 20% of the dose to dispense over a first time duration and to cause a last 20% of the dose to be disposed over a second time duration; and
the second time duration is less than two times the first time duration.

7. The method of claim 6, wherein:
the second time duration is less than about 1.5 times the first time duration.

8. The method of claim 1, wherein:
the medical injector is a wearable delivery device maintained in position against a portion of a body via an attachment surface; and
the attachment surface is configured to maintain the position absent a manually applied pressure by a user.

9. The method of claim 8, wherein:
the needle extends at an angle of between 75 degrees to 88 degrees relative to a longitudinal plane of the wearable delivery device.

10. The method of claim 8, wherein:
the attachment surface is secured against the portion of the body via at least one of an adhesive surface, a strap, a band, a sleeve, or a bandage.

11. A method of delivering a dose of a composition, comprising:

actuating a medical injector such that an energy storage member produces a force via a compressed gas within an internal volume of a housing of the medical injector on a container containing a dose of the composition, the force causing the container to move within the housing to cause a needle to extend from the housing, the movement of the container compressing a retraction spring of the medical injector;

regulating, via a control assembly positioned within the housing, a portion of the force applied directly on an elastomeric member positioned within the container to cause a movement of the elastomeric member within the container to deliver an initial portion of the dose, the medical injector having an absence of a piston coupled to the elastomeric member to cause a movement thereof;

initiating a venting of the internal volume via a vent opening defined by the housing, the vent opening being sized to maintain the force produced by the compressed gas acting on the container at a magnitude that is greater than a force applied to the container by the retraction spring during a time to deliver a final portion the dose, the force produced by the compressed gas decreasing to a magnitude that is less than the force applied by the retraction spring concurrent with the delivery of the final portion of the dose; and retracting the needle via a movement of the container within the housing in response to the force applied by the retraction spring.

12. The method of claim 11, wherein:
the control assembly includes a gas vent assembly;
the gas vent assembly includes a valve;
the gas vent assembly is configured to selectively place the internal volume of the housing in fluid communication with an exterior volume surrounding the housing; and
initiating the venting of the internal volume includes actuating the valve.

13. The method of claim 12, wherein:
the gas vent assembly includes a valve actuator; and
actuating the valve includes manually actuating the valve actuator.

14. The method of claim 12, wherein:
the vent opening is sized to establish a venting duration of at least 0.5 seconds and less than 1.5 seconds; and
the venting duration commences with the actuation of the valve of the gas vent assembly and culminating with the delivery of the final portion of the dose.

15. The method of claim 12, wherein:
the vent opening is sized to establish a venting duration of at least 5 seconds and less than 15 seconds; and the venting duration commences with the actuation of the valve of the gas vent assembly and culminating with the delivery of the final portion of the dose.

16. The method of claim 11, wherein:

the control assembly regulates the portion of the force to cause a first 20% of the dose to dispense over a first time duration and to cause a last 20% of the dose to be disposed over a second time duration; and the second time duration is less than two times the first time duration.

17. The method of claim 16, wherein:

the second time duration is less than about 1.5 times the first time duration.

18. The method of claim 11, wherein:

actuating the medical injector includes placing the medical injector against a body such that a longitudinal axis of the needle is positioned at an angle of between about 75 degrees to 105 degrees relative to an injection surface of the body.

19. The method of claim 11, wherein:

regulating the portion of the force applied directly on the elastomeric member includes reducing the force applied directly on the elastomeric member relative to the force applied to the container.

20. The method of claim 11, wherein:

the housing defines a first gas chamber;

a distal end portion of the control assembly defines a first portion of a boundary of a second gas chamber;

a proximal end portion of the elastomeric member within the container defines a second portion of the boundary of the second gas chamber; and the control assembly is configured to permit pressurized gas to pass from the first gas chamber into the second gas chamber at a reduced pressure on a condition that the needle is extended from the housing.

21. A method of delivering a dose of a composition, comprising:

actuating a medical injector such that an energy storage member produces a force via a first portion of compressed gas within a first gas chamber defined by a housing of the medical injector, the force of the first portion of compressed gas acting on a container containing a dose of the composition, the force causing the container to move within the housing to cause a needle to extend from the housing, the movement of the container compressing a retraction spring of the medical injector;

regulating, via a control assembly positioned within the housing, a flow of a second portion of gas from the first gas chamber into a second gas chamber to act directly on an elastomeric member positioned within the container, the second gas chamber being defined at least in part by the control assembly, the container, and the elastomeric member such that at least a portion of the second gas chamber is within the container, the second portion of gas within the second gas chamber applying a force directly on the elastomeric member to cause a movement of the elastomeric member within the container to deliver an initial portion of the dose;

initiating a venting of the first gas chamber via a vent opening defined by the housing, the vent opening being sized to maintain the force produced by the first portion of the compressed gas acting on the container at a magnitude that is greater than a force applied to the container by the retraction spring during a time to deliver a final portion the dose, the force produced by the first portion of the compressed gas decreasing to a magnitude that is less than the force applied by the retraction spring concurrent with the delivery of the final portion of the dose; and retracting the needle via a movement of the container within the housing in response to the force applied by the retraction spring.

22. The method of claim 21, wherein:

the control assembly is configured to permit the second portion of pressurized gas to pass from the first gas chamber into the second gas chamber at a reduced pressure on a condition that the needle is extended from the housing.

23. The method of claim 21, wherein:

the first portion of pressurized gas is at a first pressure within the first gas chamber;

the second portion of pressurized gas is at a second pressure within the second gas chamber; and the second pressure is less than the first pressure.

24. The method of claim 21, wherein:

the medical injector has an absence of a piston positioned to affect the elastomeric member.

25. The method of claim 21, wherein:

the control assembly regulates a pressure of the second portion of gas within the second gas chamber to cause a first 20% of the dose to dispense over a first time duration and to cause a last 20% of the dose to disposed over a second time duration; and the second time duration is less than two times the first time duration.

* * * * *

UNITED STATES PATENT AND TRADEMARK OFFICE
CERTIFICATE OF CORRECTION

PATENT NO. : 12,268,847 B1  
APPLICATION NO. : 17/668228  
DATED : April 8, 2025  
INVENTOR(S) : Meyers et al.

Page 1 of 2

It is certified that error appears in the above-identified patent and that said Letters Patent is hereby corrected as shown below:

In the Specification

Column 22, Line 35, change "1100," to --1100'--  
Column 22, Line 39, change "1400" to --1400'--  
Column 22, Line 48, change "1450" to --1450'--  
Column 23, Line 32, change "1217" to --1217'--  
Column 23, Line 47, change "1210)'" to --1210'--  
Column 23, Line 49, change "1217" to --1217'--  
Column 23, Line 66, change "1320" to --1320'--  
Column 24, Line 4, change "1320" to --1320'--  
Column 24, Line 24, change "1216" to --1216'--  
Column 24, Line 34, change "movement)" to --movement).--  
Column 26, Line 43, change "2108e" to --2108c'--  
Column 30, Line 34, change "3200A." to --3200A,'--  
Column 32, Line 67, change "Dow" to --flow--  
Column 36, Line 16, change "4100 . . . ." to --4100.--  
Column 38, Line 59, change "4220)." to --4220.--  
Column 51, Line 12, change "vet" to --yet--  
Column 55, Line 19, change "4340)." to --4340'.--  
Column 55, Line 37, change "6350)" to --6350--  
Column 55, Line 42, change "4340)" to --4340'--  
Column 55, Line 45, change "4340)'" to --4340'--  
Column 58, Line 48, change "7430)" to --7430--  
Column 58, Line 50, change "7440)" to --7440-- and "7450)," to --7450,--  
Column 58, Line 51, change "7460)" to --7460--  
Column 58, Line 55, change "7450)" to --7450--  
Column 58, Line 61, change "7450)" to --7450--  
Column 58, Line 62, change "7460)" to --7460--  
Column 58, Line 63, change "7440)" to --7440-- and "7440)" to --7440--  
Column 58, Line 64, change "7450)" to --7450--

Signed and Sealed this  
Sixth Day of May, 2025

Coke Morgan Stewart  
*Acting Director of the United States Patent and Trademark Office*

CERTIFICATE OF CORRECTION (continued)
U.S. Pat. No. 12,268,847 B1

Column 58, Line 66, change "7440)." to --7440.--
Column 58, Line 67, change "7470)" to --7470--
Column 59, Line 3, change "7440)." to --7440.--
Column 59, Line 6, change "7440)" to --7440--
Column 59, Line 19, change "7470)" to --7470--
Column 61, Line 12, change "7450)" to --7450--
Column 61, Line 25, change "7450)" to --7450--
Column 61, Line 41, change "7450)" to --7450--
Column 61, Line 56, change "7450)" to --7450--
Column 75, Line 3, change "granulocyte" to --recombinant human granulocyte--